US006518063B1

(12) United States Patent
Ducy et al.

(10) Patent No.: US 6,518,063 B1
(45) Date of Patent: Feb. 11, 2003

(54) OSF2/CBFA1 NUCLEIC ACIDS AND METHODS OF USE THEREFOR

(75) Inventors: Patricia Ducy, Houston, TX (US); Gérard Karsenty, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/086,663

(22) Filed: May 29, 1998

Related U.S. Application Data
(60) Provisional application No. 60/080,189, filed on Mar. 24, 1998, and provisional application No. 60/048,430, filed on May 29, 1997.

(51) Int. Cl.[7] ........................... C12N 5/00; C12N 15/63; C12N 1/20; C07H 21/04

(52) U.S. Cl. ................. 435/325; 435/320.1; 435/252.3; 536/23.5

(58) Field of Search ................... 514/44; 424/93.1; 435/69.1, 320.1, 325

(56) References Cited

U.S. PATENT DOCUMENTS

| 4,877,864 A | 10/1989 | Wang et al. ................. 530/324 |
| 4,968,590 A | 11/1990 | Kuberasampath et al. .. 530/326 |
| 5,011,691 A | 4/1991 | Oppermann et al. ......... 424/423 |
| 5,013,649 A | 5/1991 | Wang et al. ................. 435/69.1 |
| 5,106,748 A | 4/1992 | Wozney et al. ........... 435/252.3 |
| 5,108,922 A | 4/1992 | Wang et al. ............. 435/240.2 |
| 5,116,738 A | 5/1992 | Wang et al. ................. 435/69.1 |
| 5,141,905 A | 8/1992 | Rosen et al. ................. 435/69.1 |
| 5,166,058 A | 11/1992 | Wang et al. ................. 435/69.1 |
| 5,756,664 A | 5/1998 | Amann et al. ............... 530/326 |

FOREIGN PATENT DOCUMENTS

| AT | 167232 | 6/1998 |
| CA | 2092768 | 9/1993 |
| EP | 562508 | 9/1993 |
| ES | 2123582 | 1/1999 |
| JP | 05268982 | 10/1993 |
| JP | 10309148 | 11/1998 |
| JP | 11018787 | 1/1999 |
| WO | WO 98/54322 | 12/1998 |
| WO | WO 99/11787 | 3/1999 |

OTHER PUBLICATIONS

Clark TM et al. Pathology Oncology Research 5:3–15, 1999.*
Anderson WF. Nature 392 (SUPP):25–30, 1998.*
Verma IM and Somia N. Nature 389: 239–242. 1997.*
Susa M et al. Biochem Biophys Res Commun 235:680–684, 1997.*
Berger W et al. Accession No. X65724, 1992.*
Ducy, P. et al., GenBank, Accession No. AF010284., 1997.*
B.–L. Huang et al., Proc. Natl.Acad. Sci. USA, Dec. 1998, vol. 95, pp. 14669–14674.*

J. Sambrook et al., Molecular Cloning, Laboratory Manual, 2nd Edition, (Cold Spring Harbor Laboratory Press, New York) 1989, p. 11.47.*
W. Wood, Guide to Molecular Cloning Techniques,"Gene Cloning based on long oligonucleotide probes," (Academic Press, New York) vol. 152, 1987, p. 443.*
R.B. Wallace et al., Guide to Molecular Cloning Techniques, "Oligonucleotide Probes for the Screening of Recombinant DNA Libraries," (Academic Press, New York) vol. 152, 1987, pp. 432–442.*
Ahn et al., "Comparison of the human genomic structure of the Runt domain–encoding PEBP2/CBF α gene family," Gene, 168:279–280, 1996.
Armitage et al., "Peptide nucleic acid–DNA duplexes: Long range hold migration from an internally linked anthraquinone," Proc. Natl. Acad. Sci. USA, 94:12320–12325, 1997.
Aronson et al., "Groucho–dependent and –independent repression activities of runt domain proteins," Mol. Cell. Biol., 17:5581–5587, 1997.
Coffman et al., "SpRunt–1, a new member of the runt domain family of transcription factors, is a positive regulator of the aboral ectoderm–specific CyIIIA gene in a sea urchin embryos," Dev. Biol., 174:43–54, 1996.
Desbois et al., "The mouse osteocalcin gene cluster contains three genes with two separate spatial and temporal patterns of expression," J. Biol. Chem., 269(2):1183–1190, 1994.
Ducy and Karsenty, "Two distinct osteoblast–specific cis–acting elements control expression of a mouse osteocalcin gene," Mol. Cell. Biol., 15(4):1858–1869, 1995.
Ducy et al., "Osf2/Cbfa1: a transcriptional activator of osteoblast differentiation," Cell, 89:747–754, 1997.
Geoffroy et al., "A PEBP2α/AML–I–related factor increases osteocalcin promotor activity through its binding to an osteoblast–specific cis–acting element," J. Biol. Chem., 270(52):30973–30979, 1995.
Kagoshima et al., "The Runt domain identifies a new family of heteromeric transcriptional regulators," Trends Genet., 9(10):338–341, 1993.

(List continued on next page.)

Primary Examiner—Dave T. Nguyen
Assistant Examiner—Ram R. Shukla
(74) Attorney, Agent, or Firm—Fulbright & Jaworski, LLP

(57) ABSTRACT

Disclosed are methods and compositions comprising a novel osteoblast-specific transcription factor designated Osf2/Cbfa1. Also disclosed are nucleic acid segments encoding this polypeptide derived from human cell lines, and the use of these polynucleotides in a variety of diagnostic and therapeutic applications. Methods, compositions, kits, and devices are also provided for identifying compounds which are inhibitors of osteoblast differentiation, and identifying Osf2/Cbfa1 polynucleotides and polypeptides in a sample. Also disclosed are nucleic acid compositions comprising an Osf2 promoter, and the use of the promoter in heterologous and homologous gene transcription and protein production.

30 Claims, 37 Drawing Sheets

OTHER PUBLICATIONS

Figure 1A:
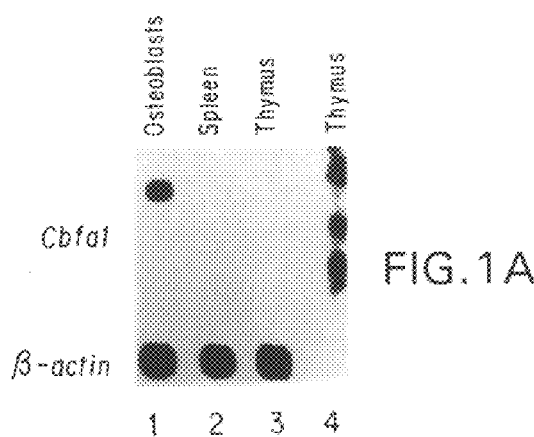

Kania et al., "The Drosophila segmentation gene runt encodes a novel nuclear regulatory protein that is also expressed in the developing nervous system," *Genes Dev.*, 4:1701–1713, 1990.

Komori et al., "Targeted disruption of Cbfa1 results in a complete lack of bone formation owing to maturational arrest of osteoblasts," *Cell*, 89:755–764, 1997.

Koppelhus et al., "Efficient in vitro inhibition of HIV–1 gag reverse transcription by peptide nucleic acid (PNA) at minimal ratios of PNA/RNA," *Nucleic Acids. Res.*, 25(11):2167–2173, 1997.

Kurokawa et al., "A conserved Cysteine residue in the runt homology domain of AML1 is required for the DNA–binding ability and the transforming activity of fibroblasts," *J. Biol. Chem.*, 271(28):16870–16876, 1996.

Kurokawa et al., "Overexpression of the AML1 proto–oncoprotein in NIH3T3 cells leads to neoplastic transformation depending on the DNA–binding and transcriptional potencies," *Oncogene*, 12:883–892, 1996.

Lee et al., "Missense mutations abolishing DNA binding of the osteoblast–specific transcription factor OSF2/CBFA1 in cleidocranial dysplasia," *Nature Genet.*, 16:307–310, 1997.

Levanon et al., "AML1, AML2, and AML3, the human members of the runt domain gene–family: cDNA structure, expression, and chromosomal localization," *Genomics*, 23:425–432, 1994.

Merriman et al., "The tissue–specific nuclear matrix protein, NMP–2, is a member of the AML/CBF/PEBP2/Runt Domain transcription factor family: interactions with the osteocalcin gene promoter," *Biochemistry*, 34:13125–13132, 1995.

Meyers et al., "Identification of AML–1 and the (8;21) translocation protein (AML–1ETO) as sequence–specific DNA–binding proteins: the runt homology domain is required for DNA binding and protein–protein interactions," *Mol. Cell. Biol.*, 13(10):6336–6345, 1993.

Mundlos et al., "Mutations involving the transcription factor CBFA1 cause cleidocranial dysplasia," *Cell*, 89(5):773–779, 1997.

Ogawa et al., "Molecular cloning and characterization of PEBP2β, the heterodimeric partner of a novel Drosophila runt–related DNA binding protein PEBP2α," *Virology*, 194:314–331, 1993.

Ogawa et al., "PEBP2/PEA2 represents a family of transcription factors homologous to the products of the Drosophila runt gene and the human AML1 gene," *Proc. Natl. Acad. Sci. USA*, 90:6859–6863, 1993.

Otto et al., "Cbfa1, a candidate gene for the cleidocranial dysplasia syndrome, is essential for osteoblast differentiation and bone development," *Cell*, 89(5):765–771, 1997.

Simeone et al., "Expression of runt in the mouse embryo," *Dev. Dyn.*, 203:61–70, 1995.

Wang et al., "Disruption of the Cbfa2 gene causes necrosis and hemorrhaging in the central nervous system and blocks definitive hematopoiesis," *Proc. Natl. Acad. Sci. USA*, 93:3444–3449, 1996.

Wang et al., "The Cbfβsubunit is essential for CBFα2 (AML1) function in vivo," *Cell*, 87:697–708, 1996.

Wijmenga et al., "Identification of a new murine runt domain–containing gene, Cbfa3, and localization of the human homolog, CBFA3, to chromosome 1p35–pter," *Genomics*, 26:611–614, 1995.

Banerjee et al., "An AML–1 consensus sequence binds an osteoblast–specific complex and transcriptionally activates the osteocalcin gene," *Proc. Nat'l. Acad. Sci. USA*, 93:4968–4973, 1996.

* cited by examiner

```
M L H S P H K Q P Q N H K C G A N F L Q E D C K K   25
A L A F K W L I S A G H Y Q P P R P T E S F K A A   50
S S I Y N R G H K F Y L E K K G G T M A S N S L F   75
S A V T P C Q Q S F F W D P S T S R R F S P P S S   100
S L Q P G K M S D V S P V V A A Q Q Q Q Q Q Q Q Q   125
Q Q Q Q Q Q Q Q Q Q Q Q Q Q Q Q Q Q Q E A A A A   150
A A A A A A A A A A A A A V P R L R P P H D N R   175
T M V E I I A D H P A E L V R T D S P N F L C S V   200
L P S H W R C N K T L P V A F K V V A L G E V P D   225
G T V V T V M A G N D E N Y S A E L R N A S A V M   250
K N Q V A R F N D L R F V G R S G R G K S F T L T   275
I T V F T N P P Q V A T Y H R A I K V T V D G P R   300
E P R R H R Q K L D D S K P S L F S D R L S D L G   325
R I P H P S M R V G V P P Q N P R P S L N S A P S   350
P F N P Q G Q S Q I T D P R Q A Q S S P P W S Y D   375
Q S Y P S Y L S Q M T S P S I H S T T P L S S T R   400
G T G L P A I T D V P R R I S D D D T A T S D F C   425
L W P S S L S K K S Q A G A S E L G P F S D P R Q   450
F P S I S S L T E S R F S N P R M H Y P A T F T Y   475
T P P V T S G M S L G M S A T T H Y H T Y L P P P   500
Y P G S S Q S Q S G P F Q T S S T P Y L Y Y G T S   525
S A S Y Q F P M V P G G D R S P S R M V P P C T T   550
T S N G S T L L N P N L P N Q N D G V D A D G S H   575
S S S P T V L N S S G R M D E S V W R P Y *        596 (SEQ ID NO:2)
```

FIG. 1B

```
              *              *              *              *              *
  1 MASNSLFSTVTPCQQNFFWDPSTSRRFSPPSSSLQPGKMSDVSPVVAAQQ
  1 --------A-----------------------------------------

51 QQQQQQQQQQQQQQQQQQQQQ------EAAAAAAAAAAAAAAAAAA-VPRL
 51 ---------------------QQQQQQ------------------A----

94 RPPHDNRTMVEIIADHPAELVRTDSPNFLCSVLPSHWRCNKTLPVAFKVV
101 --------------------------------------------------

144 ALGEVPDGTVVTVMAGNDENYSAELRNASAVMKNQVARFNDLRFVGRSGR
151 --------------------------------------------------

194 GKSFTLTITVFTNPPQVATYHRAIKVTVDGPREPRRHRQKLDDSKPSLFS
201 --------------------------------------------------

244 DRLSDLGRIPHPSMRVGVPPQNPRPSLNSAPSPFNPQGQSQITDPRQAQS
251 --------------------------------------------------

294 SPPWSYDQSYPSYLSQMTSPSIHSTTPLSSTRGTGLPAITDVPRRISDDD
301 --------------------------------------------------

244 TATSDFCLWPSTLSKKSQAGASELGPFSDPRQFPSISSLTESRFSNPRMH
351 -----------S--------------------------------------

294 YPATFTYTPPVTSGMSLGMSATTHYHTYLPPPYPGSSQSQSGPFQTSSTP
401 --------------------------------------------------

444 YLYYGTSSGSYQFPMVPGGDRSPSRMLPPCTTTSNGSTLLNPNLPNQNDG
453 ---------A----------------------------------------

494 VDADGSHSSSPTVLNSSGRMDESVWRPY  Human OSF2/CBFA1 (SEQ ID NO:74)
501 ---------------------------   Mouse Osf2/Cbfa1 (SEQ ID NO:71)
```

FIG. 7B

```
-450  CCTTAACTGCAGAGCTCTGCTCTCTACAAATGCTTAACCTTACAGGAGAGTTTGGGCTCCTTCAGCATTTGTATTCTAT
-375  TTGTGAGAGAAAGAGAGAGAGAAGAGCAAGGGGGAAAAGCCACAGTGGTAGGCAGTCCCACTTTACTTAAGA
-300  GTACTGTGAGGTCACAAACCACATGATTCTGCCTCATTGCCTCCAGTAATAGTAGTGCTTGCAAAAAAAGGATTTTAAAGCTT
-225  TTGCTTTTTTGGATTGTGTGAATGCTTCTGTGTTTTTAAAGTGTTAATCTCCGCAGTCACTACCAGCCACCGAGACCA
-150  CTCCAGGAGGACAGCAAGAAGTCTGCAAGCAGTATTTACAACAGAGGGTACAAGTTCTATCTGAAAAAAAGGAGGGACT
-75   ACAGAGTCATTTAAGGCTGCAAGCAGTATTTACAACACCATGTCAGCAGCAAACTTCTTTTGGGATCCGAGCACCAGCCGG
+1    ATGGCATCAAACAGCCTCTTCAGCAGTGTCACACCATGTCAGCAGAACAACCTTCTTTTGGGATCCGAGCACCAGCCGG
       1 M  A  S  N  S  L  F  S  T  V  T  P  C  Q  Q  N  F  F  W  D  P  S  T  S  R
75    CGCTTCAGCCCCCCCCTCCAGCAGCTGCAGCCCGGCAAATGAGCGACGTGAGCCCGGTGGTGGCTGCGCAACAG
      25 R  F  S  P  P  S  S  L  Q  P  G  K  M  S  D  V  S  P  V  V  A  Q  Q
150   CAGCAGCAACAGCAGCAGCAGCAGCAACAGCAGCAGCAGCAGCAGCAGCAGCAGCAGCAGCAGGAGGCGGCGGCG
      50 Q  Q  Q  Q  Q  Q  Q  Q  Q  Q  Q  Q  Q  Q  E  A  A  A
225   GCGGGCTGCGGCGGCGGCGGCGGCAGCGGCAGCGGCAGCAGTGCCCCGGTTGCGGCCGCCCCCAAGACAACCGC
      75 A  A  A  A  A  A  A  A  A  V  P  R  L  R  P  P  H  D  N  R
300   ACC ATGGTGGAGATCATCGCCGACCACCCGGCCGAACTCGTCCGGCCACAGCCCCAACTTCCTGTGCTCGGTG
      100 T  M  V  E  I  I  A  D  H  P  A  E  L  V  R  T  D  S  P  N  F  L  C  S  V
375   CTGCCCTCGCACTGGCGCTGCAACAAGACCCTGCCCGTGGCCTTCAAGGTGGTAGCCCTCGGAGAGGTACCAGAT
      125 P  S  H  W  R  C  N  K  T  L  P  V  A  F  K  V  V  A  L  G  E  V  P  D  G
450   GGGACTGTGGTTACTGTCATGGCGGGTAACGATGAAAATTATTCTGCTGAGCTCCGGAATGCCTCTGTGTTATG
      150 T  V  V  T  V  M  A  G  N  D  E  N  Y  S  A  E  L  R  N  A  S  A  V  M  K
525   AAAAACCAAGTAGCAAGGTTCAACGATCTGAGATTTGTGGGCCGGAGTGGACGAGGCAAGAGTTCACCTTGACC
      175 N  Q  V  A  R  F  N  D  L  R  F  V  G  R  S  G  R  G  K  S  F  T  L  T  I
600   ATAACCGTCTTCACAAATCCTCCCCAGTAGCTACCTATCACAGAGCAATTAAAGTTACAGTAGATGGACCTCGG
      200 T  V  F  T  N  P  P  Q  V  A  T  Y  H  R  A  I  K  V  T  V  D  G  P  R  E
675   GAACCCAGAAGGCACAGACAGAAGCTTGATGACTCTAAACCTAGTTGTTCTCTGACCGCCTCAGTGATTTAGGG
      225 P  R  R  H  R  Q  K  L  D  D  S  K  P  S  L  F  S  D  R  L  S  D  L  G  R
```

FIG. 7C-1

```
 750 CGCATTCCTCATCCCAGTAGTAGAGAGTAGGTGTCCCGCCTCAGAACCCAGGGCCCTCCCTGAACTCTGCACCAAGT
 250  I  P  H  P  S  M  R  V  G  V  P  P  Q  N  P  R  P  S  L  N  S  A  P  S  P
 825 CCTTTTAATCACAAGGACAGAGTCAGATTACAGACCCAGGCAGGCACAGTCTTCCCCGCTGGTCCTATGAC
 275  F  N  P  Q  G  Q  S  Q  I  T  D  P  R  Q  A  Q  S  S  P  P  W  S  Y  D  Q
 900 CAGTCTTACCCCTCCTACCTGAGCCAGATGACGTCCCGTCCATCCACTCTACCCCGCTGTCTTCCACACGG
 300  S  Y  P  S  Y  L  S  Q  M  T  S  P  S  I  H  S  T  T  P  L  S  S  T  R  G
 975 GGCACTGGGCTTCCTGCCATCACCGATGTGCCTAGGCGCATTTCAGATGATGACACTGCCACTCTGACTTCTGC
 325  T  G  L  P  A  I  T  D  V  P  R  R  I  S  D  D  D  T  A  T  S  D  F  C  L
1050 CTCTGGCCTTCCACTCTCAGTAAGAAGAGCCAGGCAGGTGCTTCAGAACTGGGCCCTTTTCAGACCCCAGGCAG
 350  W  P  S  T  L  S  K  K  S  Q  A  G  A  S  E  L  G  P  F  S  D  P  R  Q  F
1125 TTCCCAAGCATTTCATCCCTCACTGAGAGCCGCTTCTCCAACCACGAATGCAGCATCCAGCCACCTTTACTTAC
 375  S  D  S  I  S  S  L  T  E  S  R  F  S  N  P  R  M  H  Y  P  A  T  F  T  Y  T
1200 ACCCCGCCAGTCACCTCAGGCATGTCCCTCGGTATGTCGCCACCACTCACTACCACTGCCACCACCC
 400  P  P  V  T  S  G  M  S  L  G  M  S  A  T  T  H  Y  H  T  Y  L  P  P  P  Y
1275 TACCCCGGCTCTTCCCAAAGCCAGAGTGGACCCTTCCAGACCAGCAGCACTCCATATCTCTACTATGGCACTTCG
 425  P  G  S  S  Q  S  Q  S  G  P  F  Q  T  S  S  T  P  Y  L  Y  Y  G  T  S  S
1350 TCAGGATCCTATCAGTTTCCCATGGTGCCGGGGAGACCGGTCTCTCCTTCCAGAATGCTTCCGCCATGCACCACC
 450  G  S  Y  Q  F  P  M  V  P  G  G  D  R  S  P  S  R  M  L  P  P  C  T  T  T
1425 ACCTCGAATGGCAGCACGCTATTAAAATCCAAATTTGCCTAACCAGAATGATGGTGTTGACGCTGATGGAAGCCAC
 475  S  N  G  S  T  L  L  N  P  N  L  P  N  Q  N  D  G  V  D  A  D  G  S  H  S
1500 AGCAGTTCCCCAACTGTTTGAATTCTAGTGGCAGAATGGATGAATCTGTTTGGGGACCATATTGAAATTCCTCA
 500  S  S  P  T  V  L  N  S  S  G  R  M  D  E  S  V  W  R  P  Y  Z    (SEQ ID NO:74)
1575 GCAGTGGCCCAGTGTATCTGGGGGCCACATCCCACACTATCAATATATACATATATATAGAGAGAGTGCATATATA
1650 TGTTATATC-3   (SEQ ID NO:73)
```

FIG. 7C-2 hOSF2/CBFA1
18 hr. 
52 hr. 
18 S 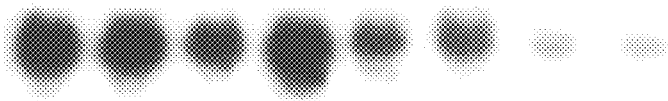
      1  2  3  4  5  6  7  8
FIG. 10

| | | |
|---|---|---|
| Osf2 | MASNSLFSAVTPCQQSFFWDPSTSRRFSPPPSSSLQPGKMSDVSPVVAAQQQQQQQQQQQQQQQ | 70 |
| Cbfa2 | MRIPV------------DASTSRRFTPPSTALSPGKMS-------------------------- | 26 |
| Osf2 | QQQQQQQEAAAAAAAAAAAAAAVPRLRPPHDNRTMVEIIADHPAELVRTDSPNFLCSVLPSHWRCN | 140 |
| Cbfa2 | ------E-------ALPLGAPDGGPALASKLRSGDRSMVEVLADHPGELVRTDSPNFLCSVLPTHWRCN | 182 |
| Osf2 | KTLPVAFKVVALGEVPDGTVVTVMAGNDENYSAELRNASAVMKNQVARFNDLRFVGRSGRGKSFTLTITV | 210 |
| Cbfa2 | KTLPIAFKVVALGDVPDGTLVTVMAGNDENYSAELRNATAAMKNQVARFNDLRFVGRSGRGKSFTLTITV | 152 |
| Osf2 | FTNPPQVATYHRAIKVTVDGPREPRRHRQKLDD-SKP-SL-FSDRLSDLGRIPHPSMRVGV----PPQNP | 273 |
| Cbfa2 | FTNPPQVATYHRAIKITVDGPREPRRHRQKLDDQTKPGSLSFSERLSELEQLRRTAMRVSPHHPAPTPNP | 222 |
| Osf2 | RPSLNSAPSPFNPQGQSQITDPRQAQSSPPWSYDQSYPSYLSQMTSPSIHSTTPLSSTRGTGLPAITDVP | 343 |
| Cbfa2 | RASLNHST-AFNPQPQSQMQDARQIQPSPPWSYDQSYQ-YLGSITSSSVHPATPISPGRASGMTSLSAEL | 290 |
| Osf2 | RRISDDDTATSDFCLWPSS-LSKKSQAGASELGPFSDPRQFPSISSLTESRFSNPRMHYP-ATFTYTPPV | 411 |

FIG. 13A

```
Cbfa2  ------------------SSRLS-----TAPDLTAFGDPRQFPTLPSIS-----DPRMHYPGA-FTYSPPV      332
Osf2   TSGMSLGMSATT---HYHTYLPPPYPGSSQSQSGPFQTSSTPY-LYYGTSSASYQFPMVPGGDRSPSRMV          477
       :::..::::       ::::::::::::::::::::::::: . :::::: ..   ::::::..
Cbfa2  TSGIGIGMSAMSSASRYHTYLPPPYPGSSQAQAGPFQTGSPSYHLYYGASAGSYQFSMV-GGERSPPRIL          401

Osf2   PPCTTTSNGSTLLNPNLPNQNDGVDADGSHSSSPTVLNSSGRMDESVWRPY      528    (SEQ ID NO:71)
       :::: ..: ..       ::::::..    . .:::::: ::
Cbfa2  PPCTNASTGAALLNPSLPSQSDVVETEGSHSNSPTNMP-PARLEEAVWRPY      451    (SEQ ID NO:75)
```

FIG. 13B

```
c-Myc        P A A K R V K L D
Osf2/Cbfa1   P R R H R Q K L D
Cbfa2        P R R H R Q K L D
CBFA2        P R R H R Q K L D
CBFA3        P R R H R Q K L E
SpRunt-1     P R R P K P K D Q
```
FIG. 14A
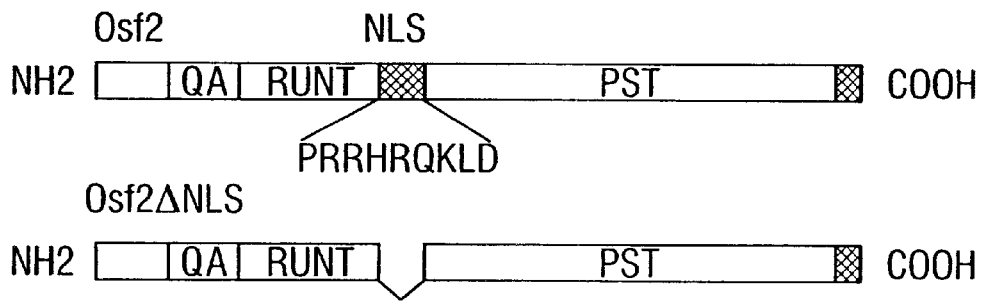
FIG. 14B
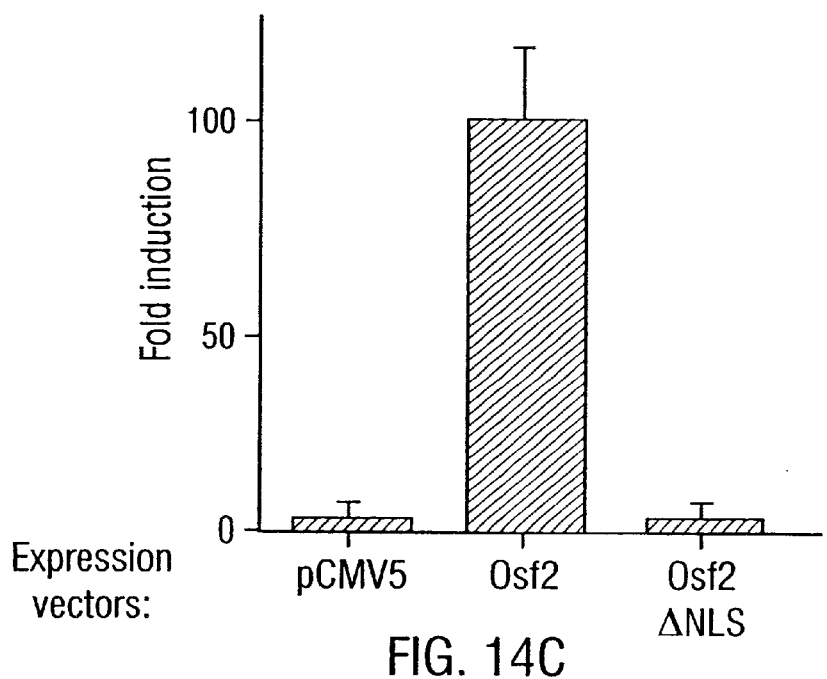
FIG. 14C Probe: α1(I)wt α1(I)m
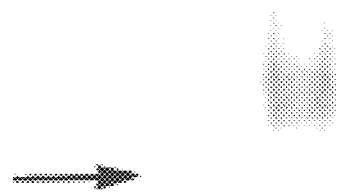
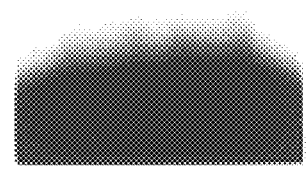
1   2
FIG.21B

SEQUENCE LISTING

<160> NUMBER OF SEQ ID NOS: 83

<210> SEQ ID NO 1
<211> LENGTH: 3334
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1

```
actttgagta ctgtgaggtc acaaaccaca tgattctgtc tctccagtaa tagtgcttgc        60
aaaaaatagg agttttaaag cttttgcttt tttggattgt gtgaatgctt cattcgcctc       120
acaaacaacc acagaaccac aagtgcggtg caaactttct ccaggaagac tgcaagaagg       180
ctctggcgtt taaatggtta atctctgcag gtcactacca gccaccgaga ccaaccgagt       240
catttaaggc tgcaagcagt atttacaaca gagggcacaa gttctatctg gaaaaaaaag       300
gagggactat ggcgtcaaac agcctcttca gcgcagtgac accgtgtcag caaagcttct       360
tttgggatcc gagcaccagc cggcgcttca gccccccctc cagcagcctg cagcccggca       420
agatgagcga cgtgagcccg gtggtggctg cgcagcagca gcaacagcag cagcagcagc       480
agcaacagca gcagcaacaa cagcaacagc aacaacagca gcagcagcag cagcagcagg       540
aggcggccgc agcagcagcg gcggcagcgg cggcggcagc agcggcggcg gccgcagtgc       600
cccgattgag gccgccgcac gacaaccgca ccatggtgga gatcatcgcg gaccacccgg       660
ccgaactggt ccgcaccgac agtcccaact tcctgtgctc cgtgctgccc tcgcactggc       720
ggtgcaacaa gaccctgccc gtggccttca aggttgtagc cctcggagag gtaccagatg       780
ggactgtggt taccgtcatg gccgggaatg atgagaacta ctccgccgag ctccgaaatg       840
cctccgctgt tatgaaaaac caagtagcca ggttcaacga tctgagattt gtgggccgga       900
gcggacgagg caagagtttc accttgacca taacagtctt cacaaatcct ccccaagtgg       960
ccacttacca cagagctatt aaagtgacag tggacggtcc ccgggaacca agaaggcaca      1020
gacagaagct tgatgactct aaacctagtt tgttctctga tcgcctcagt gatttagggc      1080
gcattcctca tcccagtatg agagtaggtg tcccgcctca gaacccacgg ccctccctga      1140
actctgcacc aagtccttttt aatccacaag gacagagtca gattacagat cccaggcagg      1200
cacagtcttc cccaccgtgg tcctatgacc agtcttaccc ctcctatctg agccagatga      1260
catccccatc catccactcc accacgccgc tgtcttccac acggggcacc gggctacctg      1320
ccatcactga cgtgccagg cgtatttcag atgatgacac tgccacctct gacttctgcc      1380
tctggccttc ctctctcagt aagaagagcc aggcaggtgc ttcagaactg ggccctttt       1440 cagaccccag gcagttccca agcatttcat ccctcactga gagccgcttc tccaacccac      1500
```

```
gaatgcacta cccagccacc tttacctaca ccccgccagt cacgtcaggc atgtccctcg    1560
gcatgtccgc caccactcac taccacacgt acctgccacc ccctacccc ggctcttccc     1620 aaagccagag tggacccttc cagaccagca gcactccata tctctactat ggtacttcgt    1680
cagcatccta tcagttccca atggtacccg ggggagaccg gtctccttcc aggatggtcc    1740
caccatgcac caccacctcg aatggcagca cgctattaaa tccaaatttg cctaaccaga    1800
atgatggtgt tgacgctgac ggaagccaca gcagttcccc aactgttttg aattctagcg    1860
gcagaatgga tgagtctgtt tggcggccat attgaaattc gtcaaccatg cccagtggc     1920 atggggggcca catcccgcat gtgttaatat atacatatat aaagagagtg cctatatatg   1980
tatattgatt agctaactag aagatttctc attcaatccc tagtcatgat cttgcaaccc    2040
taagagggtg ggggcagtca taactgggtt tcatattgtt tactatttaa gatgtcccct    2100
ttaccaagga acaaaccgtc aaggtgttg tctggtctgt tttcataagt gacctgttcc     2160
cacgccggtt cagagaggtg gactctgggt ctgggaggaa ggagagacac ttcctctctg    2220
tgctttgaaa ccacagcctc tgctgtgtgg cagccggtac actctgcaga cccgcttaca    2280
gagtcagatg tggtgcactc agaaagggac aagaggcaga gtggctgctt ctgtccgctg    2340
ccgtccactc tgccgtccac ctgttccaaa gttttccttc agacttgctg caggtactca    2400
tttgaacttt tgagttcact tttttttttt cctattctaa gaaagtgact tcaaaaatac    2460
tgatcaggac agataaattt attttaccct ttatatttc tcacttcccc catttaacca    2520
aaaagaaatc ccgttcccc tccccgttc cttctgcttc tccctttatg caaactgaaa     2580
atggcaatgc cttattatta tagccataat ggtatagtgt ttgagttggc tgtgtgttat    2640 gtgtttttt tctttttttt ctttttttaaa ttatgaatat gtgtaaaatc tgaagtaact    2700
tgctaacgtg aatggtcata aacttttaaa gatatattta taattattta atgacatttg    2760
gacatttgga acatttctta gtgtaatgat atgttgactt cggtctctaa aagtgtgctt    2820
cttcttcaat accaagtttc ttcagtgggc tagagccata tcggaaatat tgctaagcaa    2880
tctcaattcc ttcaggcata atgtgatttt ttttttttg aagataactc ccatctccaa     2940
atagtttaga tgtagtttgt tttcacgatg tatgaaggag atgctctgtt tctttctttc    3000
aggcatttga ttgcctctga cacagctttg cctttaaag caataattag ggattaaaat    3060
aacaaaaaca aaacaaaagc cacctatagc cctttaacac ttaacgtggc cccctttacta   3120 gcatgaaatg ctggagacat gtggtttcct aatttctcca ttttgggggt ggtgggagcg    3180
gggagggtgg ccattatgac tcttatcata ttaaaaagcc aatgcacaag tgattggttg    3240
aactgcagaa aagtgttctg tggtctctga gttgagcaaa actctaaatt gcaggcttcg    3300
tggttgaggg cctagtcagc tgaaagccac gcgt                                3334
```

<210> SEQ ID NO 2
<211> LENGTH: 596
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Met Leu His Ser Pro His Lys Gln Pro Gln Asn His Lys Cys Gly Ala
  1               5                  10                  15

Asn Phe Leu Gln Glu Asp Cys Lys Lys Ala Leu Ala Phe Lys Trp Leu
             20                  25                  30

-continued

```
Ile Ser Ala Gly His Tyr Gln Pro Pro Arg Pro Thr Glu Ser Phe Lys
         35                  40                  45
Ala Ala Ser Ser Ile Tyr Asn Arg Gly His Lys Phe Tyr Leu Glu Lys
     50                  55                  60
Lys Gly Gly Thr Met Ala Ser Asn Ser Leu Phe Ser Ala Val Thr Pro
 65                  70                  75                  80
Cys Gln Gln Ser Phe Phe Trp Asp Pro Ser Thr Ser Arg Arg Phe Ser
                 85                  90                  95
Pro Pro Ser Ser Ser Leu Gln Pro Gly Lys Met Ser Asp Val Ser Pro
             100                 105                 110
Val Val Ala Ala Gln Gln Gln Gln Gln Gln Gln Gln Gln Gln Gln Gln
         115                 120                 125
Gln Gln Gln Gln Gln Gln Gln Gln Gln Gln Gln Gln Gln Gln Gln Gln
     130                 135                 140
Gln Glu Ala Ala Ala Ala Ala Ala Ala Ala Ala Ala Ala Ala Ala Ala
145                 150                 155                 160
Ala Ala Ala Ala Val Pro Arg Leu Arg Pro Pro His Asp Asn Arg Thr
                 165                 170                 175
Met Val Glu Ile Ile Ala Asp His Pro Ala Glu Leu Val Arg Thr Asp
             180                 185                 190
Ser Pro Asn Phe Leu Cys Ser Val Leu Pro Ser His Trp Arg Cys Asn
         195                 200                 205
Lys Thr Leu Pro Val Ala Phe Lys Val Val Ala Leu Gly Glu Val Pro
     210                 215                 220
Asp Gly Thr Val Val Thr Val Met Ala Gly Asn Asp Glu Asn Tyr Ser
225                 230                 235                 240
Ala Glu Leu Arg Asn Ala Ser Ala Val Met Lys Asn Gln Val Ala Arg
                 245                 250                 255
Phe Asn Asp Leu Arg Phe Val Gly Arg Ser Gly Arg Gly Lys Ser Phe
             260                 265                 270
Thr Leu Thr Ile Thr Val Phe Thr Asn Pro Pro Gln Val Ala Thr Tyr
         275                 280                 285
His Arg Ala Ile Lys Val Thr Val Asp Gly Pro Arg Glu Pro Arg Arg
     290                 295                 300
His Arg Gln Lys Leu Asp Asp Ser Lys Pro Ser Leu Phe Ser Asp Arg
305                 310                 315                 320
Leu Ser Asp Leu Gly Arg Ile Pro His Pro Ser Met Arg Val Gly Val
                 325                 330                 335
Pro Pro Gln Asn Pro Arg Pro Ser Leu Asn Ser Ala Pro Ser Pro Phe
             340                 345                 350
Asn Pro Gln Gly Gln Ser Gln Ile Thr Asp Pro Arg Gln Ala Gln Ser
         355                 360                 365
Ser Pro Pro Trp Ser Tyr Asp Gln Ser Tyr Pro Ser Tyr Leu Ser Gln
     370                 375                 380
Met Thr Ser Pro Ser Ile His Ser Thr Thr Pro Leu Ser Ser Thr Arg
385                 390                 395                 400
Gly Thr Gly Leu Pro Ala Ile Thr Asp Val Pro Arg Arg Ile Ser Asp
                 405                 410                 415
Asp Asp Thr Ala Thr Ser Asp Phe Cys Leu Trp Pro Ser Ser Leu Ser
             420                 425                 430
Lys Lys Ser Gln Ala Gly Ala Ser Glu Leu Gly Pro Phe Ser Asp Pro
         435                 440                 445
```

```
Arg Gln Phe Pro Ser Ile Ser Ser Leu Thr Glu Ser Arg Phe Ser Asn
    450                 455                 460

Pro Arg Met Gly Tyr Pro Ala Thr Phe Thr Tyr Thr Pro Pro Val Thr
465                 470                 475                 480

Ser Gly Met Ser Leu Gly Met Ser Ala Thr His Tyr His Thr Tyr
                485                 490                 495

Leu Pro Pro Pro Tyr Pro Gly Ser Gln Ser Gln Ser Gly Pro Phe
            500                 505                 510

Gln Thr Ser Ser Thr Pro Tyr Leu Tyr Tyr Gly Thr Ser Ser Ala Ser
        515                 520                 525

Tyr Gln Phe Pro Met Val Pro Gly Gly Asp Arg Ser Pro Ser Arg Met
    530                 535                 540

Val Pro Pro Cys Thr Thr Thr Ser Asn Gly Ser Thr Leu Leu Asn Pro
545                 550                 555                 560

Asn Leu Pro Asn Gln Asn Asp Gly Val Asp Ala Asp Gly Ser His Ser
                565                 570                 575

Ser Ser Pro Thr Val Leu Asn Ser Ser Gly Arg Met Asp Glu Ser Val
                580                 585                 590

Trp Arg Pro Tyr
        595

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
caccaccggg ctcacgtcgc                                              20

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ctgcgctgaa gaggctgttt gacgc                                        25

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
agctgcaatc accaaccaca gca                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
```
agctgcacga tccaaccaca gca                          23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
agctgcaatc acgtaccaca gca                          23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
agctgcaatc accggccaca gca                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
agctgcaatc accagacaca gca                          23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
agctgcaatc accagccaca gca                          23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
agctgcaatc accaaacaca gca                          23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
agctgcaatc accaaccaga gca                                          23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
cgccgcaatc acctaccaca gca                                          23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
cccttcccac accacccaca cag                                          23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
aaatttagac tccaacctca gca                                          23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cgctctttgt gcaaaccaca cag                                          23

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cggggaccgt ccactgt                                                 17

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gagggcacaa gttctatctg ga                                           22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ggtggtccgc gatgatctc                                                   19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gttgagagat catctccacc                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
agcgatgatg aaccaggtta                                                  20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
ctgcgctgaa gaggctgttt ga                                               22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
cgcgtatcgt gatgtagacg tg                                               22

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
gatacgtgtg ggat                                                        14

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ctgtgaggtc accaaaccac atgattctg                                    29

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
gctttgctga cacggtgt                                                18

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
taccagccac cgagaccaac c                                            21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
ctggtcaatc tccgaggg                                                18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
agaggtacca ggatgggat                                               19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
cggggacgtc atctggctc                                               19

```
<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
ctgagccaga tgacgtcc                                                   18

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gataccactg ggccactgc                                                  19

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
ggcacagaca gaagcttgat gac                                             23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ctgtaatctg actctgtcct tg                                              22

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
taccagccac cgagaccaac agag                                            24

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
gttttgctga catggtgtca c                                               21

<210> SEQ ID NO 37
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
tttgttggtg tcttggtgtt cacgccac                                       28

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
gtggagatca tcgccgacc                                                 19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ctcgtccact ccggcccac                                                 19

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
gtggtagccc tcggagaggt ac                                             22

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
ttctgggttc ccgaggtc                                                  18

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
gcaagagttt caccttgacc                                                20

<210> SEQ ID NO 43
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
ctgaaatgcg cctaggcaca tc                                           22

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
accccaggca ggcacagtc                                               19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
ctgcctggct cttcttact                                               19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
atgatgacac tgccacctct g                                            21

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
gataccactg ggccactgc                                               19

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
aacagagtca gtgagtgctc tctaacca                                     28

<210> SEQ ID NO 49
<211> LENGTH: 28
<212> TYPE: DNA
```

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 49
ttcttttggg gtaagtgtta ccattttt                28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 50
ggccttcaag gtaagaggct accccgcc                28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 51
agtggacgag gtaggtctct gactttg                28

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 52
gaacccagaa gtaagtactc cccttttt                28

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 53
cgcatttcag gtaaagaccg tgctttaa                28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 54
agccaggcag gtgagacttt taacaatt                28

<210> SEQ ID NO 55
<211> LENGTH: 28
<212> TYPE: DNA
<213> ORGANISM: Artificial Sequence

```
<220> FEATURE:
<223> OTHER INFORMATION: Description of Artificial Sequence: Synthetic
      Primer

<400> SEQUENCE: 55
tatggtttgt attttcagtt taaggctg                                              28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
tgatgcgtat tcccgtagat ccgagcac                                              28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
gtttcctgtt ttatgtaggt ggtagccc                                              28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58 cccctttat atctgcaggc aagagttt                                               28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
atgatttgct atttccaggg cacagaca                                              28

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60 atcccctca ttttacagat gatgacac                                               28

<210> SEQ ID NO 61
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      Primer

<400> SEQUENCE: 61
ttctgttata atttttaggt gcttcaga                                              28

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62
ggacggtccc cgggaagact ctaaacctag tttg                                      34

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63
aggtttagag tcttcccggg gaccgtccac tg                                        32

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 64
tcaatcgatg actatggatc cgagcaccag c                                         31

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 65
cggggaccgt ccactg                                                          16

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Ser Phe Phe Trp Asp Pro Ser Thr Ser Arg Arg Phe Ser Pro Pro Ser
 1               5                  10                  15

<210> SEQ ID NO 67
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      Peptide

<400> SEQUENCE: 67

Pro Arg Arg His Arg Gln Lys Leu Asp Pro
 1               5                  10

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 68

Pro Arg Arg His Arg Gln Lys Leu Asp
 1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 69

Val Trp Arg Pro Tyr
 1               5

<210> SEQ ID NO 70
<211> LENGTH: 2294
<212> TYPE: DNA
<213> ORGANISM: Artificial Sequence
<220> FEATURE:
<221> NAME/KEY: CDS
<222> LOCATION: (1)..(1644)
<223> OTHER INFORMATION: Description of Artificial Sequence: Synthetic
      Primer

<400> SEQUENCE: 70
```

| | | | | | | | | | | | | | | | | |
|---|---|---|---|---|---|---|---|---|---|---|---|---|---|---|---|---|
| atg | gcg | tca | aac | agc | ctc | ttc | agc | gca | gtg | aca | ccg | tgt | cag | caa | agc | 48 |
| Met | Ala | Ser | Asn | Ser | Leu | Phe | Ser | Ala | Val | Thr | Pro | Cys | Gln | Gln | Ser | |
| 1 | | | | 5 | | | | | 10 | | | | | 15 | | |
| ttc | ttt | tgg | gat | ccg | agc | acc | agc | cgg | cgc | ttc | agc | ccc | ccc | tcc | agc | 96 |
| Phe | Phe | Trp | Asp | Pro | Ser | Thr | Ser | Arg | Arg | Phe | Ser | Pro | Pro | Ser | Ser | |
| | | | 20 | | | | | 25 | | | | | 30 | | | |
| agc | ctg | cag | ccc | ggc | aag | atg | agc | gac | gtg | agc | ccg | gtg | gtg | gct | gcg | 144 |
| Ser | Leu | Gln | Pro | Gly | Lys | Met | Ser | Asp | Val | Ser | Pro | Val | Val | Ala | Ala | |
| | | 35 | | | | | 40 | | | | | 45 | | | | |
| cag | cag | cag | caa | cag | cag | cag | cag | cag | caa | cag | cag | cag | caa | caa | | 192 |
| Gln | Gln | Gln | Gln | Gln | Gln | Gln | Gln | Gln | Gln | Gln | Gln | Gln | Gln | Gln | | |
| | 50 | | | | | 55 | | | | | 60 | | | | | |
| cag | caa | cag | caa | caa | cag | cag | cag | cag | cag | cag | cag | gag | gcg | gcc | | 240 |
| Gln | Gln | Gln | Gln | Gln | Gln | Gln | Gln | Gln | Gln | Gln | Gln | Glu | Ala | Ala | | |
| 65 | | | | | 70 | | | | | 75 | | | | | 80 | |
| gca | gca | gca | gcg | gcg | gca | gcg | gcg | gcg | gca | gca | gcg | gcg | gcg | gcc | gca | 288 |
| Ala | Ala | Ala | Ala | Ala | Ala | Ala | Ala | Ala | Ala | Ala | Ala | Ala | Ala | Ala | Ala | |
| | | | | 85 | | | | | 90 | | | | | 95 | | |
| gtg | ccc | cga | ttg | agg | ccg | ccg | cac | gac | aac | cgc | acc | atg | gtg | gag | atc | 336 |
| Val | Pro | Arg | Leu | Arg | Pro | Pro | His | Asp | Asn | Arg | Thr | Met | Val | Glu | Ile | |
| | | | 100 | | | | | 105 | | | | | 110 | | | |
| atc | gcg | gac | cac | ccg | gcc | gaa | ctg | gtc | cgc | acc | gac | agt | ccc | aac | ttc | 384 |
| Ile | Ala | Asp | His | Pro | Ala | Glu | Leu | Val | Arg | Thr | Asp | Ser | Pro | Asn | Phe | |

|   |   |   |   |   |   |   |   |   |   |   |   |   |   |   |   |   |
|---|---|---|---|---|---|---|---|---|---|---|---|---|---|---|---|---|
| | | 115 | | | | | 120 | | | | | 125 | | | | |
| ctg | tgc | tcc | gtg | ctg | ccc | tcg | cac | tgg | cgg | tgc | aac | aag | acc | ctg | ccc | 432 |
| Leu | Cys | Ser | Val | Leu | Pro | Ser | His | Trp | Arg | Cys | Asn | Lys | Thr | Leu | Pro | |
| | 130 | | | | | 135 | | | | | 140 | | | | | |
| gtg | gcc | ttc | aag | gtt | gta | gcc | ctc | gga | gag | gta | cca | gat | ggg | act | gtg | 480 |
| Val | Ala | Phe | Lys | Val | Val | Ala | Leu | Gly | Glu | Val | Pro | Asp | Gly | Thr | Val | |
| 145 | | | | | 150 | | | | | 155 | | | | | 160 | |
| gtt | acc | gtc | atg | gcc | ggg | aat | gat | gag | aac | tac | tcc | gcc | gag | ctc | cga | 528 |
| Val | Thr | Val | Met | Ala | Gly | Asn | Asp | Glu | Asn | Tyr | Ser | Ala | Glu | Leu | Arg | |
| | | | | 165 | | | | | 170 | | | | | 175 | | |
| aat | gcc | tcc | gct | gtt | atg | aaa | aac | caa | gta | gcc | agg | ttc | aac | gat | ctg | 576 |
| Asn | Ala | Ser | Ala | Val | Met | Lys | Asn | Gln | Val | Ala | Arg | Phe | Asn | Asp | Leu | |
| | | | 180 | | | | | 185 | | | | | 190 | | | |
| aga | ttt | gtg | ggc | cgg | agc | gga | cga | ggc | aag | agt | ttc | acc | ttg | acc | ata | 624 |
| Arg | Phe | Val | Gly | Arg | Ser | Gly | Arg | Gly | Lys | Ser | Phe | Thr | Leu | Thr | Ile | |
| | | 195 | | | | | 200 | | | | | 205 | | | | |
| aca | gtc | ttc | aca | aat | cct | ccc | caa | gtg | gcc | act | tac | cac | aga | gct | att | 672 |
| Thr | Val | Phe | Thr | Asn | Pro | Pro | Gln | Val | Ala | Thr | Tyr | His | Arg | Ala | Ile | |
| | 210 | | | | | 215 | | | | | 220 | | | | | |
| aaa | gtg | aca | gtg | gac | ggt | ccc | cgg | gaa | cca | aga | agg | cac | aga | cag | aag | 720 |
| Lys | Val | Thr | Val | Asp | Gly | Pro | Arg | Glu | Pro | Arg | Arg | His | Arg | Gln | Lys | |
| 225 | | | | | 230 | | | | | 235 | | | | | 240 | |
| ctt | gat | gac | tct | aaa | cct | agt | ttg | ttc | tct | gat | cgc | ctc | agt | gat | tta | 768 |
| Leu | Asp | Asp | Ser | Lys | Pro | Ser | Leu | Phe | Ser | Asp | Arg | Leu | Ser | Asp | Leu | |
| | | | | 245 | | | | | 250 | | | | | 255 | | |
| ggg | cgc | att | cct | cat | ccc | agt | atg | aga | gta | ggt | gtc | ccg | cct | cag | aac | 816 |
| Gly | Arg | Ile | Pro | His | Pro | Ser | Met | Arg | Val | Gly | Val | Pro | Pro | Gln | Asn | |
| | | | 260 | | | | | 265 | | | | | 270 | | | |
| cca | cgg | ccc | tcc | ctg | aac | tct | gca | cca | agt | cct | ttt | aat | cca | caa | gga | 864 |
| Pro | Arg | Pro | Ser | Leu | Asn | Ser | Ala | Pro | Ser | Pro | Phe | Asn | Pro | Gln | Gly | |
| | | 275 | | | | | 280 | | | | | 285 | | | | |
| cag | agt | cag | att | aca | gat | ccc | agg | cag | gca | cag | tct | tcc | cca | ccg | tgg | 912 |
| Gln | Ser | Gln | Ile | Thr | Asp | Pro | Arg | Gln | Ala | Gln | Ser | Ser | Pro | Pro | Trp | |
| | 290 | | | | | 295 | | | | | 300 | | | | | |
| tcc | tat | gac | cag | tct | tac | ccc | tcc | tat | ctg | agc | cag | atg | aca | tcc | cca | 960 |
| Ser | Tyr | Asp | Gln | Ser | Tyr | Pro | Ser | Tyr | Leu | Ser | Gln | Met | Thr | Ser | Pro | |
| 305 | | | | | 310 | | | | | 315 | | | | | 320 | |
| tcc | atc | cac | tcc | acc | acg | ccg | ctg | tct | tcc | aca | cgg | ggc | acc | ggg | cta | 1008 |
| Ser | Ile | His | Ser | Thr | Thr | Pro | Leu | Ser | Ser | Thr | Arg | Gly | Thr | Gly | Leu | |
| | | | | 325 | | | | | 330 | | | | | 335 | | |
| cct | gcc | atc | act | gac | gtg | ccc | agg | cgt | att | tca | gat | tca | gaa | ccc | agc | 1056 |
| Pro | Ala | Ile | Thr | Asp | Val | Pro | Arg | Arg | Ile | Ser | Asp | Ser | Glu | Pro | Ser | |
| | | | 340 | | | | | 345 | | | | | 350 | | | |
| acc | ttg | gac | tca | cag | tct | tcc | acc | acc | ctg | ttc | ctg | tct | cca | gag | gag | 1104 |
| Thr | Leu | Asp | Ser | Gln | Ser | Ser | Thr | Thr | Leu | Phe | Leu | Ser | Pro | Glu | Glu | |
| | | 355 | | | | | 360 | | | | | 365 | | | | |
| cct | ggc | ccc | tct | aca | gca | gct | ctg | cca | tct | cca | tcc | tcg | tcc | tgt | gag | 1152 |
| Pro | Gly | Pro | Ser | Thr | Ala | Ala | Leu | Pro | Ser | Pro | Ser | Ser | Ser | Cys | Glu | |
| | 370 | | | | | 375 | | | | | 380 | | | | | |
| ccc | cag | ccc | ttc | tct | ccc | agc | ccc | atg | ttg | ccc | cct | ctc | ctg | cag | cct | 1200 |
| Pro | Gln | Pro | Phe | Ser | Pro | Ser | Pro | Met | Leu | Pro | Pro | Leu | Leu | Gln | Pro | |
| 385 | | | | | 390 | | | | | 395 | | | | | 400 | |
| ctg | tcc | act | gcc | tcc | aca | gtg | cca | gcc | ccc | tgc | gtc | cgt | cgg | cgc | act | 1248 |
| Leu | Ser | Thr | Ala | Ser | Thr | Val | Pro | Ala | Pro | Cys | Val | Arg | Arg | Arg | Thr | |
| | | | | 405 | | | | | 410 | | | | | 415 | | |
| ggg | ctc | tac | acc | att | gtg | acc | tcc | tcc | cca | gag | gct | gca | ccc | cac | ctt | 1296 |
| Gly | Leu | Tyr | Thr | Ile | Val | Thr | Ser | Ser | Pro | Glu | Ala | Ala | Pro | His | Leu | |
| | | | 420 | | | | | 425 | | | | | 430 | | | |
| gtt | gac | tgg | atg | ccc | agc | tgc | ccc | act | gcc | acg | tcc | cct | ggt | gtc | cga | 1344 |

-continued

```
Val Asp Trp Met Pro Ser Cys Pro Thr Ala Thr Ser Pro Gly Val Arg
    435                 440                 445 ggc aag gat cat gag cgg cca cag acc atg atg gcc ccg gcc cca gct    1392
Gly Lys Asp His Glu Arg Pro Gln Thr Met Met Ala Pro Ala Pro Ala
450                 455                 460 cta gct tca gag agg ggc cac agt cag cat gca ggc cct gcc agg gat    1440
Leu Ala Ser Glu Arg Gly His Ser Gln His Ala Gly Pro Ala Arg Asp
465                 470                 475                 480 gat cat gct gaa cat cct gga acc tcc cca aag ccc tgt gct cct cca    1488
Asp His Ala Glu His Pro Gly Thr Ser Pro Lys Pro Cys Ala Pro Pro
                485                 490                 495 gcc gct gct gcc acc ttg gag gcc agt gtt ggg gac atc ctg gtg gag    1536
Ala Ala Ala Ala Thr Leu Glu Ala Ser Val Gly Asp Ile Leu Val Glu
            500                 505                 510 cta cgg aca atg aat ggc cat ctg gac atc ata gca aag gcc ctc act    1584
Leu Arg Thr Met Asn Gly His Leu Asp Ile Ile Ala Lys Ala Leu Thr
        515                 520                 525 aaa ttg gcc tct tct ctg gtg ccc cag tct cag cct gtg cct gaa gca    1632
Lys Leu Ala Ser Ser Leu Val Pro Gln Ser Gln Pro Val Pro Glu Ala
530                 535                 540 cca gat gcc aat taaaagagct ggacttctaa acaaagggat gctgaggtac        1684
Pro Asp Ala Asn
545 cacacatcct cgctgactcc tctgatcccg tctttgctgg agacaagcaa atcagcaga   1744 agagccagtt acttagcttg gtttgctcac acattggatg cccttggcct gtcactcaaa  1804 ggatagcagt gtcctgctgg ctccacgagc tgacaagctg tagactttct gtgttccctt  1864 tcaccttcca atgcccctct ctcgttctaa atccccaata gaagaagcac ccgagaagt   1924 tccagggaca aggtgattgg aaaggtatca ttccctccca gtccagcgaa ccccagcca   1984 agcgagcgga ggggagagga ggtcctatcg tcagaaacac tttctggggc cctccagca   2044 tcccttcctt gagatgctga tggtgttgcc acctccagtg gactccagtg gacttcacat  2104 atctcttctt aaagtctctt taggaaaacc aaattgattg ttttctcat ttatacctac   2164 atttcaaaga gtttgggaaa taggcaagga gggaaaagga cagagcagaa agacggtggg  2224 ggctatttag gtctttctta tgaataagag tatcatgtgt cctgataaag tgtgtgtcta  2284 tactctctga                                                        2294
```

<210> SEQ ID NO 71
<211> LENGTH: 548
<212> TYPE: PRT
<213> ORGANISM: Artificial Sequence
<220> FEATURE:
<223> OTHER INFORMATION: Description of Artificial Sequence: Synthetic

<400> SEQUENCE: 71

```
Met Ala Ser Asn Ser Leu Phe Ser Ala Val Thr Pro Cys Gln Gln Ser
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Gln Gln Gln Gln Glu Ala Ala
65                  70                  75                  80

Ala Ala Ala Ala Ala Ala Ala Ala Ala Ala Ala Ala Ala Ala Ala Ala
```

-continued

```
                    85                  90                  95

Val Pro Arg Leu Arg Pro Pro His Asp Asn Arg Thr Met Val Glu Ile
                100                 105                 110

Ile Ala Asp His Pro Ala Glu Leu Val Arg Thr Asp Ser Pro Asn Phe
            115                 120                 125

Leu Cys Ser Val Leu Pro Ser His Trp Arg Cys Asn Lys Thr Leu Pro
        130                 135                 140

Val Ala Phe Lys Val Val Ala Leu Gly Glu Val Pro Asp Gly Thr Val
145                 150                 155                 160

Val Thr Val Met Ala Gly Asn Asp Glu Asn Tyr Ser Ala Glu Leu Arg
                165                 170                 175

Asn Ala Ser Ala Val Met Lys Asn Gln Val Ala Arg Phe Asn Asp Leu
            180                 185                 190

Arg Phe Val Gly Arg Ser Gly Arg Gly Lys Ser Phe Thr Leu Thr Ile
        195                 200                 205

Thr Val Phe Thr Asn Pro Pro Gln Val Ala Thr Tyr His Arg Ala Ile
    210                 215                 220

Lys Val Thr Val Asp Gly Pro Arg Glu Pro Arg Arg His Arg Gln Lys
225                 230                 235                 240

Leu Asp Asp Ser Lys Pro Ser Leu Phe Ser Asp Arg Leu Ser Asp Leu
                245                 250                 255

Gly Arg Ile Pro His Pro Ser Met Arg Val Gly Val Pro Pro Gln Asn
            260                 265                 270

Pro Arg Pro Ser Leu Asn Ser Ala Pro Ser Pro Phe Asn Pro Gln Gly
        275                 280                 285

Gln Ser Gln Ile Thr Asp Pro Arg Gln Ala Gln Ser Ser Pro Pro Trp
    290                 295                 300

Ser Tyr Asp Gln Ser Tyr Pro Ser Tyr Leu Ser Gln Met Thr Ser Pro
305                 310                 315                 320

Ser Ile His Ser Thr Thr Pro Leu Ser Ser Thr Arg Gly Thr Gly Leu
                325                 330                 335

Pro Ala Ile Thr Asp Val Pro Arg Arg Ile Ser Asp Ser Glu Pro Ser
            340                 345                 350

Thr Leu Asp Ser Gln Ser Ser Thr Thr Leu Phe Leu Ser Pro Glu Glu
        355                 360                 365

Pro Gly Pro Ser Thr Ala Ala Leu Pro Ser Pro Ser Ser Cys Glu
    370                 375                 380

Pro Gln Pro Phe Ser Pro Ser Pro Met Leu Pro Pro Leu Leu Gln Pro
385                 390                 395                 400

Leu Ser Thr Ala Ser Thr Val Pro Ala Pro Cys Val Arg Arg Arg Thr
                405                 410                 415

Gly Leu Tyr Thr Ile Val Thr Ser Ser Pro Glu Ala Ala Pro His Leu
            420                 425                 430

Val Asp Trp Met Pro Ser Cys Pro Thr Ala Thr Ser Pro Gly Val Arg
        435                 440                 445

Gly Lys Asp His Glu Arg Pro Gln Thr Met Met Ala Pro Ala Pro Ala
    450                 455                 460

Leu Ala Ser Glu Arg Gly His Ser Gln His Ala Gly Pro Ala Arg Asp
465                 470                 475                 480

Asp His Ala Glu His Pro Gly Thr Ser Pro Lys Pro Cys Ala Pro Pro
                485                 490                 495

Ala Ala Ala Ala Thr Leu Glu Ala Ser Val Gly Asp Ile Leu Val Glu
            500                 505                 510
```

```
Leu Arg Thr Met Asn Gly His Leu Asp Ile Ile Ala Lys Ala Leu Thr
            515                 520                 525

Lys Leu Ala Ser Ser Leu Val Pro Gln Ser Gln Pro Val Pro Glu Ala
        530                 535                 540

Pro Asp Ala Asn
545
```

<210> SEQ ID NO 72
<211> LENGTH: 6178
<212> TYPE: DNA
<213> ORGANISM: Artificial Sequence
<220> FEATURE:
<223> OTHER INFORMATION: Description of Artificial Sequence: Synthetic Primer

<400> SEQUENCE: 72

| | | | | | |
|---|---|---|---|---|---|
| ggaattaatt | cggatccgta | ttccactgct | tcattttcaa | tattctttct | gtattgttaa | 60 |
| ttatgcctga | actcaccata | aattatacat | aaagcttaat | agagacctca | atccacaata | 120 |
| gccttttctg | aacccaatga | gaaatctata | cacggcaatg | aaactggcat | gcaaataaaa | 180 |
| gaactgtcaa | gacatgtact | cctgaaataa | ccctacaata | actattctaa | aggctgtgtg | 240 |
| tggtctcacc | catagatttt | ggcaagatgc | actttctccg | accacagtca | gattcatcca | 300 |
| aaagcagtgg | cactggagag | cctctgtctc | acctgtcaaa | cttgagaaac | attcttgcaa | 360 |
| agaccaccat | gagtcggtgg | agaaagccac | gctgcgacac | ctgttcttga | taagcatctt | 420 |
| ctaaagtggg | gaactccaac | aattaagcaa | atcatcctta | aaggagatat | agacagcaac | 480 |
| acccaaacct | aaatgctgag | atgttccaaa | atcaaacatg | ggtaatccag | acatcctgca | 540 |
| atatgcagag | gggccattca | taagtgatac | tgacagtctt | tccttatcat | ctaatacaat | 600 |
| ctcttaacat | tatttgccaa | cttaaaaact | atgtatcctt | ttttaatatt | tggccaacct | 660 |
| cctttgtaaa | accttaaaat | acatataaat | tttcaagtat | taaattcatc | aaaattgctg | 720 |
| aagtttgaca | actaaaagct | caatagctga | agacttataa | atgggaacat | taaatatatt | 780 |
| aaaatctgat | cttttttatga | tacattgata | catttttagc | cacatcaaat | aaaagttcac | 840 |
| ttttgctttg | ccttgacttc | atcaagttta | tggacagaag | gggaacgtat | ggatacaatg | 900 |
| gtgagagaga | caattactca | gaaaagaagg | atgcctcact | gggcttgact | caagttgggg | 960 |
| ccactaccca | acaacaaatg | ataagtcaga | cttttaaaaa | ctgcacctgg | ctctctacaa | 1020 |
| agcttacata | agaccaacag | tatctaaaat | tgtaactttg | ttgccttttg | ggtgacaggc | 1080 |
| tcctctaact | ctgttcaata | caagaacaat | tcaagtgaac | aagagagtgg | tggcctatag | 1140 |
| ggccttttcc | aagacaaggg | acaccaatta | agttctcact | tcagaataat | gtcatctgca | 1200 |
| gtaaagtcct | aaatcacaaa | gacaaagtga | caatcaaggt | tcccatgtat | taggctgccc | 1260 |
| cacacttacc | ccttactatg | caagcacaaa | agttagtttc | actttccct | agatacacta | 1320 |
| acttgcataa | ctaggatatt | attttttcttt | ggtttggtca | gaagcatgtt | tgatataaat | 1380 |
| tttattaagt | ggtagtgtat | gtaacattgc | attgtgggta | gtcgtttcct | gctttagtct | 1440 |
| ggccacatcc | tcagctgtca | tacaagcatg | ttgcccacat | tttgtgcaag | ttgtcacctt | 1500 |
| ttttaaaaaa | aaaatcttac | aaaaatgaca | cgaaagtgaa | ttgctttaat | aattataaga | 1560 |
| aacataaaat | attttataca | gatacattac | agaagtatag | accaccactc | ttcagagagc | 1620 |
| aatgcctcac | aatcagagtg | ctaatgtcat | acataacaat | atgcctaagt | aaaagagcat | 1680 |
| aaaggaaagg | gtcaagggac | agactggcag | aaataaaaca | ttcctggaca | gagctgtcaa | 1740 |

-continued

```
tgatctctaa gacctgaggt acagtacacc gcagtgtgca caagggctg cacttcagac    1800
ctgtgaggtg ctcattagtg agtgctacaa tgtcgatatt cctcaataga attttaagaa    1860
agttctgaat atatagaaac gtgaaagcat ggaaaaagaa aagtaaaaag cctggagctg    1920
gagtagaaag gaaaagaga ggaacagaaa tgaaggagga gggaccatag gagggggggt    1980
gtggagggg gaaggagggg aaggaggagg gaggaggtaa gatgtggaca ctaacttagg    2040
atgttctctc tgggcatcca atctgcatat tacatcacac ttagaaagac cactgccagg    2100
agtacacacg catgaaatca gtaaacaaga aaactgtggt acttttttaaa atattatcta    2160
atttaaaacc tcatagccaa gttcaaaata ctctgtactc acaaccagat atgctttctt    2220
atatttgtaa tataaagcat gagagttaat atctcataat cataattcag aatataaaac    2280
tataatgttt tgctaacaca gaacaatttc acgtctttaa taaaagtttg ataaatgcta    2340
ggtgaactta aacagctatg cattaaacct gaaaaagaa aaattaccca ccaatggaaa    2400
acacaaatta ctaaatatta agttaaaatg aattaagaaa gtccctagcc caagtctcat    2460
aagcagacta ttttaagcca gagtgggcac ctagagtttg ttagtcattt tcttactgtt    2520
tcgattaaaa gaatagaaaa gcaacaacta tacatccaaa ggaatccttc tttagagcac    2580
agatattggc acagtattgg taaagtaagg ctactgtgtt caagtgcaag caggaaccga    2640
tcaaataaaa atcaattcaa atggtaacat tgaagaaatg tatagtattt aagatattac    2700
tatactgtta tattcacatg tcttgatatt ttaagaactt tgacaaatct gaaaaaatta    2760
ttaaattgta aaaaaacaag aaagcaagac aataatttca tgatttaaga ctgatttcaa    2820
atttaaagct gtatttcatt gttattgcat gaaaacacag aatttatagg gcacaactaa    2880
acttgttact tacttcacag caattgctag catatcctcc aaaaggatta catttaaaag    2940
atctttaaag agagtctgtg gtttccattt ctgaatataa gcatggtaaa agtctctaaa    3000
caagcgcttt ctgccatggc ttttcaaagc tggctccctc tctccatctc tagcagccat    3060
ttctaaggaa atgcagtcag tatcaaagat gttaccactc accagtgttg tctttaaatt    3120
tccaccacag tgtacaggtt gctcctgagt ctagtttgaa ttgggagggg tacgtggaca    3180
atgaatgcat aaatttaacc acaaatgtaa cattcctgtt tttatcctgc agaatgtga    3240
tggactatac acaatacata aaggccacgt tcagcaacct ctactaaact cttgtatcat    3300
gagatacaga ccataactca cagacacagg aaatagggtt aggttacctg caaaacagac    3360
catgtgacta ctcatctgat aaatgagatg gtggtaaaat ttattcaaat tcattttaga    3420
tcaatttgaa taccaaaatg tatatacctt ttttttaaaaa atgtaaggga aaaattattg    3480
catgaaaaat taggacataa aagacctggg cactctaaaa gaaaagcatt tgcttactat    3540
cctatagcaa ctacgcaaac atcttcaact gccaagtgct gtgattcctt gtacatatgg    3600
aactaagttc agaaactcca caattttat agacaaaacc cttttttttat ttactttgaa    3660
taatagagat aaagatcaca ctggcacact ttatttatga aagaggataa tagagtaact    3720
tttttctcct ctgcatgaat aatgacccta atgaaaact tcagtataaa tatctgtttt    3780
acagtaaaac atgagtctag cctcaaaaat caaacaaaag aatgtatttc tgtggttttg    3840
tcattaaaac tttattctga aaattaaat aaataaacct agattcttga aaataaggg    3900
gttaaaagca ttaccatgtc tttccagtat atagagaata aatgtttaaa gaatcttatg    3960
aacatgattt catagataac tttaactaag aggaaacaaa aacagacaat gagttatttt    4020
ggggtgtaca gacacaagaa tattttactt ctgtcaccct ctaagtcact ccctcttacc    4080
tccactgtgc accccaaata atttcttgta cttctgtgcc cccacccacc atcacagtca    4140
```

```
tccgttccat gccactcctg gttaccatca cactaggaag aaatctaaca tgcaaattca    4200
gagtggcgtg gataaatggc aaaaaatgcc taggaaattg gtctgctcgc ctttataatg    4260
tttgttgaaa aatcctccat cgctcccaac taatgaaaac aggaagctct attcataaat    4320
gtgaaattca ctgcctatga tatataatca tcctaataag aaaatgagct ctagacatac    4380
atgtccaaga gggcaaaaga agagatagtt tcccaaagat ggtttcaatt ttcttctgaa    4440
tcagaattag caaatcaaga cgactaacat actctgtctg tgtgcattat tccttactac    4500
acacagcatt ttgtaattta tttcaaagct tccattataa acaacaaaaa cttacagttt    4560
ctgttaaccc cctctattct gagctatgga aattactgca tatttcatta tatatgcaga    4620
actgcaccca aagtcctgtt acagtcactg tccacgctga tgaaagaatt atacaaaaca    4680
tttctttgaa agataaaatc caatcataca gaaaactaac attagtccaa caaaatgtcc    4740
accacaattc ctgacatttg ttttttaaga tcttcaaagt aaccatggga tgatggcaaa    4800
aataatgtaa acgatactaa ttacatttaa tctttattgt aagagccgcc acgtaataaa    4860
aaaaaaaaaa aatcaactac acagccatga tttaatattt gtaaaggaat ccccaggcta    4920
acacttttgt gacagccaat tacagtcgat cccgatcccg gcaaggagtt tgcaagcaga    4980
gctctggaaa ggtaaactcc tttttacaat gagttacaga tccccaagct taggaagaca    5040
agcaaaaggc aaacagaagg aagcagccac cctgggaaat ccgaagcagc cttgcaagtg    5100
atacaatccc aagatgcgaa ttactgcaaa gcagcactgt tgctcagaac gccacacact    5160
cagttgagac aattttgctc acttttccat agacataata atgaaggaaa gggaggaggg    5220
gtagagaaga gagatgaaaa agcagaggag ggaaggggga gtagggaggt ggcagaaagg    5280
aaaagcctta gctacagagt tctgctctcc agaggcttaa ccttacagga gtgtgggctc    5340
cttcagcatt tgtgttctag ccaaatcctc atgagtcaca aaaattaaaa agctataacc    5400
ttctgaatgc caggaaggcc ttaccacaag cctttttgtca gagggagaaa gggagagaga    5460
gagggagaga gagagggaga gagggaggga gagaggaagg gaaggagaga cagaggaaca    5520
cccataagta aagagacaga aggaaggaaa gggagaggac aagagaagag aaaggaggga    5580
ggggagggga gaaggaaaaa gattgagaaa gaggagggga agagagcaag gggaagccac    5640
agtggtaggc agtcccactt tactttgagt actgtgaggt cacaaaccac atgattctgt    5700
ctctccagta atagtgcttg caaaaaatag gagtttaaa gcttttgctt ttttggattg      5760
tgtgaatgct tcattcgcct cacaaacaac cacagaacca caagtgcggt gcaaactttc    5820
tccaggaaga ctgcaagaag gctctggcgt ttaaatggtt aatctctgca ggtcactacc    5880
agccaccgag accaaccgag tcagtgagtg ctctaaccac agtccatgca ggaatagtag    5940
gtccttcaaa tatttgctca ctccgttttg ttttgtttcc ttgcttttca catgttacca    6000
gctacataat ttcttgacag aaaaaaataa atataaagtc tatgtactcc aggcatactg    6060
tacaactaaa acagggactg ggtatggttt gtattttcag tttaaggctg caagcagtat    6120
ttacaacaga gggcacaagt tctatctgga aaaaaagga gggactatgg cgtcaaac      6178
```

<210> SEQ ID NO 73
<211> LENGTH: 6
<212> TYPE: DNA
<213> ORGANISM: Artificial Sequence
<220> FEATURE:
<223> OTHER INFORMATION: Description of Artificial Sequence: Synthetic Primer

<400> SEQUENCE: 73

```
aataaa                                                           6

<210> SEQ ID NO 74
<211> LENGTH: 6
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 74 aaccac                                                           6

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75

Gly Ala Ser Glu Leu
 1               5

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 76

Arg Arg His Arg
 1

<210> SEQ ID NO 77
<211> LENGTH: 6
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 77 accaca                                                           6

<210> SEQ ID NO 78
<211> LENGTH: 2156
<212> TYPE: DNA
<213> ORGANISM: Artificial Sequence
<220> FEATURE:
<221> NAME/KEY: CDS
<222> LOCATION: (498)..(2060)
<223> OTHER INFORMATION: Description of Artificial Sequence: Synthetic
      Primer

<400> SEQUENCE: 78
agaggaggca aaaaggcaga ggttgagcgg ggagtacaaa ggaaagccct taactgcaga      60
gctctgctct acaaatgctt aaccttacag gagtttgggc tccttcagca tttgtattct    120
atttgtgaga gaaagagaga gagagaaaga gcaaggggga aaagccacag tggtaggcag    180
tcccacttta cttaagagta ctgtgaggtc acaaaccaca tgattctgcc tctccagtaa    240
tagtgcttgc aaaaaaaagg attttaaagc ttttgctttt ttggattgtg tgaatgcttc    300
```

```
attcgcctca caaacaacca cagaaccaca agtgcggtgc aaactttctc caggaggaca    360
gcaagaagtc tctggttttt aaatggttaa tctccgcagg tcactaccag ccaccgagac    420
caacagagtc atttaaggct gcaagcagta tttacaacag agggtacaag ttctatctga    480
aaaaaaaagg agggact atg gca tca aac agc ctc ttc agc aca gtg aca       530
                    Met Ala Ser Asn Ser Leu Phe Ser Thr Val Thr
                     1               5                  10 cca tgt cag caa aac ttc ttt tgg gat ccg agc acc agc cgg cgc ttc      578
Pro Cys Gln Gln Asn Phe Phe Trp Asp Pro Ser Thr Ser Arg Arg Phe
             15                  20                  25 agc ccc ccc tcc agc agc ctg cag ccc ggc aaa atg agc gac gtg agc      626
Ser Pro Pro Ser Ser Ser Leu Gln Pro Gly Lys Met Ser Asp Val Ser
         30                  35                  40 ccg gtg gtg gct gcg caa cag cag cag caa cag cag cag caa cag          674
Pro Val Val Ala Ala Gln Gln Gln Gln Gln Gln Gln Gln Gln Gln
 45                  50                  55 cag cag cag cag cag caa cag cag cag cag cag gag gcg gcg gcg          722
Gln Gln Gln Gln Gln Gln Gln Gln Gln Gln Gln Glu Ala Ala Ala
 60                  65                  70                  75 gcg gct gcg gcg gcg gcg gcg gct gcg gcg gcg gca gct gca gtg ccc      770
Ala Ala Ala Ala Ala Ala Ala Ala Ala Ala Ala Ala Ala Val Pro
                 80                  85                  90 cgg ttg cgg ccg ccc cac gac aac cgc acc atg gtg gag atc atc gcc      818
Arg Leu Arg Pro Pro His Asp Asn Arg Thr Met Val Glu Ile Ile Ala
             95                 100                 105 gac cac ccg gcc gaa ctc gtc cgc acc gac agc ccc aac ttc ctg tgc      866
Asp His Pro Ala Glu Leu Val Arg Thr Asp Ser Pro Asn Phe Leu Cys
         110                 115                 120 tcg gtg ctg ccc tcg cac tgg cgc tgc aac aag acc ctg ccc gtg gcc      914
Ser Val Leu Pro Ser His Trp Arg Cys Asn Lys Thr Leu Pro Val Ala
 125                 130                 135 ttc aag gtg gta gcc ctc gga gag gta cca gat ggg act gtg gtt act      962
Phe Lys Val Val Ala Leu Gly Glu Val Pro Asp Gly Thr Val Val Thr
 140                 145                 150                 155 gtc atg gcg ggt aac gat gaa aat tat tct gct gag ctc cgg aat gcc     1010
Val Met Ala Gly Asn Asp Glu Asn Tyr Ser Ala Glu Leu Arg Asn Ala
                 160                 165                 170 tct gct gtt atg aaa aac caa gta gca agg ttc aac gat ctg aga ttt     1058
Ser Ala Val Met Lys Asn Gln Val Ala Arg Phe Asn Asp Leu Arg Phe
             175                 180                 185 gtg ggc cgg agt gga cga ggc aag agt ttc acc ttg acc ata acc gtc     1106
Val Gly Arg Ser Gly Arg Gly Lys Ser Phe Thr Leu Thr Ile Thr Val
         190                 195                 200 ttc aca aat cct ccc caa gta gct acc tat cac aga gca att aaa gtt     1154
Phe Thr Asn Pro Pro Gln Val Ala Thr Tyr His Arg Ala Ile Lys Val
 205                 210                 215 aca gta gat gga cct cgg gaa ccc aga agg cac aga cag aag ctt gat     1202
Thr Val Asp Gly Pro Arg Glu Pro Arg Arg His Arg Gln Lys Leu Asp
 220                 225                 230                 235 gac tct aaa cct agt ttg ttc tct gac cgc ctc agt gat tta ggg cgc     1250
Asp Ser Lys Pro Ser Leu Phe Ser Asp Arg Leu Ser Asp Leu Gly Arg
                 240                 245                 250 att cct cat ccc agt atg aga gta ggt gtc ccg cct cag aac cac ggg     1298
Ile Pro His Pro Ser Met Arg Val Gly Val Pro Pro Gln Asn His Gly
             255                 260                 265 ccc tcc ctg aac tct gca cca agt cct ttt aat cca caa gga cag agt     1346
Pro Ser Leu Asn Ser Ala Pro Ser Pro Phe Asn Pro Gln Gly Gln Ser
         270                 275                 280
```

```
cag att aca gac ccc agg cag gca cag tct tcc ccg ccg tgg tcc tat      1394
Gln Ile Thr Asp Pro Arg Gln Ala Gln Ser Ser Pro Pro Trp Ser Tyr
    285                 290                 295 gac cag tct tac ccc tcc tac ctg agc cag atg acg tcc ccg tcc atc      1442
Asp Gln Ser Tyr Pro Ser Tyr Leu Ser Gln Met Thr Ser Pro Ser Ile
300                 305                 310                 315 cac tct acc acc ccg ctg tct tcc aca cgg ggc act ggg ctt cct gcc      1490
His Ser Thr Thr Pro Leu Ser Ser Thr Arg Gly Thr Gly Leu Pro Ala
                320                 325                 330 atc acc gat gtg cct agg cgc att tca gat gat gac act gcc acc tct      1538
Ile Thr Asp Val Pro Arg Arg Ile Ser Asp Asp Asp Thr Ala Thr Ser
            335                 340                 345 gac ttc tgc ctc tgg cct tcc act ctc agt aag aag agc cag gca ggt      1586
Asp Phe Cys Leu Trp Pro Ser Thr Leu Ser Lys Lys Ser Gln Ala Gly
        350                 355                 360 gct tca gaa ctg ggc cct ttt tca gac ccc agg cag ttc cca agc att      1634
Ala Ser Glu Leu Gly Pro Phe Ser Asp Pro Arg Gln Phe Pro Ser Ile
    365                 370                 375 tca tcc ctc act gag agc cgc ttc tcc aac cca cga atg cac tat cca      1682
Ser Ser Leu Thr Glu Ser Arg Phe Ser Asn Pro Arg Met His Tyr Pro
380                 385                 390                 395 gcc acc ttt act tac acc ccg cca gtc acc tca ggc atg tcc ctc ggt      1730
Ala Thr Phe Thr Tyr Thr Pro Pro Val Thr Ser Gly Met Ser Leu Gly
                400                 405                 410 atg tcc gcc acc act cac tac cac acc tac ctg cca cca ccc tac ccc      1778
Met Ser Ala Thr Thr His Tyr His Thr Tyr Leu Pro Pro Pro Tyr Pro
            415                 420                 425 ggc tct tcc caa agc cag agt gga ccc ttc cag acc agc agc act cca      1826
Gly Ser Ser Gln Ser Gln Ser Gly Pro Phe Gln Thr Ser Ser Thr Pro
        430                 435                 440 tat ctc tac tat ggc act tcg tca gga tcc tat cag ttt ccc atg gtg      1874
Tyr Leu Tyr Tyr Gly Thr Ser Ser Gly Ser Tyr Gln Phe Pro Met Val
    445                 450                 455 ccg ggg gga gac cgg tct cct tcc aga atg ctt ccg cca tgc acc acc      1922
Pro Gly Gly Asp Arg Ser Pro Ser Arg Met Leu Pro Pro Cys Thr Thr
460                 465                 470                 475 acc tcg aat ggc agc acg cta tta aat cca aat ttg cct aac cag aat      1970
Thr Ser Asn Gly Ser Thr Leu Leu Asn Pro Asn Leu Pro Asn Gln Asn
                480                 485                 490 gat ggt gtt gac gct gat gga agc cac agc agt tcc cca act gtt ttg      2018
Asp Gly Val Asp Ala Asp Gly Ser His Ser Ser Ser Pro Thr Val Leu
            495                 500                 505 aat tct agt ggc aga atg gat gaa tct gtt tgg cga cca tat              2060
Asn Ser Ser Gly Arg Met Asp Glu Ser Val Trp Arg Pro Tyr
        510                 515                 520 tgaaattcct cagcagtggc ccagtggtat ctgggggcca catcccacac tatcaatata    2120
tacatatata gagagagtgc atatatatgt tatatc                              2156

<210> SEQ ID NO 79
<211> LENGTH: 521
<212> TYPE: PRT
<213> ORGANISM: Artificial Sequence
<220> FEATURE:
<223> OTHER INFORMATION: Description of Artificial Sequence: Synthetic

<400> SEQUENCE: 79

Met Ala Ser Asn Ser Leu Phe Ser Thr Val Thr Pro Cys Gln Gln Asn
 1               5                  10                  15

Phe Phe Trp Asp Pro Ser Thr Ser Arg Arg Phe Ser Pro Pro Ser Ser
                20                  25                  30
```

-continued

```
Ser Leu Gln Pro Gly Lys Met Ser Asp Val Ser Pro Val Ala Ala
         35                  40                  45
Gln Gln Gln Gln Gln Gln Gln Gln Gln Gln Gln Gln Gln Gln Gln
 50                  55                  60
Gln Gln Gln Gln Gln Gln Glu Ala Ala Ala Ala Ala Ala Ala Ala
 65                  70                  75                  80
Ala Ala Ala Ala Ala Ala Ala Ala Val Pro Arg Leu Arg Pro Pro
                 85                  90                  95
His Asp Asn Arg Thr Met Val Glu Ile Ile Ala Asp His Pro Ala Glu
             100                 105                 110
Leu Val Arg Thr Asp Ser Pro Asn Phe Leu Cys Ser Val Leu Pro Ser
             115                 120                 125
His Trp Arg Cys Asn Lys Thr Leu Pro Val Ala Phe Lys Val Val Ala
 130                 135                 140
Leu Gly Glu Val Pro Asp Gly Thr Val Thr Val Met Ala Gly Asn
145                 150                 155                 160
Asp Glu Asn Tyr Ser Ala Glu Leu Arg Asn Ala Ser Ala Val Met Lys
             165                 170                 175
Asn Gln Val Ala Arg Phe Asn Asp Leu Arg Phe Val Gly Arg Ser Gly
             180                 185                 190
Arg Gly Lys Ser Phe Thr Leu Thr Ile Thr Val Phe Thr Asn Pro Pro
             195                 200                 205
Gln Val Ala Thr Tyr His Arg Ala Ile Lys Val Thr Val Asp Gly Pro
             210                 215                 220
Arg Glu Pro Arg Arg His Arg Gln Lys Leu Asp Asp Ser Lys Pro Ser
225                 230                 235                 240
Leu Phe Ser Asp Arg Leu Ser Asp Leu Gly Arg Ile Pro His Pro Ser
                 245                 250                 255
Met Arg Val Gly Val Pro Pro Gln Asn His Gly Pro Ser Leu Asn Ser
             260                 265                 270
Ala Pro Ser Pro Phe Asn Pro Gln Gly Gln Ser Gln Ile Thr Asp Pro
             275                 280                 285
Arg Gln Ala Gln Ser Ser Pro Pro Trp Ser Tyr Asp Gln Ser Tyr Pro
 290                 295                 300
Ser Tyr Leu Ser Gln Met Thr Ser Pro Ser Ile His Ser Thr Thr Pro
305                 310                 315                 320
Leu Ser Ser Thr Arg Gly Thr Gly Leu Pro Ala Ile Thr Asp Val Pro
                 325                 330                 335
Arg Arg Ile Ser Asp Asp Asp Thr Ala Thr Ser Asp Phe Cys Leu Trp
             340                 345                 350
Pro Ser Thr Leu Ser Lys Lys Ser Gln Ala Gly Ala Ser Glu Leu Gly
             355                 360                 365
Pro Phe Ser Asp Pro Arg Gln Phe Pro Ser Ile Ser Ser Leu Thr Glu
             370                 375                 380
Ser Arg Phe Ser Asn Pro Arg Met His Tyr Pro Ala Thr Phe Thr Tyr
385                 390                 395                 400
Thr Pro Pro Val Thr Ser Gly Met Ser Leu Gly Met Ser Ala Thr Thr
                 405                 410                 415
His Tyr His Thr Tyr Leu Pro Pro Tyr Pro Gly Ser Ser Gln Ser
             420                 425                 430
Gln Ser Gly Pro Phe Gln Thr Ser Thr Pro Tyr Leu Tyr Tyr Gly
             435                 440                 445
```

-continued

```
Thr Ser Ser Gly Ser Tyr Gln Phe Pro Met Val Pro Gly Asp Arg
    450                 455                 460

Ser Pro Ser Arg Met Leu Pro Pro Cys Thr Thr Thr Ser Asn Gly Ser
465                 470                 475                 480

Thr Leu Leu Asn Pro Asn Leu Pro Asn Gln Asn Asp Gly Val Asp Ala
                    485                 490                 495

Asp Gly Ser His Ser Ser Pro Thr Val Leu Asn Ser Ser Gly Arg
                500                 505                 510

Met Asp Glu Ser Val Trp Arg Pro Tyr
        515                 520

<210> SEQ ID NO 80
<211> LENGTH: 596
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 80

Met Leu His Ser Pro His Lys Gln Pro Gln Asn His Lys Cys Gly Ala
 1               5                  10                  15

Asn Phe Leu Gln Glu Asp Cys Lys Lys Ala Leu Ala Phe Lys Trp Leu
                20                  25                  30

Ile Ser Ala Gly His Tyr Gln Pro Pro Arg Pro Thr Glu Ser Phe Lys
            35                  40                  45

Ala Ala Ser Ser Ile Tyr Asn Arg Gly His Lys Phe Tyr Leu Glu Lys
        50                  55                  60

Lys Gly Gly Thr Met Ala Ser Asn Ser Leu Phe Ser Ala Val Thr Pro
65                  70                  75                  80

Cys Gln Gln Ser Phe Phe Trp Asp Pro Ser Thr Ser Arg Arg Phe Ser
                85                  90                  95

Pro Pro Ser Ser Ser Leu Gln Pro Gly Lys Met Ser Asp Val Ser Pro
                100                 105                 110

Val Val Ala Ala Gln Gln Gln Gln Gln Gln Gln Gln Gln Gln Gln Gln
            115                 120                 125

Gln Gln Gln Gln Gln Gln Gln Gln Gln Gln Gln Gln Gln Gln Gln Gln
        130                 135                 140

Gln Glu Ala Ala Ala Ala Ala Ala Ala Ala Ala Ala Ala Ala Ala Ala
145                 150                 155                 160

Ala Ala Ala Ala Val Pro Arg Leu Arg Pro Pro His Asp Asn Arg Thr
                165                 170                 175

Met Val Glu Ile Ile Ala Asp His Pro Ala Glu Leu Val Arg Thr Asp
            180                 185                 190

Ser Pro Asn Phe Leu Cys Ser Val Leu Pro Ser His Trp Arg Cys Asn
        195                 200                 205

Lys Thr Leu Pro Val Ala Phe Lys Val Val Ala Leu Gly Glu Val Pro
    210                 215                 220

Asp Gly Thr Val Val Thr Val Met Ala Gly Asn Asp Glu Asn Tyr Ser
225                 230                 235                 240

Ala Glu Leu Arg Asn Ala Ser Ala Val Met Lys Asn Gln Val Ala Arg
                245                 250                 255

Phe Asn Asp Leu Arg Phe Val Gly Arg Ser Gly Arg Gly Lys Ser Phe
            260                 265                 270

Thr Leu Thr Ile Thr Val Phe Thr Asn Pro Pro Gln Val Ala Thr Tyr
        275                 280                 285
```

-continued

```
His Arg Ala Ile Lys Val Thr Val Asp Gly Pro Arg Glu Pro Arg Arg
    290                 295                 300
His Arg Gln Lys Leu Asp Asp Ser Lys Pro Ser Leu Phe Ser Asp Arg
305                 310                 315                 320
Leu Ser Asp Leu Gly Arg Ile Pro His Pro Ser Met Arg Val Gly Val
                325                 330                 335
Pro Pro Gln Asn Pro Arg Pro Ser Leu Asn Ser Ala Pro Ser Pro Phe
                340                 345                 350
Asn Pro Gln Gly Gln Ser Gln Ile Thr Asp Pro Arg Gln Ala Gln Ser
                355                 360                 365
Ser Pro Pro Trp Ser Tyr Asp Gln Ser Tyr Pro Ser Tyr Leu Ser Gln
    370                 375                 380
Met Thr Ser Pro Ser Ile His Ser Thr Thr Pro Leu Ser Ser Thr Arg
385                 390                 395                 400
Gly Thr Gly Leu Pro Ala Ile Thr Asp Val Pro Arg Arg Ile Ser Asp
                405                 410                 415
Asp Asp Thr Ala Thr Ser Asp Phe Cys Leu Trp Pro Ser Ser Leu Ser
                420                 425                 430
Lys Lys Ser Gln Ala Gly Ala Ser Glu Leu Gly Pro Phe Ser Asp Pro
                435                 440                 445
Arg Gln Phe Pro Ser Ile Ser Ser Leu Thr Glu Ser Arg Phe Ser Asn
    450                 455                 460
Pro Arg Met Gly Tyr Pro Ala Thr Phe Thr Tyr Thr Pro Pro Val Thr
465                 470                 475                 480
Ser Gly Met Ser Leu Gly Met Ser Ala Thr Thr His Tyr His Thr Tyr
                485                 490                 495
Leu Pro Pro Pro Tyr Pro Gly Ser Ser Gln Ser Gln Ser Gly Pro Phe
                500                 505                 510
Gln Thr Ser Ser Thr Pro Tyr Leu Tyr Tyr Gly Thr Ser Ser Ala Ser
    515                 520                 525
Tyr Gln Phe Pro Met Val Pro Gly Gly Asp Arg Ser Pro Ser Arg Met
                530                 535                 540
Val Pro Pro Cys Thr Thr Thr Ser Asn Gly Ser Thr Leu Leu Asn Pro
545                 550                 555                 560
Asn Leu Pro Asn Gln Asn Asp Gly Val Asp Ala Asp Gly Ser His Ser
                565                 570                 575
Ser Ser Pro Thr Val Leu Asn Ser Ser Gly Arg Met Asp Glu Ser Val
                580                 585                 590
Trp Arg Pro Tyr
        595

<210> SEQ ID NO 81
<211> LENGTH: 521
<212> TYPE: PRT
<213> ORGANISM: Homo sapiens

<400> SEQUENCE: 81

Met Ala Ser Asn Ser Leu Phe Ser Thr Val Thr Pro Cys Gln Gln Ser
  1               5                  10                  15
Phe Phe Trp Asp Pro Ser Thr Ser Arg Arg Phe Ser Pro Pro Ser Ser
                 20                  25                  30
Ser Leu Gln Pro Gly Lys Met Ser Asp Val Ser Pro Val Val Ala Ala
             35                  40                  45
Gln Gln Gln Gln Gln Gln Gln Gln Gln Gln Gln Gln Gln Gln Gln Gln
```

-continued

```
                50                  55                  60
Gln Gln Gln Gln Gln Gln Gln Glu Ala Ala Ala Ala Ala Ala Ala Ala
 65                  70                  75                  80
Ala Ala Ala Ala Ala Ala Ala Ala Val Pro Arg Leu Arg Pro Pro
                 85                  90                  95
His Asp Asn Arg Thr Met Val Glu Ile Ile Ala Asp His Pro Ala Glu
                100                 105                 110
Leu Val Arg Thr Asp Ser Pro Asn Phe Leu Cys Ser Val Leu Pro Ser
                115                 120                 125
His Trp Arg Cys Asn Lys Thr Leu Pro Val Ala Phe Lys Val Val Ala
            130                 135                 140
Leu Gly Glu Val Pro Asp Gly Thr Val Val Thr Val Met Ala Gly Asn
145                 150                 155                 160
Asp Glu Asn Tyr Ser Ala Glu Leu Arg Asn Ala Ser Ala Val Met Lys
                165                 170                 175
Asn Gln Val Ala Arg Phe Asn Asp Leu Arg Phe Val Gly Arg Ser Gly
            180                 185                 190
Arg Gly Lys Ser Phe Thr Leu Thr Ile Thr Val Phe Thr Asn Pro Pro
            195                 200                 205
Gln Val Ala Thr Tyr His Arg Ala Ile Lys Val Thr Val Asp Gly Pro
    210                 215                 220
Arg Glu Pro Arg Arg His Arg Gln Lys Leu Asp Asp Ser Lys Pro Ser
225                 230                 235                 240
Leu Phe Ser Asp Arg Leu Ser Asp Leu Gly Arg Ile Pro His Pro Ser
                245                 250                 255
Met Arg Val Gly Val Pro Pro Gln Asn Pro Arg Pro Ser Leu Asn Ser
            260                 265                 270
Ala Pro Ser Pro Phe Asn Pro Gln Gly Gln Ser Gln Ile Thr Asp Pro
            275                 280                 285
Arg Gln Ala Gln Ser Ser Pro Trp Ser Tyr Asp Gln Ser Tyr Pro
    290                 295                 300
Ser Tyr Leu Ser Gln Met Thr Ser Pro Ser Ile His Ser Thr Thr Pro
305                 310                 315                 320
Leu Ser Ser Thr Arg Gly Thr Gly Leu Pro Ala Ile Thr Asp Val Pro
                325                 330                 335
Arg Arg Ile Ser Asp Asp Asp Thr Ala Thr Ser Asp Phe Cys Leu Trp
            340                 345                 350
Pro Ser Thr Leu Ser Lys Lys Ser Gln Ala Gly Ala Ser Glu Leu Gly
            355                 360                 365
Pro Phe Ser Asp Pro Arg Gln Phe Pro Ser Ile Ser Ser Leu Thr Glu
    370                 375                 380
Ser Arg Phe Ser Asn Pro Arg Met His Tyr Pro Ala Thr Phe Thr Tyr
385                 390                 395                 400
Thr Pro Pro Val Thr Ser Gly Met Ser Leu Gly Met Ser Ala Thr Thr
                405                 410                 415
His Tyr His Thr Tyr Leu Pro Pro Tyr Pro Gly Ser Ser Gln Ser
            420                 425                 430
Gln Ser Gly Pro Phe Gln Thr Ser Ser Thr Pro Tyr Leu Tyr Tyr Gly
            435                 440                 445
Thr Ser Ser Gly Ser Tyr Gln Phe Pro Met Val Pro Gly Gly Asp Arg
    450                 455                 460
Ser Pro Ser Arg Met Val Pro Pro Cys Thr Thr Thr Ser Asn Gly Ser
465                 470                 475                 480
```

-continued

```
Thr Leu Leu Asn Pro Asn Leu Pro Asn Gln Asn Asp Gly Val Asp Ala
                485                 490                 495

Asp Gly Ser His Ser Ser Ser Pro Thr Val Leu Asn Ser Ser Gly Arg
            500                 505                 510

Met Asp Glu Ser Val Trp Arg Pro Tyr
        515                 520

<210> SEQ ID NO 82
<211> LENGTH: 528
<212> TYPE: PRT
<213> ORGANISM: Mus musculus

<400> SEQUENCE: 82

Met Ala Ser Asn Ser Leu Phe Ser Ala Val Thr Pro Cys Gln Gln Ser
  1               5                  10                  15

Phe Phe Trp Asp Pro Ser Thr Ser Arg Arg Phe Ser Pro Pro Ser Ser
             20                  25                  30

Ser Leu Gln Pro Gly Lys Met Ser Asp Val Ser Pro Val Val Ala Ala
         35                  40                  45

Gln Gln Gln Gln Gln Gln Gln Gln Gln Gln Gln Gln Gln Gln Gln Gln
 50                  55                  60

Gln Gln Gln Gln Gln Gln Gln Gln Gln Gln Gln Gln Glu Ala Ala
 65                  70                  75                  80

Ala Ala Ala Ala Ala Ala Ala Ala Ala Ala Ala Ala Ala Ala Ala
                 85                  90                  95

Val Pro Arg Leu Arg Pro Pro His Asp Asn Arg Thr Met Val Glu Ile
            100                 105                 110

Ile Ala Asp His Pro Ala Glu Leu Val Arg Thr Asp Ser Pro Asn Phe
            115                 120                 125

Leu Cys Ser Val Leu Pro Ser His Trp Arg Cys Asn Lys Thr Leu Pro
            130                 135                 140

Val Ala Phe Lys Val Val Ala Leu Gly Glu Val Pro Asp Gly Thr Val
145                 150                 155                 160

Val Thr Val Met Ala Gly Asn Asp Glu Asn Tyr Ser Ala Glu Leu Arg
                165                 170                 175

Asn Ala Ser Ala Val Met Lys Asn Gln Val Ala Arg Phe Asn Asp Leu
            180                 185                 190

Arg Phe Val Gly Arg Ser Gly Arg Gly Lys Ser Phe Thr Leu Thr Ile
            195                 200                 205

Thr Val Phe Thr Asn Pro Pro Gln Val Ala Thr Tyr His Arg Ala Ile
            210                 215                 220

Lys Val Thr Val Asp Gly Pro Arg Glu Pro Arg Arg His Arg Gln Lys
225                 230                 235                 240

Leu Asp Asp Ser Lys Pro Ser Leu Phe Ser Asp Arg Leu Ser Asp Leu
                245                 250                 255

Gly Arg Ile Pro His Pro Ser Met Arg Val Gly Val Pro Pro Gln Asn
            260                 265                 270

Pro Arg Pro Ser Leu Asn Ser Ala Pro Ser Pro Phe Asn Pro Gln Gly
            275                 280                 285

Gln Ser Gln Ile Thr Asp Pro Arg Gln Ala Gln Ser Ser Pro Pro Trp
        290                 295                 300

Ser Tyr Asp Gln Ser Tyr Pro Ser Tyr Leu Ser Gln Met Thr Ser Pro
305                 310                 315                 320

Ser Ile His Ser Thr Thr Pro Leu Ser Ser Thr Arg Gly Thr Gly Leu
```

-continued

```
                    325                 330                 335
Pro Ala Ile Thr Asp Val Pro Arg Arg Ile Ser Asp Asp Thr Ala
                340                 345                 350
Thr Ser Asp Phe Cys Leu Trp Pro Ser Ser Leu Ser Lys Lys Ser Gln
                355                 360                 365
Ala Gly Ala Ser Glu Leu Gly Pro Phe Ser Asp Pro Arg Gln Phe Pro
370                 375                 380
Ser Ile Ser Ser Leu Thr Glu Ser Arg Phe Ser Asn Pro Arg Met His
385                 390                 395                 400
Tyr Pro Ala Thr Phe Thr Tyr Thr Pro Pro Val Thr Ser Gly Met Ser
                405                 410                 415
Leu Gly Met Ser Ala Thr Thr His Tyr His Thr Tyr Leu Pro Pro Pro
                420                 425                 430
Tyr Pro Gly Ser Ser Gln Ser Gln Ser Gly Pro Phe Gln Thr Ser Ser
                435                 440                 445
Thr Pro Tyr Leu Tyr Tyr Gly Thr Ser Ser Ala Ser Tyr Gln Phe Pro
                450                 455                 460
Met Val Pro Gly Gly Asp Arg Ser Pro Ser Arg Met Val Pro Pro Cys
465                 470                 475                 480
Thr Thr Thr Ser Asn Gly Ser Thr Leu Leu Asn Pro Asn Leu Pro Asn
                485                 490                 495
Gln Asn Asp Gly Val Asp Ala Asp Gly Ser His Ser Ser Ser Pro Thr
                500                 505                 510
Val Leu Asn Ser Ser Gly Arg Met Asp Glu Ser Val Trp Arg Pro Tyr
                515                 520                 525

<210> SEQ ID NO 83
<211> LENGTH: 451
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 83

Met Arg Ile Pro Val Asp Ala Ser Thr Ser Arg Arg Phe Thr Pro Pro
1               5                   10                  15
Ser Thr Ala Leu Ser Pro Gly Lys Met Ser Glu Ala Leu Pro Leu Gly
                20                  25                  30
Ala Pro Asp Gly Gly Pro Ala Leu Ala Ser Lys Leu Arg Ser Gly Asp
                35                  40                  45
Arg Ser Met Val Glu Val Leu Ala Asp His Pro Gly Glu Leu Val Arg
        50                  55                  60
Thr Asp Ser Pro Asn Phe Leu Cys Ser Val Leu Pro Thr His Trp Arg
65                  70                  75                  80
Cys Asn Lys Thr Leu Pro Ile Ala Phe Lys Val Val Ala Leu Gly Asp
                85                  90                  95
Val Pro Asp Gly Thr Leu Val Thr Val Met Ala Gly Asn Asp Glu Asn
                100                 105                 110
Tyr Ser Ala Glu Leu Arg Asn Ala Thr Ala Ala Met Lys Asn Gln Val
                115                 120                 125
Ala Arg Phe Asn Asp Leu Arg Phe Val Gly Arg Ser Gly Arg Gly Lys
        130                 135                 140
Ser Phe Thr Leu Thr Ile Thr Val Phe Thr Asn Pro Pro Gln Val Ala
145                 150                 155                 160
```

-continued

```
Thr Tyr His Arg Ala Ile Lys Ile Thr Val Asp Gly Pro Arg Glu Pro
            165                 170                 175

Arg Arg His Arg Gln Lys Leu Asp Asp Gln Thr Lys Pro Gly Ser Leu
            180                 185                 190

Ser Phe Ser Glu Arg Leu Ser Glu Leu Glu Gln Leu Arg Arg Thr Ala
        195                 200                 205

Met Arg Val Ser Pro His His Pro Ala Pro Thr Pro Asn Pro Arg Ala
        210                 215                 220

Ser Leu Asn His Ser Thr Ala Phe Asn Pro Gln Pro Gln Ser Gln Met
225                 230                 235                 240

Gln Asp Ala Arg Gln Ile Gln Pro Ser Pro Pro Trp Ser Tyr Asp Gln
            245                 250                 255

Ser Tyr Gln Tyr Leu Gly Ser Ile Thr Ser Ser Ser Val His Pro Ala
            260                 265                 270

Thr Pro Ile Ser Pro Gly Arg Ala Ser Gly Met Thr Ser Leu Ser Ala
            275                 280                 285

Glu Leu Ser Ser Arg Leu Ser Thr Ala Pro Asp Leu Thr Ala Phe Gly
        290                 295                 300

Asp Pro Arg Gln Phe Pro Thr Leu Pro Ser Ile Ser Asp Pro Arg Met
305                 310                 315                 320

His Tyr Pro Gly Ala Phe Thr Tyr Ser Pro Pro Val Thr Ser Gly Ile
            325                 330                 335

Gly Ile Gly Met Ser Ala Met Ser Ser Ala Ser Arg Tyr His Thr Tyr
            340                 345                 350

Leu Pro Pro Pro Tyr Pro Gly Ser Ser Gln Ala Gln Ala Gly Pro Phe
            355                 360                 365

Gln Thr Gly Ser Pro Ser Tyr His Leu Tyr Tyr Gly Ala Ser Ala Gly
        370                 375                 380

Ser Tyr Gln Phe Ser Met Val Gly Gly Glu Arg Ser Pro Pro Arg Ile
385                 390                 395                 400

Leu Pro Pro Cys Thr Asn Ala Ser Thr Gly Ala Ala Leu Leu Asn Pro
                405                 410                 415

Ser Leu Pro Ser Gln Ser Asp Val Val Glu Thr Glu Gly Ser His Ser
            420                 425                 430

Asn Ser Pro Thr Asn Met Pro Pro Ala Arg Leu Glu Glu Ala Val Trp
            435                 440                 445

Arg Pro Tyr
    450
```

OSF2/CBFA1 NUCLEIC ACIDS AND METHODS OF USE THEREFOR

The present application is a continuing application of U.S. Provisional Application Serial No. 60/080,189 filed Mar. 24, 1998, which was a continuing application of U.S. Provisional Application Serial No. 60/048,430 filed May 29, 1997, the entire contents of each of which is specifically incorporated herein by reference in its entirety.

The United States government has rights in the present invention pursuant to grant numbers DE11290 and AR41059 from the National Institutes of Health.

1.0 BACKGROUND OF THE INVENTION

1.1 Field of the Invention

The present invention relates generally to the field of molecular biology, and in particular, skeletogenesis. More particularly, certain embodiments concern nucleic acid segments comprising a gene that encodes a novel osteoblast-specific transcription factor, designated Osf2/Cbfa1. In certain embodiments, the invention concerns the use of these polynucleotide and polypeptide compositions to regulate osteoblast differentiation, and stimulate bone tissue formation, growth, repair and regeneration. Methods are also provided for identifying Osf2/Cbfa1 and Osf2/Cbfa1-related genes and polypeptides from biological samples, as well as methods and kits for identifying compounds that interact with Osf2/Cbfa1 polypeptides or polynucleotides, as well as compounds that alter or inhibit osteogenesis in an organism.

1.2 Description of Related Art
1.2.1 Bone Development

Regulatory factors involved in bone repair are known to include systemic hormones, cytokines, growth factors, and other molecules that regulate growth and differentiation. Various osteoinductive agents have been purified and shown to be polypeptide growth-factor-like molecules. These stimulatory factors are referred to as bone morphogenetic or morphogenic proteins (BMPs), and have also been termed osteogenic bone inductive proteins or osteogenic proteins (OPs). Several BMP- (or OP-) encoding genes have now been cloned and characterized; these have been assigned the common designations of BMP-1 through BMP-8. Although the BMP terminology is widely used, it may prove to be the case that there is an OP counterpart term for every individual BMP (Alper, 1994). Likewise, additional genes encoding OPs and BMPs are still being identified.

BMPs 2–8 are generally thought to be osteogenic, although BMP-1 is a more generalized morphogen (Shimell et al., 1991). BMP-3 is also called osteogenin (Luyten et al., 1989) and BMP-7 is also called OP-1 (Ozkaynak et al., 1990). BMPs are related to, or part of, the transforming growth factor-β (TGF-β) superfamily, and both TGF-β1 and TGF-β2 also regulate osteoblast function (Seitz et al., 1992). Several BMP (or OP) nucleotide sequences and polypeptides have been described in U.S. Pat. Nos. 4,795,804; 4,877,864; 4,968,590; and 5,108,753; including, specifically, BMP-1 disclosed in U.S. Pat. No. 5,108,922; BMP-2A (currently referred to as BMP-2) in U.S. Pat. Nos. 5,166,058 and 5,013,649; BMP-2B (currently referred to as BMP-4) disclosed in U.S. Pat. No. 5,013,649; BMP-3 in U.S. Pat. No. 5,116,738; BMP-5 in U.S. Pat. No. 5,106,748; BMP-6 in U.S. Pat. No. 5,187,076; BMP-7 in U.S. Pat. No. 5,108,753 and U.S. Pat. No. 5,141,905; and OP-1, COP-5 and COP-7 in U.S. Pat. No. 5,011,691 (each of which is specifically incorporated herein by reference in its entirety).

Other growth factors or hormones that have been reported to have the capacity to stimulate new bone formation include acidic fibroblast growth factor (Jingushi et al., 1990); estrogen (Boden et al., 1989); macrophage colony stimulating factor (Horowitz et al., 1989); and calcium regulatory agents such as parathyroid hormone (PTH) (Raisz and Kream, 1983). Skeletal development is a multi-step process. It includes patterning of skeletal elements, commitment of mesenchymal cells to chondrogenic and osteogenic lineages, followed by the terminal differentiation of precursor cells into three specialized cell types: the chondrocyte in cartilage, the osteoblast and osteoclast in bone. Many genes encoding either growth factors or transcription factors were shown through genetic studies in mice to control patterning of skeletal elements (Luo et al.; 1996a, 1996b). These genetic analyses showed also that mutations in these genes do not severely affect the differentiation of the skeleton specific cell types suggesting that patterning and cell differentiation in the skeleton are achieved through different genetic pathways. Consistent with this hypothesis, genes such as PTHrP and c-fos were shown to control chondrocyte and osteoclast differentiation respectively, without affecting skeletal patterning (Karaplis et al., 1994; Wang et al., 1992; Johnson et al., 1992). Little is known, however, about the molecular determinants specifically responsible for controlling osteogenesis, and in particular, osteoblast differentiation.

Analysis of Osf2, the osteoblast nuclear activity polypeptide that binds to OSE2, showed that it is immunologically related to the Cbfa transcription factors (Geoffroy et al., 1995; Merriman et al., 1995). The Cbfa proteins are the mouse homologues of Runt, a Drosophila pair-rule gene product required for neurogenesis and sexual differentiation (Gergen and Wieschaus, 1985; Kania et al., 1990). Runt and the Cbfa proteins have a high degree of homology in their DNA-binding domain, a 128-amino-acid long motif called the runt domain (Kagoshima et al., 1993). The mouse genome contains three known runt homologues encoding numerous isoforms with well-characterized expression patterns (Ogawa et al., 1993a; Bae et al., 1992; Wijmenga et al., 1995; Simeone et al., 1995). None of the described Cbfa transcripts has been shown to be expressed exclusively or predominantly in bone, suggesting that still unknown member(s) of the Cbfa family control osteoblast-specific expression of Osteocalcin. This prompted the search for such a novel member or members.

1.2.2 Transcription Factors

The control of all biological processes results from a balance between various positive and negative-acting factors which interact with DNA regulatory elements and with each other. These protein factors play a critical role in controlling the expression of proteins, and thus are critical to both normal and pathological processes. Understanding these protein factors and how they modulate gene expression is key to strategies for the development of agents to control disease initiation and progression.

Gene-specific transcription factors provide a promising class of targets for novel therapeutics directed to these and other human diseases for the following reasons. One, transcription factors offer substantial diversity. Over 300 gene-specific transcription factors have been described, and the human genome may encode as many as 3000. Hence, they provide as plentiful a target source as cell-surface receptors. Two, transcription factors offer substantial specificity. Each and every factor offers unique molecular surfaces to target. Three, transcription factors are known to be involved in human disease. For example, many tumors are associated with the activation of a specific oncogene. A third of known proto-oncogenes and three fourths of all anti-oncogenes are transcription factors.

Transcription factors are capable of sequence-specific interaction with a portion of a gene or gene regulatory region. The interaction may be directed sequence-specific binding where the transcription factor directly contacts the nucleic acid or indirect sequence-specific binding mediated or facilitated by other auxiliary proteins where the transcription factor is tethered to the nucleic acid by a direct nucleic acid binding protein. In addition, some transcription factor demonstrate induced or synergistic binding. A broad range of transcription factor-nucleic acid complexes provide useful targets. The gene and/or transcription factor may be derived from a host or from an infectious or parasitic organism. As examples, a host may be immunomodulated (e.g., by controlling inflammation or hypersensitivity) by modulating the DNA binding of a transcription factor involved in immune cell activation; or vital, bacterial, or other microbial disease progression may be inhibited by disrupting the DNA binding of a host, vital or other microbial transcription factor involved in vital or other microbial gene transcription.

1.3 Deficiencies in the Prior Art

What is lacking in the prior art, inter alia, are polynucleotide compositions that encode polypeptides that possess osteoblast-specific transcription factor activity. Also lacking are methods of regulating transcription of genes involved in skeletogenesis, and in particular, those involved in expression of osteoblast-specific genes.

2.0 SUMMARY OF THE INVENTION

The present invention overcomes these and other limitations in the prior art by providing for the first time, an osteoblast-specific transcription factor that regulates differentiation along osteoblastic lineages. The invention provides methods that overcomes the prior limitations that regulate transcription of genes involved in skeletogenesis.

In a first embodiment, the invention provides novel polynucleotide compositions comprising an Osf2/Cbfa1 gene, that encodes the first osteoblast-specific transcription factor identified, the Osf2/Cbfa1 polypeptide disclosed herein. Also provided are methods for the use of this gene and its regulatory sequences (including its promoter and enhancer elements) in the regulation and expression of specific genes, including those involved in osteogenesis. The invention also provides antibodies reactive with Osf2/Cbfa1, and a variety of related immunological methods, compositions, and devices. The methods of the invention also provide for the use of Osf2/Cbfa1 gene and Osf2/Cbfa1 polypeptide compositions in the regulation of heterologous genes positioned under the control of Osf2/Cbfa1 and Osf2/Cbfa-derived nucleic acid sequences. In illustrative embodiments, Osf2/Cbfa1 has been shown to regulate the expression of genes in mesenchymal cells that are required for osteoblast differentiation, and Osf2/Cbfa1 polypeptides have been shown to possess osteoblast-specific transcription factor activity.

In a second embodiment, the present invention provides a method of specifically transcribing a gene, and in particular, an osteoblast-specific gene. The method generally involves providing to a cell an amount of an Osf2/Cbfa1 composition effective to specifically transcribe the gene of interest. Such genes may be homologous or heterologous genes, and may include genes derived from a variety of sources, including mammalian sources. In exemplary embodiments, the inventors have demonstrated the occurrence of a variety of osteoblast-specific genes which may be controlled by the disclosed transcription factor active polypeptides including polypeptides such as, but not limited to, osteocalcin, α1 and α2, type I collagen, osteopontin, and bone sialoprotein.

In exemplary embodiments, the inventors have identified cell lines and cell types suitable for the present methods, including, but not limited to, Ros25, C3H10T42, C2C12, NIH3T3, F9, MC3T3E1, primary fibroblasts, myoblasts, chondrocytes, adipocytes, and marrow stromal cells.

In a third embodiment the invention provides methods for promoting the expression of an osteoblast-specific gene in a cell. These methods generally involve providing to a cell, an amount of an Osf2/Cbfa1 composition effective to promote the expression of the osteoblast-specific gene in the cell.

A fourth embodiment of the invention concerns a method for promoting the expression of a selected gene in a cell. The method generally involves providing to the cell, an expression system which contains one or more genes of interest which are positioned under the transcriptional control of an OSE2 element, and further providing to the cell an amount of an Osf2/Cbfa1 composition effective to promote the expression of the gene.

A fifth embodiment of the invention concerns a method of detecting a nucleic acid segment comprising at least one OSE2 element. This method generally involves contacting a population of nucleic acid segments suspected of containing one or more OSE2 elements with at least one Osf2/Cbfa1 composition under conditions and for a period of time effective to permit the binding of the Osf2/Cbfa1 composition(s) to the OSE2 element(s), and detecting the complex(es) so bound.

A sixth embodiment of the invention relates to a method of identifying an OSE2 element. This method generally involves contacting a sample suspected of containing an OSE2 element with an Osf2/Cbfa1 composition under conditions effective to allow binding of the Osf2/Cbfa1 composition to the OSE2 element, and detecting the bound complex.

The invention also provides a method of inducing osteoblast differentiation. This method comprises providing to an osteoblast progenitor cell an amount of an Osf2/Cbfa1 composition effective to induce differentiation of the progenitor cell. Exemplary cell cells include Ros25, C3H10T42, C2C12, NIH3T3, F9, MC3T3E1, primary fibroblast myoblasts, chondrocytes, adipocytes, and marrow stromal cells.

In yet another embodiment, there is provided a method for the production of an antibody that binds immunologically to an Osf2/Cbfa1 polypeptide, and in particular a mammalian Osf2/Cbfa1 polypeptide. This method generally comprises administering to an animal an immunologically-effective amount of an Osf2/Cbfa1 polypeptide composition. In one such method, co-administration of an adjuvant to the animal is contemplated to be particularly useful in producing an immune response in the animal, and the formation of antibodies specific for the particular Osf2/Cbfa1- or Osf2/Cbfa1-derived polypeptide, peptide, or epitope.

The invention also provides a method for identifying compounds which regulate, alter, or modulate the activity of an Osf2/Cbfa1 polypeptide or polynucleotide. This method generally comprises exposing a cell that expresses an Osf2/Cbfa1 polypeptide to at least one compound or signal whose ability to modulate the activity of the Osf2/Cbfa1 polypeptide is sought to be determined, and thereafter monitoring the cell for a change that is a result of the modulation of Osf2/Cbfa1 activity. Such an assay is particularly contemplated to be useful in the identification of agonists, antagonists and/or allosteric modulators of Osf2/Cbfa1. For example, recombinant Osf2/Cbfa1-producing cells may be contacted with one or more test compounds, and the modulating effect(s) thereof can then be evaluated by comparing the Osf2/Cbfa1-mediated response in the presence and absence of test compound, or relating the Osf2/Cbfa1-mediated response of test cells, or control cells (i.e. cells that do not express Osf2/Cbfa1), to the presence of the compound.

As used herein, a compound or signal that modulates the activity of Osf2/Cbfa1 refers to a compound that alters the activity of Osf2/Cbfa1 in such a way that the activity of Osf2/Cbfa1 is different in the presence of the compound or signal (as compared to the absence of said compound or signal).

A further aspect of the invention provides methods for screening compounds (e.g., synthetic peptides, peptide analogs, peptidomimetics, small molecule inhibitors, etc.) which inhibit or reduce the binding of an Osf2/Cbfa1 polypeptide with a polynucleotide. Being a promoter-specific transcription factor, Osf2/Cbfa1 is an important target for therapeutic intervention e.g., by means of a chemical entity affecting the factor's capability of binding to the DNA. Therefore, the inventors contemplate that screening for such chemical entities may be performed e.g., by means of a cell-based assay, an in vitro assay for Osf2/Cbfa1 function and/or rational drug design. Cell-based assays for screening can be designed e.g., by constructing cell lines in which the expression of a reporter protein, i.e. an easily assayable protein, is dependent on Osf2/Cbfa1. Such an assay enables the detection of compounds that directly antagonize Osf2/Cbfa1, or compounds that inhibit other cellular functions required for the activity of Osf2/Cbfa1.

In yet another embodiment, the present invention provides an isolated Osf2/Cbfa1 promoter element. Preferably the promoter element comprises a contiguous nucleic acid sequence of at least 17 nucleic acids from SEQ ID NO:72. As such, promoter elements contemplated to be useful in the practice of the present invention include those elements which comprise at least 18, at least 19, at least 20, at least 21, at least 22, at least 23, at least 24, at least 25, and at least 26 contiguous nucleic acids from SEQ ID NO:72. Moreover, sequence elements which comprise at least 27, 28, 29, 30, 31, 32, 33, 34, 35, 36, 37, 38, 39, or 40 or so contiguous nucleotides from SEQ ID NO:72 are also contemplated to be useful in the practice of the present invention, and are useful in promoting the expression of a gene operably linked to one or more of these promoter element sequences. This promoter element may comprise enhancer, inducer, and/or silencer elements that may be involved in controlling the cell-specific expression of the gene. In illustrative embodiments, the operably-linked gene may be any gene for which expression is desired to produce a polypeptide product from such gene. The gene may be a native, or mutated gene, and may be either homologous or heterologous. In certain embodiments, the expression of heterologous gene sequences from the Osf2/Cbfa1 promoter is contemplated to be useful in cells where expression of the gene under the control of its own promoter is either inefficient or impossible.

In illustrative embodiments, the Osf2/Cbfa1 promoter element may comprise a nucleic acid sequence having from about 60% to about 65%, to about 70%, to about 75%, to about 80%, to about 85%, to about 90%, to about 95%, even up to and including about 96%, about 97%, about 98%, or about 99% or greater sequence identity with a contiguous nucleic acid sequence of at least about 17 or so nucleotides from SEQ ID NO:72. Of course, the percent identity to a contiguous nucleic acid sequence from SEQ ID NO:72 need not be limited to the specific percentages given, but is also meant to include all integers between about 60% and about 99% identity, such as percentage identities of about 86%, 87%, 88%, and 89%, or even about 91% or 92% or 93% or 94%, etc. identity with a contiguous nucleic acid sequence of at least about 17 or so nucleotides from SEQ ID NO:72. In fact, all such sequences are contemplated to fall within the scope of the present invention, so long as the particular sequence retains an ability to promote transcription of a nucleic acid segment operably linked to the DNA sequence comprising the Osf2/Cbfa1 promoter element. The inventors contemplate that the particular nucleic acid segment to be transcriptionally controlled (or promoted) by such an Osf2/Cbfa1 promoter polynucleotide may comprise one or more polynucleotides selected from the group consisting of homologous genes, heterologous genes, ribozymes, protein nucleic acids, and antisense constructs.

Another embodiment of the invention is an antisense nucleic acid segment which is complementary to a contiguous nucleotide sequence of at least about 17 or so nucleotides from SEQ ID NO:1 or SEQ ID NO:72. When it is desirable to negatively, or "down-regulate" the expression of a particular gene or nucleic acid segment in a particular cell, the inventors contemplate that preparation of such antisense constructs will be useful in altering the activity of Osf2/Cbfa1 in a cell. Alternatively, if an antisense construct complementary to a contiguous nucleotide sequence from the Osf2/Cbfa1 promoter sequence (SEQ ID NO:72) such constructs may also be used to regulate the activity of any heterologous gene placed downstream of, and operably linked to, such an Osf2/Cbfa1 promoter.

Antisense constructs are well-known in the art, and in their simplest terms, relate to the use of antisense mRNA to reduce or lessen the transcription or translation or otherwise impair the net production of the encoded polypeptide. The preparation and use of such antisense constructs are described in detail hereinbelow.

A further embodiment of the invention concerns the preparation of ribozymes utilizing a promoter comprising a contiguous nucleotide sequence selected from SEQ ID NO:72. Means for preparing ribozymes using heterologous promoters operably linked to a ribozyme sequence are also well-known in the art, and described in detail hereinbelow.

In important aspects of the present invention, there are provided DNA constructs comprising one or more Osf2 promoters operably linked to or operatively positioned with respect to one or more heterologous genes. Exemplary heterologous genes which are contemplated to be useful include, but are not limited to, reporter genes such as GFP, GUS, lac, lux, β-lactamase, xylE, α-amylase, a tyrosinase gene, and aequorin; cell cycle control genes such as Rb, p53, a cell cycle dependent kinase, a CDK kinase or a cyclin gene.

A further aspect of the present invention provides a method of expressing a heterologous nucleic acid segment in a cell. The method generally involves transforming said cell with a vector comprising a heterologous nucleic acid segment operatively linked to at least one Osf2 promoter and culturing the cell under conditions effective to express the heterologous nucleic acid segment from the promoter. Preferably, the Osf2 promoter comprises a substantially contiguous nucleic acid sequence of at least about 17 contiguous nucleotides from SEQ ID NO:72 that retains the ability to promote transcription of a heterologous polynucleotide operably linked to the promoter. Most preferred are the smallest contiguous regions of SEQ ID NO:72 that retain the transcriptional activity of an Osf2/Cbfa1 promoter and that are capable of promoting the expression of such a heterologous gene. Preferably, the cell is an animal cell such as that from a human, monkey, hamster, caprine, feline, canine, equine, porcine, lupine, or murine. Of course, in certain embodiments, particularly in the preparation of recombinant vectors and the like, it may be desirable to prepare the constructs of the present invention for use in bacterial cells such as E. coli or salmonellas including S. typhimurium cells or in yeast.

In another embodiment the present invention provides a method of changing the characteristics of a cell. Characteristics include, but are not limited to, differentiation state, transformation state, color, fluorescence, antibiotic resistance, metabolic activity, or RNA expression profile.

In an illustrative embodiment, the present invention relates to a recombinant vector comprising an Osf2 promoter sequence from SEQ ID NO:72, or a substantially equivalent sequence that retains the transcriptional activity of the Osf2 promoter, operatively linked to a heterologous nucleic acid segment, in such an orientation as to control expression of said segment. The recombinant vector may be a plasmid, a cosmid, a YAC, a BAC, or a viral vector. Viral vectors include, but are not limited to, a bacteriophage vector, a Raus sarcoma virus vector, a p21 virus vector, an adeno-associated virus vector, and adenoviral vectors. Adenovirus vectors may be replication deficient of replication competent. In certain embodiments, the recombinant vector may be dispersed in a pharmaceutically acceptable solution.

2.1 Methods for Identifying Compositions Involved in Cell Differentiation

The polynucleotides and proteins of the present invention may be used to identify molecules that control cell differentiation in the osteoblastic, chondrocytic and fibroblastic pathways. This can be achieved by ectopic expression (i.e. expression of the gene where it is normally not expressed) in cell culture studies and in transgenic mice. Moreover, the gene may also be used to screen (using a yeast two hybrid system, protein-protein interactions, or by immunoassay) for the proteins that interact with Osf2 or that regulate Osf2 expression or function. The nucleic acid compositions of the invention may also be used to identify regulatory sequences that control Osf2/Cbfa1 expression in cells of the osteoblastic lineage by DNA transfection studies and generation of transgenic mice lines. Antibodies generated against the novel protein may be used to perform DNA-binding assays to determine if the protein binds to other genes expressed in osteoblasts.

2.2 OSF2/CBFA1 Nucleic Acid Compositions

The invention provides nucleic acid sequences encoding an Osf2/Cbfa1 polypeptide. As used herein, an "Osf2/Cbfa1 gene" means a nucleic acid sequence encoding an Osf2/Cbfa1 polypeptide. Preferred Osf2/Cbfa1 genes include mammalian Osf2/Cbfa1 genes, and in particular those from humans. A preferred nucleic acid sequence encoding an Osf2/Cbfa1 gene is the nucleotide sequence of SEQ ID NO:1 or substantially homologous variants, fusion proteins, or antigenically-active peptide fragments thereof. Also provided are nucleic acid sequences encoding an alternatively spliced variant of an Osf2/Cbfa1 polypeptide (SEQ ID NO:70) and a nucleic acid sequence that comprises an Osf2/Cbfa1 promoter (SEQ ID NO:72).

It is expected that the genes encoding Osf2/Cbfa1 polypeptides will vary in nucleic acid sequence from species to species, and even from strain to strain or cell line to cell line within a species, but that the variation in nucleic acid sequence will not preclude hybridization between sequences encoding the Osf2/Cbfa1 polypeptides of various species, cell lines, and strains under moderate to strict hybridization conditions. It is also contemplated that the genes encoding Osf2/Cbfa1 polypeptides from various strains may vary in nucleic acid sequences, but that the variation will not preclude hybridization between sequences encoding an Osf2/Cbfa1 polypeptides from various species, cell lines and strains under moderate to stringent hybridization conditions.

As used herein, a variant of an Osf2/Cbfa1 polypeptide means any polypeptide encoded, in whole or in part, by a nucleic acid sequence which hybridizes under moderate to stringent hybridization conditions to the nucleic acid sequence of SEQ ID NO:1 or SEQ ID NO:70, which encodes an Osf2/Cbfa1 polypeptide isolated from the human osteoblastic cell line designated SaOS, as well as from other human osteosarcoma cell lines.

One of skill in the art will understand that variants of Osf2/Cbfa1 polypeptides include those proteins encoded by nucleic acid sequences which may be amplified using one or more of the Osf2/Cbfa1 nucleic acid sequence disclosed in SEQ ID NO:1 or SEQ ID NO:70.

In related embodiments, the invention also comprises strain variants of Osf2/Cbfa1 polypeptides and nucleic acid segments encoding Osf2/Cbfa1 polypeptides, in particular, the Osf2/Cbfa1 genes which encode the Osf2/Cbfa1 polypeptide. The amino acid sequences of Osf2/Cbfa1 polypeptides claimed herein are disclosed in SEQ ID NO:2 (native Osf2/Cbfa1) and SEQ ID NO:71 (a splice variant of Osf2/Cbfa1).

Aspects of the invention concern the identification of such protein and peptide variants using diagnostic methods and kits described herein. In particular, methods utilizing Osf2/Cbfa1 gene sequences as nucleic acid hybridization probes and/or anti-Osf2/Cbfa1 antibodies in western blots or related analyses are useful for the identification of such variants. The identity of potential variants of Osf2/Cbfa1 polypeptides may also be confirmed by transcriptional assays as described in Section 5.

As used herein, an Osf2/Cbfa1 polypeptide means an isolated protein (or an epitope, variant, or active fragment thereof) derived from a mammalian species which has the ability to modulate osteoblast differentiation. Preferably, an Osf2/Cbfa1 polypeptide is encoded by a nucleic acid sequence having the sequence of SEQ ID NO:1 or SEQ ID NO:70, or a sequence which hybridizes to the sequence of SEQ ID NO:1 or SEQ ID NO:70. Alternatively, an Osf2/Cbfa1 polypeptide may be defined as a polypeptide which comprises a contiguous amino acid sequence from SEQ ID NO:2 or SEQ ID NO:71, or which protein comprises the entire amino acid sequence of SEQ ID NO:2 or SEQ ID NO:71.

In the present invention, an Osf2/Cbfa1 polypeptide composition is also understood to comprise one or more polypeptides that are immunologically reactive with antibodies generated against an Osf2/Cbfa1 polypeptide, particularly a protein having the amino acid sequence disclosed in SEQ ID NO:2 or SEQ ID NO:71; or the protein encoded by the Osf2/Cbfa1 nucleic acid sequence disclosed in SEQ ID NO:1 or SEQ ID NO:70, or to active fragments, or to variants thereof.

Likewise, an Osf2/Cbfa1 polypeptide composition of the present invention is understood to comprise one or more polypeptides that are capable of eliciting antibodies that are immunologically reactive with one or more Osf2/Cbfa1 polypeptides encoded by one or more contiguous Osf2/Cbfa1 nucleic acid sequences contained in SEQ ID NO:1 or SEQ ID NO:70, or to active fragments, or to strain variants thereof, or to one or more nucleic acid sequences which hybridize to one or more of these sequences under conditions of moderate to high stringency. Particularly preferred proteins include the amino acid sequence disclosed in SEQ ID NO:2 or SEQ ID NO:71.

As used herein, an active fragment of an Osf2/Cbfa1 polypeptide includes a whole or a portion of an Osf2/Cbfa1 polypeptide which is modified by conventional techniques, e.g., mutagenesis, or by addition, deletion, or substitution, but which active fragment exhibits substantially the same structure and function as a native Osf2/Cbfa1 polypeptide as described herein.

Other aspects of the present invention concern isolated DNA segments and recombinant vectors encoding one or more Osf2/Cbfa1 polypeptides, in particular, the Osf2/Cbfa1 polypeptide from mammalian, and preferably, human sources, and the creation and use of recombinant host cells through the application of DNA technology, that express one or more Osf2/Cbfa1 gene products. As such, the invention concerns DNA segments comprising an isolated gene that encodes an Osf2/Cbfa1 polypeptide that includes an amino acid sequence essentially as set forth by a contiguous sequence from SEQ ID NO:2 or SEQ ID NO:71. These DNA segments are represented by those that include an Osf2/Cbfa1 nucleic acid sequence essentially as set forth by a contiguous sequence from SEQ ID NO:1 or SEQ ID NO:70, respectively.

Compositions that include a purified Osf2/Cbfa1 polypeptide that has a contiguous amino acid sequence essentially as set forth by the amino acid sequence of SEQ ID NO:2 or SEQ ID NO:71 are also encompassed by the invention.

Regarding the novel Osf2/Cbfa1 polypeptides, the present invention concerns DNA segments, that can be isolated from virtually any source, that are free from total genomic DNA and that encode one or more proteins having osteoblast-specific transcription factor activity. DNA segments encoding one or more Osf2/Cbfa1-like species may also encode proteins, polypeptides, subunits, functional domains, antigenic epitopes, binding domains, and/or the like.

As used herein, the term "DNA segment" refers to a DNA molecule that has been isolated free of total genomic DNA of a particular species. Therefore, a DNA segment encoding an Osf2/Cbfa1 polypeptide refers to a DNA segment that contains one or more Osf2/Cbfa1 coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified Osf2/Cbfa1 gene refers to a DNA segment including Osf2/Cbfa1 coding sequences and, in certain aspects, regulatory sequences, isolated substantially away from other naturally occurring genes or protein encoding sequences. Preferably the sequence encodes an Osf2/Cbfa1 polypeptide, and more preferably, comprises an Osf2/Cbfa1 gene, in particular, an Osf2/Cbfa1 gene isolated from a mammalian cell line such as the Osf2/Cbfa1 gene isolated from human cell lines including one designated SaOS. In this respect, the term "gene" is used for simplicity to refer to a functional protein, polypeptide or peptide encoding unit. As will be understood by those in the art, this functional term includes both genomic sequences, extra-genomic and plasmid-encoded sequences and smaller engineered gene segments that express, or may be adapted to express, proteins, polypeptides or peptides. Such segments may be naturally isolated, or modified synthetically by the hand of man.

"Isolated substantially away from other coding sequences" means that the gene of interest, in this case, a gene encoding an Osf2/Cbfa1 polypeptide, forms the significant part of the coding region of the DNA segment, and that the DNA segment does not contain large portions of naturally-occurring coding DNA, such as large chromosomal fragments or other functional genes or polypeptide coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an Osf2/Cbfa1 polypeptide species that comprises an amino acid sequence essentially as set forth in SEQ ID NO:2 or SEQ ID NO:71, or biologically-functional equivalents thereof. In other particular embodiments, the invention concerns isolated DNA segments and recombinant vectors incorporating DNA sequences that comprises a sequence essentially as set forth in SEQ ID NO:1 or SEQ ID NO:70, or biologically-functional equivalents or strains variants thereof.

The term "a sequence essentially as set forth in SEQ ID NO:1 or SEQ ID NO:70" means that the sequence substantially corresponds to a portion of the DNA sequence listed in SEQ ID NO:1 or SEQ ID NO:70, and has relatively few nucleotides that are not identical to, or a biologically functional equivalent of, the nucleic acid sequence of SEQ ID NO:1 or SEQ ID NO:70. Such nucleotide sequences are also considered to be essentially as those disclosed herein when they encode essentially the same amino acid sequences as disclosed, or that they encode biologically functional equivalent amino acids tot hose as disclosed herein. In particular, preferred nucleotide sequences are those which encode the amino acid sequence of SEQ ID NO:2 or SEQ ID NO:71, or biologically functional equivalents thereof.

Likewise, the term "a sequence essentially as set forth in SEQ ID NO:70" means that the sequence substantially corresponds to a portion of the DNA sequence listed in SEQ ID NO:70, and has relatively few nucleotides that are not identical to, or a biologically functional equivalent of, the nucleic acid sequence of SEQ ID NO:70. Such nucleotide sequences are also considered to be essentially as those disclosed herein when they encode essentially the same amino acid sequences as disclosed, or that they encode biologically functional equivalent amino acids tot hose as disclosed herein. In particular, preferred nucleotide sequences are those which encode the amino acid sequence of SEQ ID NO:71, or biologically functional equivalents thereof.

The term "biologically functional equivalent" is well understood in the art and is further defined in detail herein (e.g., see Illustrative Embodiments). Accordingly, sequences that have between about 70% and about 80%; or more preferably, between about 81% and about 90%; or even more preferably, between about 91% and about 99%; of amino acids that are identical or functionally equivalent to the amino acids disclosed herein, will be sequences that are "essentially as set forth in SEQ ID NO:2" or "essentially as set forth in SEQ ID NO:71".

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1 and has relatively few nucleotides residues that are not identical, or functionally equivalent, to the nucleotide residues of SEQ ID NO:1. Again, DNA segments that encode proteins exhibiting an Osf2/Cbfa1 polypeptide-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various upstream or downstream regulatory or structural genes. It will also include a splice variant of an Osf2/Cbfa1 gene that has limited or no biologic activity, but which may act as a naturally-occurring "dominant negative" regulator of Osf2/Cbfa1 activity.

Naturally, the present invention also encompasses DNA segments that are complementary, or essentially complementary, to the sequence set forth in SEQ ID NO:1, SEQ ID NO:70, or SEQ ID NO:72. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, SEQ ID NO:70, or SEQ ID NO:72, under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1, SEQ ID NO:70, or SEQ ID NO:72, such as about 14 nucleotides, and that are up to about 10,000 or about 5,000 base pairs in length, with segments of about 3,000 being preferred in certain cases. DNA segments with total lengths of about 2,000, about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid sequence disclosed in SEQ ID NO:1, SEQ ID NO:70, or SEQ ID NO:72 or to the amino acid sequence disclosed in SEQ ID NO:2 or SEQ ID NO:71. Recombinant vectors and isolated DNA segments may therefore variously include the Osf2/Cbfa1 coding regions themselves, coding regions bearing selected alterations or modifications in the basic coding region, or they may encode larger polypeptides that nevertheless include an Osf2/Cbfa1 polypeptide coding region or may encode biologically functional equivalent polypeptides that have variant amino acids sequences.

The DNA segments of the present invention encompass biologically functional equivalent Osf2/Cbfa1 polypeptides and Osf2/Cbfa1-derived peptides, in particular those Osf2/Cbfa1 polypeptides isolated from mammals, and particularly humans. DNA segments isolated from mammalian species which are homologous to Osf2/Cbfa1-encoding nucleic acid sequences are particularly preferred for use in the methods disclosed herein. Such sequences may arise as a consequence of codon redundancy and functional equivalency that are known to occur naturally within nucleic acid sequences and the proteins thus encoded. Alternatively, functionally equivalent polypeptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the Osf2/Cbfa1 coding regions are aligned within the same expression unit with other polypeptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter or an enhancer. The promoter (or enhancer) may be in the form of the promoter or enhancer that is naturally associated with an Osf2/Cbfa1 polypeptide gene (SEQ ID NO:72), as may be obtained by isolating the 5' non-coding sequences located upstream of the coding segment, for example, using recombinant cloning and/or PCR™ technology, in connection with the compositions disclosed herein. The enhancer may be obtained by isolating the 5' non-coding sequence located upstream of the coding sequence; by isolating the 3' non-coding sequence located downstream of the coding sequences; or by isolating one or more intronic sequences located within the gene that contain one or more enhancer regions, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an Osf2/Cbfa1 gene in its natural environment. Such promoters may include Osf2/Cbfa1 promoters themselves, or promoters normally associated with other genes, and in particular other transcription factor genes, or promoters isolated from any bacterial, viral, eukaryotic, or mammalian cell. Naturally, it will be important to employ a promoter that effectively directs the expression of the Osf2/Cbfa1-encoding DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant polypeptides.

Prokaryotic expression of nucleic acid segments of the present invention may be performed using methods known to those of skill in the art, and will likely comprise expression vectors and promoter sequences such as those provided by tac, ara, trp, lac, lacUV5 or T7. When expression of the recombinant Osf2/Cbfa1 polypeptides is desired in eukaryotic cells, a number of expression systems are available and known to those of skill in the art. An exemplary eukaryotic promoter system contemplated for use in high-level expression is the Pichia expression vector system available from Pharmacial LKB Biotechnology.

In connection with expression embodiments to prepare one or more recombinant Osf2/Cbfa1 polypeptides or Osf2/Cbfa1-derived peptides, it is contemplated that longer DNA segments will most often be used, with DNA segments encoding the entire Osf2/Cbfa1 polypeptide or one or more functional domains, epitopes, ligand binding domains, subunits, etc. therefore being most preferred. However, it will be appreciated that the use of shorter DNA segments to direct the expression of an Osf2/Cbfa1 polypeptide or an Osf2/Cbfa1-derived peptide or epitopic core region, such as may be used to generate anti-Osf2/Cbfa1 antibodies, also falls within the scope of the invention. DNA segments that encode peptide antigens from about 15 to about 100 amino acids in length, or more preferably, from about 15 to about 50 amino acids in length are contemplated to be particularly useful.

The Osf2/Cbfa1 gene and DNA segments derived therefrom may also be used in connection with somatic expression in an animal or in the creation of a transgenic animal. Again, in such embodiments, the use of a recombinant vector that directs the expression of the full length or active Osf2/Cbfa1 polypeptide is particularly contemplated. Expression of Osf2/Cbfa1 transgenes in animals is particularly contemplated to be useful in the production of anti-Osf2/Cbfa1 antibodies and the regulation or modulation of osteoblast differentiation.

2.3 Probes and Primers for OSF2/CBFA1 Gene Segments

In addition to their use in directing the expression of Osf2/Cbfa1, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:1, SEQ ID NO:70, or SEQ ID NO:72 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to Osf2/Cbfa1-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to SEQ ID NO:1, SEQ ID NO:70, or SEQ ID NO:72, are particularly contemplated as hybridization probes for use in, e.g., Southern and Northern blotting. This would allow an Osf2/Cbfa1 polypeptide or regulatory gene product to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 14 and about 100 nucleotides, but larger contiguous complementarity stretches may be used, according to the length complementary sequences one wishes to detect.

The use of a hybridization probe of about 14–25 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1, SEQ ID NO:70, or SEQ ID NO:72, or to any continuous portion of the sequence, from about 14–25 nucleotides in length up to and including the full length sequence, that one wishes to utilize as a probe or primer. The choice of probe and primer sequences may be governed by various factors, such as, by way of example only, one may wish to employ primers from towards the ternini of the total sequence.

The process of selecting and preparing a nucleic acid segment that includes a contiguous sequence from within SEQ ID NO:1, SEQ ID NO:70, or SEQ ID NO:72, may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of the entire Osf2/Cbfa1 gene or gene fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related Osf2/Cbfa1 genes.

Of course, for some applications, for example, where one desires to prepare mutants employing a mutant primer strand hybridized to an underlying template or where one seeks to isolate one or more Osf2/Cbfa1-encoding sequences from related species, functional equivalents, or the like, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

2.4 Vectors Comprising and Host Cells Expressing OSF2/CBFA1- and OSF2/CBFA1-Derived Polynuclotides Recombinant clones expressing the Osf2/Cbfa1-encoding nucleic acid segments may be used to prepare purified peptide antigens as well as mutant or variant protein species in significant quantities. The selected antigens, and variants thereof, are proposed to have significant utility in regulating, modulating, altering, changing, increasing, and/or decreasing osteoblast differentiation. For example, it is proposed that these antigens, or peptide variants, or antibodies against such antigens may be used in immunoassays to detect Osf2/Cbfa1 antibodies or as vaccines or immunotherapeutic to modulate osteoblast differentiation.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence.

The Osf2 promoter may be used to express the Osf2/Cbfa1-encoding nucleic acid segments of the present invention. This allows the expression of these proteins to have the same tissue specificity and other activities as the endogenous gene. Similarly, one or more heterologous genes may be operably linked to the Osf2 promoter of the present invention to allow expression of one or more heterologous genes in a manner similar to that of the endogenous Osf2 gene.

Particular aspects of the invention concern the use of plasmid vectors for the cloning and expression of recombinant peptides, and particular peptides incorporating either native, or site-specifically mutated Osf2/Cbfa1 epitopes. The generation of recombinant vectors, transformation of host cells, and expression of recombinant proteins is well-known to those of skill in the art. Prokaryotic hosts are preferred for expression of the peptide compositions of the present invention. Some examples of prokaryotic hosts are *E. coli* strains JM101, XL1-Blue™, RR1, LE392, B, $\chi^{1776}$ (ATCC 31537), and W3110 (F−, λ−, prototrophic, ATCC 273325). Enterobacteriaceae species such as *Salmonella typhimurium* and *Serratia marcescens*, and other Gram-negative hosts such as various Pseudomonas species may also find utility in the recombinant expression of genetic constructs disclosed herein.

Alternatively, Gram-positive cocci such as *S. aureus, S. pyogenes, S. dysgalactiae, S. epidermidis, S. zooepidemicus, S. xylosus*, and *S. hominus*, and bacilli such as *Bacillus subtilis, B. cereus, B. thuringiensis*, and *B. megaterium* may also be used for the expression of these constructs and the isolation of native or recombinant peptides therefrom.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be typically transformed using vectors such as pBR322, or any of its derivatives (Bolivar et al., 1977). pBR322 contains genes for ampicillin and tetracycline resistance and thus provides ready means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). The use of recombinant and native microbial promoters is well-known to those of skill in the art, and details concerning their nucleotide sequences and specific methodologies are in the public domain, enabling a skilled worker to construct particular recombinant vectors and expression systems for the purpose of producing compositions of the present invention.

In addition to the preferred embodiment expression in prokaryotes, eukaryotic microbes, such as yeast cultures may also be used in conjunction with the methods disclosed herein. *Saccharomyces cerevisiae*, or common baker's yeast is the most commonly used among eukaryotic microorganisms, although a number of other species may also be employed for such eukaryotic expression systems. For expression in Saccharomyces, the plasmid YRp7, for example, is commonly used (Stinchcomb et al., 1979; Kingsman et al., 1979; Tschumper and Carbon, 1980). This plasmid already contains the trpL gene which provides a selection marker for a mutant strain of yeast lacking the ability to grow in tryptophan, for example ATCC 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphatedehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3N of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphatedehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

A particular aspect of this invention provides novel ways in which to utilize recombinant Osf2/Cbfa1-derived peptides, nucleic acid segments encoding these peptides, recombinant vectors and transformed host cells comprising Osf2/Cbfa1-derived DNA segments. As is well known to those of skill in the art, many such vectors and host cells are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a polypeptide of interest (e.g., an Osf2/Cbfa1-derived epitopic sequence) and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various regulatory sequences.

After identifying an appropriate epitope-encoding nucleic acid molecule, it may be inserted into any one of the many vectors currently known in the art, so that it will direct the expression and production of the polypeptide epitope of interest when incorporated into a host cell. In a recombinant expression vector, the coding portion of the DNA segment is positioned under the control of a promoter. The promoter may be in the form of the promoter which is naturally associated with an Osf2/Cbfa1-encoding nucleic acid segment, as may be obtained by isolating the 5' non-coding sequences located upstream of the coding segment, for example, using recombinant cloning and/or PCR™ technology, in connection with the compositions disclosed herein. Direct amplification of nucleic acids using the PCR™ technology of U.S. Pat. Nos. 4,683,195 and 4,683,202 (each specifically incorporated herein by reference) are particularly contemplated to be useful in such methodologies.

In certain embodiments, it is contemplated that particular advantages will be gained by positioning the Osf2/Cbfa1-encoding DNA segment under the control of a recombinant, or heterologous, promoter. As used herein, a recombinant or heterologous promoter is intended to refer to a promoter that is not normally associated with an Osf2/Cbfa1 gene segment in its natural environment. Such promoters may include those normally associated with other transcription factor-encoding genes, and/or promoters isolated from any other bacterial, viral, eukaryotic, or mammalian cell. Naturally, it will be important to employ a promoter that effectively directs the expression of the DNA segment in the particular cell containing the vector comprising an Osf2/Cbfa1 epitope-encoding nucleic acid segment.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. For eukaryotic expression, preferred promoters include those such as a CMV promoter, an RSV LTR promoter, a β-actin promoter, an insulin promoter, an SV40 promoter alone, or an SV40 promoter either alone, or in combination with one or more enhancers, such as an SV40 enhancer. Prokaryotic expression of nucleic acid segments of the present invention may be performed using methods known to those of skill in the art, and will likely comprise expression vectors and promoter sequences such as a tac, ara, trp, lac, lacUV5 or T7 promoter.

2.5 Pharmaceutical Compositions

Another aspect of the present invention includes novel compositions comprising isolated and purified Osf2/Cbfa1 polypeptides, Osf2/Cbfa1-derived peptides, synthetic modifications of these epitopic peptides, peptides derived from site-specifically-mutagenized nucleic acid segments encoding such peptides, polynucleotides, and/or antibodies specific for Osf2/Cbfa1 and Osf2/Cbfa1-derived peptides and polypeptides. It will, of course, be understood that one or more than one Osf2/Cbfa1-encoding nucleic acid segment may be used in the methods and compositions of the invention. The nucleic acid delivery methods may thus entail the administration of one, two, three, or more, Osf2/Cbfa1 nucleic acid segments encoding one or more transcription factors. The maximum number of nucleic acid segments that may be applied is limited only by practical considerations, such as the effort involved in simultaneously preparing a large number of nucleic acid segment constructs or even the possibility of eliciting an adverse cytotoxic effect.

The particular combinatio o nucleic acid segments may be two or more distinct nucleic acid segments; or it may be such that a nucleic acid segment from one gene encoding Osf2/Cbfa1 is combined with another nucleic acid segment and/or another peptide or protein such as a cytoskeletal protein, cofactor targeting protein, chaperone, or other biomolecule such as a vitamin, hormone or growth factor gene. Such a composition may even further comprise one or more nucleic acid segments or genes encoding portions or all of one or more cell-surface receptors or bone-specific targeting proteins capable of interacting with the polypeptide product of the Osf2/Cbfa1-encoding nucleic acid segment.

In using multiple nucleic acid segments, they may be combined on a single genetic construct under control of one or more promoters, or they may be prepared as separate constructs of the same or different types. Thus, an almost endless combination of different nucleic acid segments and genetic constructs may be employed. Certain combinations of nucleic acid segments may be designed to, or their use may otherwise result in, achieving synergistic effects on inhibiting osteoblast differentiation and/or stimulation of an immune response against peptides derived from translation of such nucleic acid segments. Any and all such combinations are intended to fall within the scope of the present invention. Indeed, many synergistic effects have been described in the scientific literature, so that one of ordinary skill in the art would readily be able to identify likely synergistic combinations of nucleic acid segments, or even nucleic acid segment-peptide combinations.

It will also be understood that, if desired, the nucleic acid segment or gene encoding a particular Osf2/Cbfa1-derived peptide may be administered in combination with further agents, such as, e.g., proteins or polypeptides or various pharmaceutically-activeagents. So long as the composition comprises a nucleic acid segment encoding all or portions of an Osf2/Cbfa1 polypeptide, there is virtually no limit to other components which may also be included, given that the additional agents do not cause a significant adverse effect upon contact with the target cells or host tissues. The nucleic acids may thus be delivered along with various other agents as required in the particular instance. The formulation of pharmaceutically-acceptable excipients and carrier solutions are well-known to those of skill in the art, as is the development of suitable dosing and treatment regimens for using the particular compositions herein described in oral, parenteral, and/or intravenous administration and formulation.

2.6 Methods of Preparing OSF2/CBFA1 Pharmaceutical Compositions

The Osf2/Cbfa1 pharmaceutical compositions disclosed herein may be prepared and delivered in a variety of formulations and methods depending upon the particular application. For example, in the case of oral administration, the disclosed compositions may be formulated with an inert diluent or with an assimilable edible carrier, or they may be enclosed in hard- or soft-shell gelatin capsule, or they may be compressed into tablets, or they may be incorporated directly with the food of the diet. For oral therapeutic administration,the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-releas preparation and formulations.

Likewise, for oral administration, the compositions of the invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate, dispersed in dentifrices, including: gels, pastes, powders and slurries, or added in a therapeutically effective amount to a paste dentifrice that may include water, binders, abrasives, flavoring agents, foaming agents, and humectants.

Alternatively, in certain embodiments, it may be desirable to administer the Osf2/Cbfa1 pharmaceutical compositions disclosed herein either parenterally, intravenously, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

2.7 Therapeutic, Diagnostic and Immunological Kits

The invention also encompasses Osf2/Cbfa1-derived peptide antigen compositions together with pharmaceutically-acceptable excipients, carriers, diluents, adjuvants, and other components, such as additional peptides, antigens, cell membrane preparations, or even attenuated whole-cell compositions as may be employed in the formulation of particular vaccines.

Using the peptide antigens described herein, the present invention also provides methods of generating an immune response, which methods generally comprise administering to an animal, a pharmaceutically-acceptable composition comprising an immunologically effective amount of an Osf2/Cbfa1-derived peptide composition. Preferred animals include mammals, and particularly humans. Other preferred animals include murines, bovines, equines, porcines, canines, and felines. The composition may include partially or significantly purified Osf2/Cbfa1-derived peptide epitopes, obtained from natural or recombinant sources, which polypeptides may be obtainable naturally or either chemically synthesized, or alternatively produced in vitro from recombinant host cells expressing DNA segments encoding such epitopes. Smaller peptides that include reactive epitopes, such as those between about 30 and about 100 amino acids in length will often be preferred. The antigenic polypeptides may also be combined with other agents, such as other peptides or nucleic acid compositions, if desired.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various therapeutic embodiments.

Further means contemplated by the inventors for generating an immune response in an animal includes administering to the animal, or human subject, a pharmaceutically-acceptable composition comprising an immunologically effective amount of a nucleic acid composition encoding a peptide epitope, or an immunologically effective amount of an attenuated live organism that includes and expresses such a nucleic acid composition. The "immunologically effective amounts" are those amounts capable of stimulating a B cell and/or T cell response.

Immunoformulations of this invention, whether intended for vaccination, treatment, or for the generation of antibodies specific to Osf2/Cbfa1 and related proteins. Antigenic functional equivalents of these proteins and peptides also fall within the scope of the present invention. An "antigenically functional equivalent" polypeptide is one that incorporates an epitope that is immunologically cross-reactive with one or more epitopes derived from the Osf2/Cbfa1 polypeptides disclosed. Antigenically functional equivalents, or epitopic sequences, may be first designed or predicted and then tested, or may simply be directly tested for cross-reactivity.

The identification or design of suitable Osf2/Cbfa1 epitopes, and/or their functional equivalents, suitable for use in immunoformulations, vaccines, or simply as antigens (e.g., for use in detection protocols), is a relatively straight-forward matter. For example, one may employ the methods of Hopp (as disclosed in U.S. Pat. No. 4,554,101, which is specifically incorporated herein by reference) in the identification and preparation of epitopes from amino acid sequences on the basis of hydrophilicity. These methods, described in several other papers, and software programs based thereon, can also be used to identify epitopic core sequences. For example, Chou and Fasman (1974a,b; 1978a, b; 1979); Jameson and Wolf (1988); Wolf et al. (1988); and Kyte and Doolittle (1982) all address this subject in several scientific publications. The amino acid sequence of these "epitopic core sequences" may then be readily incorporated into peptides, either through the application of peptide synthesis or recombinant technology.

It is proposed that the use of shorter antigenic peptides, e.g., about 25 to about 50, or even about 15 to 25 amino acids in length, that incorporate modified epitopes of Osf2/Cbfa1 will provide advantages in certain circumstances, for example, in the preparation of vaccines or in immunologic detection assays. Exemplary advantages include the ease of preparation and purification, the relatively low cost and improved reproducibility of production, and advantageous biodistribution.

In still further embodiments, the present invention concerns immunodetection methods and associated kits. It is contemplated that the polypeptides of the invention may be employed to detect antibodies having reactivity therewith, or, alternatively, antibodies prepared in accordance with the present invention, may be employed to detect Osf2/Cbfa1 polypeptides. Either type of kit may be used in the immunodetection of Osf2/Cbfa1 compositions. The kits may also be used in antigen or antibody purification, as appropriate.

In general, the preferred immunodetection methods will include first obtaining a sample suspected of containing an Osf2/Cbfa1-specific antibody, such as a biological sample from a patient, and contacting the sample with a first Osf2/Cbfa1 polypeptide under conditions effective to allow the formation of an immunocomplex (primary immune complex). One then detects the presence of any primary immunocomplexes that are formed.

Contacting the chosen sample with the Osf2/Cbfa1-derived polypeptide under conditions effective to allow the formation of (primary) immune complexes is generally a matter of simply adding the polypeptide composition to the sample. One then incubates the mixture for a period of time sufficient to allow the added antigens to form immune complexes with, i.e. to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first polypeptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies and the remaining bound label is then detected.

For diagnostic purposes, it is proposed that virtually any sample suspected of containing either the antibodies of interest may be employed. Exemplary samples include clinical samples obtained from a patient such as blood or serum samples, bronchoalveolar fluid, ear swabs, sputum samples, middle ear fluid or even perhaps urine samples may be employed. This allows for the diagnosis of meningitis, otitis media, pneumonia, bacteremia and postpartum sepsis. Furthermore, it is contemplated that such embodiments may have application to non-clinical samples, such as in the titering of antibody samples, in the selection of hybridomas, and the like. Alternatively, the clinical samples may be from veterinary sources and may include such domestic animals as cattle, sheep, and goats. Samples from feline, canine, and equine sources may also be used in accordance with the methods described herein.

In related embodiments, the present invention contemplates the preparation of kits that may be employed to detect the presence of Osf2/Cbfa1-derived epitope-specific antibodies in a sample. Generally speaking, kits in accordance with the present invention will include a suitable polypeptide together with an immunodetection reagent, and a means for containing the polypeptide and reagent.

The immunodetection reagent will typically comprise a label associated with an Osf2/Cbfa1 polypeptide, or associated with a secondary binding ligand. Exemplary ligands might include a secondary antibody directed against the first Osf2/Cbfa1 polypeptide or antibody, or a biotin or avidin (or streptavidin) ligand having an associated label. Detectable labels linked to antibodies that have binding affinity for a human antibody are also contemplated, e.g., for protocols where the first reagent is an Osf2/Cbfa1 peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

2.8 OSF2/CBFA1 Antibody Compositions

In another aspect, the present invention contemplates an antibody that is immunoreactive with a polypeptide of the invention. As stated above, one of the uses for Osf2/Cbfa1 peptides according to the present invention is to generate antibodies. Reference to antibodies throughout the specification includes whole polyclonal and monoclonal antibodies, and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. An antibody can be a polyclonal or a monoclonal antibody. In a preferred embodiment, an antibody is a polyclonal antibody. Means for preparing and characterizing antibodies are well known in the art (See, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for Osf2/Cbfa1 and Osf2/Cbfa1-derived peptides and/or epitopes may be prepared using conventional immunization techniques, as will be generally known to those of skill in the art. A composition containing antigenic Osf2/Cbfa1 epitopes can be used to immunize one or more experimental animals, such as a rabbit or mouse, which will then proceed to produce specific antibodies against epitope-containing Osf2/Cbfa1 peptides. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i.e. B-cells of different lineage. Monoclonal antibodies, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e. the percentage of clone reacting with the same molecular determinant, is at least 80%. Even higher clonality—90%, 95% or greater—is contemplated.

To obtain monoclonal antibodies, one would also initially immunize an experimental animal, often preferably a mouse, with an Osf2/Cbfa1 polypeptide or Osf2/Cbfa1-derived peptide or epitope-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting monoclonal antibodies against Osf2/Cbfa1-derivedepitopes. Hybridomas which produce monoclonal antibodies to the selected antigens are identified using standard techniques, such as immunoprecipitation, ELISA and Western blot methods. Hybridoma clones can then be cultured in liquid media and the culture supernatant purified to provide the Osf2/Cbfa1 and Osf2/Cbfa1-derived epitope-specific monoclonal antibodies.

It is proposed that the monoclonal antibodies of the present invention will find useful application in standard immunochemical procedures, such as immunoprecipitation, ELISA and Western blot methods, as well as other procedures which may utilize antibody specific to the Osf2/Cbfa1 or Osf2/Cbfa1-derived epitopes.

Additionally, it is proposed that monoclonal antibodies specific to the particular Osf2/Cbfa1-derived peptide may be utilized in other useful applications. For example, their use in immunoabsorben protocols may be useful in purifying native or recombinant peptide species or synthetic or natural variants thereof.

In general, both poly- and monoclonal antibodies against these peptides may be used in a variety of embodiments. For example, they may be employed in antibody cloning protocols to obtain cDNAs or genes encoding the peptides disclosed herein or related proteins. They may also be used in inhibition studies to analyze the effects of Osf2/Cbfa1-derived peptides in cells or animals. Anti-Osf2/Cbfa1 epitope antibodies will also be useful in immunolocalization studies to analyze the distribution of Osf2/Cbfa1 various cellular events, for example, to determine the cellular or tissue-specific distribution of the Osf2/Cbfa1 peptides under different physiological conditions. A particularly useful application of such antibodies is in purifying native or recombinant Osf2/Cbfa1 or Osf2/Cbfa1-derived peptides, for example, using an antibody affinity column. The operation of all such immunological techniques will be known to those of skill in the art in light of the present disclosure.

2.9 Antibody Generation Methods and Formulations Thereof

Means for preparing and characterizing antibodies are well known in the art (see, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4-1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol./vol.) PEG, by Gefter et al. (1977). The use of electrically induced fusion methods is also appropriate (Goding, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines may also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.10 Epitopic Core Sequences

The present invention is also directed to Osf2/Cbfa1 polypeptide compositions, free from total cells and other polypeptides, which comprise a purified Osf2/Cbfa1 polypeptide which incorporates an epitope that is immunologically cross-reactive with one or more of the Osf2/Cbfa1-specific antibodies of the present invention.

As used herein, the term "incorporating an epitope(s) that is immunologically cross-reactive with one or more anti-Osf2/Cbfa1 antibodies" is intended to refer to a peptide or protein antigen which includes a primary, secondary or tertiary structure similar to an epitope located within an Osf2/Cbfa1 polypeptide. The level of similarity will generally be to such a degree that monoclonal or polyclonal antibodies directed against the Osf2/Cbfa1 polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Osf2/Cbfa1 epitopes and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to Osf2/Cbfa1-related sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on Osf2/Cbfa1 epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar™ software, DNAStar, Inc., Madison, Wis.) may also be useful in designing synthetic epitopes and epitope analogs in accordance with the present disclosure.

The peptides provided by this invention are ideal targets for use as vaccines or immunoreagents for the regulation or modulation of osteoblast differentiation, and in particular, that caused by the transcription factor Osf2/Cbfa1. In this regard, particular advantages may be realized through the preparation of synthetic Osf2/Cbfa1 peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

To confirm that a polypeptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e. based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as an Osf2/Cbfa1 or Osf2/Cbfa1-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between Osf2/Cbfa1 and any test antigen, one would first label Osf2/Cbfa1 with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to a known antibody. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label.

The reactivity of the labeled antigen, e.g., an Osf2/Cbfa1-derived peptide, in the absence of any test antigen would be the control high value. The control low value would be obtained by incubating the labeled antigen with an excess of unlabeled antigen, when competition would occur and reduce binding. A significant reduction in labeled antigen reactivity in the presence of a test antigen is indicative of a test antigen that is "cross-reactive", i.e. that has binding affinity for the same antibody. "A significant reduction", in terms of the present application, may be defined as a reproducible (i.e. consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.11 Methods of Using Osf2/Cbfa1 Nucleic Acid Sequences

As mentioned, in certain aspects, the DNA sequence information provided by the present disclosure allows for the preparation of relatively short DNA (or RNA) sequences having the ability to specifically hybridize to nucleic acid sequences encoding portions of the Osf2/Cbfa1 gene, which the inventors have identified as an osteoblast-specific transcription factor. In these aspects, nucleic acid probes of an appropriate length are prepared based on a consideration of the natural sequence and the size of the particular DNA segment used. Such DNA segments may be those of native Osf2/Cbfa1 or Osf2/Cbfa1-derived, or alternatively, may be DNA sequences which have undergone site-specific mutations to generate any of the novel peptides disclosed herein. The ability of such nucleic acid probes to specifically hybridize to the corresponding Osf2/Cbfa1 nucleic acid sequences lend them particular utility in a variety of embodiments. However, other uses are envisioned, including the expression of protein products, the use of the sequence information for the preparation of mutant species primers, or primers for use in preparing other genetic constructions. Such primers may also be used as diagnostic compositions for the isolation and identification of epitope-encoding nucleic acid segments from transcription factors related to Osf2/Cbfa1.

To provide certain of the advantages in accordance with the present invention, the preferred nucleic acid sequence employed for hybridization studies or assays would include sequences that have, or are complementary to, at least an about 14 or 15 to about 20 or so nucleotide stretch of the sequence, although sequences of about 30 to about 50 or so nucleotides are also envisioned to be useful. A size of at least 14–15 or 20 nucleotides in length helps to ensure that the fragment will be of sufficient length to form a duplex molecule that is both stable and selective. Molecules having complementary sequences over stretches greater than 14–15 or 20 bases in length are generally preferred, though, in order to increase stability and selectivity of the hybrid, and thereby improve the quality and degree of specific hybrid molecules obtained. Thus, one will generally prefer to design nucleic acid molecules having Osf2/Cbfa1-gene-complementary stretches of 14–15 to 20–25 nucleotides, or even longer, such as about 30, or about 50, or about 100, or even about 200 nucleotides, where desired. Such fragments may be readily prepared by, for example, directly synthesizing the fragment by chemical means, by application of nucleic acid reproduction technology, such as the PCR™ technology of U.S. Pat. No. 4,683,202, or by introducing selected sequences into recombinant vectors for recombinant production.

The inventors further contemplate that such DNA segments will have utility in the overexpression of Osf2/Cbfa1-derived peptide epitopes described herein, and the preparation of recombinant vectors containing native and site-specific-mutagenized DNA segments comprising particular epitope regions from the Osf2/Cbfa1 gene.

The invention will find particular utility as the basis for diagnostic hybridization assays for detecting Osf2/Cbfa1-specific RNA or DNA in clinical samples. Exemplary clinical samples that can be assayed for the presence of Osf2/Cbfa1 or Osf2/Cbfa1-encoding nucleic acids include middle ear fluid, sputum, bronchoalveolar fluid and the like. Such samples may be of human, murine, equine, bovine, feline, porcine, or canine origins. A variety of hybridization techniques and systems are known that can be used in connection with the hybridization aspects of the invention, including diagnostic assays such as those described in U.S. Pat. No. 4,358,535, incorporated herein by reference. Samples derived from non-human mammalian sources, including animals of economic significance such as domestic farm animals, may also provide the basis for clinical specimens.

Accordingly, the nucleotide sequences of the invention are important for their ability to selectively form duplex molecules with complementary stretches of the nucleic acid segments encoding Osf2/Cbfa1 epitopes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one may desire to employ lower or reduced stringency hybridization conditions. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated Osf2/Cbfa1-encoding clones. In particular embodiments, mutant clone colonies growing on solid media that contain variants of the Osf2/Cbfa1 gene could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of these genes may be utilized to identify those clones growing on solid media that contain sequence variants of the entire genes. These clones can then be grown to obtain desired quantities of the variant nucleic acid sequences or the corresponding antigens.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, that are capable of giving a detectable signal. In preferred diagnostic embodiments, one will likely desire to employ an enzyme tag such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., middle ear effusion, bronchoalveolarlavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Detection of a Cbfa-related mRNA in osteoblasts, cloning and expression of the mouse Osf2/Cbfa1 cDNA. Poly (A)+ RNA isolated from mouse primary osteoblasts (lane 1), spleen (lane 2) and thymus (lanes 3 and 4) were analyzed by Northern blot, using as a probe a fragment of Cbfa1 cDNA encoding the runt domain. Equivalent amount of intact mRNA were run in lanes 1–3 as indicated by hybridization to a β-actin probe. Lane 4 represents a 20-fold longer exposure of lane 3.

FIG. 1B. Amino acid sequence of SEQ ID NO:2 Osf2/Cbfa1. The initiation codons are shown in boldface type, the runt domain is underlined.

Figure 1C:
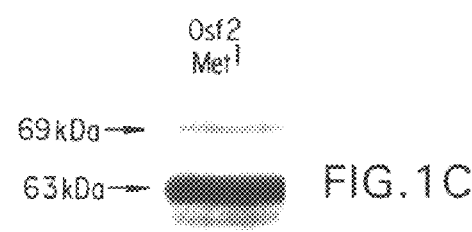

FIG. 1C. In vitro transcription/translation of Osf2/Cbfa1 cDNA. Translation products were resolved on a 10% SDS-polyacrylamide gel.

Figure 1D:
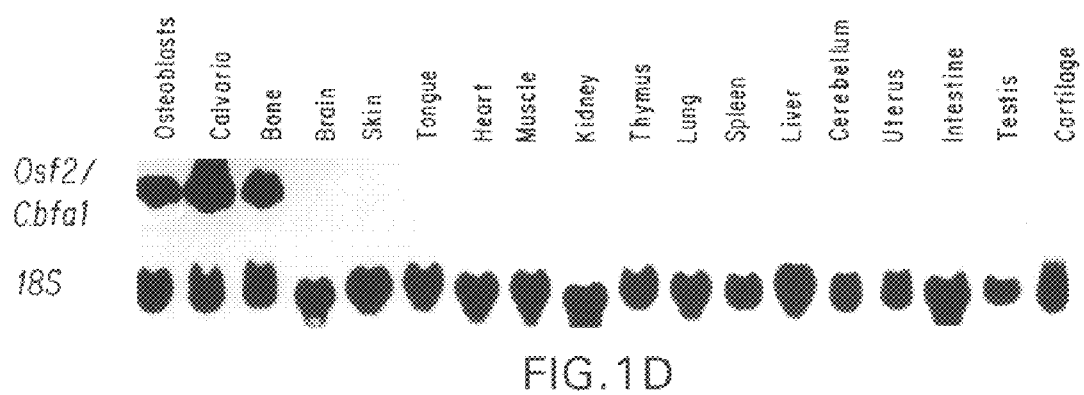

FIG. 1D. Expression of Osf2/Cbfa1 in tissues of adult mice. Total RNA (15 μg per lane) was isolated from adult mouse tissues and analyzed by Northern blot using an Osf2/Cbfa1-specific probe. The blot was reprobed with an 18S rDNA cDNA probe to account for RNA loading and transfer efficiency.

Figure 2A:
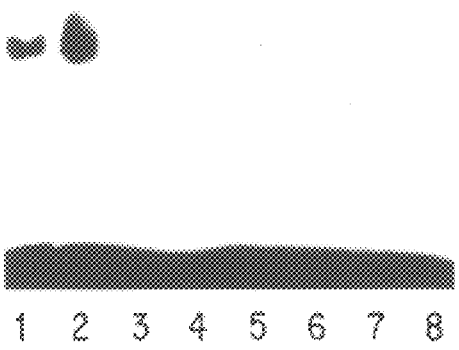

FIG. 2A. Binding of Osf2/Cbfa1 to OSE2 and activation of OG2 promoter activity. DNA binding was analyzed by EMSA. DNA-protein complexes were resolved from free DNA on a 5% polyacrylamide gel and visualized by autoradiography. His-Osf2/Cbfa1 was incubated with $^{32}$P labeled wild-type (lane 1) or mutated OSE2 (lanes 2–8) oligonucleotides. Mutations within the mutated OSE2 oligonucleotides are presented in Table 1. The asterisk denotes the mutation used for subsequent DNA cotransfection studies. (FIG. 2C–FIG. 2F).

Figure 2B:

FIG. 2B. Abolition of His-Osf2/Cbfa1 binding to OSE2 by an anti-Cbfa antiserum. A preimmune serum (lane 2) or antiserum (lane 3) to a peptide sequence present in Osf2/Cbfa1 was included in the binding reaction as indicated.

Figure 2E:
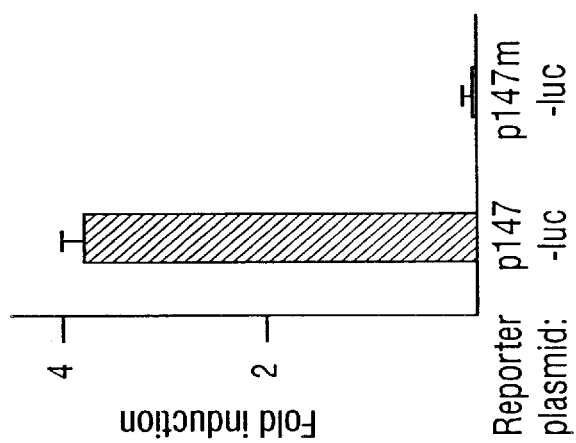
Figure 2D:
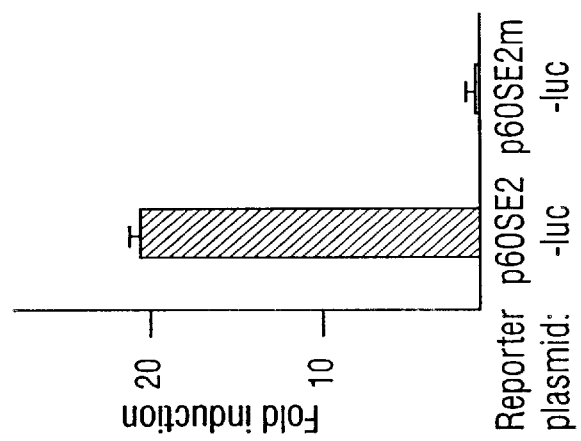
Figure 2C:
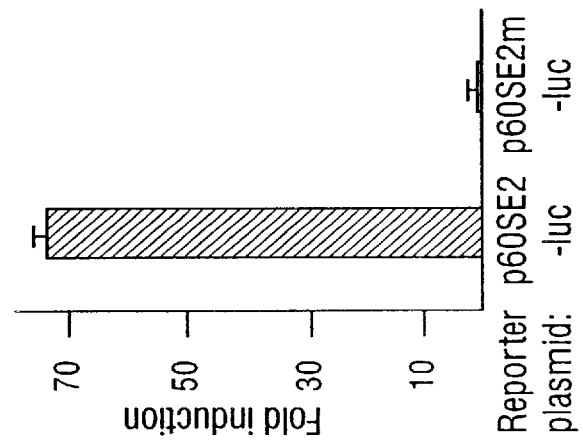

FIG. 2C. Transcriptional activity of Osf2/Cbfa1 in F9 teratocarcinoma cells.

FIG. 2D. Transcriptional activity of Osf2/Cbfa1 in C3H10T1/2 fibroblastic cells.

FIG. 2E. Activation of the 147-bp OG2 promoter by Osf2/Cbfa1 in C3H10T1/2 cells. Cells were cotransfected with Luciferase-fusion constructs as reporter plasmids, pCMV (open bars) or pCMV-Osf2/Cbfa1 (black bars) as effector plasmids, and pSVβ-gal plasmid as an internal control of transfection efficiency. Data are presented as fold activation relative to the activity obtained with the pCMV effector plasmid. Values represent average of luciferase to β-galactosidase ratios obtained from 4 independent transfection studies, with error bars representing the standard deviation of the mean.

Figure 3:
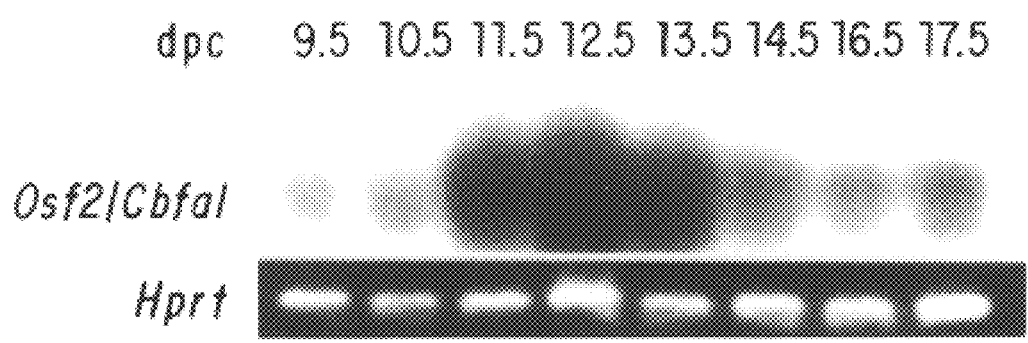

FIG. 3. Osf2/Cbfa1 expression during mouse development. RT-PCR™ analysis of Osf2/Cbfa1 expression during development. An aliquot of RT-PCR™ products obtained from 9.5 to 17.5 day-old embryos were electrophoresed and hybridized with an Osf2/Cbfa1 specific probe. Amplification of Hprt exon 2 was used as an internal control in each reaction. dpc=days post coitum. Section in situ hybridization was performed using antisense $^{35}$S-labeled Osf2/Cbfa1, α1(II) collagen and Mgp riboprobes. Osf2/Cbfa1 expression was determined in 12.5 dpc mouse embryo. Mesenchymal condensations of the developing skull, ribs, vertebrae, forelimb and hindlimb expressed Osf2/Cbfa1, whereas the chondrocytes of the Meckel's cartilage did not. α1(II) collagen expression was determined in the differentiated chondrocytes of the Meckel's cartilage of 12.5 dpc embryo. Osf2/Cbfa1 expression was also assessed in the developing skull of a 14.5 dpc mouse embryo. Prominent Osf2/Cbfa1 expression is present in the primordia of the maxilla and nasal bone, extends to the frontal bone, and marks the ossification centers of the basisphenoid and basioccipital bones. Osf2/Cbfa1 transcripts were also present in the ribs proper but not in chondrocytes of the chondrocostal ribs where αa(II) collagen was highly expressed. Osf2/Cbfa1 mRNA was detected in every bone examined, but absent from other tissues. Osf2/Cbfa1 was also expressed in the ossification centers of the vertebrae but not in the surrounding chondrocytes or the fibroblasts of the skin.

Figure 4A:
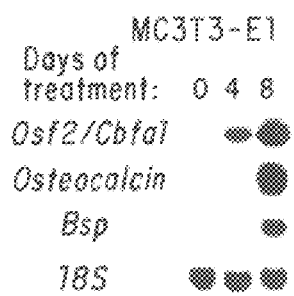

FIG. 4A. Regulation of Osf2/Cbfa1 expression is osteoblast culture. Total RNA (15 μg per lane) was isolated at different time points from cultured cells treated with regulators of differentiation or with vehicle, and analyzed by Northern blot. Equivalent amounts of intact RNA were run in each lane as indicated by hybridization to an 18S rRNA cDNA probe. Differentiationof MC3T3-E1 osteogenic cells cultured in presence of ascorbic acid (50 μg/ml).

Figure 4B:
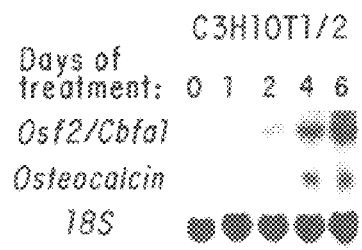

FIG. 4B. Regulation of Osf2/Cbfa1 expression is osteoblast culture. Total RNA (15 μg per lane) was isolated at different time points from cultured cells treated with regulators of differentiation or with vehicle, and analyzed by Northern blot. Equivalent amounts of intact RNA were run in each lane as indicated by hybridization to an 18S rRNA cDNA probe. Differentiation of C3H10T1/2 fibroblasts cultured in presence of BMP7 (200 ng/ml). Note the appearance of Osf2/Cbfa1 transcripts before Osteocalcin transcripts.

Figure 4C:
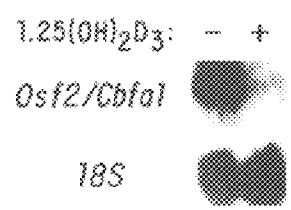

FIG. 4C. Regulation of Osf2/Cbfa1 expression by 1,25 $(OH)_2D_3$. Mouse primary osteoblasts were cultured in the presence or absence of $1,25(OH)_2D_3$ $10^{-8}$ M for 6 h before RNAs were prepared for Northern analysis.

Figure 5A:
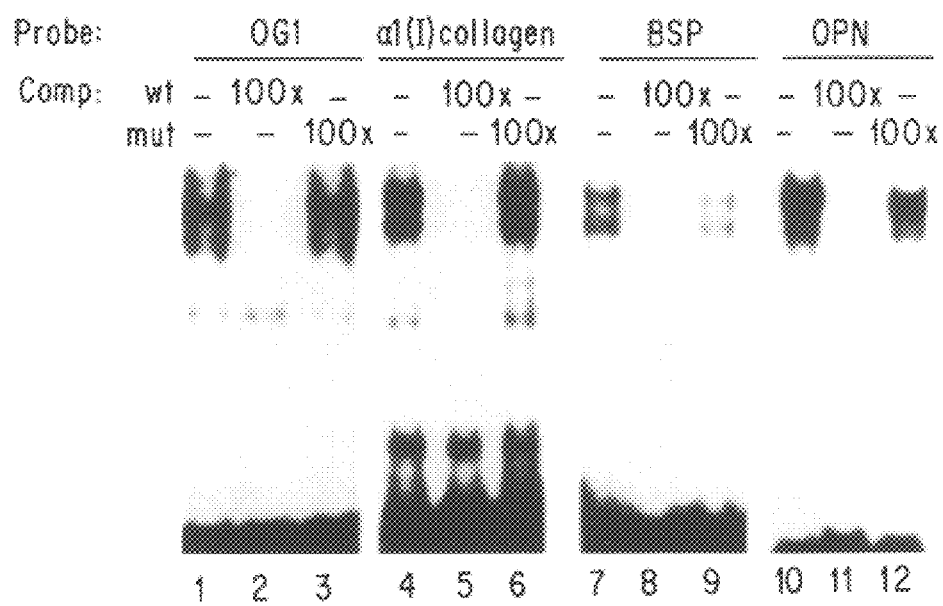

FIG. 5A. sf2/Cbfa1 binds to and regulates the expression of several genes expressed in osteoblasts. DNA-binding studies. Labeled double-stranded oligonucleotides corresponding to the OSE2 elements present in the promoters of OG1,α1(I)collagen, Bsp, and Osteopontin (OPN) (see Table 2) were used in EMSA. DNA binding was performed using osteoblast nuclear extracts as a source of proteins. Probes were as follows: lanes 1–3: OSE2 of OG1; lanes 4–6: OSE2 of α1(I)collagen; lanes 7–9: OSE2 of Bsp; lanes 10–12: OSE2 of Osteopontin.

Figure 5B:
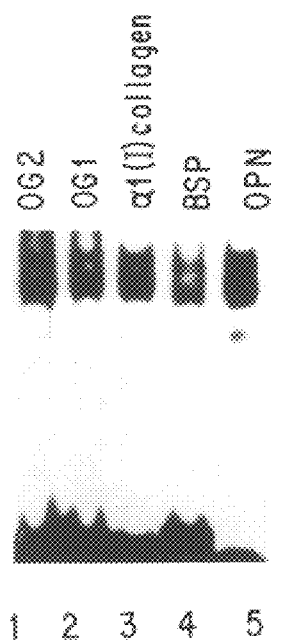

FIG. 5B. NA-binding studies. Labeled double-stranded oligonucleotides corresponding to the OSE2 elements present in the promoters of OG1,α1(I)collagen, Bsp, and Osteopontin (OPN) (see Table 2) were used in EMSA. DNA binding performed with His-Osf2/Cbfa1. Labeled probes were as follows, lane 1: OSE2 of OG2; lane 2: OSE2 of OG1; lane 3: OSE2 of α1(I)collagen; lane 4: OSE2 of Bsp; lane 5: OSE2 of Osteopontin.

Figure 5D:
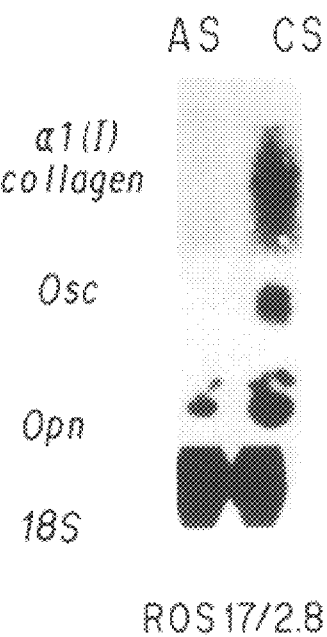
Figure 5C:
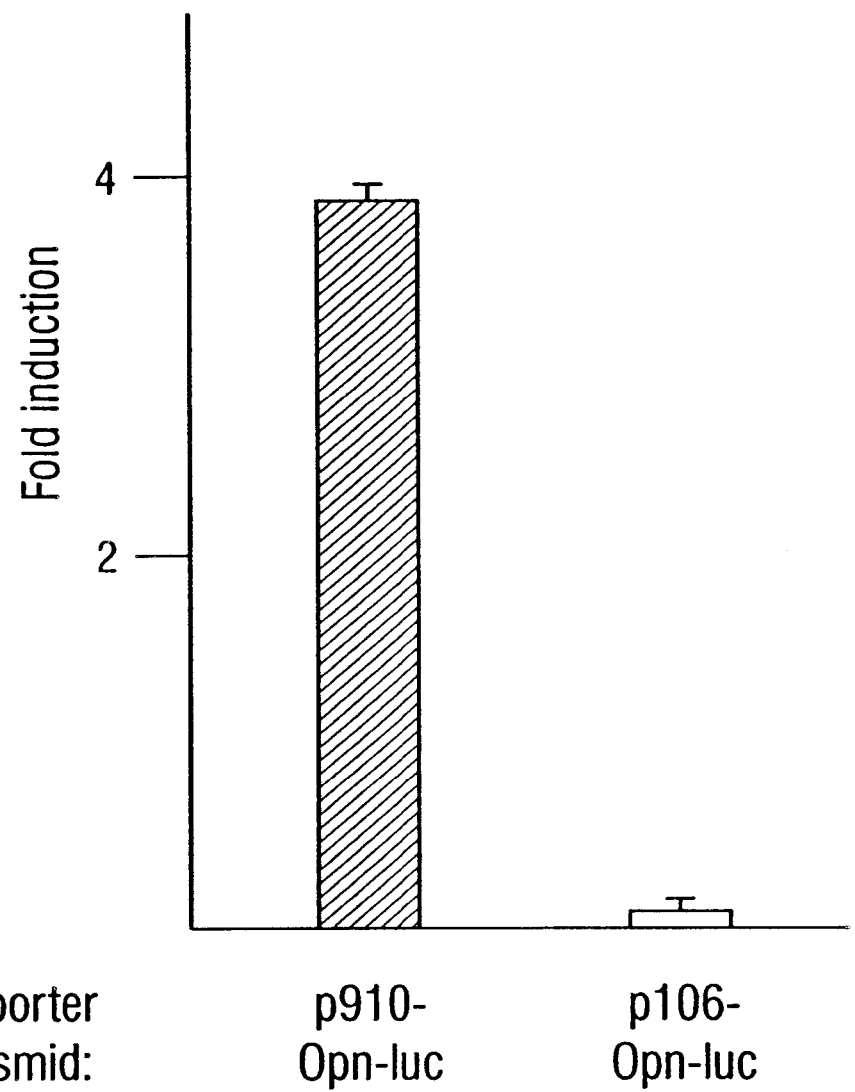

FIG. 5C. Activation of the Osteopontin promoter fragment containing an OSE2 sequence by Osf2/Cbfa1. F9 cells were cotransfected with p910-Opn-luc that contains the OSE2 element or with p106-Opn-luc that does not contain the OSE2 element, along with pCMV or pCMV-Osf2/Cbfa1.

FIG. 5D. Effect of Osf2/Cbfa1 antisense oligonucleotide on osteoblast-specific gene expression. Rat ROS17/2.8 osteoblastic cells were transfected with antisense (AS) or control scrambled (CS) oligonucleotide. RNAs were prepared after 40 h and analyzed for the expression of α1(I) collagen, Osteocalcin and Osteopontin. The blot was reprobed with an 18S rRNA cDNA probe to account for RNA loading and transfer efficiency.

Figure 6A:
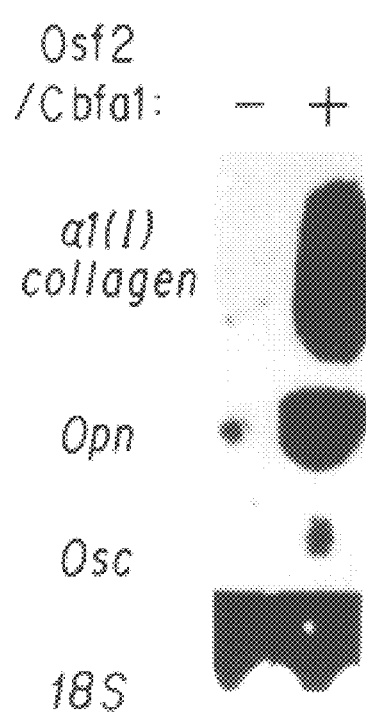

FIG. 6A. Osf2/Cbfa1 can induce expression of osteoblast-specific genes in nonosteoblastic cell lines. Total RNA (15 μg) from MC3T3-E1 calvaria cells were collected 40 h after transient transfection with pCMV or pCMV-Osf2/Cbfa1. Northern blot analysis was performed using probes for α1(I)collagen, Bsp, Osteocalcin, and Osteopontin transcripts. Equivalent amounts of intact RNA were run in each lane as indicated by hybridizationto an 18S rRNA cDNA probe.

Figure 6B:
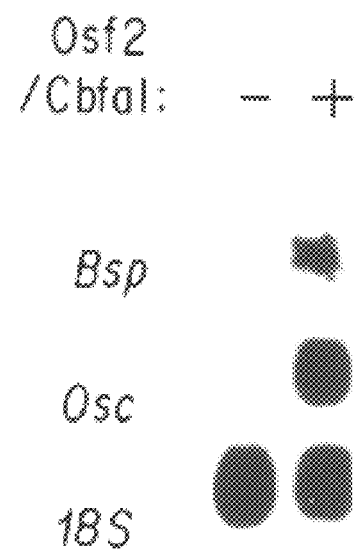

FIG. 6B. Osf2/Cbfa1 can induce expression of osteoblast-specific genes in nonosteoblastic cell lines. Total RNA (15 μg) from C3H10T1/2 fibroblastic cells was collected 40 h after transient transfection with pCMV or pCMV-Osf2/Cbfa1. Northern blot analysis was performed using probes for α1(I)collagen, Bsp, Osteocalcin, and Osteopontin transcripts. Equivalent amounts of intact RNA were run in each lane as indicated by hybridizationto an 18S rRNA cDNA probe.

Figure 7A:
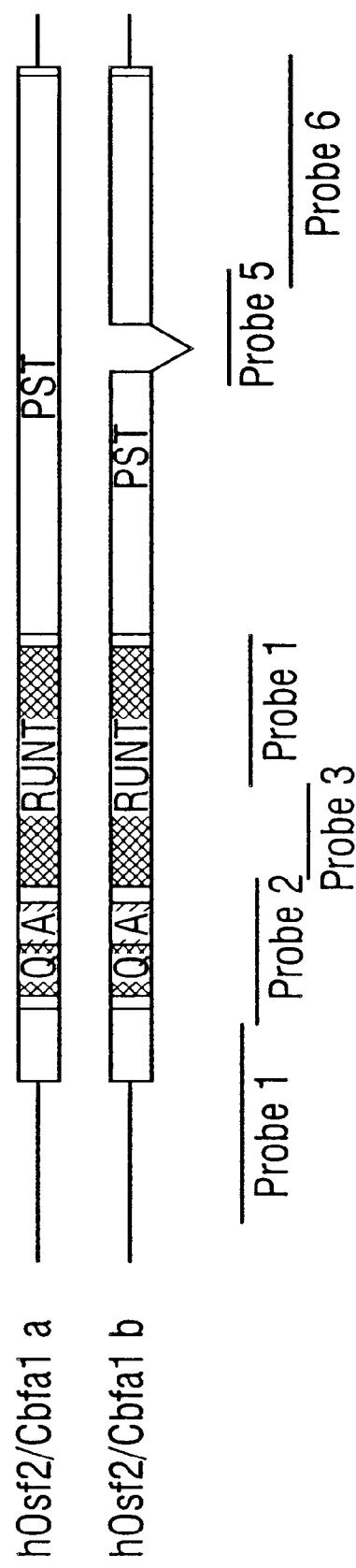

FIG. 7A. Schematic representation of the two human OSF2/CBFA1 transcripts (hOSF2/CBFA1a and hOSF2/CBFA1b). The open reading frames are represented as boxes, established 3' and 5' untranslated sequences are shown as lines. The 66 bp in-frame deletion in the hOSF2/CBFA1b transcript is represented by connecting lines. The probes derived from the hOSF2/CBFA1a cDNA that were used for Southern and Northern analysis and screening of the λ-fixII human genomic library are shown below hOSF2/CBFA1b. Q, glutamine stretch (23 residues); A, alanine stretch (17 residues); RUNT, runt domain; PST, proline/serine/threonine rich region.

FIG. 7B. Comparison of the deduced amino acid sequence of human (upper sequence) SEQ ID NO:79 and mouse (lower sequence) SEQ ID NO:82 Osf2/Cbfa1 polypeptides. The sequences were aligned to optimize the amino acid sequence homology. Dashes in the mouse amino-acid sequence represent matching residues. Gaps in the human sequence indicated as dashes are introduced to maximize homology of pairing amino acids.

FIG. 7C. Nucleotide and deduced amino acid sequence of the human OSF2/CBFA1a cDNA SEQ ID NO:78. Numbering of the nucleotide and amino acid sequences is indicated on the left, numbering of the nucleotide is relative to the translation start site at +1, the numbering of the amino acids is presented in italic. The translation start and stop codons are indicated in bold. The runt domain is boxed and the 22 amino acid alternative spliced sequence is underlined.

Figure 8A:
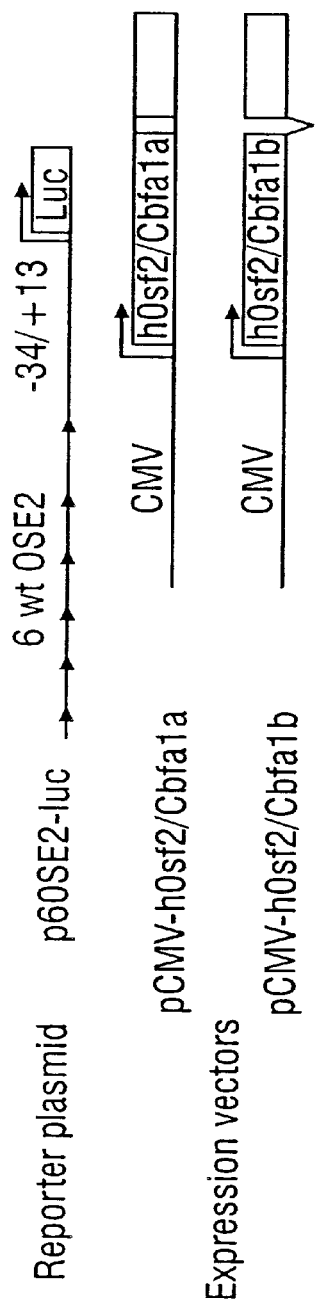

FIG. 8A. Representation of the reporter plasmid and expression vectors: the reporter plasmid p6OSE2-luc contains six copies of the wild-type OSE2 oligonucleotide cloned upstream of the −34/+13 mOG2 promoter-luciferase fusion gene; the expression vectors contain the OSF2/CBFA1a and b cDNAs cloned downstream of the CMV promoter in the correct orientation.

Figure 8B:
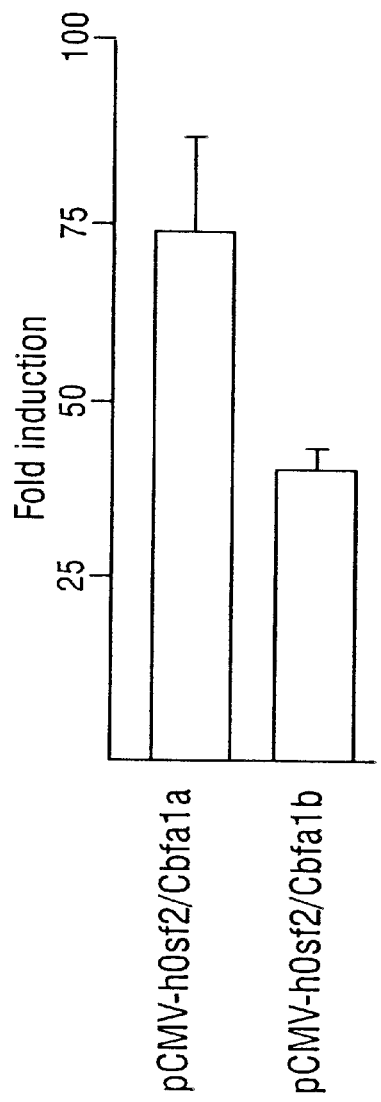

FIG. 8B. F9 mouse teratocarcinoma cells were transiently transfected with 5 μg of the reporter plasmid in presence of 5 μg of the indicated expression vector. Values are expressed relative to the basal activity of p6OSE2-luc which was set at 1. Data represent results from 3 independent transfection studies.

Figure 9:
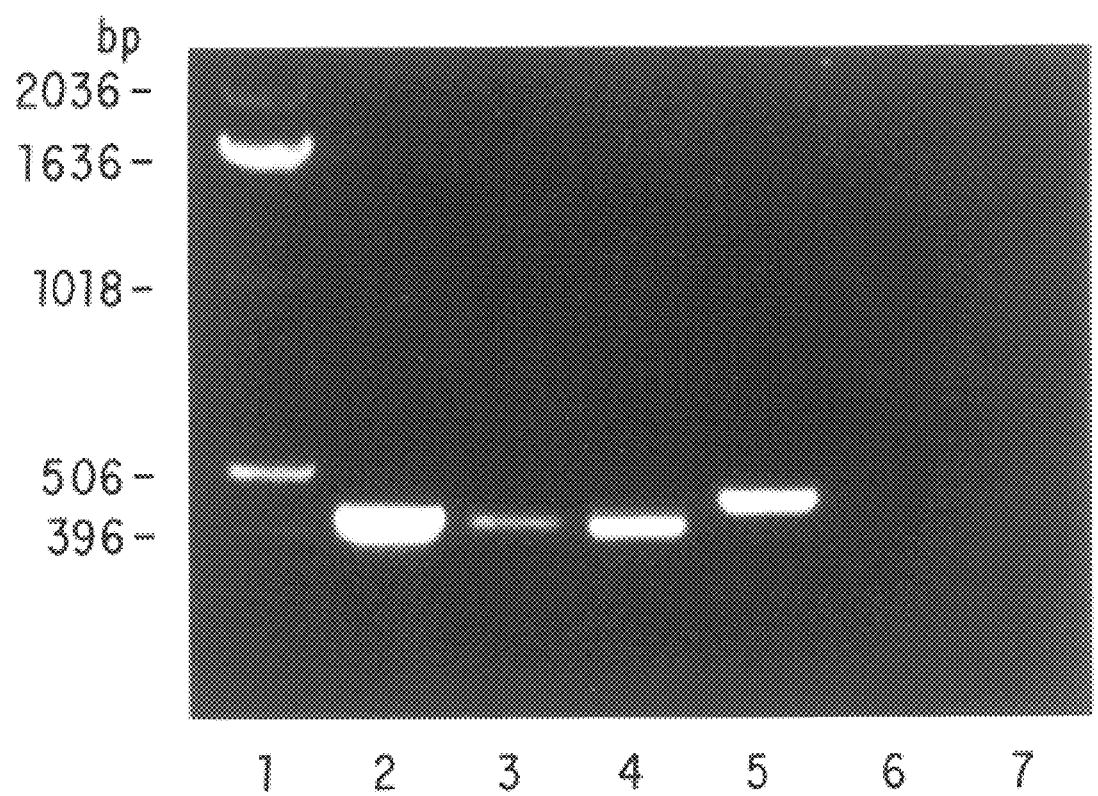

FIG. 9. Characterization of the 5' untranslated region (UTR). An RT-PCR™ analysis of human OSF2/CBFA1 expression in human bone and SaOS-2 osteosarcoma cells was performed using as 5' primers oligonucleotides located in the 5' untranslated region (UTR) of the human OSF2/CBFA1 cDNA (Lanes 2, 3 and 4) or in the 5' UTR of the originally described mouse Cbfa1 cDNA (Lanes 5, 6 and 7) and a 3' primer located at the 5' end of the runt domain. Marker 1 kb ladder (Lane 1), control plasmid hOSF2 (Lane 2), bone RNA (Lane 3), SaOS-2 RNA (Lane 4), control plasmid pBS312 containing the originally described mouse Cbfa1 cDNA (Lane 5), bone RNA (Lane 6), SaOS-2 RNA (Lane 7).

FIG. 10. Northern blot analysis of human OSF2/CBFA1 expression. Total RNA (15 μg/lane) from SaOS-2 (Lane 1), Molt 4 (Lane 2), transformed fibroblasts (Lane 3), transformed chondrocytes (Lane 4), lung (Lane 5), kidney (Lane 6), uterus (Lane 7) and spleen (Lane 8) were hybridized with $^{32}$P-labeled human OSF2/CBFA1 cDNA. The 18S rRNA cDNA hybridization was performed to ensure the integrity of the RNA.

Figure 11A:
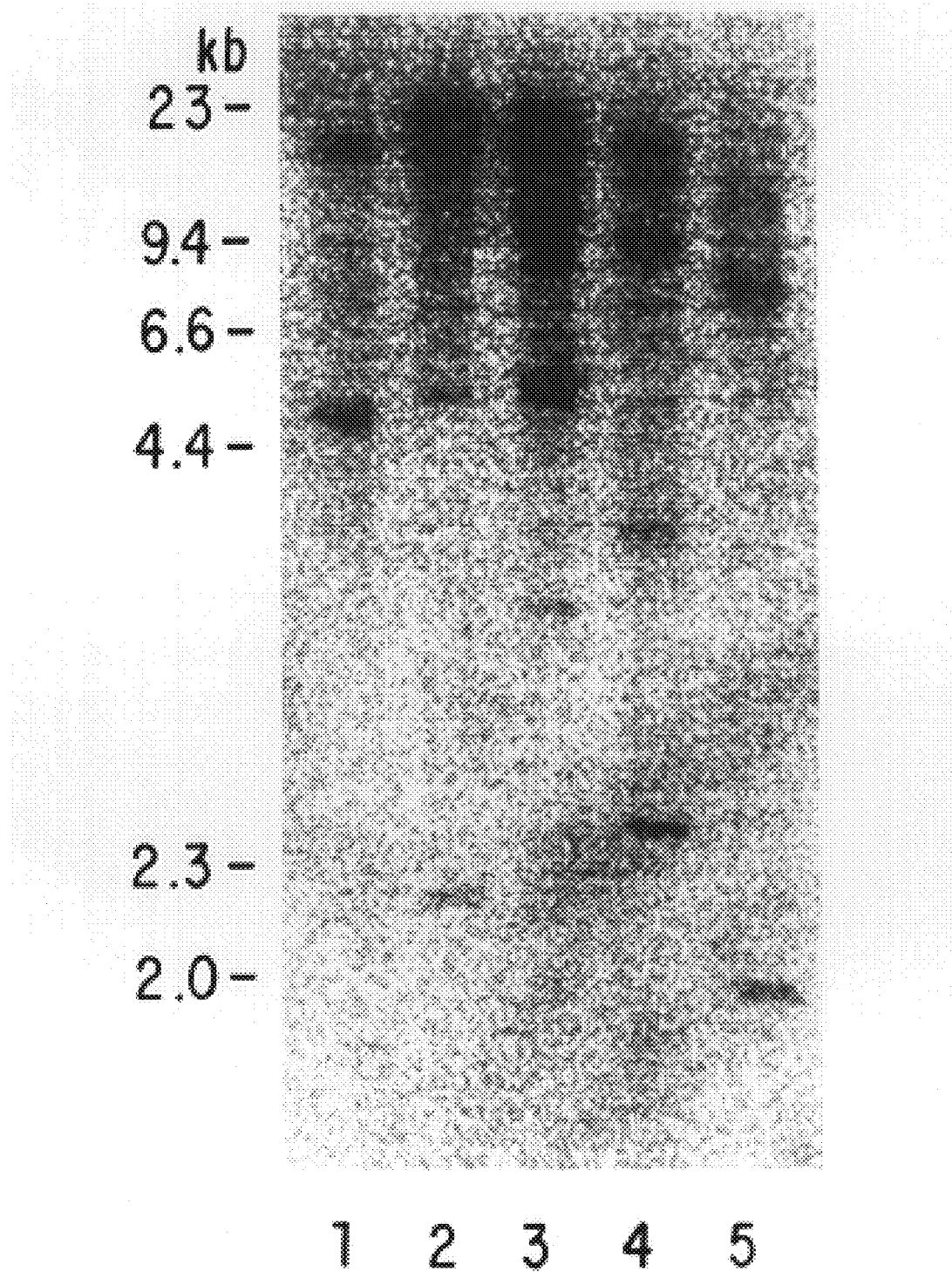

FIG. 11A. Southern blot analysis of human genomic DNA. Human genomic DNA (10 μg/lanes) was digested with BamHI, HindIII, SpeI, XbaI and EcoRI (Lanes 1 to 5) and hybridized with the hOSF2/CBFA1 cDNA as probe.

Figure 11B:
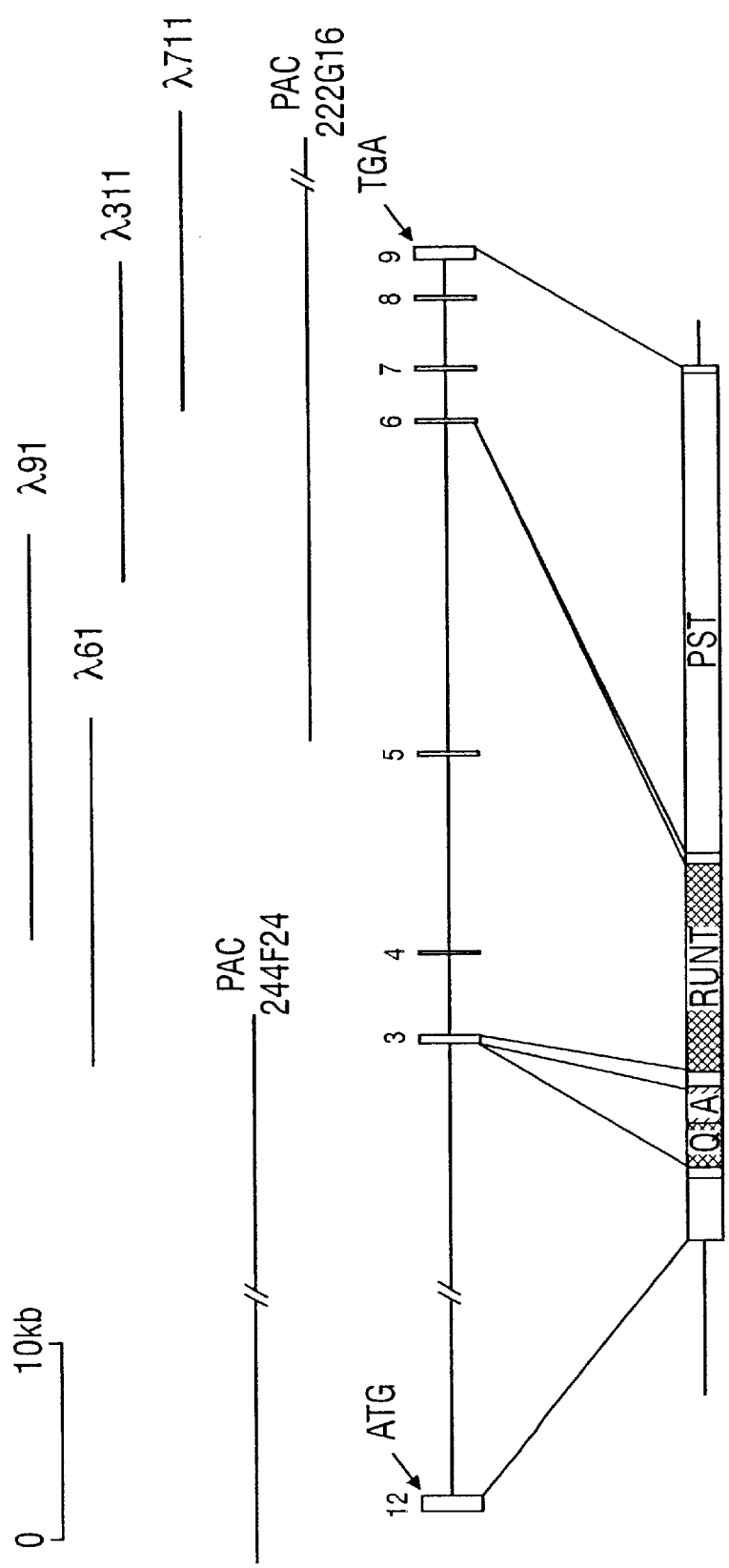

FIG. 11B. Physical map of the human Osf2/Cbfa1 gene based upon λ phage and PAC clones. Exons (numbered from 1 to 9) are indicated by open boxes, with connected lines indicating the introns. The lines above the genomic structure represent the λ phage and PAC clones from RNA.

Figure 12A:
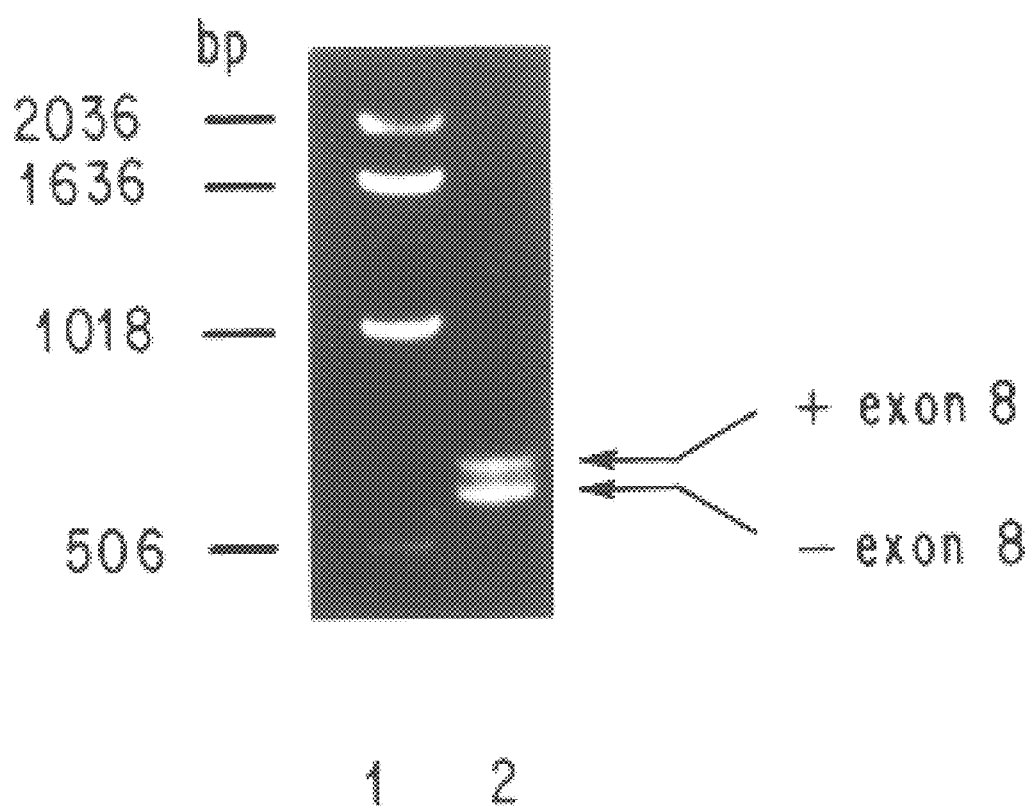

FIG. 12A. Evidence of an alternative splicing event around the exon 8 of the OSF2/CBFA1 gene. RT-PCR™ of SaOS-2 osteosarcoma cells mRNA and identification of two differentially spliced transcripts. The oligonucleotides used as primers for PCR™ amplification were located in exons 7 and 9. Lane 1, marker 1 kb ladder; lane 2, PCR™ products from SaOS-2 RNA.

Figure 12B:
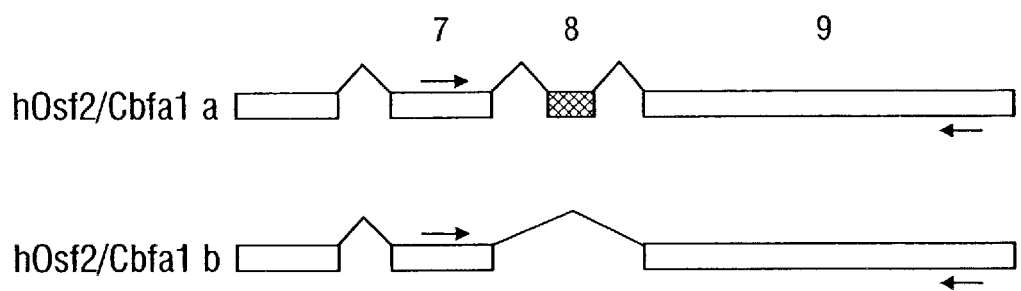

FIG. 12B. Schematic representation of the alternative splicing event around the exon 8 generating the OSF2/CBFA1a and b transcripts. Exons are represented by open boxes except exon 8 which is indicated as a black box. The splicing events are represented by connected lines. The primers used for the PCR™ amplification are indicated by arrows.

FIG. 13. Alignment of the amino acid sequences of Osf2 SEQ ID NO:82 and Cbfa1 SEQ ID NO:83. Hyphens denote gaps inserted to maximize sequence alignment. Identical residues are indicated by a colon, and similar ones are indicated by a dot. The N-terminal 19 amino acids (AD 1), and the QA domain (AD2), that are unique to Osf2 are double-underlined. The runt domain is underlined and the C-terminal 27 amino acids of AD3 are shown in boldface type and underlined. The Osf2 sequence is from Ducy et al. (1997), and the Cbfa2 sequence is from Bae et al. (1993).

FIG. 14A. Identification of a Myc-related NLS sequence in Osf2. Comparison of the NLS sequences of Runt-related proteins, with that of c-Myc. Basic residues are indicated in bold, and residues that are identical in at least three of the proteins shown are underlined.

FIG. 14B. Identification of a Myc-related NLS sequence in Osf2. Schematic representation of the wild-type Osf2 and Osf2ΔNLS expression constructs.

FIG. 14C. Identification of a Myc-related NLS sequence in Osf2. Transcriptional activity of wild-type Osf2 and Osf2ΔNLS lacking the basic 9-amino acid stretch (NLS), in transient transfection assays done with p6OSE2-luc reporter in COS7 cells. The fold induction of luciferase activity, normalized to βgal activity are shown. The values represent the mean of 9 independent transfection studies. Error bars represent standard deviation of the mean.

Figure 14D:
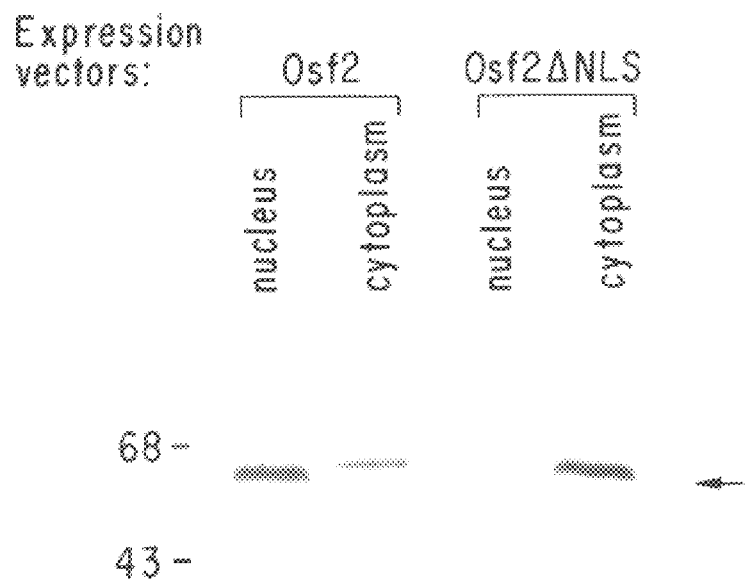

FIG. 14D. Identification of a Myc-related NLS sequence in Osf2. Immunoblot analysis of COS7 cells transfected with wild-type Osf2 or Osf2ΔNLS expression constructs. Cytoplasmic and nuclear fractions were prepared from transfected cells, and subjected to immunoblot analysis with rabbit polyclonal anti-Osf2 antibody. Molecular size markers (in kilodaltons) are shown on the left.

Figure 15A:
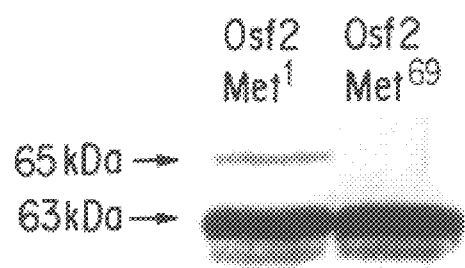

FIG. 15A. Identification of transactivationdomains in Osf2. In vitro transcription and translation of Osf2 cDNA. Osf2Met$^1$ and Osf2Met$^{69}$ constructs were transcribed and translated in vitro, and the "$^{35}$S-labeled proteins were subjected to SDS-PAGE analysis, followed by autoradiography.

Figure 15B:
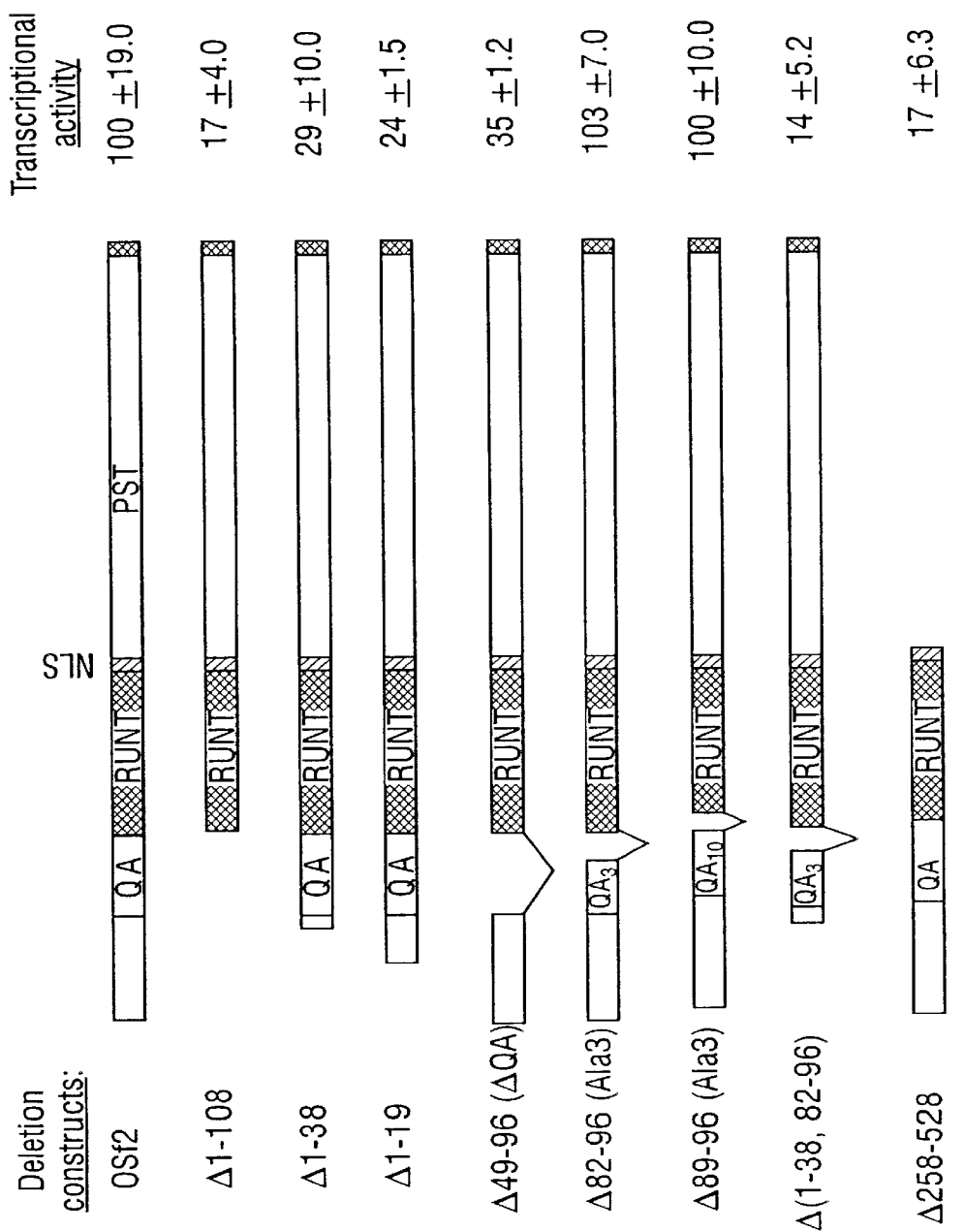

FIG. 15B. Identification of transactivation domains in Osf2. Transcriptional activities of Osf2 deletion mutants. Deletions of Osf2 were cloned in pCMV5 expression vector, and transfections were carried out with p6OSE2-luc reporter, as described herein. Numbers shown on the left indicate the amino acids deleted. Values shown at the right are the means±standard deviation of 9 independent transfection studies.

Figure 16A:
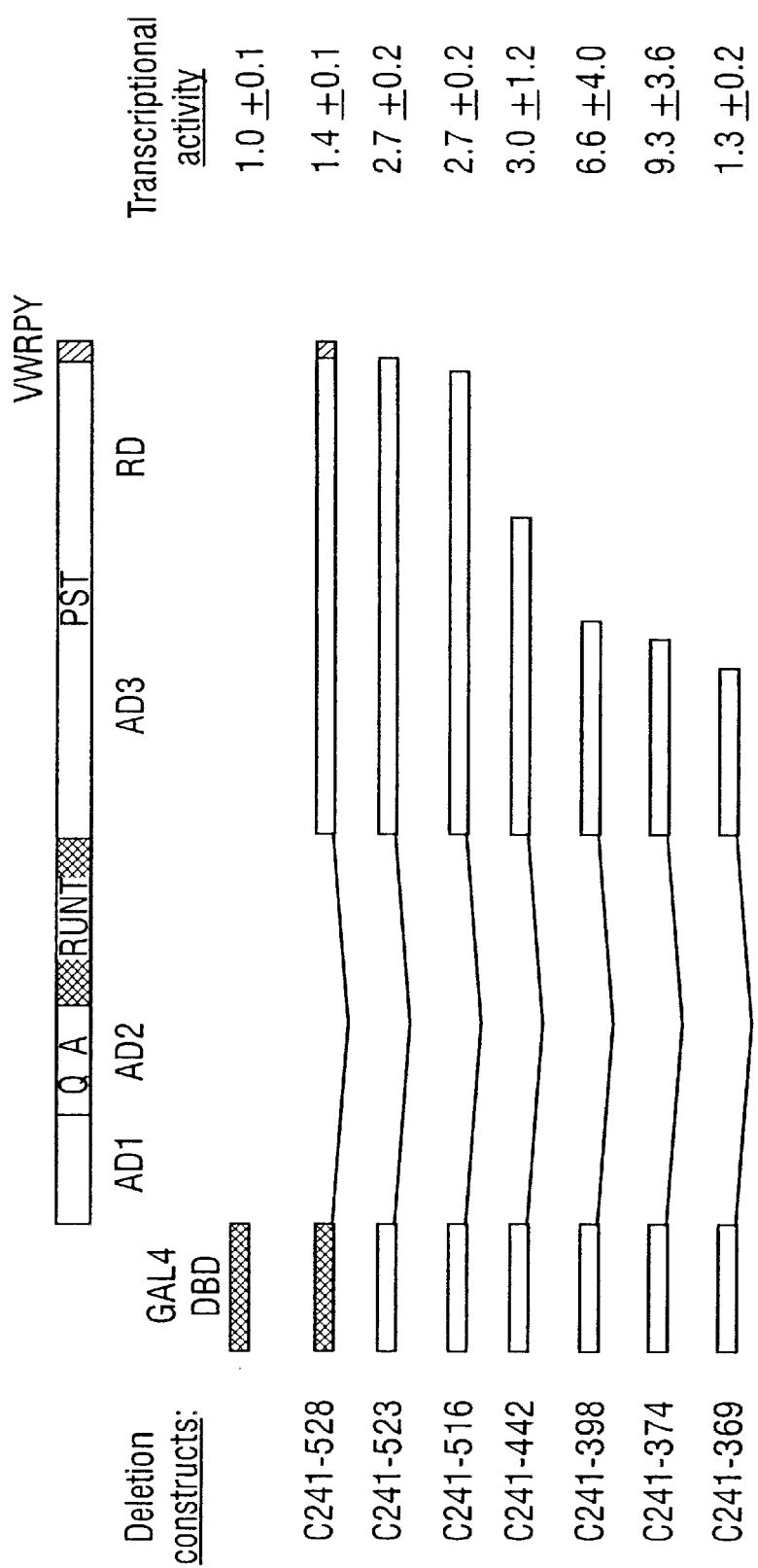

FIG. 16A. Identification of activation and repression domains in the PST region of Osf2. Transcriptional activity of the PST domain deletion constructs. DNA cotransfection studies were performed in COS7 cells with pGAL4SVluc as the reporter construct. Luciferase activity in cell extracts was assayed as described in Materials and Methods. Values shown are the averages of 4 independent transfection studies done in triplicate.

Figure 16B:
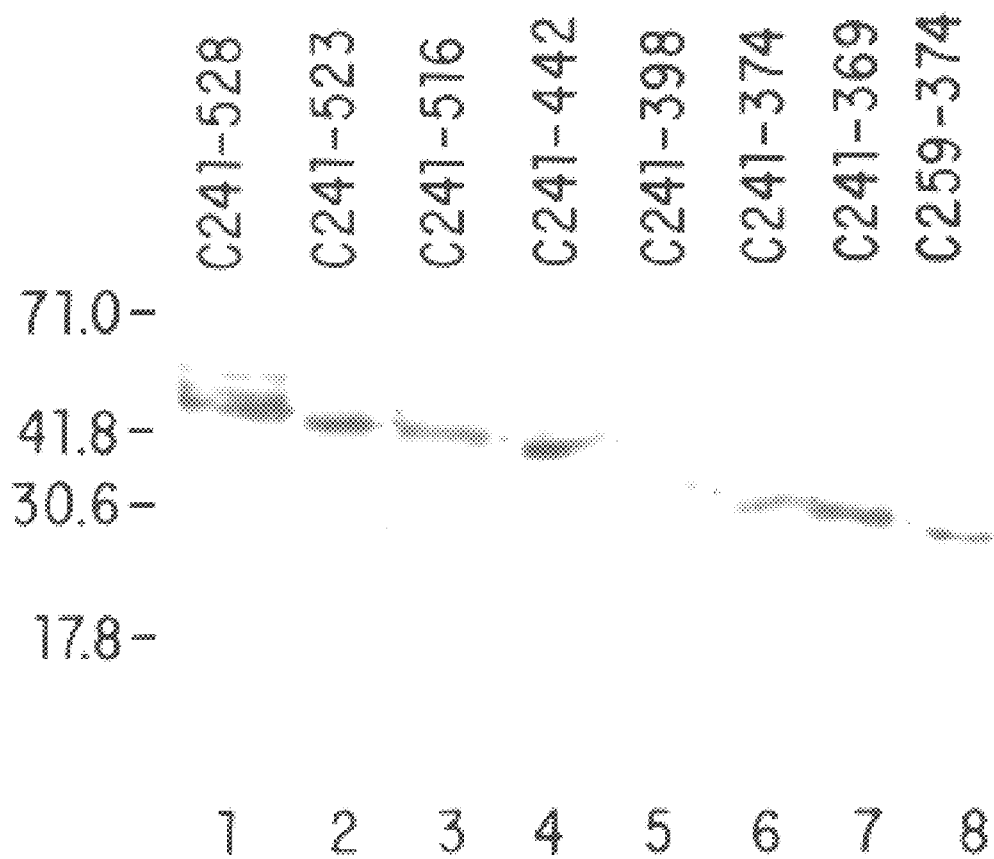

FIG. 16B. Identification of activation and repression domains in the PST region of Osf2. Immunoblot analysis of extracts from transfected cells. Expression of the GAL4-fusion proteins in transfected cells was verified by immunoblot analysis using anti-GAL4DBD antibody. Molecular size markers (in kilodaltons) are shown on the left.

Figure 16C:
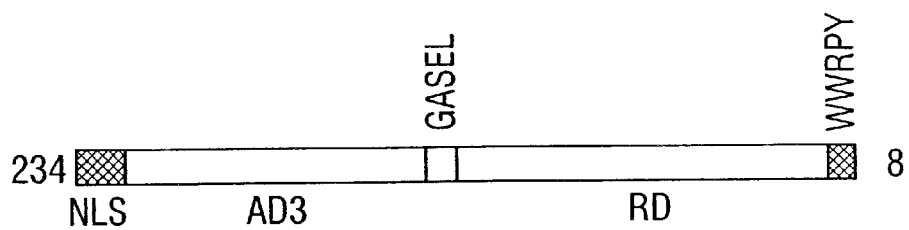

FIG. 16C. Identification of activation and repression domains in the PST region of Osf2. Schematic representatio o the various functional domains in the PST region of Osf2.

Figure 16D:
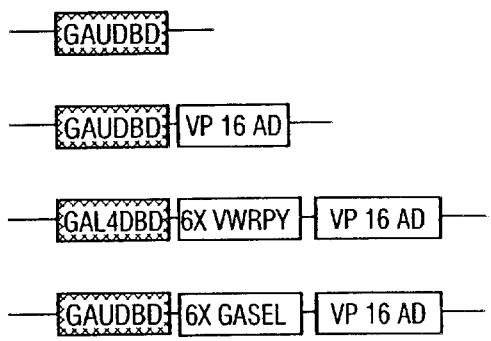

FIG. 16D. Identification of activation and repression domains in the PST region of Osf2. Schematic representation of the GAL4-VP 16 constructs used to determine the function of the VWRPY motif.

Figure 16E:
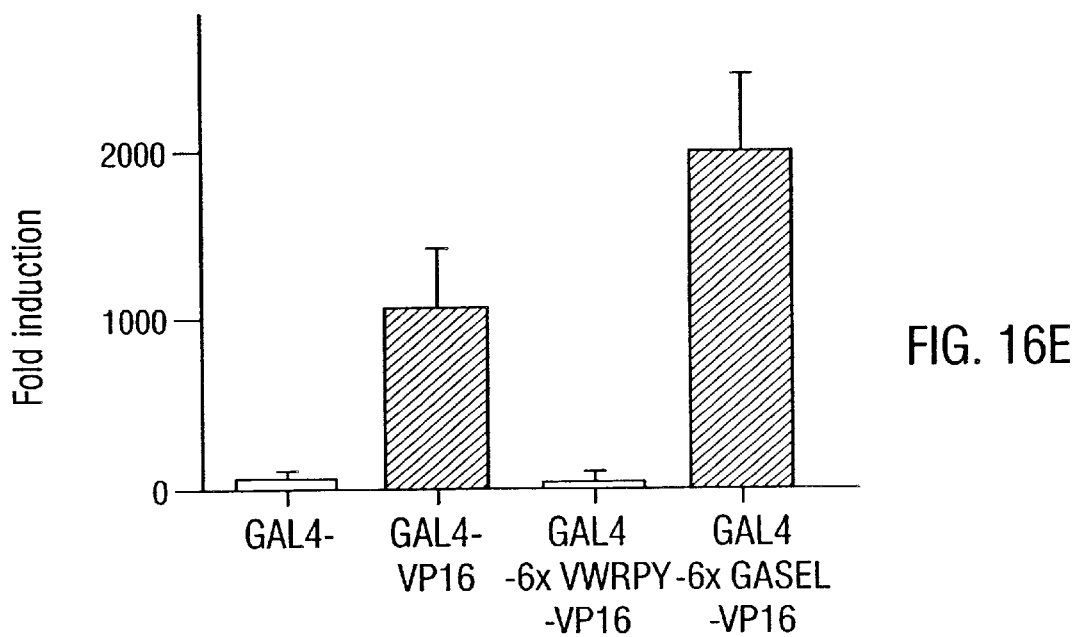

FIG. 16E. Identification of activation and repression domains in the PST region of Osf2. Fold induction of luciferase activity in extracts from COS7 cells transfected with the GAL4-VP16 constructs shown in panel D. Values represent the means of 9 independent transfection studies.

Figure 17:
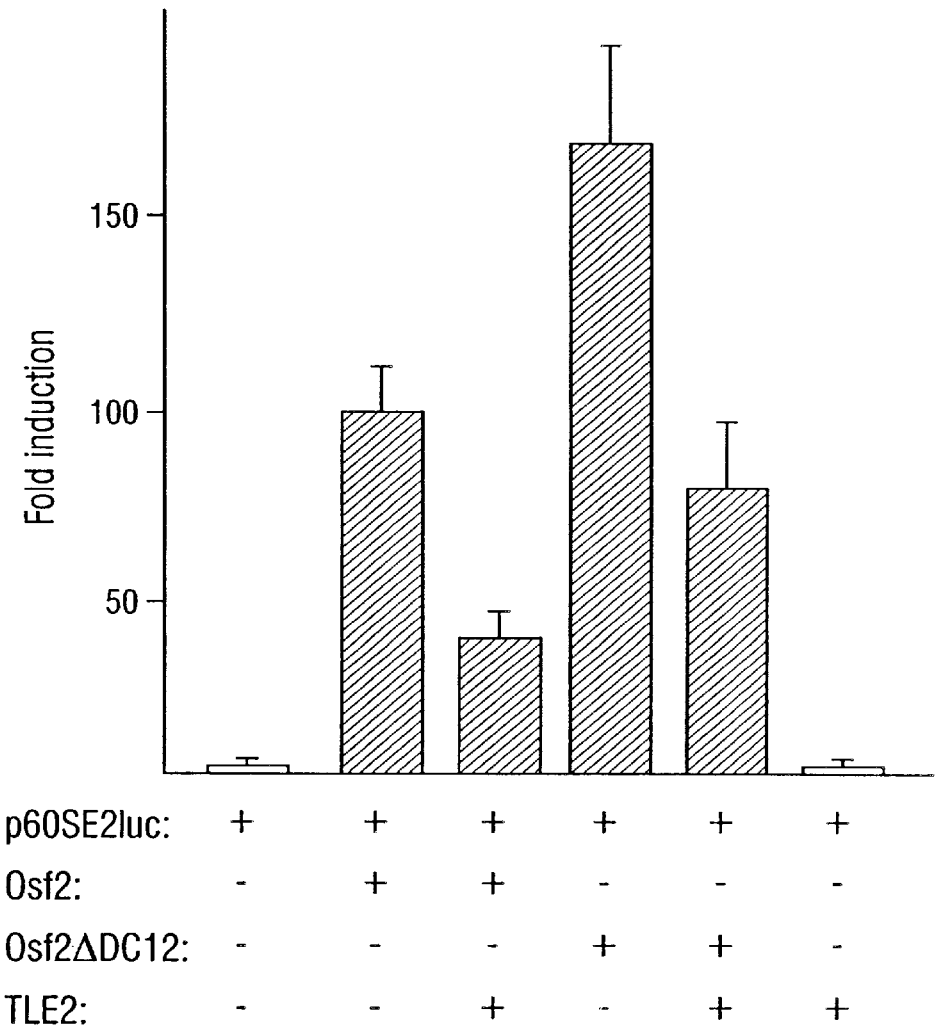

FIG. 17. Effect of TLE2 on the transactivationability of Osf2 and Osf2ΔC12. DNA cotransfection studies were performed in COS7 cells with Osf2 or Osf2ΔC12, and p6OSE2luc reporter, in the presence or absence of the TLE2 expression construct, pcDNA3-TLE2. Values indicate the fold induction of luciferase activity, and are the means of 9 independent transfection studies.

Figure 18B:
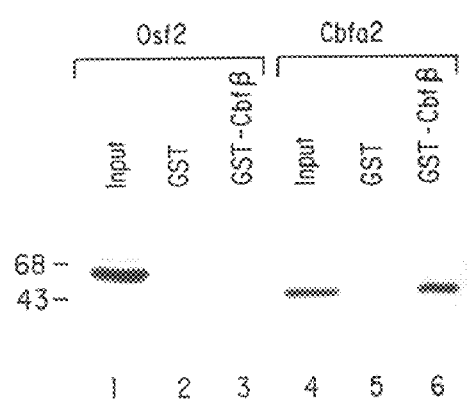
Figure 18A:
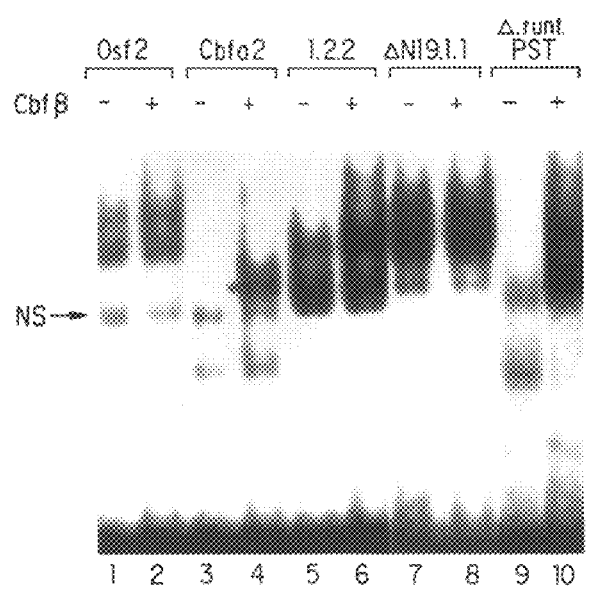

FIG. 18A. The QA domain prevents heterodimerization of Osf2 with Cbfβ. EMSA done with labeled double-stranded OSE2 oligonucleotide, and equivalent amounts of the Histidine-tagged wild-type and mutant proteins, in the presence or absence of Cbfβ. The nonspecific band (NS) is indicated by an arrow. Arrowheads indicate the supershifted complexes seen in lanes 4 and 10.

FIG. 18B. The QA domain prevents heterodimerization of Osf2 with Cbfβ. In vitro binding assay. The GST protein and GST-Cbfβ fusion protein immobilized on glutathione-agarose beads were incubated with in vitro translated $^{35}$S-labeled Osf2 (lanes 2 and 3) or Cbfa2 (lanes 5 and 6). The bound proteins were then analyzed on a SDS-polyacrylamidegel, followed by autoradiography. The input amounts of $^{35}$S-labeled Osf2 (lane 1) and Cbfa2 (lane 4) are shown.

Figure 18C:
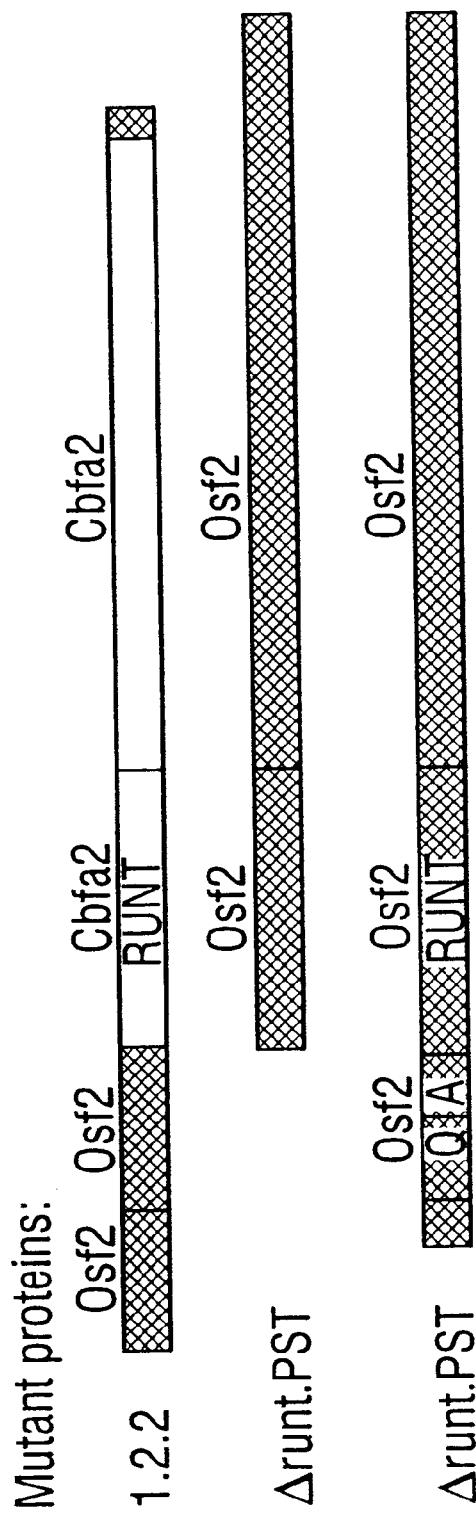

FIG. 18C. The QA domain prevents heterodimerization of Osf2 with Cbfβ. Schematic representation of the Osf2 and Cbfa2 chimeric constructs.

Figure 19:
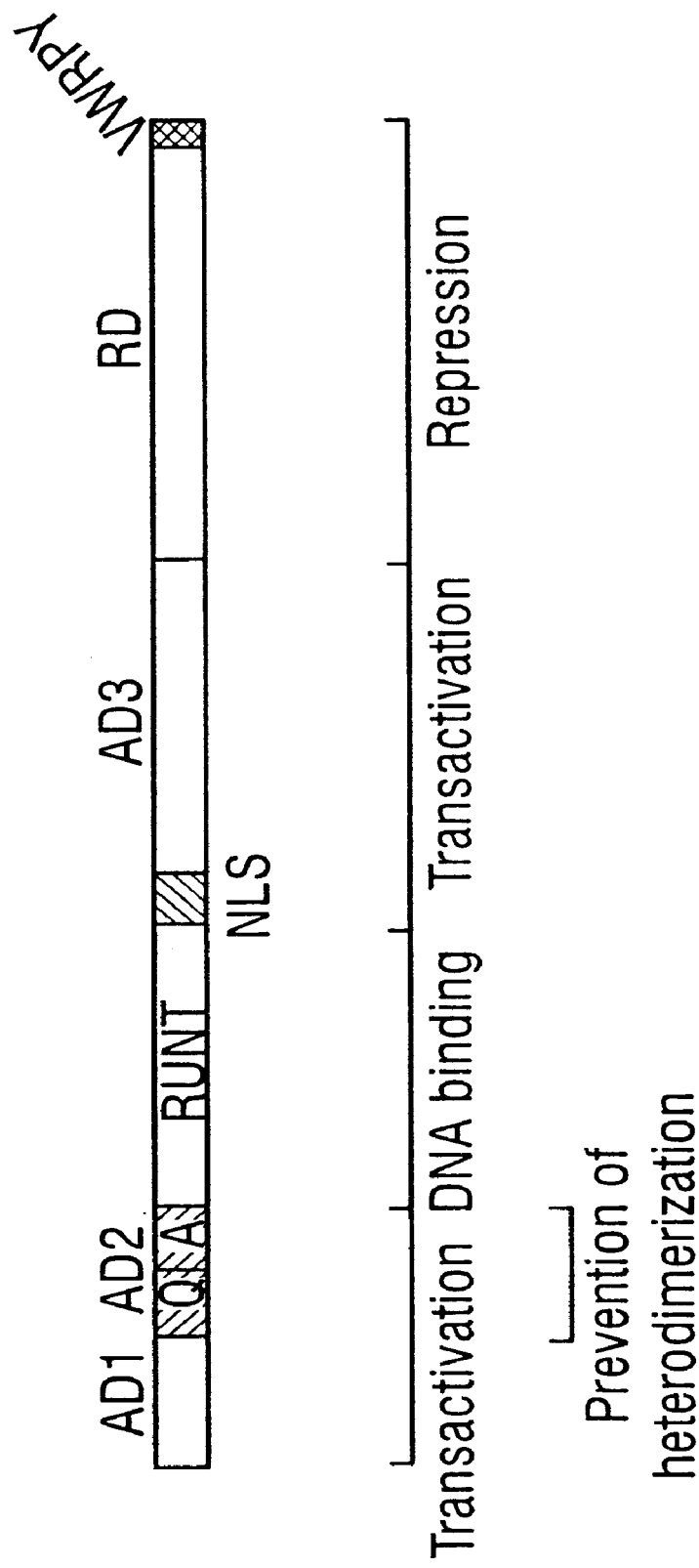

FIG. 19. Schematic representation of the various functional domains of Osf2. The location of the different activation domains and the repression domain, as well as the N-terminal region comprising the QA domain that is thought to prevent heterodimerization of Osf2 with Cbfβ, are shown.

Figure 20A:
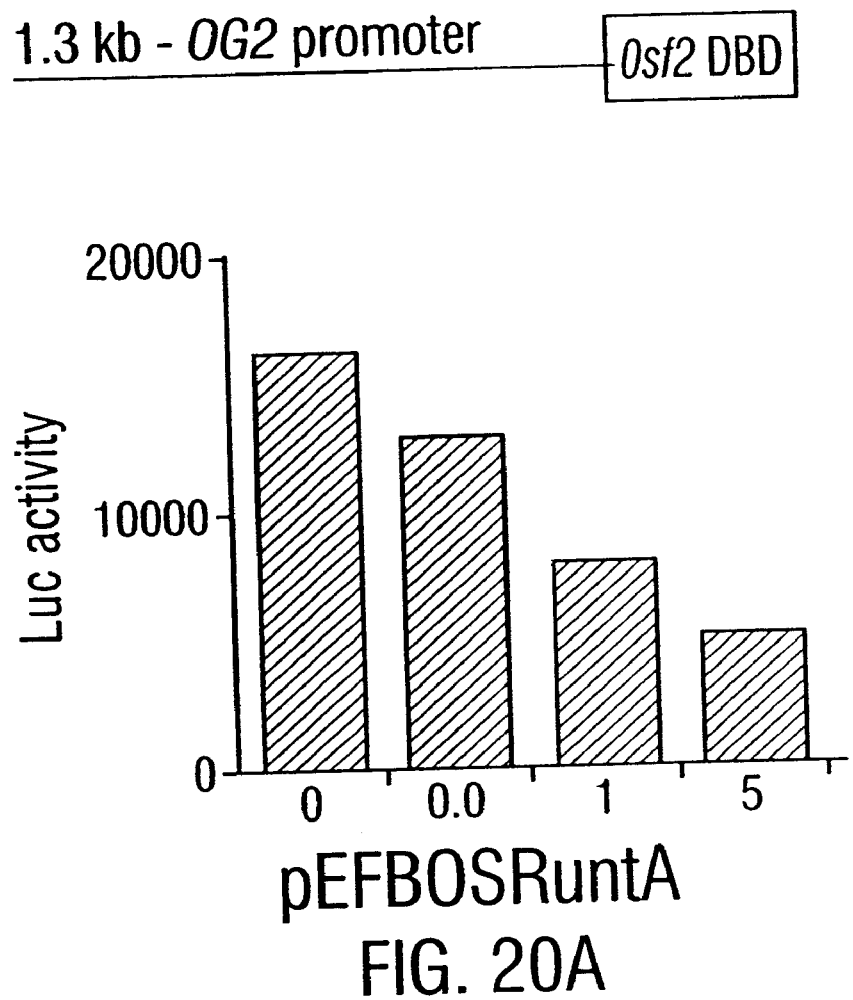

FIG. 20A. Inhibition of Osf2 induction of an Osteocalcin promoter-luciferase chimeric gene by ΔOsf2.

Figure 20B:

FIG. 20B. Indication that transgene expression was only in bone. RNA integrity was confirmed by detection of expression of the Hprt gene.

Figure 21A:
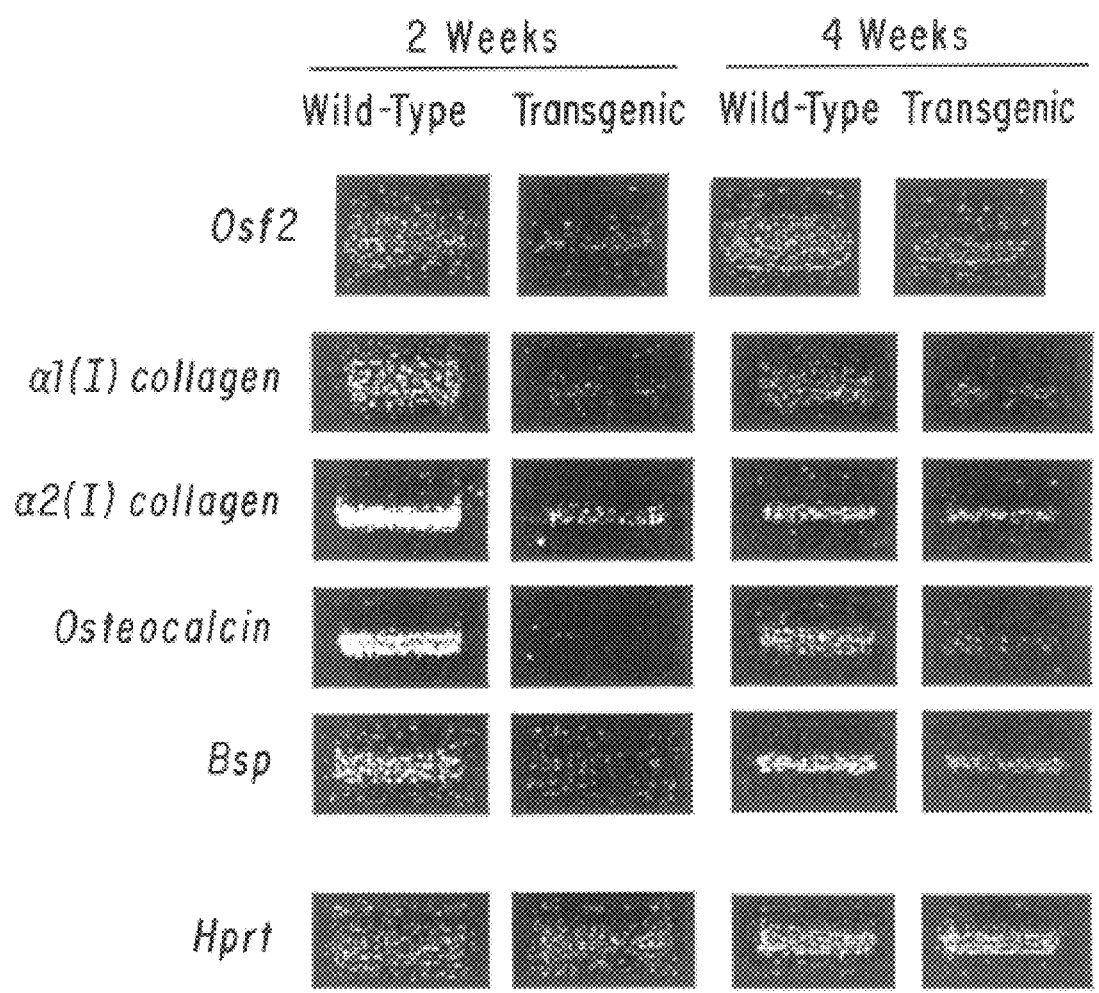

FIG. 21A. Comparison of expression of osteoblast-specific genes including Osf2 in wild-type and transgenic animals. As indicated, expression was determined at 2 wk and 4 wk.

FIG. 21B. Electromobility shift assay (EMSA) using osteoblast nuclear extracts and oligonucleotides containing wild-type (α1(I)wt) OSE2 elements or OSE2 elements containing a 2-bp mutation (α1(I)m).

Figure 21C:
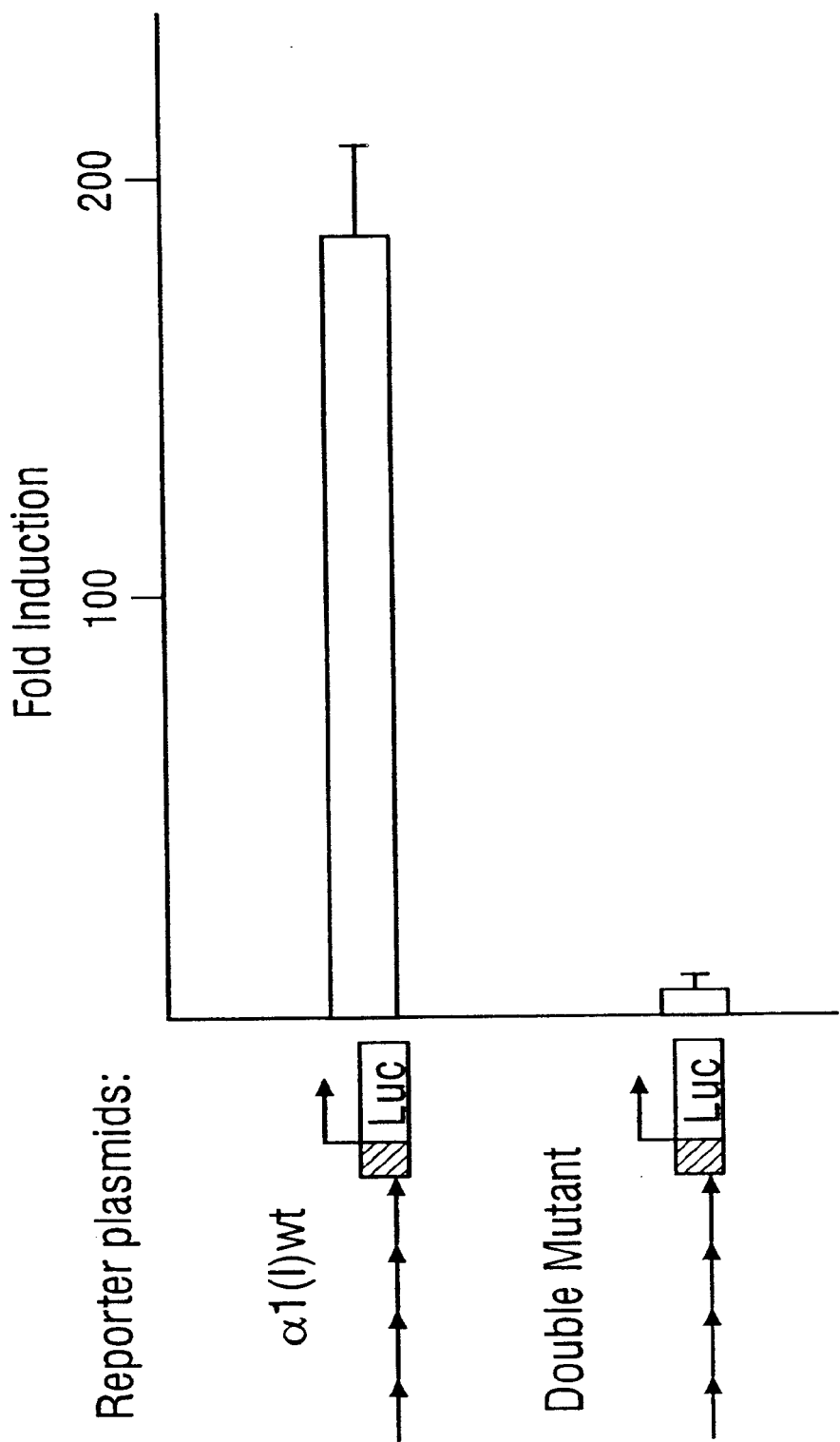

FIG. 21C. Comparison of Osf2 induced expression in cells containing a reporter construct containing multimers or the wild type OSE2α1(I) and multimers of a mutated OSE2α1(I) site.

4.0 DESCRIPTION OF ILLUSTRATIVE EMBODIMENTS

4.1 Bone Remodeling

Vertebrates constantly remodel bone. Bone remodeling includes bone resorption by osteoclasts followed by bone formation by osteoblasts. Defects in bone resorption and formation are linked to the development of several osteogenic human diseases and disorders, e.g., osteoporosis, osteosclerosis, osteogenesis imperfecta, and failure of bone repair. The term osteoporosis refers to a heterogeneous group of disorders where bone resorption overcomes bone formation, leading to low bone mass and fractures. Clinically, osteoporosis is segregated into type I andtype II. Type I osteoporosis occurs predominantlyin middle-aged women and is most frequently associated with estrogen loss at the menopause, while osteoporosis type II is associated with advancing age.

Osteogenesis imperfecta (OI) refers to a group of inherited connective tissue diseases characterized by bone and soft connective tissue fragility (Byers and Steiner, 1992; Prockop, 1990). Males and females are affected equally, and the overall incidence is currently estimated to be 1 in 5,000–14,000 live births. Hearing loss, dentinogenesis imperfecta, respiratory insufficiency, severe scoliosis and emphysema are just some of the conditions that are associated with one or more types of OI.

Failure of bone repair also is associated with significant complications in clinical orthopedic practice, for example, fibrous non-union following bone fracture, implant interface failures and large allograft failures. Although methods to stimulate or complement bone repair have been proposed in conjunction with each of the disease states mentioned here, there still remains a significant need for added understanding of such disease, as well as improved treatment protocols for bone-related disorders.

Osteocalcin, also called bone Gla protein because of the presence of γ-carboxyglutamic acid (Gla) residues, is the most abundant non-collagenous protein (NCP) of the bone extracellular matrix, comprising about 10–20% of NCP's. It contains between 46 and 50 amino acids, depending upon the species, and exhibits a $Ca^{2+}$ binding function. It binds strongly to hydroxylapatite in vitro. It is synthesized only by osteoblasts and odontoblasts and is dependent on vitamin K. In the presence of calcium, osteocalcin undergoes a transition to an α-helical conformation in which all Gla side chains are located on the same face of one α-helix. Gla residues are spaced at intervals of about 5.4 Å, closely paralleling the interatomic separation of $Ca^{2+}$ in the hydroxyapatite lattice. In other work, the inventors have demonstrated a role for osteocalcin in increasing bone formation.

4.2 Bone One Disease and Disorders

Bone diseases are a significant health problem around the world. For example, an estimated 20–25 million people are at increased risk for fracture because of site-specific bone loss. The cost of treating osteoporosis in the United States is currently estimated to be in the order of $10 billion per year. Demographic trends, i.e. the gradually increasing age of the U.S. population, suggest that these costs may increase 2–3 fold by the year 2020 if a safe and effective treatment is not found. While accurate estimates of the health care costs for OI are not available, the morbidity and mortality associated with this disease, resulting from the extreme propensity to fracture (OI types I–IV) and the deformation of abnormal bone following fracture repair (OI types II–IV), are significant.

Presently, conventional methods for treating bone disease are "after the fact," and rely primarily on enhancing fracture repair. Unfortunately, significant morbidity and mortality are associated with prolonged bed rest in the elderly, especially those who have suffered hip fracture. While new methods clearly are needed for stimulating fracture repair, thus restoring mobility in patients before the complications arise, it also is important to develop new methods which focus on fracture prevention, not fracture repair. This will require a more detailed understanding of bone metabolism and how this metabolism is altered in disease states. The present invention provides the tools with which to accomplish this goal, as well as further insights into the function of an important bone-related protein, osteocalcin.

4.3 Osteocalcin

Osteocalcin, also called bone γ-carboxyglutamic acid (Gla) protein or BGP, is an abundant $Ca^{2+}$ binding protein indigenous to the organic matrix of bone, dentin, and possibly other mineralized tissues. The name osteocalcin (osteo, Greek for bone; calc, Latin for lime salts; in, protein) derives from the $Ca^{2+}$ affinity of this protein and the abundance of this protein in bone tissue (1–20% of noncollagen protein, depending on species, age and site). Osteocalcin is one of the ten most abundant proteins of the human body, and the most predominant Gla protein in bone.

Osteocalcin contains 46–50 amino acid residues ($M_r$=5, 210–5,889), depending on the species. Osteocalcin is distinguished by its normal content of Gla residues, although the human protein may contain only two Gla. The vitamin K-dependent biosynthesis of osteocalcin occurs in bone. Vitamin K is involved as a cofactor in the synthesis of Gla by posttranslational enzymatic carboxylation of certain glutamic acid residues in polypeptide chains. Osteocalcin is secreted in the bone matrix just after the onset of bone mineralization.

The primary structure of osteocalcin has been determined for more than 13 different species. Osteocalcins of all species share extensive amino acid sequence identity. Common features include the location of Gla at residues 17, 21 and 24, and the disulfide loop Cys-23-Cys-29. Hydroxyproline occurs at position 9 in most of the species. The amino terminus of osteocalcin exhibits considerable sequence variation in contrast to the strongly conserved central portion of the molecule, which is the locus of the Gla residues and the $Ca^{2+}$ binding site.

Osteocalcin has specific calcium-binding properties. Circular dichroism and ultraviolet spectroscopy have verified the existence of α-helical conformation in osteocalcin and have further shown that millimolar levels of $Ca^{2+}$ or other specific cations are required to offset electrostatic repulsion if the highly anionic osteocalcin molecule is to achieve its full potential of approximately 40% α-helix. In the presence of calcium, osteocalcin undergoes a transition to an α-helical conformation in which all Gla side chains are located on the same face of one α-helix.

Osteocalcin in free solution binds between 2 and 3 mol $Ca^{2+}$/mol protein with a dissociation constant ranging from 0.8 to 3 mM. Various cations have competitive binding properties which also induce the α-helical conformational transition. Calcium ions induce this transition with a midpoint of 0.75 mM for chicken osteocalcin. Helical conformation is important for the adsorption of osteocalcin to hydroxyapatite. The affinity of metal-free osteocalcin for hydroxyapatite is increased fivefold by addition of 5 mM $Ca^{2+}$.

Binding sites for $Ca^{2+}$ are probably formed by carboxyl groups of Gla residues, as well as by opposing carboxyls of aspartic acid and glutamic acid in the two helical domains of osteocalcin. The interaction of Gla with $Ca^{2+}$ is such that only two of the six to nine likely coordination sites are occupied. Thus the sequestered $Ca^{2+}$ is available for other types of interaction. This key feature of Gla proteins is compatible with their relatively high dissociation constant ($K_d$) for $Ca^{2+}$ (mM range), as well as the probable extracellular action of these proteins where plasma [$Ca^{2+}$] prevails. This feature distinguishes Gla proteins as a class from intracellular $Ca^{2+}$ binding proteins of the "EF-hand" type )in which Gla residues have not been found), where bound $Ca^{2+}$ is virtually fully coordinated and $K_d$ values are typically in the micromolar range. Candidate ligands for sharing in the interaction of $Ca^{2+}$ bound to Gla residues of osteocalcin include other $Ca^{2+}$ binding proteins, acidic phospholipid surfaces, and calcium phosphate mineral surfaces, such as hydroxyapatite.

The adsorption affinity of osteocalcin for hydroxyapatite may be an important factor in the mineral dynamics of bone. The transition of brushite ($CaHPO_4.2H_2O$) to hydroxyapatite [$Ca_{10}(PO_4)_6(OH)_2$] is inhibited by very low concentrations of osteocalcin. Osteocalcin also inhibits precipitation of hydroxyapatite from supersaturated solutions and from seeded hydroxyapatite systems but has no affect on $Ca^{2+}$- phospholipid-PO$_4$-dependent crystallization. The protein binds poorly to amorphous calcium phosphate of unspecified surface area. Osteocalcin adsorption to fluoroapatite [Ca$_{10}$(PO$_4$)$_6$F$_2$] exhibits a fivefold greater affinity constant than hydroxyapatite, which may account for some of the disparate effects of fluoride in bone mineral metabolism. Because on the average there is only about one molecule of osteocalcin for each microcrystal of hydroxyapatite in bone, the binding site on the microcrystal (lateral surface vs. end) could strongly affect the kinetics of mineral crystallization and/or dissolution.

Osteocalcin appears to be a specific product of osteoblasts. The human osteocalcin gene has been localized to chromosome 1 by analysis of mouse-human somatic cell hybrids. Another gene of importance to bone, alkaline phosphatase, is also on human chromosome 1. The rat osteocalcin gene has been isolated from a rat genomic DNA library. Sequence analysis indicates that the mRNA is represented in a segment of DNA comprised of four exons and three introns. Although the introns in the rat gene are larger, its overall organization is similar to the human gene. Typical sequences associated with most genes transcribed by RNA polymerase II are found in 5'-flanking regions of the rat gene (e.g., TATA, CAAT, AP1, and AP2). In addition, consensus sequences have been identified for cyclic nucleotide-responsive elements and several hormone receptor sites (estrogen, thyroid hormone). Also present are AG-rich clusters, the putative vitamin D-responsive elements; within the 1,000 nucleotides immediately upstream from the transcription initiation site are sequences that support 1,25(OH)$_2$D$_3$-dependent transcription of the rat osteocalcin gene.

The mouse osteocalcin gene has also been cloned and studied. There is a cluster of three genes highly homologous in their coding sequences but transcribed in two distinct spatial and temporal patterns. The three genes are clustered within a 23-kb span of genomic DNA and arranged in the same transcriptional orientation. The genes are named (5' to 3') osteocalcin gene 1 (OG1) osteocalcin gene 2 (OG2), and osteocalcin-related gene (ORG). OG1 and OG2 are expressed only in bone and late during development. ORG is expressed in kidney, but not in bone, and earlier during development.

The coding sequence of OG2 is identical to the published sequence of the mouse osteocalcin cDNA. Like the osteocalcin gene in human and rat, OG2 contains four exons and a 5'-untranslated region with a typical TATA box, CCAAT box, and a vitamin D response element. OG1 has the same exon-intron structure as OG2, and its coding sequence is 98% similar to the coding sequence of OG2. The differences are six substitution mutations in exon 1. The 5'-untranslated region of OG1 is 93% homologous to the 5'-untranslated region of OG2 over 1 kb; in particular the TATA and CCAAT boxes and the vitamin D response element are all present, at the same distance from the start site of transcription. The 3'-untranslated regions of OG1 and OG2 are highly similar over more than 1 kb.

The organization of ORG, in contrast, has several differences. This gene has apparently the same exon-intron structure as OG1 and OG2, and its coding sequence is 96% similar to OG2. There are two substitution mutations in the putative exon 2 and seven substitution mutations in the last exon, the exon coding for the mature protein. These mutations do not affect the glutamic acid residues, the recognition sequence of the vitamin K-dependent carboxylase, or create a stop codon.

The major difference between ORG and the two other genes is a 4-kb DNA fragment located upstream from the initiator that had no homology to any sequences in the two other genes. 5' of this 4 kb DNA fragment there is a segment of DNA 93% homologous to the 5'-untranslated region of OG1 and OG2 over 1 kb. The 3'-untranslated region of ORG is similar to corresponding regions of OG1 and OG2. ORG contains an additional exon and uses a different promoter than OG1 and OG2.

The three genes of the mouse osteocalcin cluster are transcribed in two distinct spatial patterns. OG1 and OG2 are transcribed only in bone, which is consistent with their virtually identical structure. ORG is transcribed in kidney and lung, but not bone.

The three genes of the mouse osteocalcin cluster have two different temporal patterns of expression. Transcription of ORG begins first in mouse embryos, as early as gestation of 10.5 days. Transcription of OG1 and OG2 starts at day 15.5, when osteogenesis begins.

4.4 OSF2/CBFA1: A Transcriptional Activator of Osteoblast Differentiation

The osteoblastis the bone-forming cell. The molecularbasis of osteoblast-specificgene expression and differentiation is unknown. An osteoblast-specific cis-acting element termed OSE2 in the Osteocalcin promoter was previously identified. The cDNA encoding Osf2/Cbfa1 has been cloned, the protein that binds to OSE2. Osf2/Cbfa1 expression is initiated in the mesenchymal condensations of the developing skeleton, is strictly restricted to cells of the osteoblast lineage thereafter, and is regulated by BMP7 and vitamin D$_3$. Osf2/Cbfa1 binds to and regulates the expression of multiple genes expressed in osteoblasts. Finally, forced expression of Osf2/Cbfa1 in nonosteoblastic cells induces the expression of the principal osteoblast-specific genes. This work represents the first identification of an osteoblast-specific transcription factor that has been shown to act as a regulator of osteoblast differentiation.

4.5 Affinity Chromotography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsor the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of antibodies from solution wherein the matrix contains Osf2/Cbfa1 peptide epitopes such as those derived from Osf2/Cbfa1, covalently-coupled to a Sepharose CL6B or CL4B. This matrix binds the antibodies of the present invention directly and allows their separation by elution with an appropriate gradient such as salt, GuHCl, pH, or urea.

Since antibodies, including monoclonal antibodies, to the Osf2/Cbfa1 epitopes of the present invention are described herein, the use of immunoabsorbent techniques to purify these peptides, or their immunologically cross-reactive variants, is also contemplated. It is proposed that useful antibodies for this purpose may be prepared generally by the techniques disclosed hereinbelow, or as is generally known in the art for the preparation of monoclonals (see, e.g., U.S. Pat. Nos. 4,514,498 and 4,740,467), and those reactive with the desired polypeptides selected. The development of immunoaffinity chromatography media, matrices, and columns may be of particular use in the isolation and purification of Osf2/Cbfa1-derived polypeptides and/or antibodies.

4.6 Methods of Nucleic Acid Delivery and DNA Transfection

In certain embodiments, it is contemplated that the nucleic acid segments disclosed herein will be used to transfect appropriate host cells. Technology for introduction of DNA into cells is well-known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984), direct microinjection (Capecchi, 1980; Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Curiel et al., 1991; Wagner et al., 1992; Wu and Wu, 1987; Wu and Wu, 1988). Some of these techniques may be successfully adapted for in vivo or ex vivo use.

Moreover, the use of viral vectors (Lu et al., 1993; Eglitis and Anderson, 1988; Eglitis et al., 1988), including retroviruses, baculoviruses, adenoviruses, adenoassociatedviruses, vaccinia viruses, Herpes viruses, and the like are well-known in the art, and are described in detail herein.

4.7 Liposomes and Nanocapsules

In certain embodiments, the inventors contemplate the use of liposomes and/or nanocapsules for the introduction of particular peptides or nucleic acid segments into host cells. In particular, the Osf2/Cbfa1 peptides of the present invention may be formulated for delivery in solution with DMSO or encapsulated in liposomes.

Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977; Couvreur, 1988 which describes the use of liposomes and nanocapsulesin the targeted antibiotic therapy of intracellular bacterial infections and diseases). Recently, liposomes were developed with improved serum stability and circulation half-times (Gabizon and Papahadjopoulos, 1988; Allen and Chonn, 1987).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems.

Liposomes have been used effectively to introduce genes, drugs (Heath and Martin, 1986; Heath et al., 1986; Balazsovits et al., 1989), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the Osf2/Cbfa1 peptides of the present invention. Nanocapsules can generally entrap compounds in a stable and reproducible way (Henry-Michelin et al., 1987). To avoid side effects due to intracellular polymeric overloading, such ultrafine particles (sized around 0.1 μm) should be designed using polymers able to be degraded in vivo. Biodegradable polyalkylcyanoacrylate nanoparticles that meet these requirements are contemplated for use in the present invention, and such particles may be are easily made, as described (Couvreur et al., 1984; 1988).

4.8 Expression of OSF2/CBFA1-Derived Epitopes

For the expression of Osf2/Cbfa1-derivedepitopes, once a suitable clone or clones have been obtained, whether they be native sequences or genetically-modified, one may proceed to prepare an expression system for the recombinant preparation of Osf2/Cbfa1-derived epitopes. The engineering of DNA segment(s) for expression in a prokaryotic or eukaryotic system may be performed by techniques generally known to those of skill in recombinant expression. It is believed that virtually any expression system may be employed in the expression of Osf2/Cbfa1-derived epitopes.

Osf2/Cbfa1-derived epitopes may be successfully expressed in eukaryotic expression systems, however, it is also envisioned that bacterial expression systems may be preferred for the preparation of Osf2/Cbfa1-derivedepitopes for all purposes. The DNA sequences encoding the full-length, truncated, site-specifically modified, mutagenized, or derivitized Osf2/Cbfa1peptide may be separately expressed in bacterial systems, with the encoded proteins being expressed as fusions with β-galactosidase, ubiquitin, *Schistosoma japonicum* glutathione S-transferase, *S. aureus* Protein A, maltose binding protein, and the like. It is believed that prokaryotic expression systems, and particularly bacterial expression systems will ultimately have advantages over eukaryotic expression in terms of ease of use and quantity of materials obtained thereby.

It is proposed that transformation of host cells with DNA segments encoding such epitopes will provide a convenient means for obtaining Osf2/Cbfa1-derived epitope peptides. Genomic or extra-chromosomal sequences are suitable for eukaryotic expression when present in appropriate expression vectors, and under suitable conditions to permit expression of the encoded protein, as the host cell will, of course, process the nucleic acid transcripts to yield functional mRNA for subsequent translation into protein.

It is similarly believed that almost any eukaryotic expression system may be utilized for the expression of Osf2/Cbfa1-derived epitopes (e.g., baculovirus-based, glutamine synthase-based or dihydrofolate reductase-based systems) may be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e. 3' of) the chosen promoter.

Where eukaryotic expression is contemplated, one will also typically desire to incorporate into the transcriptional unit which includes Osf2/Cbfa1-derived epitope-encoding DNA sequences, an appropriate polyadenylation site (e.g., 5'-AATAAA-3') (SEQ ID NO:73) if one was not contained within the original cloned segment. Typically, the poly-A addition site is placed about 30 to 2000 nucleotides "downstream" of the termination site of the protein at a position prior to transcription termination.

It is contemplated that virtually any of the commonly employed host cells can be used in connection with the expression of Osf2/Cbfa1-derived epitopes in accordance herewith. Examples include cell lines typically employed for eukaryotic expression such as 239, AtT-20, HepG2, VERO, HeLa, CHO, WI 38, BHK, COS-7, RIN and MDCK cell lines.

It is contemplated that Osf2/Cbfa1-derived epitopic peptides may be "overexpressed", i.e. expressed in increased levels relative to its natural expression in human cells, or even relative to the expression of other proteins in a recombinant host cell containing Osf2/Cbfa1-derived epitope-encoding DNA segments. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant polypeptide in comparison to the level in natural Osf2/Cbfa1-derived peptide-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding an Osf2/Cbfa1-derived epitope peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e. they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventors have noticed that the level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection study; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

4.9 Detection of Peptide and Antibody Compositions

It will be further understood that certain of the polypeptides may be present in quantities below the detection limits of typical staining procedures such as Coomassie brilliant blue or silver staining, which are usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently-, or colloidal gold-tagged. Means for the labeling and detection of such two-step secondary antibody techniques are well-known to those of skill in the art.

4.10 Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of the disclosed proteins and peptides is not limited to such assays, and that other useful embodiments include RIAs and other non-enzyme linked antibody binding assays and procedures.

In preferred ELISA assays, polypeptides incorporating the novel protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween™. These added agents also tend to assist in the reduction of nonspecific background. The layered antisera is then allowed to incubate for, e.g., from 2 to 4 h, at temperatures preferably on the order of about 25° to about 27° C. Following incubation, the antisera-contacted surface is washed so as to remove non-immunocomplexed material. A preferred washing procedure includes washing with a solution such as PBS/Tween™, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human gig for a period of time and under conditions that favor the development of immunocomplex formation (e.g., incubation for 2 h at room temperature in a PBS-containing solution such as PBS-Tween™).

After incubation with the second labeled or enzyme-tagged antibody, and subsequent to washing to remove unbound material, the amount of label is quantified, e.g., by incubation with a chromogenic substrate such as urea and bromocresol purple or 2,2'-azino-di-(3-ethylbenzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

4.11 Immunoprecipitation

The antibodies of the present invention are particularly useful for the isolation of Osf2/Cbfa1 polypeptide antigens by immunoprecipitation. Immunoprecipitation involves the separation of the target antigen component from a complex mixture, and is used to discriminate or isolate minute amounts of protein. In an alternative embodiment the antibodies of the present invention are useful for the close juxtaposition of two antigens. This is particularly useful for increasing the localized concentration of antigens, e.g., enzyme-substrate pairs.

In a related embodiment, antibodies of the present invention are useful for regulating the activity of Osf2/Cbfa1. Detection of the binding between the antibodies and antigenic compositions may be accomplished by using radioactively labeled antibodies or alternatively, radioactively-labeled Osf2/Cbfa1 polypeptides derived therefrom. Alternatively, assays employing biotin-labeled antibodies are also well-known in the art as described (Bayer and Wilchek, 1980).

4.12 Western Blots

The compositions of the present invention will find great use in immunoblot or western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods for use in conjunction with Western blotting include enzymatically-,radiolabel-, or fluorescently-tagged secondary antibodies against various peptide moieties are considered to be of particularuse in this regard.

4.13 Screening Assays

Host cells that have been transformed may be used in the screening of natural and artificially derived compounds or mixtures to select those that are capable of complexing with the Osf2/Cbfa1 polypeptides of the present invention. This could be useful in the search for compounds that inhibit or otherwise disrupt, or even enhance the ability of Osf2/Cbfa1 to modulate osteoblast differentiation. It is contemplated that effective pharmaceutical agents may be developed by identifying compounds that complex with the particular Osf2/Cbfa1 epitopes, including, for example, compounds isolated from natural sources, such as plant, animal and marine sources, and various synthetic compounds. Natural or man-made compounds that may be tested in this manner may also include various minerals and proteins, peptides or antibodies.

4.14 Mutagenesis of Polypeptides and Polypeptide Encoding DNAs

In certain embodiments, it is desirable to prepare mutant polypeptides and/or polynucleotides that encode them. Once the structure of the desired peptide to be mutagenized has been analyzed, it may often be desirable to introduce one or more mutations into either the polypeptide sequencer, alternatively, into the DNA sequence encoding the Osf2/Cbfa1-derived polypeptide for the purpose of producing a mutated peptide with altered biological properties, and in particular, increased transcription factor activity, increased peptide stability, and or decreased toxicity.

To that end, the present invention encompasses both site-specific mutagenesis methods and random mutagenesis of a nucleic acid segment encoding a channel-inhibitory polypeptide of the present invention. Using the assay methods described herein, one may then identify mutants arising from these procedures which have improved channel inhibitory activity, increased peptide stability, and or decreased toxicity.

The means for mutagenizing a DNA segment encoding a polypeptide are well-known to those of skill in the art. Modifications may be made by random, or site-specific mutagenesis procedures. The nucleic acid may be modified by altering its structure through the addition or deletion of one or more nucleotides from the sequence.

Mutagenesis may be performed in accordance with any of the techniques known in the art such as and not limited to synthesizing an oligonucleotide having one or more mutations within the sequence of a particular polypeptide.

In particular, site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159 (each of which is specifically incorporated herein by reference in its entirety). Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, specifically incorporated herein by reference in its entirety, describes an alternative method of amplification similar to LCR for binding probe pairs to a target sequence.

Qbeta Replicase™, described in Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having 3' and 5' end sequences of non-Cry-specific DNA and an internal sequence of a Cry-specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a cry-specific expressed nucleic acid.

Still other amplification methods described in Great Britain Pat. Appl. No. 2 202 328, and in Intl. Pat. Appl. Publ. No. PCT/US89/01025, each of which is incorporated herein by reference in its entirety, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has polypeptide-specific sequences. Following polymerization, DNA/RNA hybrids are digested with RNase H while double stranded DNA molecules are heat denatured again. In either case the single stranded DNA is made fully double stranded by addition of second polypeptide-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate polypeptide-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e., new templates are not produced from the resultant RNA transcripts. Other amplification methods include "RACE" (Frohman, 1990), and "one-sided PCR™" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.15 Ribozmes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Harnpel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecula interaction betwee the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al., 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/ or other chemical or biological molecules). Other in vitro uses of ribozymes of this invention are well known in the art, and include detection of the presence of mRNA associated with an IL-5 related condition. Such RNA is detected by determining the presence of a cleavage product after treatment with a ribozyme using standard methodology.

4.16 Biological Functional Equivalents

Modification and changes may be made in the structure of the peptides of the present invention and DNA segments which encode them and still obtain a functional molecule that encodes a polypeptide with desirable characteristics. The following is a discussion based upon changing the amino acids of a protein to create an equivalent, or even an improved, second-generation molecule. The amino acid changes may be achieved by changing the codons of the DNA sequence, according to Table 1.

For example, certain amino acids may be substituted for other amino acids in a protein structure without appreciable loss of interactive binding capacity with structures such as, for example, antigen-bindingregions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies,

TABLE 1

| Amino Acids | | | Codons | | | | |
| --- | --- | --- | --- | --- | --- | --- | --- |
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | | antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8);

tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamate and asparagine; and valine, leucine and isoleucine.

4.17 Characteristics of the OSF2 Promoter

The present invention provides promoter regions allowing expression of functional RNA. Although a functional RNA may be an mRNA, it may also be anti-sense RNA or RNA with enzymatic properties such as a ribozyme.

In a preferred embodiment, the invention discloses and claims the Osf2 promoter region. The Osf2 promoter region is substantially comprised within the 6178 bp nucleic acid sequence of SEQ ID NO:72. The inventors contemplate that smaller contiguous nucleic acid sequences comprised within SEQ ID NO:72 will maintain the characteristics of the Osf2 promoter.

4.18 Expression Vectors

The present invention contemplates an expression vector comprising a polynucleotide of the present invention. Thus, in one embodiment an expression vector is an isolated and purified DNA molecule comprising a promoter of the present invention operatively linked to a coding region that encodes a polypeptide, which coding region is operatively linked to a transcription-terminating region, whereby the promoter drives the transcription of the coding region.

In another embodiment, the promoter of the present invention is operatively linked to a coding region that encodes a functional RNA. A functional RNA may encode for a polypeptide(mRNA), be a tRNA, have ribozyme activity, or be an antisense RNA.

As used herein, the term "operatively linked" means that a promoter is connected to a functional RNA in such a way that the transcription of that functional RNA is controlled and regulated by that promoter. Means for operatively linking a promoter to a functional RNA are well known in the art.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.19 Expression in Animal Cells

The inventors contemplate that an Osf2 promoter comprising a contiguous nucleic acid sequence from SEQ ID NO:72, or a substantially identical nucleic acid sequence thereto, may also be utilized to promote the expression of homologous or heterologous genes in transformed host cells. Such cells are preferably animal cells, including mammalian cells such as those obtained from a human or other primate, murine, canine, bovine, equine, epine, or porcine species. The cells may be transformed with one or more vectors comprising a promoter operably linked to a gene segment of interest, such that the promoter (either alone or in combination with one or more enhancer elements) is sufficient to promote the expression of a polypeptide product encoded by the operably linked gene of interest. Such gene may be a native or mutagenized gene, a gene fusion, a gene encoding a protein fusion, or a gene encoding a truncated form of the polypeptide of interest.

4.19.1 Polypeptides

A variety of different polypeptides may be expressed according to the present invention. Proteins can be grouped generally into two categories—secreted and non-secreted—discussions of each are detailed below.

First, it is contemplated that many proteins will not have a single sequence but, rather, will exists in many forms. These forms may represent allelic variation or, rather, mutant forms of a given protein. Second, it is contemplated that various proteins may be expressed advantageously as "fusion" proteins. Fusions are generated by linking together the coding regions for two proteins, or parts of two proteins.

This generates a new, single coding region that gives rise to the fusion protein. Fusions may be useful in producing secreted forms of proteins that are not normally secreted or producing molecules that are immunologically tagged. Tagged proteins may be more easily purified or monitored using antibodies to the tag. A third variation contemplated by the present invention involves the expression of protein fragments. It may not be necessary to express an entire protein and, in some cases, it may be desirable to express a particular functional domain, for example, where the protein fragment remains functional but is more stable, or less antigenic, or both.

4.19.1.1 Secreted Proteins

Expression of several proteins that are normally secreted can be engineered into animal cells. The cDNAs encoding a number of useful human proteins are available. Examples would include soluble CD-4, Factor VIII, Factor IX, von Willebrand Factor, t-PA, urokinase, hirudin, interferons, TNF, interleukins, hematopoietic growth factors, antibodies, albumin, leptin, transferin and nerve growth factors.

Peptide hormones are grouped into three classes with specific examples given for each. These classes are defined by the complexity of their post-translational processing. Class I proteins generally are considered to include growth hormone, prolactin, placental lactogen, luteinizing hormone, follicle-stimulating hormone, chorionic gonadotropin, and thyroid-stimulating hormone. These require relatively limited proteolytic processing followed by storage and stimulated release from secretory granules.

Class II is represented human peptide hormones such as adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, and somatostatin. Further proteolytic processing is required, with both endoproteases and carboxypeptidases processing of larger precursor molecules occurring in the secretory granules.

Class III includes, for example, Calcium Metabolism Peptides such as calcitonin, calcitonin gene related peptide (CGRP), β-calcitonin gene related peptide, hypercalcemia of malignancy factor (1–40) (PTH-rP), parathyroid hormone-related protein (107–139) (PTH-rP), and parathyroid hormone-related protein (107–111) (PTH-rP); Gastrointestinal Peptides, such as cholecystokinin (27–33) (CCK), galanin message associated peptide, preprogalanin (65–105), gastrin I, gastrin releasing peptide, glucagon-like peptide (GLP-1), pancreastatin, pancreatic peptide, peptide YY, PHM, secretin, and vasoactive intestinal peptide (VIP); and Pituitary Peptides, such as oxytocin, vasopressin (AVP), and vasotocin; Enkephalins, such as enkephalinamide, and metorphinamide (adrenorphin). Also included in Class III are peptides such as alpha melanocyte stimulating hormone (α-MSH), atrial natriuretic factor (5–28) (ANF), amylin, amyloid P component (SAP-1), corticotropin releasing hormone (CRH), growth hormone releasing factor (GHRH), luteinizing Hormone-releasing hormone (LHRH), neuropeptide Y, substance K (Neurokinin A), substance P, and thyrotropin releasing hormone (TRH). In addition to the proteolytic processing found in the Class II peptides, amidation of the C-terminus is required for proper biological function.

4.19.1.2 Non-Secreated Proteins

Expression of non-secreted proteins can be engineered into animal cells. Two general classes of such proteins can be defined. The first are proteins that, once expressed in cells, stay associated with the cells in a variety of destinations. These destinations include the cytoplasm, nucleus, mitochondria, endoplasmic reticulum, golgi, membrane of secretory granules and plasma membrane. Non-secreted proteins are both soluble and membrane associated. The second class of proteins are ones that are normally associated with the cell, but have been modified such that they are now secreted by the cell. Modifications would include site-directed mutagenesis or expression of truncations of engineered proteins resulting in their secretion as well as creating novel fusion proteins that result in secretion of a normally non-secreted protein.

Cells engineered to produce such proteins could be used for either in vitro production of the protein or for in vivo, cell-based therapies. In vitro production would entail purification of the expressed protein from either the cell pellet for proteins remaining associated with the cell or from the conditioned media from cells secreting the engineered protein. In vivo, cell-based therapies would either be based on secretion of the engineered protein or beneficial effects of the cells expressing a non-secreted protein.

The cDNAs encoding a number of therapeutically useful human proteins are available. These include cell surface receptors, transporters and channels such as GLUT2, CFTR, leptin receptor, sulfonylurea receptor, β-cell inward rectifying channels, etc. Other proteins include protein processing enzymes such as PC2 and PC3, and PAM, transcription factors such as IPF1, and metabolic enzymes such as adenosine deaminase, phenylalanine hydroxylase, glucocerebrosidase.

4.19.2 Genetic Constructs

Also contemplated are DNA expression plasmids designed to optimize production of heterologous proteins. These include a number of enhancers/promoters from both viral and mammalian sources that drive expression of the genes of interest in animal cells. Elements designed to optimize messenger RNA stability and translatability in animal cells are defmed.

4.19.2.1 Vector Backbone

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product of interest is under the transcriptional control of an Osf2 promoter that comprises a substantially contiguous nucleic acid sequence from SEQ ID NO:72. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter fuictions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

In preferred embodiments of the invention, the expression construct comprises a virus or engineered construct derived from a viral genome. The ability of certain viruses to enter cells via receptor-mediatedendocytosis and to integrate into host cell genome and express viral genes stably and efficiently have made them attractive candidates for the transfer of foreign genes into mammalian cells (Ridgeway, 1988; Nicolas and Rubenstein, 1988; Temin, 1986). The first viruses used as gene vectors were DNA viruses including the papovaviruses (simian virus 40, bovine papilloma virus, and polyoma) (Ridgeway, 1988) and adenoviruses (Ridgeway, 1988). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

4.19.2.2 Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Also contemplated as an element of the expression cassette is a terminator. These elements can serve to enhance message levels and to minimize read through from the cassette into other sequences.

4.19.2.3 Selectable Markers

In certain embodiments of the invention, the delivery of a nucleic acid in a cell may be identified in vitro or in vivo by including a marker in the expression construct. The marker would result in an identifiable change to the transfected cell permitting ready identification of expression. Usually the inclusion of a drug selection marker aids in cloning and in the selection of transformants, for example, neomycin, puromycin, hygromycin, DHFR, GPT, zeocin and histidinol. Alternatively, enzymes such as herpes simplex virus thymidine kinase (tk) (eukaryotic) or chloramphenicol acetyltransferase (CAT) (prokaryotic) may be employed, as well as markers such as green fluorescentprotein, luciferase, and the like. Immunologic markers also can be employed. The selectable marker employed is not believed to be important, so long as it is capable of being expressed simultaneously with the nucleic acid encoding a gene product. Further examples of selectable markers are well known to one of skill in the art.

4.19.2.4 Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Yang et al., 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

4.19.3 In Vivo Delivery and Treatment Protocols

It may be desirable to introduce genetic constructs to cells in vivo. There are a number of ways in which nucleic acids may be introduced into cells. Several methods are outlined below.

4.19.3.1 Adenovirus

One of the preferred methods for in vivo delivery of one or more heterologous genes operably linked to an Osf2 promoter involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of an adenovirus. Knowledge of the genetic organization or adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

4.19.3.2 Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglyco protein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the fuiction of flanking genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hesdorffer et al., 1990).

4.19.3.3 Other Viral Vectors as Expression Constructs

Other viral vectors may be employed as expression constructs in the present invention. Vectors derived from viruses such as vaccinia virus (Ridgeway, 1988; Coupar et al., 1988) adeno-associated virus (AAV) (Ridgeway, 1988; Hermonat and Muzycska, 1984) and herpesviruses may be employed. They offer several attractive features for various mammalian cells (Friedmann, 1989; Ridgeway, 1988; Couparet al., 1988; Horwichet al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

4.19.3.4 Non-Viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, the preferred mechanism for delivery is via viral infection where the expression construct is encapsidated in an infectious viral particle.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct comprising an Osf2 promoter may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1989.). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

In a further embodiment of the invention, the expression construct comprising an Osf2 promoter may be entrapped in one or more nanocapsules, liposomes, or other lipid based DNA delivery agent. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1991; Wu et al., 1991; Wu et al., 1988).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. No. 0,273,085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. U.S. Pat. No. 5,399,346 (incorporated herein in its entirety), discloses exemplary ex vivo therapeutic methods.

4.20 Protein Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference.

4.20.1 Methods of Making PNAs

According to Corey, PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Further discussed by Corey are desired modifications of PNAs for given applications. Modifications can be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Parridge et al., 1995; Boffa et al., 1995; Landsdorp et al., 1996; Gambacorti-Passeriniet al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

4.20.2 Physical Properties of PNAs

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destablized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-proteinthat extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

4.20.3 Applications of PNAs

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

4.21 Viral Expression Vectors

The present invention contemplates a viral expression vector comprising one or more of the polynucleotide sequences of the present invention. Viral expression vectors are typically replication-defectiveviruses that have been engineered to optimally express a heterologous gene product when introduced into a recombinant host cell. Of course, replication-competent viral expression vectors exist and may be used to express the polynucleotide of the present invention. Often optimal expression is by means of introduction of a heterologous promoter into the viral genome. Other viral expression vectors utilize a promoter already contained within the virus.

To facilitate the introduction of the heterologous polynucleotide into the expression vector, many viral expression vectors also contain a multiple cloning region (MCR). The MCR is often a region of DNA engineered to contain a large number of restriction enzyme cleavage sites. When an expression vector contains an MCR, the MCR is placed such that the polynucleotide, when cloned into the MCR in the correct orientation, will be operably linked to the promoter. As used herein, the term "operably linked" means that a promoter is connected to a polynucleotide in such a way that the transcription of that polynucleotide is controlled and regulated by that promoter. Means for operably linking a promoter to a polynucleotide are well known in the art.

In one embodiment, a viral expression vector is an isolated and purified DNA molecule comprising a promoter operably linked to a polynucleotide of the present invention, which polynucleotide is operably linked to a transcription-terminating region, whereby the promoter drives the transcription of the coding region.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polynucleotide of the present invention to which it is operably linked.

A viral expression vector may be derived from any of a number of viruses including retroviruses, adenoviruses, adeno-associated viruses, baculoviruses, vaccinia viruses, togaviruses, and bacteriophage. However, given the state of the art of molecular biology, the inventors contemplate that essentially any viral genome may be used as a viral expression vector.

4.21.1 Retroviral Expression Vectors

Many viral expression vectors are derived from viruses of the retroviridae family. This family includes the murine leukemia viruses, the mouse mammary tumor viruses, the human foamy viruses, Rous sarcoma virus, and the immunodeficiency viruses, including human, simian, and feline. Considerations when designing retroviral expression vectors are discussed in Comstock et al. (1997).

Excellent murine leukemia virus (MLV)-based viral expression vectors have been developed by Kim et al. (1998). In creating the MLV vectors, Kim et al. found that the entire gag sequence, together with the immediate upstream region, could be deleted without significantly affecting viral packaging or gene expression. Further, it was found that nearly the entire U3 region could be replaced with the immediately-early promoter of human cytomegalovirus without deleterious effects. Additionally, MCR and internal ribosome entry sites (IRES) could be added without adverse effects. Based on their observations, Kim et al. have designed a series of MLV-based expression vectors comprising one or more of the features described above.

As more has been learned about human foamy virus (HFV), characteristics of HFV that are favorable for its use as an expression vector have been discovered. These characteristics include the expression of pol by splicing and start of translation at a defined initiation codon. Other aspects of HFV viral expression vectors are reviewed in Bodem et al. (1997).

Murakami et al. (1997) describe a Rous sarcoma virus (RSV)-based replication-competent avian retrovirus vectors, IR1 and IR2 to express a heterologous gene at a high level. In these vectors, the IRES derived from encephalomyocarditis virus (EMCV) was inserted between the env gene and the heterologous gene. The IR1 vector retains the splice-acceptorsite that is present downstream of the env gene while the IR2 vector lacks it. Murakami et al. have shown high level expression of several different heterologous genes by these vectors.

Recently, a number of lentivirus-based retroviral expression vectors have been developed. Kafri et al. (1997) have shown sustained expression of genes delivered directly into liver and muscle by a human immunodeficiency virus (HIV)-based expression vector. One benefit of the system is the inherent ability of HIV to transduce non-dividing cells. Because the viruses of Kafri et al. are pseudotyped with vesicular stomatitis virus G glycoprotein (VSVG), they can transduce a broad range of tissues and cell types.

4.22.2 Adenoviral Expression Vectors

A large number of adenovirus-based expression vectors have been developed. One reason for such a large number is the vectors utility as a preferred gene therapy agent. Adenovirus expression vectors and methods of using such vectors are the subject of a number of United States patents, including U.S. Pat. No. 5,698,202, U.S. Pat. No. 5,616,326, U.S. Pat. No. 5,585,362, and U.S. Pat. No. 5,518,913, all incorporated herein by reference.

Additional adenoviral constructs are described in Khatri et al. (1997) and Tomanin et al (1997). Khatri et al. describe novel ovine adenovirus expression vectors and their ability to infect bovine nasal turbinate and rabbit kidney cells as well as a range of human cell type, including lung and foreskin fibroblasts as well as liver, prostate, breast, colon and retinal lines. Tomanin et al. describe adenoviral expression vectors containing the T7 RNA polymerase gene. When introduced into cells containing a heterologous gene operably linked to a T7 promoter, the vectors were able to drive gene expression from the T7 promoter. The authors suggest that this system may be useful for the cloning and expression of genes encoding cytotoxic proteins.

4.23.3 Poxviral Expression Vectors

Poxviruses are widely used for the expression of heterologous genes in mammalian cells. Over the years, the vectors have been improved to allow high expression of the heterologous gene and simplify the integration of multiple heterologous genes into a single molecule. In an effort to diminish cytopathic effects and to increase safety, vaccinia virus mutant and other poxviruses that undergo abortive infection in mammalian cells are receiving special attention (Oertli et al., 1997). The use of poxviruses as expression vectors is reviewed in Carroll and Moss (1997).

4.24.4 Togaviral Expression Vectors

Togaviral expression vectors, which includes alphaviral expression vectors have been used to study the structure and function of proteins and for protein production purposes. Attractive features of togaviral expression vectors are rapid and efficient gene expression, wide host range, and RNA genomes (Huang, 1996). Also, recombinant vaccines based on alphaviral expression vectors have been shown to induce a strong humoral and cellular immune response with good immunological memory and protective effects (Tubulekas et al., 1997). Alphaviral expression vectors and their use are discussed in Lundstrom (1997).

In one interesting study, Li and Garoff(1 996) use Semliki Forest virus (SFV) expression vectors to express retroviral genes and to produce retroviral particles in BHK-21 cells.

The particles produced by this method had protease and reverse transcriptase activity and were infectious. Furthermore, no helper virus could be detected in the virus stocks. Therefore, this system has features that are attractive for its use in gene therapy protocols.

4.24.5 Baculoviral Expression Vectors

Baculoviral expression vectors have traditionally been used to express heterologous proteins in insect cells. Examples of proteins include mammalian chemokine receptors (Wang et al., 1997), reporter proteins such as green fluorescent protein (Wu et al., 1997), and FLAG fusion proteins (Wu et al., 1997; Koh et al., 1997). Recent advances in baculoviral expression vector technology, including their use in virion display vectors and expression in mammalian cells is reviewed by Possee (1997). Other reviews on baculoviral expression vectors include Jones and Morikawa (1996) and O'Reilly (1997).

5.0 EXAMPLES

The following examples are included to demonstrate preferred embodiments of the invention. It should be appreciated by those of skill in the art that the techniques disclosed in the examples which follow represent techniques discovered by the inventor to fuiction well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation and Characterization of an OSF2/CBFA1 Protein That Regulates Osteocalcin Promoter Activity This example describes the identification, cloning, sequencing and characterization of Osf2/Cbfa1, the factor that binds to the OSE2 element. Osf2/Cbfa1 has several functional features that identify it as the first transcriptional regulator of osteoblast differentiation. Osf2/Cbfa1 expression is restricted during development and after birth to cells of the osteoblast lineage, and is regulated by osteoblast differentiating agents such as bone morphogenetic protein 7 (BMP7) and 1,25(OH)$_2$ vitamin D$_3$ (1,25(OH)$_2$D$_3$). Osf2/Cbfa1 binds to OSE2 elements present in the promoter of multiple genes expressed in osteoblasts and regulates the expression of these genes. Lastly, forced expression of Osf2/Cbfa1 in non-osteoblastic cell lines induces the expression of several osteoblast-specific genes.

5.1.1 Methods 5.1.1.1 Cloning the OSF2/CBFA1 cDNA cDNA was prepared using poly (A)$^+$ RNA from primary osteoblast cultures obtained by sequential digestion of calvaria from 2-day-old mice (Ducy and Karsenty, 1995) and as primers a mixture of oligo-dT and random oligonucleotides. The cDNA library was built in λgt11 bacteriophage using EcoRI adaptors EcoRI adapters (Promega, Madison, Wis.) were ligated to each end of the cDNAs. Excess of adapters were removed by ethanol precipitation. cDNAs having ligated adapters were ligated to λgt11 bacteriophage dephosphorylated EcoRI digested arms (Stratagene, La Jolla, Calif.). Bacteriophage DNA was packaged with viral proteins using Gigapack II Gold extracts (Stratagene, La Jolla, Calif.). E. coli bacteria (Y1088, Y1089, Y1090, Stratagene, La Jolla, Calif.) were infected with these viruses and plated following the manufacturer's instructions (Stratagene, La Jolla, Calif.). Plaque screening was performed at low stringency (37° C., 20% formamide, 10% dextran sulfate, 6×SSC [1×SSC is 0.15 M NaCl plus 0.015 sodium citrate) for 20 hr at 37° C. using as probe the Asp718/HindIII fragment (+1431/+1687) encoding part of Cbfa1 runt domain (Ogawa et al., 1993a). Phage inserts were liberated from the phage arms by EcoRI digestion, gel purified and ligated into dephosphorylated EcoRI digested pBSKS(−) plasmid (Stratagene, La Jolla, Calif.) and sequenced using conventional methods. Ligation anchored-PCR™ was performed on primary osteoblasts total RNA treated by DNase I (Boehringer Mannheim, Indianapolis, Ind.) according to Ansari-Lari et al. (1996).

The primers used for cDNA synthesis and specific nested PCR™ were:

5'-CACCACCGGGCTCACGTCGC-3' (SEQ ID NO:3) and

5'-CTGCGCTGAAGAGGCTGTTTGACGC-3' (SEQ ID NO:4), respectively. Initial denaturation: 5 min at 94° C., 40 cycles: 1 min at 94° C. denaturation, 1 min at 62° C. annealing, 1 min at 72° C. elongation, Final elongation: 15 min at 17° C.

Sequence analyses and alignments were performed using MacVector software (Oxford Molecular Group, Campbell, Calif.). Plasmid containing full-length Osf2/Cbfa1 was in vitro transcribed/translated using the TnT kit (Promega, Promega, Madison, Wis.) and [$^{35}$S]-methionine for 90 min at 30° C. $^{35}$S-labeled proteins were analyzed by SDS-PAGE.

5.1.1.2 Plasmids

For production of recombinant Osf2/Cbfa1 an AcyI/XbaI (+311/+3334) fragment of the Osf2/Cbfa1 cDNA encoding the full-length protein was ligated in frame with coding sequence for the 6 histidine residues in the pV2a vector (Van Dyke et al., 1992). The expression plasmid for Osf2/Cbfa1 (pCMV-Osf2/Cbfa1) was constructed by inserting Osf2/Cbfa1 cDNA under transcriptional control of the CMV promoter region of the pCMV5 plasmid (Meyers et al., 1995). The reporter plasmids p6OSE2-luc, p6OSE2m-luc, p147-luc, and p147m-luc were described previously (Ducy and Karsenty 1995; Zhang et al., 1997). p910-Opn-luc was obtained by cloning of the −910/+90 PstI fragment of the mouse Osteopontin promoter into pGL2 vector (Promega). p106-Opn-luc was subsequently generated by deletion of the −910 to −106 fragment.

5.1.1.3 Production of Recombinant OSF2/CBFA1 and DNA-binding Assays

His-tagged Osf2/Cbfa1 polypeptide (His-Osf2/Cbfa1) was enriched on Ni-bound imminodiacetic acid agarose resin (Qiagen, Santa Clarita, Calif.) according to the manufacturer's instructions, aliquoted, and stored at −80° C. For EMSA, labeled double-stranded oligonucleotides were prepared as previously described (Ducy and Karsenty 1995). The oligonucleotides used in this study are presented in Table 2. Approximately 5 fmol of labeled probe was added to the recombinant protein in 10 µl of a buffer containing 20 mM Tris-HCl [pH 8], 10 mM NaCl, 3 mM EGTA, 0.05% Nonidet P-40®, 5 mM dithiothreitol, and 2 µg Poly(dI.dC) .poly(dI.dC). After incubation at room temperature for 10 min, loading buffer was added (5% glycerol, 2 mM Tris-HCl [pH 8], 0.025% xylene cyanole/bromophenol blue), and samples were subjected to electrophoresis on a 5% polyacrylamide gel in 0.25×TBE at 160 V for 90 min. The gels were dried and autoradiographed. For competition studies, the indicated amount of double-stranded unlabeled oligonucleotide was added to the binding reaction with the other components. For studies using the anti-CBFA antiserum (Meyers et al., 1995), this antiserum or a 10-fold excess of preimmune serum was added when indicated, to the reaction mixture 30 min before adding the probe.

5.1.1.4 RNA Analysis

RNA was isolated from cultured cells with RNAzOL™ (Cinna/Biotecx Lab, Houston, Tex.) following the manufacturer's instructions. RNA from mouse embryos and tissue of adult mice was isolated using the guanidinium thiocyanate-CsCl gradient method as described (Sambrook et al., 1989). Briefly, total or poly(A)+ RNA was fractionated by electrophoresis on agarose-formaldehyde denaturing gel and transferred to Hybond-N+™ (Amersham, Arlington Heights, Ill.). Probes used include the first 336-bp of Osf2/Cbfa1 untranslated and coding sequences, the Asp718/HindIII fragment (+1431/+1687) encoding part of the runt domain of Cbfa1, the mouse osteocalcin cDNA, the mouse osteopontin cDNA, the mouse α1(I) collagen cDNA and an 18S rRNA cDNA (Ambion, Austin, Tex.). Hybridization was carried out at 60° C. in 6.6% SDS and 0.33 M sodium phosphate buffer, pH 7.2. Final washes were in 0.2 or 0.5×SSC and 0.1% SDS at 60° C. for twice 25 min.

TABLE 2

DNA SEQUENCES USED IN EMSA

| Source | Sequence[a] | SEQ ID NO: |
|---|---|---|
| Osteocalcin OSE2 | 5'-AGCTGCAATCACC<u>AACCAC</u>AGCA-3' | 5 |
| mutant 1 | 5'-AGCTGCACGATCC<u>AACCAC</u>AGCA-3' | 6 |
| mutant 2 | 5'-AGCTGCAATCACGTACCACAGCA-3' | 7 |
| mutant 3 | 5'-AGCTGCAATCACCGGCCACAGCA-3' | 8 |
| mutant 4 | 5'-AGCTGCAATCACCAGACACAGCA-3' | 9 |
| mutant 5 | 5'-AGCTGCAATCACCAGCCACAGCA-3' | 10 |
| mutant 6 | 5'-AGCTGCAATCACCAAACACAGCA-3' | 11 |
| mutant 7 | 5'-AGCTGCAATCACCAACCAGAGCA-3' | 12 |
| OG1 OSE2 | 5'-CGCCGCAATCACC<u>TACCAC</u>AGCA-3' | 13 |
| α1(I) collagen OSE2 | 5'-CCCTTCCCACACC<u>ACCCAC</u>ACAG-3' | 14 |
| Bsp OSE2 | 5'-AAATTTAGACTCC<u>AACCTC</u>AGCA-3' | 15 |
| Osteopontin OSE2 | 5'-CGCTCTTTGTGCA<u>AACCAC</u>ACAG-3' | 16 |

[1]The OSE2 core binding site is underlined. The mutations are in bold.

For RT-PCR™ analysis, DNAse I-treated total RNA from mouse embryos at various stages of development were reverse transcribed using oligo-dT and Runt-specific 5'-CGGGGACCGTCCACTGT-3' (SEQ ID NO:17) primers. cDNAs were amplified for 30 cycles using the primers 5'-GAGGGCACAAGTTCTATCTGGA-3' (SEQ ID NO:18) and 5'-GGTGGTCCGCGATGATCTC-3' (SEQ ID NO:19). PCR™ products were separated on agarose gel, transferred to Hybond-N+ (Amersham), and hybridized with a 32P probe encompassing the first 336-bp of Osf2/Cbfa1 untranslated and coding sequences. Primers 5'-GTTGAGAGATCATCTCCACC-3' (SEQ ID NO:20) and 5'-AGCGATGATGAACCAGGTTA-3' (SEQ ID NO:21) were used to amplified exon 2 of the Hprt gene as a control of cDNA quality and loading.

5.1.1.5 In Situ Hybridization

The 336 bp fragment of Osf2/Cbfa1 cDNA containing 5' untranslated and coding sequence, the mouse MGP cDNA (Luo et al., 1997), and the 3' untranslated region of the mouse α1(II) collagen cDNAs cloned into pBSKS(−) (Stratagene), were used to generate antisense riboprobes, using either T3 or T7 RNA polymerase. Section in situ hybridization procedures were as described (Sundin et al., 1990) with the following modification. Sections of 8-μm were mounted onto poly-lysine-treatedslides. The hybridization and post-hybridization washes were performed as described (Wilkinson, 1992). Briefly, the sections were hybridized overnight at 50° C. The stringency washes were at 62° C. Exposure times were 2 to 16 days. Autoradiography, Hoechst 33258 staining, and photography were performed as described (Sundin et al., 1990).

5.1.1.6 Cell Culture and Induction of Osteoblastic Differentiation

Mouse F9 teratocarcinoma cells were cultured in EMEM/10% fetal bovine serum (FBS; GIBCO, Gaithersburg, Md.). C3H10T1/2 fibroblasts were cultured in DMEM/10% FBS. The murine MC3T3-E1 calvaria cell line was maintained in a α-MEM/10% FBS. Rat osteosarcoma ROS17/2.8 cells were maintained in DMEM/F12/10% FBS. For induction of osteoblast differentiation C3H10T1/2 fibroblasts were plated at a density of $2 \times 10^4$ cells/cm$^2$. After 24 h (t$_o$), this medium was replaced by fresh mixture complemented with 200 ng/ml of BMP7 or with vehicle for 12 h, as described (Zhang et al., 1997).

5.1.1.7 DNA Transfections

F9 and C3H10T1/2 cells were cotransfected with each reporter plasmid (5 μg), 5 μg of expression plasmid, and 2 μg of pSVβ-gal using the calcium phosphate coprecipitation procedure (Sambrook et al., 1989). After transfection the cells were washed twice with PBS (150 mM NaCl, 10 mM sodium phosphate [pH 7.2]), and regular medium was added for 24 h. Cells were harvested and lysed by three cycles of freeze-thawing. β-galactosidase activities present in each lysate, measured by a colorimetric enzyme assay (Ausubel et al., 1997) using resorufin β-D-galactopyranoside (Boehringer Mannheim) as a substrate, were used to normalize the transfection efficiency between different studies. DNA cotransfections (Ausubel et al., 1997) were performed in duplicates and repeated at least four times with quantitatively and qualitatively similar results. Luciferase activities were assayed using a Monolight 2010 luminometer (Analytical Luminescence Laboratory, San Diego, Calif.) and D-luciferin substrate (Analytical Luminescence Laboratory) in 100 mM Tris-HCl [pH 7.8], 5 mM ATP, 15 mM MgSO$_4$, 1 mM dithiothreitol (DTT). For overexpression studies, expression plasmids were transfected for 4 h with Lipofectamin (GIBCO) following the manufacturer's instructions. RNA were harvested 40 h after transfection. Antisense (5'-CTGCGCTGAAGAGGCTGTTTGA-3'; SEQ ID NO:22) and control scrambled (5'-CGCGTATCGTGATGTAGACGTG-3'; SEQ ID NO:23) oligonucleotides corresponding to a region 105-bp downstream of Osf2/Cbfa1 AUG sequence were synthesized in the phosphothioate modified condition (Midlands, Inc., Midlands, Tex.). 0.1 μM were transfected for 5 h using Lipofectamin (GIBCO), RNAs were isolated 40 h after transfection.

5.1.2 Results 5.1.2.1 Isolation of OSF2/CBFA1, an Osteoblast-specific CBFA cDNA

Given the immunological similarity between the CbfA proteins and Osf2 (Geoffroy et al., 1995; Merriman et al., 1995), the inventors searched for a Cbfa-related mRNA in osteoblasts. Northern blot analysis was performed using poly (A)+RNA from mouse thymus and spleen, two tissues in which Cbfa1, Cbfa2, and Cba3 are expressed, and from primary osteoblasts. When this filter was hybridized with a probe containing sequences coding for the runt domain of Cbfa1, a gene thought to be expressed in T lymphocytes (Satake et al., 1995), a transcript was detected in osteoblasts that was at least 20 fold more abundant than the signal detected in thymus (FIG. 1A, lanes 1, 3, and 4). Based on this finding, a mouse osteoblast cDNA library was screened at reduced stringency using the same probe as above. Three independent clones encoding the same protein were identified. This cDNA was called Osf2/Cbfa1 because it encodes the factor binding to OSE2 and is encoded by the Cbfa1 gene.

Osf2/Cbfa1 contains a glutamine/alanine-rich domain close to its N-terminal end, a runt domain, and a proline/serine/threonine-rich (PST) domain at its C-terminal end (FIG. 1B). The sequences coding for the runt and PST domains are identical in Osf2/Cbfa1 and the originally described Cbfa1, however, these two transcripts differ totally in their 5' end. Osf2/Cbfa1 encodes a different amino-acid stretch 5' of the glutamine/alanine domain and has a totally different 5' untranslated sequences. The identify of the 3' part of the nucleotide sequence between Osf2/Cbfa1 and Cbfa1 suggests that Osf2/Cbfa1 originates from the Cbfa1 gene. This was confirmed by the existence of exons coding for Osf2/Cbfa1 5' sequences in the Cbfa1 gene. The 5' end of Osf2/Cbfa1 contains two ATG codons in frame with the predicted coding sequence. In vitro transcription/translation of Osf2/Cbfa1 cDNA yielded two polypeptide species running at 63 kDa and 69 kDa respectively (FIG. 1C) indicating that both ATG codons may function as translational initiators, although the ATG codon at position 69 appeared to be the most efficient initiator.

The OSE2-binding activity is detectable exclusively in osteoblast nuclear extracts. Therefore, Northern blot analysis was performed to determine whether Osf2/Cbfa1 expression was restricted to osteoblasts in adult mice. As shown in FIG. 1D, Osf2/Cbfa1 transcripts were detectable only in bone and osteoblasts but in no other tissues examined. In particular, no Osf2/Cbfa1 expression was detected in thymus and spleen, two organs where the other CbfAs are expressed, or in tissues containing fibroblasts (skin), myoblasts (muscle, heart), or chondrocytes (cartilage), three other cell types of mesenchymal origin. Identical results were obtained by RT-PCR™ analysis followed by Southern hybridization with an Osf2/Cbfa1 specific probe.

5.1.2.2 OSF2/CBFA1 Increases Osteocalcin Promoter Activity Through its Binding to OSE2

The binding of Osf2/Cbfa1 to the OSE2 element present in the OG2 promoter was analyzed using a histidine-tagged recombinant Osf2/Cbfa1 polypeptide (His-Osf2/Cbfa1) in electrophoretic mobility shift assay (EMSA). A series of mutated OSE2 elements were compared with the wild-type OSE2 element for their ability to bind His-Osf2/Cbfa1 (FIG. 2A). Any single or double bp mutation within the 5'-AACCAC-3' (SEQ ID NO:74) sequence abolished binding of His-Osf2/Cbfa1 (FIG. 2A, lanes 3–8), while a mutation located outside this core sequence did not affect His-Osf2/Cbfa1 binding to DNA (FIG. 2A, lane 2). To demonstrate that Osf2/Cbfa1 and the OSE2-binding activity present in osteoblast nuclear extracts are related, an anti-Cbfa1 antiserum was used in EMSA that abolishes binding of nuclear extracts to OSE2 (Geoffroy et al., 1995). As shown in FIG. 2B, this antiserum abolished binding of His-Osf2/Cbfa1 to OSE2 while a preimmune serum did not.

The transcriptional activity of Osf2/Cbfa1 was assessed by DNA cotransfection studies. These studies were initially performed in F9 mouse teratocarcinoma cells, which do not express either Osteocalcin or the Cbfa genes (Ducy and Karsenty, 1995; Furukawa et al., 1990), and so provide a null background. The activity of a construct containing six copies of OSE2 oligonucleotides cloned upstream of the Osteocalcin basal promoter (p6OSE2-luc) was stimulated more than 70-fold upon cotransfection with the Osf2/Cbfa1 expression vector. This effect was abolished by a 2 bp mutation in OSE2 that abolishes binding of His-Osf2/Cbfa1 (p6OSE2m-luc) (FIG. 2C). Similar results were obtained when the DNA cotransfections were performed in another cell line in which Osf2/Cbfa1 is not expressed in the C3H10T1/2 fibroblasts (FIG. 2D). Osf2/Cbfa1 could also transactivate an Osteocalcin promoter fragment (−147/+13) containing a single wild-type OSE2 element (p147-Luc) (FIG. 2E). Thus, Osf2/Cbfa1 binds specifically to the OSE2 element present in the OG2 promoter and can activate transcription through this binding.

5.1.2.3 OSF2/CBFA1 Expression Marks the Cells of the Osteoblast Lineage During Development To determine when Osf2/Cbfa1 expression is initiated during mouse development RT-PCR™ analysis was performed followed by Southern blot hybridization using RNAs from mouse embryos of different stages (FIG. 3). Surprisingly, Osf2/Cbfa1 expression reached a peak in 12.5 days post-coitum (dpc) embryos whereas the first ossification center cannot be observed before 14.5 dpc (Kaufman, 1992). Based on this analysis section in situ hybridization studies were performed at several key stages of skeletal development.

The first important step during skeletal development is the formation of mesenchymal cell condensations. This mesenchymal condensations are identifiable at 12.5 dpc mouse embryos the only chondrocytes to be fully differentiated reside in the Meckel's cartilage (Kaufinan, 1992). Importantly, these cells expressed α1(II) collagen, a marker of the chondrocytic lineage, but not Osf2/Cbfa1 suggesting that its expression is restricted to undifferentiated mesenchymal cells and to cells of the osteoblast lineage but is mutually exclusive with the differentiated chondrocyte phenotype. There was no detectable Osf2/Cbfa1 expression in any internal organ.

In 14.5 dpc mouse embryos there is no mineralized bone yet but the first ossification centers appear in the skull. At that stage, as was the case in 12.5 dpc embryos, Osf2/Cbfa1 was expressed in every developing skeletal element of the skull and of the rest of the skeleton. Its expression was now clearly restricted to cells of the osteoblast lineage and to the perichondrium, and was absent in differentiated chondrocytes. For instance, in the rib cage Osf2/Cbfa1 expression was restricted to the ribs proper (Kaufinan, 1992), that will ossify first, but was totally absent in the chondrocostal cartilage where α1(II) collagen was expressed at the highest. A similar exclusive pattern of expression of Osf2/Cbfa1 and α1(II) collagen was also observed in developing long bones.

Lastly, in situ hybridization was performed on 16.0 dpc embryos. At this stage, ossification centers are now present in most of the skeleton but not all bones are mineralized as assessed by alizarin red staining of skeletal preparations (Kaufman, 1992). Final ossification will occur through two distinct pathways. In the skull, the mesenchymal cells will differentiate directly in osteoblasts (intramembranous ossification). In the rest of the skeleton, the cells of the mesenchymal condensations will differentiate first in chondrogenic cells that will be replaced by osteoblasts (endochondral ossification) (Erlebacher et al., 1995).

In the skull of 16.0 dpc embryos; the nasal, frontal, basosphenoid and basooccipital bones and the mandibles expressed high levels of Osf2/Cbfa1 mRNA. Osf2/Cbfa1 expression was detected in bones such as the manubrium sterni, the sternebrae and the hyoid bone, 12 to 24 h before mineralization of these structures occurs (Kaufinan, 1992). As before, no Osf2/Cbfa1 expression was detectable in the chondrocytes of the Meckel's cartilage or of the manubrium sterni, in the fibroblasts of the skin or in any soft tissues examined. In the axial skeleton, Osf2/Cbfa1 was expressed in the cells of the ossification centers of caudal vertebrae, two days before they became mineralized (Kaufman, 1992). In a control study on adjacent sections, the expression of Matrix gla protein (Mgp), a gene expressed in chondrocytes but not in osteoblasts (Luo et al., 1997), was mutually exclusive with Osf2/Cbfa1 expression during vertebrae development. Mgp-expressing chondrocytes surrounded the ossification centers where Osf2/Cbfa1-expressing cells resided.

In summary, Osf2/Cbfa1 expression occurs early during skeletal development, is restricted to cells of the mesenchymal condensations and of the osteoblast lineage and can be detected before osteoblasts are fully differentiated and able to mineralize a matrix. Moreover, Osf2/Cbfa1 transcripts are detectable in all bones examined, regardless of their embryologic origin and their mechanisms of ossification: intramembranous or endochondral. This early expression of Osf2/Cbfa1 strongly suggests that it may regulate the expression of multiple gene in developing osteoblasts.

5.1.2.4 OSF2/CBFA1 Expression is Regulated by Osteoblast Differentiating Agents

Next it was asked whether Osf2/Cbfa1 expression was regulated by vitamins, growth factors and hormones known to affect osteoblast differentiation and if it preceded the expression of known markers of the osteoblast phenotype in in vitro models of osteoblast differentiation. The MC3T3-E1 cells (Sudo et al., 1983) are derived from mouse calvaria. They do not express osteoblast-specific genes such as Bone sialoprotein (Bsp) or Osteocalcin unless they are cultured for 6 to 8 days in the presence of ascorbic acid, an agent known to promote osteoblast differentiation (Reynolds, 1967). As shown in FIG. 4A, Osf2/Cbfa1 was the first gene characteristic of the osteoblast phenotype to be expressed in MC3T3-E1 cells treated with ascorbic acid. Its expression preceded Bsp and Osteocalcin expression of several days. The C3H10T1/2 fibroblasts are not committed to the osteoblast lineage and do not normally express any osteoblast-specific genes. However, treatment of these cells with BMP2 and BMP7 can induce osteoblast differentiation (Piccolo et al., 1996). When C3H10T1/2 cells were cultured in the presence of BMP7 alone, Osf2/Cbfa1 expression was induced before the expression of Osteocalcin and Osteopontin (FIG. 4B). Lastly, $1,25(OH)_2D_3$, one of the major hormones regulating bone remodeling, inhibits mouse Osteocalcin expression. This effect involves the abolition of binding of osteoblast nuclear extracts to OSE2 (Zhang et al., 1997). Consistent with this observation, treatment of primary mouse osteoblasts with $1,25(OH)_2D_3$ nearly abolished Osf2/Cbfa1 expression (FIG. 4C).

5.1.2.5 OSF2/CBFA1 Affects Gene Expression in Osteoblasts

The developmental pattern of expression of Osf2/Cbfa1 suggests that it may be required for the establishment of the osteoblast phenotype and therefore should regulate the expression of the principal genes expressed in osteoblasts. The inventors searched for OSE2-like elements in the promoter of genes such as, Osteocalcin gene 1 (OG1), $\alpha 1(I)$ collagen, Bsp, and Osteopontin and in each case found such element. The ability of these various OSE2 elements to bind Osf2/Cbfa1 was examined by EMSA using as probes oligonucleotides covering each site and as source of proteins osteoblast nuclear extracts or His-Osf2/Cbfa1. In each case, when using osteoblast nuclear extracts, the generation of a protein DNA-complex that could be competed away by a wild-type OSE2 oligonucleotide but not by a mutant OSE2 oligonucleotide was observed (FIG. 5A). Likewise, His-Osf2/Cbfa1 was found to bind labeled oligonucleotides containing the OSE2 sequences present in OG1, $\alpha 1(I)$ collagen, BSP and Osteopontin promoters (FIG. 5B).

The functional relevance of the binding of Osf2/Cbfa1 to the promoter of these genes was tested by DNA cotransfection studies and by oligonucleotide antisense studies. In DNA cotransfections the activity of a fragment of the mouse Osteopontin promoter that includes the OSE2 sequence was increased 4-fold upon cotransfection with Osf2/Cbfa1 expression vector in F9 cells while a deletion of this element abolished this effect (FIG. 5C). In a different assay Osf2/Cbfa1 antisense oligonucleotides were transfected in ROS17/2.8 osteoblastic cells and RNA harvested 40 h later. The Osf2/Cbfa1 antisense oligonucleotide but not the control oligonucleotide led to an abolition of $\alpha 1(I)$ collagen expression, and a marked decrease in the level of expression of Osteocalcin, and Osteopontin (FIG. 5D). Inhibition of the expression of these genes was not due to a toxic effect of the treatment since cell viability was identical in the antisense oligonucleotides treated and control plates. These studies indicate that Osf2/Cbfa1 regulates expression of important genes expressed in osteoblasts and suggest that Osf2/Cbfa1 may be required for the establishment of the differentiated osteoblast phenotype.

5.1.2.6 OSF2/CBFA1 Induces Osteoblast Differentiation of Non-Osteoblastic Cell Lines Taken together, the results presented above raised the hypothesis that Osf2/Cbfa1 could induce osteoblast differentiation of non-osteoblastic cells. To test this hypothesis DNA transfections were performed of two cell lines that normally express neither Osf2/Cbfa1 nor genes characteristic of the osteoblasts phenotype such as $\alpha 1(I)$ collagen, Bsp, and Osteocalcin. The MC3T3-E1 calvarial cells are considered to be undifferentiated cells committed to the osteoblast lineage. They do not express osteoblast specific genes when cultured in the absence of ascorbic acid. Northern blot analyses of MC3T3-E1 cells transiently transfected with Osf2/Cbfa1 cDNA or with the empty vector showed that forced expression of Osf2/Cbfa1 in these cells led to Bsp, Osteocalcin and $\alpha 1(I)$ collagen expression whereas transfection of the empty vector did not have this effect (FIG. 6A).

Another cell line of great interest is the C3H10T1/2 line since these cells are pluripotent fibroblasts that are not committed to the osteoblast lineage. Indeed, they can acquire a myoblast, an adipocyte or even a chondrocyte phenotype but not an osteoblast phenotype following treatment with 5-azacytidine (Taylor and Jones, 1979). Transient transfection of C3H10T1/2 cells with Osf2/Cbfa1 expression vector led to the induction of Bsp, Osteopontin, and Osteocalcin expression while transfection of the empty vector did not (FIG. 6B). This ability of Osf2/Cbfa1 to induce osteoblast gene expression was not observed in transformed or differentiated cell lines such as rat chondrosarcomaor C2C12 myoblasts.

5.1.3 Summary 5.1.3.1 OSF2/CBFA1

Genes controlling cell-specific differentiation in the skeleton are only beginning to be identified. To date, these studies have shed light primarily on chondrocyte and osteoclast differentiation (Karaplis et al., 1994; Wang et al., 1992; Johnson et al., 1992). To understand the mechanisms of osteoblast differentiation, the inventors studied the regulation of expression of Osteocalcin, the most osteoblast-specific gene. The inventors report here the cloning of Osf2/Cbfa1, the first osteoblast-specific transcription factor that has many features of a determinant of osteoblast differentiation.

Several experimental arguments indicate that Osf2/Cbfa1 is encoded by the Cbfa1 gene, one of the three known mouse homologues of the Drosophila genes runt and lozenge (Kania et al., 1990; Ogawa et al., 1993a,b; Daga et al., 1996). First, the analysis of the genomic structure of Cbfa1 showed exons encoding Osf2 5' end separated from the exon encoding the Glutamine/Alanine domain by a large intron. Second, genetic evidence in human and mouse demonstrates the role of Cbfa1 in osteoblast differentiation in absence of any other abnormality. Third, in RT-PCR™ studies, the inventors could only amplify sequences corresponding to the 5' end of Osf2/Cbfa1 raising the possibility that the 5' sequence originally ascribed to Cbfa1 is unrelated to this gene. Extensive PCR™ analysis with oligonucleotides designed to amplify novel CbfAs and repeated screening of the mouse osteoblast cDNA library at low stringency have failed to identify other Cbfa transcripts indicating that Osf2/Cbfa1 is the predominant if not the only Cbfa transcript expressed in osteoblasts.

5.1.3.2 OSF2/CBFA1 Expression and Regulation

The osteoblast differentiates from a mesenchymal progenitor through an unknown genetic pathway. Since there is no morphologic feature specific of the osteoblast the osteoblast phenotype can only be defined by the concomitant expression of several genes: Type I collagen, Bone sialoprotein, and Osteocalcin which is the most specific to osteoblast, and other less specific genes such as Osteopontin, and by the ability to mineralize an ECM (Aubin and Liu, 1996). The first identifiable osteoblast appears relatively late during development at 14.5 dpc in the mouse (Kaufinan, 1992).

In situ hybridization studies show that Osf2/Cbfa1 is the earliest molecular marker of the osteoblast lineage. Its expression could already be observed in mesenchymal condensations of the developing skull, axial, and appendicular skeleton in 12.5 dpc embryos. Importantly, at that stage of skeletal development, the cells present in the mesenchymal condensations of the future axial and appendicular skeleton express many genes specific of the chondrocyte phenotype (Horton, 1993). The expression of Osf2/Cbfa1 in these cells at 12.5 dpc indicates that they may have the potential to become osteoblasts, and implies that there may be a common progenitor cell for the osteoblast and the chondrocyte in the mesenchymal condensations. At later stages of skeletal development, in 14.5 dpc and 16.0 dpc embryos when cell differentiation is more advanced, Osf2/Cbfa1 expression was restricted to the subset of cells that will become osteoblasts or that had already osteoblast features but was not detectable in differentiated chondrocytes. No other cell types in developing mouse embryos expressed Osf2/Cbfa1 to a detectable level.

Consistent with its expression in osteoblast progenitors, Osf2/Cbfa1's expression was regulated by growth factors and hormones affecting osteoblast differentiation. The BMPs are secreted signaling molecules that can induce the cascade of events leading to bone formation during development (Kingsley, 1994). Here, BMP7 was shown to induce Osf2/Cbfa1 expression in cells where it is not normally expressed, raising the hypothesis that Osf2/Cbfa1 may be one of the nuclear targets in the BMP signal transduction pathway in osteoblasts. It was shown earlier that in mouse, Osteocalcin expression is down regulated by $1,25(OH)_2D_3$ through an indirect mechanism. $1,25(OH)_2D_3$ treatment of primary osteoblast culture abolishes binding of osteoblast nuclear extracts to OSE2 (Zhang et al., 1997). The down regulation of Osf2/Cbfa1 expression by $1,25(OH)_2D_3$ reported here is in agreement with previous studies performed using crude nuclear extracts (Zhang et al., 1997) and is consistent with a growing body of clinical evidence suggesting that $1,25(OH)_2D_3$ may prevent osteoblast terminal differentiation and causes aplastic bone disease (Goodman et at, 1994).

5.1.3.3 OSF2/CBFA1 Function During Osteoblast Differentiation

Osf2/Cbfa1 pattern of expression and its regulation by a BMP suggest that it may play a much broader role in osteoblast-specific gene expression and differentiation. Consistent with this hypothesis, Osf2/Cbfa1 binding sites were identified in the promoter of four genes mostly expressed in osteoblasts: the two Osteocalcin genes, α1(I) collagen, Bsp, and of another gene, Osteopontin, which is expressed in osteoblasts and other cell types. Each of these elements was able to bind the Osf2/Cbfa1 activity present in osteoblast nuclear extracts as well as recombinant Osf2/Cbfa1. The functional relevance of these Osf2/Cbfa1 binding sites is supported by three different lines of evidence. First, in DNA cotransfection studies Osf2/Cbfa1 increased the activity of a fragment of the Osteopontin promoter or the Osteocalcin promoter containing an OSE2 element. Second, oligonucleotide antisense studies showed a dramatic decrease in the level of α1(I) collagen, Osteocalcin, and Osteopontin expression in an osteoblast cell line. Third, and more important, analysis of Osf2/Cbfa1 function indicated that it is sufficient for osteoblast differentiation as assessed by the induction of osteoblast-specific genes expression in non-osteoblast cells in cell culture studies. This ability of Osf2/Cbfa1 to induce osteoblast-specific gene expression in non-osteoblast cells suggests that Osf2/Cbfa1 is required for the differentiation of mesenchymal cells along the osteoblast lineage in vivo. In agreement with the cell culture studies Cbfa1-deficient mice lack osteoblasts.

5.1.3.4 OSF2/CBFA1 and Skeletal Diseases

Many skeletal dysplasias and familial forms of osteoporosis have yet to be explained at the molecular level. For a transcription factor like Osf2/Cbfa1 to be responsible for a genetic disease it would have to be a generalized defect involving intramembranous and endochondral bone formation. Genetic mapping of Cbfa1 showed that it maps at the same location as the gene responsible for cleidocranial dysplasia in humans (Mundlos et al., 1995) and in mice (Ccd mouse mutant, Sillence et al., 1987). Moreover, molecular analysis detected non-sense mutations of the Cbfa1 gene in patients with cleidocranial dysplasia and strong genetic evidence indicates that Cbfa1 is deleted in the Ccd mouse, demonstrating the importance of this gene in osteoblast differentiation in vivo. The functional analysis of each domain of Osf2/Cbfa1 is not completed but the existence of a long stretch of alanine residues at its N-terminal end is striking. A mutation lengthening the alanine stretch in Hoxd13 causes synpolydactyly, an inherited skeletal malformation of the hands and feet (Muragaki et al., 1996). It is possible that lengthening of the alanine stretch in Osf2/Cbfa1 could cause disorders of bone, such as familial forms of juvenile osteoporosis. Lastly, Osf2/Cbfa1 belongs to a family of transcription factors involved in oncogenic transformation, and for which rearrangements have been shown to cause leukemia (Okuda et al., 1996; Speck and Tracy, 1995). Thus, it will be important to search for rearrangements of the Cbfa1 gene in osteosarcoma, the most frequent malignant bone tumor.

5.2 Example 2

Genomic Organization, Expression of the Human CBFA1 Gene

The runt/Cbfa gene family is highly conserved between Drosophila and human (Kagoshima et al., 1993; Ogawa et al., 1993a,b). These genes encode transcription factors whose DNA binding domain, the runt domain, is a 128 amino acid polypeptide whose amino acid sequence is highly conserved between Drosophila and human proteins. Three human CBFA genes, CBFA1, CBFA2 and CBFA3, have recently been identified (Levanon et al., 1994; Ahn et al., 1996; Wijmenga et al., 1995). CBFA2, formerly known as AML-2, has been the focus of many investigations since it is disrupted in the t(8;21) translocation observed in some forms of acute myelogenous leukemia (Speck and Tracy, 1995; Nucifora and Rowley, 1995; Ito, 1996). Consistent with this clinical observation, deletion of the Cbfa2 gene through gene targeting in mice leads to an arrest in hematopoiesis early during development (Wang et al., 1996a,b).

Example 1 described the important biological properties of another member of this family, CBFA1. It showed that Osf2/Cbfa1, a transcript of the mouse Cbfa1 gene is an osteoblast-specific transcription factor that controls the expression of many genes expressed in osteoblasts and can induce osteoblast differentiation of nonosteoblastic cells. Otto et al. (1997) showed that the deletion of the Cbfa1 gene in mice leads to a total absence of osteoblasts due to an arrest in their differentiation. Cbfa1 maps to mouse chromosome 17 and to human chromosome 6p21 (Bae et al., 1995; Levanon et al., 1994). Cleidocranial dysplasia (CDD), a defect in skeletal ossification, has been mapped to these chromosomes in mouse and human, respectively (Sillence et al., 1987; Mundlos et al., 1995). CCD is an autosomal dominantly inherited generalized skeletal disorder characterized by aplasia of the clavicles, delay in closure of the fontanelles and cranial sutures, brachycephalia, prognathism, irregularities in dentition and structural abnormalities of most of the bones of the skeleton. Otto et al. (1997) showed strong suggestive evidence that Cbfa1 is deleted in mouse CCD, Mundlos et al. (1995) showed deletion of CBFA1 and nonsense mutations in patients with CCD and identified two missense mutations in the CBFA1 gene that abolish DNA binding. Thus, CBFA1 appears to be an important regulator of osteoblast differentiation in mouse and human.

During the cloning and characterization of the mouse Osf2/Cbfa1 cDNA, 5' sequences were uncovered that were previously unknown in any Cbfa1 transcript. This finding and the biological importance of this gene in human and mouse skeletal development prompted the cloning and analysis of the human Osf2/Cbfa1 cDNA and the human Osf2/Cbfa1 gene. This example describes the cloning and characterization of the human gene.

5.2.1 Materials and Methods 5.2.1.1 Cloning of the OSF2/CBFA1 cDNA

Cloning of the human OSF2/CBFA1 cDNA was performed by RT-PCR™ using SaOS-2 osteosarcoma cells as source of total RNA. Total RNA was prepared using the guanidium thiocyanate-CsCl gradient method (Sambrook et al., 1989). The cDNA was generated using an oligo(dT) primer or a primer (5'-GATACGTGTGGGAT-3'; SEQ ID NO:24) designed from the partial human CBFA1 cDNA sequence available in the GenBank. The complete coding sequence was generated by amplification through PCR™ of four overlapping fragments. The primers used for the amplification were designed according to the mouse Osf2/Cbfa1 cDNA sequence:

FA5'-CTGTGAGGTCACCAAACCACATGATTCTG-3' (SEQ ID NO:25)
RA5'-GCTTTGCTGACACGGTGT-3' (SEQ ID NO:26)
FB5'-TACCAGCCACCGAGACCAACC-3' (SEQ ID NO:27)
RB5'-CTGGTCAATCTCCGAGGG-3' (SEQ ID NO:28)
FC5'-AGAGGTACCAGFATGGGAT-3' (SEQ ID NO:29)
RC5'-CGGGGACGTCATCTGGCTC-3' (SEQ ID NO:30)
FD5'-CTGAGCCAGATGACGTCC-3' (SEQ ID NO:31)
RD5'-GATACCACTGGGCCACTGC-3' (SEQ ID NO:32)

Each PCR™ product was subcloned in pBluescript (Stratagene, La Jolla, Calif.) and sequenced. The full length cDNA was then generated using unique restriction sites as cloning sites.

5.2.1.2 Souther Blot Analysis

For Southern blot analysis, human genomic DNA prepared from spleen tissue (Strauss, 1994) was digested with various restriction endonucleases (HindIII, BamHI, SpeI, XbaI and EcoRI), fractionated on a 0.8% agarose gel in 1×TBE and transferred onto Hybond-N$^+$® membrane (Amersham, Arlington Heights, Ill.). The hybridization was performed using radiolabeled Osf2/Cbfa1 cDNA as a probe and washed at 65° C. in 0.2×SSC/0.1% SDS for 30 min twice.

5.2.1.3 Cloning of the Human CBFA1 Gene

To elucidate the genomic organization of the CBFA1 gene several libraries of human genomic DNA were used. A λ-FixII human genomic library (Stratagene, La Jolla, Calif.) was screened using several radiolabeled probes derived from the cDNA (FIG. 7A). The probes 1, 2, 3, 4, and 6 were generated by restriction digestion of the full-length cDNA and probe 5 by PCR™ amplification. Hybridization was carried out at 52° C. overnight in 6×SSC/10% dextran sulfate/5×Denhardt's solution/0.5% SDS/20% formamide/200 µg/ml denatured fish sperm DNA. The washings were performed at 0.1% SDS in SSC buffer. Washing conditions such as time, temperature and SSC concentration were adapted to the length of the probe. The insert of the isolated Cbfa1 λ phage clones were subcloned into pBluescript® and characterized by restriction digest. Overlapping inserts were further analyzed by hybridization analysis using oligonucleotides as probes in order to determine the position of the intron-exon boundaries as well as limited DNA sequencing. This analysis failed to generate clones covering the entire gene and prompted the screening of a human PAC library.

The human genomic PAC library was screened by two rounds of PCR™ amplification and by Southern blot hybridization. Two sets of oligonucleotide were used. The first set was located in the runt domain:

F65'-GGCACAGACAGAAGCTTGATGAC-3' (SEQ ID NO:33)
R65'-CTGTAATCTGACTCTGTCCTTG-3' (SEQ ID NO:34)

and the second at the 5' end of the cDNA:

FE5'-TACCAGCCACCGAGACCAACAGAG-3' (SEQ ID NO:35)
RE5'-GTTTTGCTGACATGGTGTCAC-3' (SEQ ID NO:36).

The Southern blot was hybridized with the full length cDNA as described below. A 1.8 kb BamHI/BglII restriction fragment of the PAC genomic clone that covered the 5' end of the gene was subcloned into the BamHII site of pBluescript® plasmid in order to determine the transcription starting site by primer extension.

5.2.1.4 Determination of Intron-exon Boundaries

A Southern blot analysis from each positive clone digested with BamHI, HindIII, EcoRI and NotI was hybridized with oligonucleotides (18 to 28 mers) containing various parts of the cDNA sequence. Oligonucleotides were purchased from Genosys (Houston, Tex.) and end-labeled by T4 polynucleotide kinase (Pharmacia, Piscataway, N.J.). The Southern hybridization was carried out as previously described (Brown, 1993) and the membranes were rinsed with 6×SSC, 0.01% sodium pyrophosphate at 45° C. for 10 min. The nucleotide sequences of intron-exon boundaries were determined by the dideoxynucleotide chain termination method (Sequenase® v.2.0, United States Biochemical Corp., Cleveland, Ohio) using appropriate oligonucleotides as primers. The genomic sequences were compared with the cDNA sequence to establish the intron-exon boundaries.

5.2.1.5 Primer Extension Analysis

Total RNA was isolated from the SaOS-2 human osteosarcoma cell line. A synthetic oligonucleotide specific for CBFA1 transcripts corresponding to the CBFA1 cDNA sequence from +25 to +53 was designed as follows:

5'-TTTGTTGGTGTCTTGGTGTTCACGCCAC-3' (SEQ ID NO:37)

Primer extension studies were performed as previously described (Chen, 1990). Reverse transcription studies were carried out for 1 h at 45° C. with AMV reverse transcriptase as specified by the manufacturer (Life Science Inc., St. Petersburg, Fla.). After alkaline hydrolysis of the RNA, the extended products were ethanol precipitated and electrophoresedin a denaturing 6% polyacrylamide gel together with a sequencing reaction.

5.2.1.6 Long-Expand PCR™ Amplification

Two hundred ng to 1 μg of phage, PAC or human genomic DNA was used as template to amplify the introns and determine the position of the intron-exon boundaries of the human Osf2/Cbfa1. The primers were designed along the cDNA sequence to confirm the intron-exon structure already described (Ogawa et al., 1993a) for the mouse homologue:

(Intron 1, FE and RE;

Intron 3, F13, 5'-GTGGAGATCATCGCCGACC-3', (SEQ ID NO:38)

R4, 5'-CTCGTCCACTCCGGCCCAC-3'; (SEQ ID NO:39)

Intron 4, F4, 5'-GTGGTAGCCCTCGGAGAGGTAC-3', (SEQ ID NO:40)

R5,5'-TTCTGGGTTCCCGAGGTC-3'; (SEQ ID NO:41)

Intron 5, F5, 5'-GCAAGAGTTTCACCTTGACC-3', (SEQ ID NO:42)

R6; Intron 6, F6 and R7, 5'-CTGAAATGCGCCTAGGCACATC-3'; (SEQ ID NO:43)

Intron 7, F7, 5'-ACCCCAGGCAGGCACAGTC-3', (SEQ ID NO:44)

R8, 5'-CTGCCTGGCTCTTCTTACT-3'; (SEQ ID NO:45)

Intron 9, F9, 5'-ATGATGACACTGCCACCTCTG-3', (SEQ ID NO:46)

RD, 5'-GATACCACTGGGCCACTGC-3') (SEQ ID NO:47).

The amplification was performed using the long-expand template PCR™ kit (Boehringer Mannheim, Indianapolis, Ind.) and was carried out according to the manufacturer's recommendations. The DNA fragments were purified from 0.7% agarose gel and sequenced using internal primers.

5.2.1.7 Northern Blot Analysis

Total RNA was isolated on guanidium thiocyanate-CsCl gradient from various human tissues, from human cell lines or from human transformed fibroblasts and chondrocytes as previously described (Sambrook et al., 1989). The RNA were loaded on a 1% formaldehyde-agarose gel and transferred onto Hybond-N+ nylon membrane (Amersham, Arlington Heights, Ill.). The filter was hybridized with a probe specific for the hOsf2/Cbfa1 gene located in the 5' end of the cDNA (FIG. 7A, probe 1). The 18S rRNA probe was used as an internal control. The hybridization was carried out at 60° C. in 6.6% SDS/0.33 M sodium phosphate buffer pH 7.2 and the washings performed at 60° C. in 0.2×SSC/0.1% SDS two times each 30 min.

5.2.1.8 DNA Transfection Studies

The mouse F9 teratocarcinoma cell line was used for the DNA transfection studies. The cells were plated on 10-cm dishes at a density of 5×10$^5$ cells/dish. Cells were transfected by the calcium phosphate coprecipitation method (Chen and Okayama, 1987), using 5 μg of reporter plasmid, 5 μg of expression plasmid and 2 μg of pRSV/βGal as previously described (Geoffroy et al., 1995). The p6OSE2-luc plasmid containing six copies of the wild-type OSE2 oligonucleotide in front of the −34/+13 mOG2 promoter-luciferase (luc) was used as reporter plasmid (Ducy and Karsenty, 1995). The pCMV-hOSF2/CBFA1a and pCMV-hOSF2/CBFA1b were used as expression plasmids. They contain respectively the full length hOSF2/CBFA1a cDNA and the hOSF2/CBFA1b cDNA lacking exon 8 in correct orientation downstream from the CMV promoter. Luciferase and β-galactosidase activities were assayed as previously described (Geoffroy et at, 1995).

5.2.2 Results 5.2.2.1 Isolation and Characterization of 2 Full Length Human OSF2/CBFA1 cDNAs The human OSF2/CBFA1 cDNA was cloned by RT-PCR™ using SaOS-2 human osteosarcoma RNA. Surprisingly, two cDNAs, OSF2/CBFA1a and OSF2/CBFA1b, were generated. OSF2/CBFA1a had an open reading frame of 521 amino acids. The homology with the mouse Osf2/Cbfa1 was 98% at the amino-acid level (FIG. 7B). The glutamine/alanine rich domain at the N terminal, the runt domain and the proline/serine/threonine(PST) rich domain were all present. hOSF2/CBFA1b had the same nucleotide sequence except for a 66 bp in-frame deletion in the PST domain.

This 66-bp segment encodes a putative 22 amino-acid exon that was not present in the partial human CBFA1 cDNA deposited in GenBank. Since this in-frame deletion is located in the putative transcriptional activation domain, DNA co-transfection studies were performed to test if its absence affects the transcriptional activity of the protein.

The DNA co-transfection studies were performed in the F9 mouse teratocarcinoma cell line that does not express any of the Cbfa1 genes. The reporter plasmid contained the luciferase (luc) gene driven by the minimal −34/+13 mouse osteocalcin gene 2 (mOG2) promoter and six copies of the wild-type OSE2 oligonucleotide cloned upstream (p6OSE2-luc). The expression vectors contained either the OSF2/CBFA1a or OSF2/CBFA1b driven by the CMV promoter. Transfection of OSF2/CBFA1a leads to a 75-fold increase in luciferase activity of p6OSE2-luc while co-transfection using OSF2/CBFA1b leads to a 40-fold increase in luciferase activity, indicating that these 22 amino acids are part of the transcription activation domain of OSF2/CBFA1 (FIG. 8).

The nucleotide sequence of the 5' untranslated region (5'UTR) in the OSF2/CBFA1a and OSF2/CBFA1b are identical to each other and closely related to the same sequences described in the mouse Osf2/Cbfa1 cDNA but differ completely from the originally described sequence of the mouse Cbfa1 transcript (Ogawa et al., 1993a) (FIG. 7C). To address this discrepancy, oligonucleotides containing sequences either of the 5'UTR of the previously published mouse Cbfa1 cDNA (Cbfa1) or of the 5'UTR of OSF2/CBFA1 cDNAs were generated and used to perform RT-PCR™ using a 3' primer located at the 5' end of the runt domain. This 3' primer contains sequences that are identical in both human and mouse. As shown in FIG. 9, amplification with the 5'UTR OSF2/CBFA1 oligonucleotide yielded a band of the expected size (FIG. 9, lanes 2–4) and sequence whereas amplification with the 5'UTR Cbfa1 oligonucleotide failed to generate any band in bone RNA (FIG. 9, lanes 6, 7). This result, consistent with the analysis of the mouse transcripts, raised the possibility of a complex splicing pattern at the 5' end of the CBFA1 gene and was an incentive to analyze the genomic structure of the human CBFA1.

5.2.2.2 Expression Analysis

To determine the size of the transcript(s) and the tissue-specific expression of the hOSF2/CBFA1 gene, a Northern blot analysis was performed using total RNA isolated from various human tissues, cell lines and transformed cells (FIG. 10). The hybridization was performed using a probe specific for the human OSF2/CBFA1 gene located in the 5' end of the gene (FIG. 7A). hOSF2/CBFA1 is expressed in osteoblastic cell lines but not in any other cell lines or tissues. This result is in agreement with the osteoblast-specific expression of the gene in mouse. When the same blot was exposed 3 times longer, no transcript in any other cell lines and tissues could be detected. (FIG. 10).

5.2.2.3 Genomic Structure of the OSF2/CBFA1 Gene

Initially, a Southern blot of human genomic DNA digested with different restriction endonucleases (BamHI, HindIII, SpeI XbaI and EcoRI) was probed with the human full length cDNA. As shown in FIG. 11, each reaction digest generated multiple bands that hybridized with this probe.

A human λ-fixII genomic library was screened using six different probes, each of them covering the OSF2/CBFA1 cDNA sequence (FIG. 7A). Multiple positive clones were isolated.

Using restriction enzyme sites present within the cDNA (BamHI, HindIII, EcoRI, NotI) in combination with a Southern blot hybridization analysis, the relative position of the λ clones to each other was determined and a restriction map of the gene was established. Four independent but overlapping clones were selected that covered most of the gene for further analysis (FIG. 10). Hybridization with oligonucleotides located in the exonic sequence, permitted the determination of the relative position of most exons in the gene. At this point of the analysis, the 5' part of the gene was not entirely covered by these clones. Thus, a PAC human genomic library was screened in order to characterize the entire gene structure. Two PAC clones were isolated, one covering the 3' part of the gene (222G16) and the second the 5' part (244F24) (FIG. 11). Similarly, the position of restriction enzyme sites and Southern blot hybridization analysis were used to determine the relative position of the PAC clones to the λ clone-map. Information available regarding the structure of the mouse Cbfa1 gene (Ahn et al., 1996) was also used to determine the putative position of the intron-exon boundaries of the human gene. According to this analysis, oligonucleotides bordering the putative exons were designed in order to amplify from these clones the intronic sequences and to determine by sequencing the intron-exon boundaries. Furthermore, the size of most of the introns was confirmed by PCR™ amplification using the λ phage, PAC and human genomic DNA as template. The intron 1 was identified by direct sequencing after PCR™ amplification of genomic DNA. The long-expand template PCR™ system was needed to amplify most of the other introns (3, 4, 6, 7 and 8) that were too large to be amplified by conventional PCR™ reaction. The relative size of the intron 2 that could not be amplified by this technique was estimated from the established map (FIG. 11).

The size of intron 2 was determined after mapping of the exons 2 and 3 in the restriction map of the PAC 244F24 insert. The same oligonucleotides that were used for the intron amplifications were used to sequence through the exons to determine the sequence of the intron-exon boundaries. The length of the introns and the sequence of most intron-exon boundaries are indicated in Table 3. Analysis of the gene sequence shows that the entire coding sequence (1566 bp) is encoded by 8 exons (exons 2 to 9).

TABLE 3

| Exon (bP)[a] | 5' Splice Junction[b] | SEQ ID NO. | Intron (kb)[c] | 3' Splice Junction[b] | SEQ ID NO. | Exon |
|---|---|---|---|---|---|---|
| 1 | AACAGAGTCAgtgagtgctctctaacca | 48 | 1 (0.2) | tatggtttgtattttcagTTTAAGGCTG | 55 | 2 |
| 2 (123) | TTCTTTTGGGgtaagtgttaccattttt | 49 | 2 (75) | tgatgcgtattcccgtagATCCGAGCAC | 56 | 3 |
| 3 (366) | GGCCTTCAAGgtaagaggctaccccgcc | 50 | 3 (4) | gtttcctgttttatgtagGTGGTAGCCC | 57 | 4 |
| 4 (156) | AGTGGACGAGgtaggtctctgactttg | 51 | 4 (10) | cccctttatatctgcagGCAAGAGTTT | 58 | 5 |
| 5 (106) | GAACCCAGAAgtaagtactccccttttt | 52 | GT | atgatttgctatttccagGGCACAGACA | 59 | 6 |
| 6 (174) | NA[d] | | 6 (15) | NA | | 7 |
| 7 (162) | CGCATTTCAGgtaaagaccgtgctttaa | 53 | 7 (3.5) | atcccctcattttacagATGATGACAC | 60 | 8 |
| 8 (66) | AGCCAGGCAGgtgagactttaacaatt | 54 | 8 (2) | ttctgttataatttttagGTGCTTCAGA | 61 | 9 |

[a]Length (bp) of the coding sequence in each exon.
[b]The exonic and intronic sequences are uppercase and lowercase letters, respectively. The gt/ag consensus sequences of splice junctions are indicated in bold. The 5' end of the mouse Cbfa1 coding sequence is underlined.
[c]Approximate length (kb) of the intronic sequences.
[d]NA, Not Available.

5.2.2.4 Determination of the Transciption Start Site of CBFA1

A primer extension study was performed to identify precisely the start site of transcription of CBFA1. In this study, a 28 base oligonucleotide containing sequences corresponding to the first exon of the human CBFA1 gene from +25 to +28 was annealed with 15 μg of total RNA from SaOS-2 cells. SaOS-2 RNA was chosen because the CBFA1 gene is highly expressed in these cells. A sequencing reaction using a genomic clone as a template and the same oligonucleotide as primer run in parallel with the primer extension identified a single start site (FIG. 12).

5.2.2.5 Evidence of Alternative Splicing of Exon 8

As discussed above, the 5' end of the human and mouse OSF2/CBFA1 cDNAs is different from the 5' end of the previously reported CBFA1 transcript. Interestingly, the sequence originally described as the 5' end of CBFA1 is entirely present at the 3' end of the 75 kb intron 2. This result suggests the existence of a cryptic splice acceptor site in this large intron. Once the complete genomic structure of the CBFA1 gene has been deciphered, this information was used to determine unambiguously that the 66 bp in frame deletion in OSF2/CBFA1b cDNA was due to an alternative splicing event around exon 8. Primers corresponding to sequences present in exons 7 and 9 were designed and used in an RT-PCR™ reaction using SaOS-2 osteosarcoma cells as a source of RNA. As shown in FIG. 12, two distinct bands were generated. The upper band contained sequences of exons 7, 8 and 9, while the lower band contained only sequences of exons 7 and 9.

It is clear that (1) the human CBFA1 gene is composed of 9 exons and 8 introns spanning at least 120 kb; (2) there is evidence of alternative splicing events at the 3' end of the gene that affects the function of the protein; (3) the 5' end of the gene is very similar to the 5' end of the mouse OSF2/CBFA1 cDNA and is unrelated to the 5' end of the originally described mouse Cbfa1 transcript; (4) in fact, the 5' end of the originally described CBFA1 transcript is present at the end of intron 2; and (5) as is the case in the mouse, the gene is expressed only in cell of osteoblastic origin. The human CBFA1 gene is mutated in CCD and is thought to be a master gene responsible for osteoblast differentiation in vertebrates.

5.3 Example 3

Expression Cloning in E. Coli

Based on the Southwestern assay it is possible to perform a Southwestern screening of a bacterial expression library. In this assay a cDNA library is cloned into a bacterial expression vector and screened with labeled monomers or multimers of OSE2. The library is plated and 5 protein-fusion expression is induced by incubation on filters impregnated with IPTG. A $^{32}$P labeled single or concatenated wt OSE2 oligonucleotide is used to probe the filters, using the same buffer as the one used in GRA. Positive phage clones are replated and probed as for the first screening until they reach 100% purity. The specificity of binding of positive clones is tested on a fourth screening by probing filters with the wt probe and its mutated version(s), to determine whether the positive clones isolated fail to bind to multimers of a mutated OSE2 sequence.

5.4 Example 4

Yeast One-Hybrid Cloning System

In this procedure, the OSE2-binding site is cloned upstream of an inactive yeast promoter linked to the His3 gene. A cDNA library is cloned into a yeast expression vector in which the polypeptides encoded by the cDNAs are fused to the acidic transcription activation domain of the yeast transcription factor Gal 4. If a cDNA encodes a polypeptide that binds the OSE2 sequence, colonies become His$^+$. This system can be considered a eukaryotic Southwestern cloning system. The advantage of this yeast cloning system over the Southwestern cloning system of bacterially-expressed protein is that the selection occurs in the yeast cells with a processed protein and in the presence of TBP-associated factors (TAFs), histones, and other chromatin proteins.

5.5 Example 5

Analysis of Transcriptional Activity of OSF2/CBFA1

Using a clone consisting of a large fragment (50 kb) of 5' untranslated sequence of the Osf2/Cbfa1 gene, the transcriptional activity of this large promoter fragment may be analyzed by generating 5' deletion mutants of this promoter, fusing them to the bacterial lacZ gene and generating transgenic mice by pronuclei injection. The activity of the various promoter fragments may be analyzed by staining with β-galactosidase transgenic mice harboring promoter fragments of various size. To obtain additional regulatory elements beyond the initial 50 kb clone, larger fragments (i.e. up to about 500 kb) of the 5' untranslated sequence may be isolated, as well as long fragments up to about 500 kb of 3' untranslated sequence.

To identify protein(s) which interact with Osf2/Cbfa1, a radiolabeled Osf2/Cbfa1 polypeptide may be used to screen an osteoblast expression library. Portions of Osf2/Cbfa1 cDNA may also be used as "baits" to look for gene product (s) interacting with it through the use of the yeast two-hybrid system. In this system, the "prey" is an osteoblast cDNA library, a somite cDNA library, or a cDNA library prepared from mesenchymal condensations. Genes isolated using one of these two assays are then sequenced, their pattern of expression characterized by Northern blot analysis and in situ hybridization and their function defined by gene deletion studies.

To study the regulation of expression of Osf2/Cbfa1 by hormones such as vitamin D3, sexual steroids, glucocorticoids and parathromone, morphogens such as retinoic acids and growth factors such as sonic, Indian and desert hedgehogs, the bone morphogenetic proteins, the fibroblast growth factors and the parathormone related peptide, nonosteoblastic cells or primary osteoblasts may be placed in culture and treated with one or more of the hormones, morphogens, growth factors or vehicle.

Osf2/Cbfa1 cDNA may also be placed in front of an osteocalcin promoter or an α1(II) collagen promoter to prepare constructs used to generate transgenic mice, to overexpress the gene in osteoblasts, or ectopically express it in chondrocytes.

In related studies, the inventors contemplate the generation of a mouse strain where the Osf2/Cbfa1 gene is inactivated only after birth. Such an animal is contemplated to be useful in the creation of an animal model for osteoporosis.

5.6 Example 6

Two OSF2/CBFA1 Domains Determine Transactivation Function and Inability to Heterodimerize with CBFβ

The Runt/Cbfa family of proteins comprises a group of transcription factors that have recently emerged as major regulators of organogenesis in invertebrates and vertebrates. This family includes Runt and Lozenge, two Drosophila proteins (Kania et al., 1990; Daga et al., 1996), and Cbfa1, 2, and 3, in mouse and human (Ogawa et al., 1993a; Bae et al., 1993; Bae et al., 1995). In addition, Runt homologs have been identified in C. elegans and sea urchin (Ito and Bae, 1997; Coffman et al., 1996). This evolutionary conservation further underscores the biological importance of these proteins. Genetic and biochemical analyses in Drosophila, mice, and humans have shown that runt and lozenge in Drosophila, Cbfa2 and Osf2 in mice and humans play crucial roles in neurogenesis, eye development, hematopoiesis, and skeletogenesis, respectively (Kania et al., 1990; Daga et al., 1996; Okuda et al., 1996; Ducy et al., 1997; Komori et al., 1997; Lee et al., 1997; Mundlos et al., 1997; Otto et al., 1997).

The mechanism by which these transcription factors control various cell differentiation programs and organogenesis processes remains largely unknown. All the Runt-related proteins share a common 128 amino acid motif called the runt domain that acts as their DNA-binding domain (Kagoshima et al., 1993). Runt and the Cbfa proteins bind to the consensus site 5'-TGT/cGGT-3' (Meyers et al., 1993), which is found in the control regions of numerous genes involved in various developmental processes. These proteins are capable of binding to DNA as monomers, but it has been shown that both Runt and Cbfa2 (formerly known as AML1), can heterodimerize with a ubiquitously expressed partner protein called Cbfβ (Golling et al., 1996; Ogawa et al., 1993b). Cbfβ does not directly bind to DNA, but increases the affinity of Runt and Cbfa2 for DNA (Golling et al., 1996; Bae et al., 1994).

Mice heterozygous for the Cbfa1 inactivation have a delay in ossification, recapitulating the phenotype of a classical mouse mutant termed cleidocranial dysplasia (ccd) (Selby and Selby, 1978; Sillence et al., 1987). In humans, there is also a skeletal dysplasia called CCD, and the phenotype of the patients is similar to that observed in mouse CCD (Jones, 1997). CCD patients have been shown to have either deletion, insertion or missense mutations in the CBFA1 gene that abolish DNA-binding (Mundlos et al., 1997; Lee et al., 1997). Taken together, these results demonstrate that Osf2 is a key regulator of skeletogenesis whose function is nonredundant with the function of other genes and whose level of expression must be kept within tight limits.

In contrast to the wealth of knowledge available for the other members of this family, such as runt and Cbfa2, nothing is known about the mechanisms by which Osf2 controls osteoblast gene expression. A comparison of Osf2 and the other Runt-related proteins reveals the existence of two regions conserved with other members of this family: the runt domain, and the PST domain located at the C-terminal end of the runt domain (FIG. 13). However, Osf2 contains three domains that are not present in other Runt-related and Cbfa proteins (FIG. 13). The first one is a stretch of 19 amino acid residues at the amino terminus that was not present in the original partial cDNA of Cbfa1 (Ogawa et al., 1993a). The second is a unique glutamine-alanine domain (QA domain) located N-terminal to the runt domain. This domain contains 29 glutamine residues in a row, followed by a stretch of 18 alanine residues. Mutational analysis in CCD patients suggests that the alanine stretch within the QA domain influences the transcriptional activity of the protein, although it must be said that the phenotype of the patients is different from the classical CCD phenotype (Mundlos et al., 1997). Finally, there is a stretch of 27 amino acids in the PST domain that has no homology with sequences present in the PST domains of other Runt-related proteins.

To understand the mechanism by which Osf2 controls osteoblast differentiation, the inventors identified domains responsible for nuclear localization, transcriptional functions, as well as domains involved in regulating heterodimerization. Analysis show that Osf2 has a unique functional organization among other Runt-related proteins. Indeed, the first 19 amino acids and the QA domain control largely the transactivation function, and the QA domain additionally prevents heterodimerization of Osf2.

5.6.1 Materials and Methods 5.6.1.1 Plasmids

The Osf2 cDNA cloned in pBluescript KS(-) and pCMV5 (Ducy et al., 1997) was used for generating deletion mutants in the pCMV5 expression vector. Osf2 lacking the 9-amino acid nuclear localization signal (Osf2ΔNLS) was generated by the 2-step PCR™ strategy (Ausubel et al., 1994), using the following oligonucleotides:

5'-GGACGGTCCCCGGGAAGACTCTAAACCT AGTTTG-3' (NLS-F) (SEQ ID NO:62) and

5'-AGGTTTAGAGTCTTCCCGGGGACCGTCCACTG-3' (NLS-R) (SEQ ID NO:63). Osf2Δ1-108 was generated by inserting a 1275 bp NcoI fragment of the Osf2 coding sequence in pCMV5, with the ATG codon in the NcoI site serving as a translational initiator; Δ1-38, by inserting an 1856 bp PstI fragment in PstI-digested pCMV5, with the ATG codon immediately downstream of the PstI site intended to serve as a translational initiator; Δ1-19, by PCR™ amplification of the 5' region of the Osf2 coding sequence using the following primers:

5'-TCAATCG<u>ATG</u>ACTATGGATCCGAGCACCAGC-3' (DEL5° F) (SEQ ID NO:64) and

5'-CGGGGACCGTCCACTG-3' (R3) (SEQ ID NO:65); the PCR™ product was digested with BstEII, and the resulting 5'-end/BstEII fragment was ligated to Δ1-38 that was digested with MluI (end-filled) and BstEII. The ATG codon (underlined) in the DEL5'F primer was intended to serve as the initiator of translation. The QA domain was deleted by removing the, FspI-NotI and NotI-NotI fragments, followed by religation, and A82-96 was generated by removing the NotI fragment, followed by religation of pCMV5-Osf2. A PCR™ amplified molecule that had the Osf2 coding sequence with a 24 bp internal deletion was cloned in pCMV5 to get Δ89-96. Δ(1-38, 82-96) was made by removing the NotI fragment, followed by religation of Δ1-38. Δ258-528 was made by removal of the BsmI-BsmI and BsmI-XbaI fragments from pCMV5-Osf2, followed by religation.

For analysis of the functional domains in the PST region, full-length or fragments of the PST coding sequence were cloned in the vector pSG424 (Sadowski and Ptashne, 1989), in frame with a sequence coding for the GAL4 DNA-binding domain (amino acids 1–147). Fragments of the coding sequence were obtained using suitable restriction sites or were PCR™ amplified using appropriate primers, and cloned.

The constructs GAL4-6x VWRPY-VP16, and GAL4-6x GASEL-VP16 were made by inserting synthetic double-stranded oligonucleotides (that would code for 6 copies of either the VWRPY (SEQ ID NO:69) or the GASEL (SEQ ID NO:75) sequence), in the Asp718 site, in between sequences coding for GAL4DBD and the VP16 activation domain. The TLE2 expression construct was obtained by digesting a TLE2 cDNA with EcoRV and XbaI, followed by ligation to pcDNA3 cut with the same enzymes. Osf2ΔC12 was generated by inserting an EcoRI fragment (obtained from pCMV5-Osf2) into pCMV5 cut with the same enzyme. The reporter plasmid p6OSE2-luc has been previously described (Ducy and Karsenty, 1995), and the pGAL4SV-luc reporter plasmid (that has a luc reporter gene driven by 5 copies of $UAS_G$ cloned upstream of the SV40 minimal promoter) was obtained from Jennifer Philhower, Science Park Research Division, M. D. Anderson Cancer Center, Smithville, Tex.

For bacterial expression of recombinant proteins, the coding sequences for Cbfa2 and Cbfβ were cloned downstream, and in frame, with a sequence coding for six histidine residues in pTrcHis vectors (Invitrogen, San Diego, Calif.). His-Osf2 expression construct has been previously described (Ducy et al., 1997). For the domain-swapping study, the Chimeric construct 1.2.2 was generated by PCR™ amplifying fragments of Osf2 and Cbfa2 coding sequences, and ligating them in frame to a sequence coding for six histidine residues in the vector pV2a (Van Dyke et al., 1992). ΔN19.1.1 was made by removing a BamHI fragment at the 5'-end of the Osf2 coding sequence, followed by religation of the His-Osf2 expression construct. Δ.runt.PST was made by inserting a 1275-bp NcoI fragment in pTrcHis vector. For in vitro binding assays, the Cbfβ coding sequence was cloned in frame with a sequence coding for GST in the expression vector pGEX-2T. The integrity of all the constructs were verified by DNA sequencing.

For in vitro transcription and translation, Osf2Met$^{69}$ was generated by deletion of the 189-bp 5'-end/DraI fragment of the original Osf2 cDNA. Osf2Met$^1$ [the original Osf2 cDNA cloned in pBluescript II KS(-)] and Osf2Met$^{69}$ cDNAs were transcribed and translated in vitro using the TNT kit (Promega, Madison, Wis.), according to manufacturer's instructions, and the labeled proteins were analyzed by SDS-PAGE.

5.6.1.2 Cell Culture and DNA Transfection

The kidney cell line COS7 was grown in DMEM/10% fetal bovine serum (GIBCO-BRL). 3×10$^5$ cells/dish were transfected with 5 μg of reporter plasmid (p6OSE2-luc or pGAL4SV-luc), 5 μg of the expression construct, and 2 μg of pRSVβgal. Following transfection, the cells were washed twice with phosphate-buffered-saline (PBS) and incubated with the appropriate medium for 24 h. Cells were harvested in 0.3 ml of 0.25 M Tris-HCl, lysed by freeze-thawing, and subjected to a colorimetric β-galactosidase activity assay, using resorufm-β-D-galactopyranoside (Sigma Chemical Co., St. Louis, Mo.) as substrate. 20 μl of cell extract was used for measuring luciferase activity with a Monolight 2010 luminometer (Analytical Luminescence Laboratory), using D-luciferin substrate, in luciferase reaction buffer (100 mM Tris-HCl, pH 7.8; 5 mM ATP; 15 mM MgSO$_4$; 1 mM DTT). Luciferase activity values were adjusted to β-gal values to normalize for transfection efficiency.

5.6.1.3 Generation of Recombinant Fusion Proteins, DNA-binding Assays, and In Vitro Binding Assays For protein production, bacterial cells were induced with 2 mM IPTG, and the fusion proteins were enriched using Ni-NTA agarose resin (Qiagen Chatsworth, Calif.) as per the manufacturer's guidelines. DNA-binding assays were performed with 5 fmol of $^{32}$P-labeled double-stranded OSE2 oligonucleotides, in a buffer containing 20 mM Tris-HCl, pH 8.0, 10 mM NaCl, 3 mM EGTA, 0.05% NP-40, 5 mM DTT, and 2 μg of poly (dI.dC).poly (dI.dC), with equivalent amounts of wild type or mutant proteins. The reactions were incubated for 10 min at room temperature and then electrophoresed on a 8% polyacrylamide gel (Ducy et al., 1997). For in vitro binding assays, the GST and GST-Cbfβ proteins were eluted with reduced glutathione or used as such bound to the beads. The proteins were checked for purity and quantified before use. $^{35}$S-labeled Osf2 and Cbfa2 were synthesized in rabbit reticulocyte lysate using coupled in vitro transcription and translation (TNT kit, Promega). Typically, 100 ng of fusion protein bound to glutathione-agarose beads was used for each assay, while the amount of labeled protein in the assay was determined using fluorography. In vitro binding assay was carried out as described in Ausubel et al. (1994).

5.6.1.4 Cellular Fractionation and Immunofluoresence Analyses

1×10$^6$ COS7 cells were transfected with either wild-type Osf2 or Osf2ΔMNLS, using the calcium phosphate coprecipitation method (Ausubel et al., 1994). Cytoplasmic and nuclear fractions were prepared from transfected cells, separated on SDS-PAGE, and subjected to immunoblot analysis with rabbit polyclonal anti-Osf2 antibody (generated against the peptide sequence SFFWDPSTSRRFSPPS (SEQ ID NO:66), present at the N terminus of Osf2) and horse radish peroxidase-conjugated anti-rabbit gig, followed by ECL detection (Amersham, Arlington Heights, Ill.). For immunofluorescence, 2 days after transfection, the cells were plated on slides, washed with PBS buffer and fixed in 3.7% formaldehyde at room temperature for 10 min, followed by permeabilizationwith 0.1% Triton X-100. Blocking was done for 30 min in 5% goat serum/3% BSA. The cells were then incubated with anti-Osf antibody at a dilution of 1:150 in blocking buffer for 1 h at room temperature, followed by a wash with blocking buffer, and then with PBS. Rhodamine-conjugated goat anti-rabbit gig was then used at a dilution of 1:10,000. Slides were then mounted using 50% glycerol, and the staining pattern of Osf2 was visualized by confocal microscopy.

5.6.2 Results 5.6.2.1 Identification of a Myc-related Nuclear Localization Signal (NLS) in OSF2

To identify the transcription activation domain(s) of Osf2 through a deletion mutagenesis approach, the shortest possible NLS in Osf2 was delineated. The NLS was originally assigned to a broad region of the protein containing the runt domain and the entire PST domain of Cbfa1 (Lu et al., 1995). To define a shorter NLS, the inventors compared the sequence of Osf2 to known NLS sequences. Stretches of basic amino acid residues have been shown to be responsible for targeting proteins to the nucleus (Dingwall and Laskey, 1991; Nigg, 1997). The inventors found, overlapping the runt and PST domains of Osf2, a stretch of 9 amino acids (PRRHRQKLD) (SEQ ID NO:67), including 5 basic residues (in bold), that is highly homologous to the known NLS of c-Myc (FIG. 14A). This sequence contains a short motif, RRHR (SEQ ID NO:76), that has been shown to be responsible for nuclear localization of various proteins (Nigg, 1997). Moreover, this 9-amino acid sequence is present at the same location in several other Runt-related proteins (CBFA2, Cbfa2, CBFA3 and SpRunt-1) (FIG. 14A), suggesting that this stretch of amino acids may act as a common NLS in these proteins.

To test whether this 9-amino acid stretch acts as an NLS in Osf2, an in-frame deletion of this motif was constructed in the full-length coding sequence. This mutant Osf2 (Osf2ΔNLS) was cloned in the pCMV5 expression vector (FIG. 14B), and checked for its ability to activate transcription from p6OSE2-luc, a construct containing 6 copies of a canonical Osf2 binding site (OSE2) (Ducy and Karsenty, 1995) in COS7 cells that do not express the Cbfa genes (Kurokawa et al., 1996a). Osf2ΔNLS failed to drive expression of the luc reporter, while wild-type Osf2 did activate transcription under the same conditions (FIG. 14C). To determine that this lack of transactivation by Osf2ΔNLS was due to the inability of the mutant protein to get translocated to the nucleus, cellular fractionation and immunolocalization analyses were performed. Extracts from transfected cells were separated into nuclear and cytosolic fractions and subjected to immunoblot analysis using a polyclonal antibody directed against Osf2. The wild-type protein was found predominantly in the nuclear fraction, whereas Osf2ΔNLS was found only in the cytosolic fraction (FIG. 14D). Lastly, indirect immunofluorescence analysis of transfected cells revealed the presence of the wild-type protein in the nucleus, while Osf2ΔNLS was localized in the cytosol. Thus, these studies identify the 9-amino acid stretch (PRRHRQKLD) (SEQ ID NO:68) as a sequence necessary and sufficient for nuclear localization of Osf2.

5.6.2.2 The First 19 Amino Acids Comprise One Activation Domain

The 5' end of Osf2 has two ATG codons in frame with the predicted coding sequence. The one at position 1 (Met$^1$) is in a poor context for translational initiation, whereas the one at position 69 (Met$^{69}$) is in an appropriate context for translational initiation (Kozak, 1987). To test the respective efficiencies of these two potential translational initiators, two constructs were generated, one containing both ATG codons (Osf2Met$^1$) and the other containing only the second ATG codon (Osf2Met$^{69}$), and tested them in an in vitro transcription/translation assay. As shown in FIG. 15A, Met$^{69}$ is by far the best, if not the only translational initiator. For that reason, the inventors considered the protein initiating from Met$^{69}$ as the full-length protein in the rest of this study.

To identify regions of Osf2 responsible for transcriptional activation, a series of deletion mutants was generated that all contained the NLS and assayed their ability to transactivate the OSE2-dependent luciferase reporter construct (p6OSE2-luc) in DNA cotransfection studies. Surprisingly, a deletion of the entire N-terminal end of Osf2 that left only the runt and PST domains intact (Δ1-108) resulted in an 80% decrease in the transactivation ability of the protein (FIG. 15B). This suggested that, unlike what has been proposed for Cbfa2 (Bae et al., 1994), the major transactivation domain of Osf2 is not located in the PST domain but in the N-terminal part of the molecule. This prompted the inventors to generate additional deletion mutants of this region of Osf2 to delineate the transactivation domains.

A deletion of the first 38 amino acid residues (Δ1-38) which left only the QA, runt, and PST domains intact, led to a 70% decrease in transactivation. This region is made up of two parts: the first 19 amino acids that are unique to Osf2 and are not present in the partial Cbfa1 cDNA initially identified, and the next 21 amino acids that show a high degree of similarity (85%) with the corresponding amino acids of Cbfa2 (FIG. 13). Interestingly, deletion of the first 19 amino acids (Δ1-19) resulted in a 75% decrease in transactivation ability, indicating that they constitute a transactivation domain that is unique to Osf2 and was called AD1 (Activation Domain 1).

5.6.2.3 The QA Domain Forms a Second Activation Domain

The transactivation function of the QA domain was analyzed. Deletion of the QA domain alone (Δ49-96) resulted in a 75% decrease in the transactivation ability of the protein, indicating that the QA domain has a transactivation function. For that reason, this region was termed AD2. The identification of the QA domain as a transactivation domain is generally consistent with the known function of glutamine stretches as activators of transcription (Gerber et al., 1994) and with the fact that lengthening the alanine stretch results in a loss of function of Osf2 in a CCD patient (Mundlos et al., 1997). To assess the respective importance of the glutamine and alanine residues in the QA domain, additional deletion mutants of Osf2 were generated (FIG. 15B). A deletion of 8 of the 18 alanines (Δ89-96) did not affect the transactivation function of Osf2. This is in agreement with genetic analysis demonstrating that similar polymorphisms do not cause phenotype abnormalities in humans (Mundlos et al., 1997). A deletion of 15 of the 18 alanine residues (Δ82-96) also had no effect on the transactivation function of Osf2. Next, the entire N-terminal part of Osf2 (AD1) and 15 of the 18 alanine residues was deleted, leaving in place only the glutamine residues [Δ(1-38,82-96)]. This deletion mutant had the same transactivating ability as Δ1-38 which contains the QA, runt and PST domains, demonstrating that within the QA domain, it is the glutamine stretch that bears most, if not all, of the transactivation function. All of the mutant proteins tested above were found to be expressed in equivalent amounts and were capable of binding to the OSE2 element.

5.6.2.4 Identification of Activation and Repression Domains in the PST Region of OSF2

Deletion of the entire PST domain of Osf2 (Δ258-528) also resulted in an 80% decrease in the transactivation ability of the protein (FIG. 15B) indicating the presence of additional transactivation domain(s) within the PST region. However this latter activation domain may not act independently of AD1 and AD2, since the deletion mutant containing only the runt and PST domains was nearly inactive. To localize this third activation domain and to avoid any possible functional interference with AD1 and AD2, the Osf2 PST domain was fused to the heterologous DNA-binding domain of the yeast transcription factor GAL4 (DBD, amino acids 1–147) (FIG. 16A), and the ability of this construct was tested to transactivate a luciferase reporter construct driven by 5 copies of the GAL4 upstream activation sequence (UAS$_G$) that was cloned upstream of an SV40 minimal promoter. Using that assay, the PST domain (C241–528) had no transcriptional activity. The absence of transactivation observed may reflect the existence of multiple activation and repression subdomains.

Deletions were also made from the C-terminal end of the PST region. Deletion of the last 5 amino acid residues (VWRPY) (C241-523) (SEQ ID NO:69) which are identical in all Runt-related proteins (Aronson et al., 1997), led to a significant and reproducible increase in activation (FIG. 16A), suggesting that this short motif has a repression function by itself. Further C-terminal deletions extending to amino acid 374 (C241–374) resulted in a progressive increase in the level of expression of the reporter gene (FIG. 16A), indicating that the repression domain (RD) is 154 amino acids long and located between amino acids 374 and 528.

Removal of amino acids 370 to 374 (GASEL) (SEQ ID NO:75) resulted in a total loss of transcriptional activity (FIG. 16A), demonstrating that these 5 amino acids are a critical part of the transactivation domain. Interestingly, this GASEL (SEQ ID NO:75) motif is located in a broader region of the Osf2 PST domain that is the most divergent with the PST domain of Cbfa2 (FIG. 13). Deletions made from the N-terminal end of the PST domain led to a progressive decrease in transactivation, suggesting that the entire N-terminal half of the PST domain, up to the GASEL (SEQ ID NO:75) motif (135 amino acids long) is required for transactivation. This region was termed AD3. To determine if the GAL4 fusion proteins were being made, extracts from transfected cells-were used for immunoblot analysis using a monoclonal antibody directed against GAL4DBD. FIG. 16B shows that cells transfected with a plasmid coding for each of the chimeric proteins tested above expressed the recombinant proteins. FIG. 16C shows a schematic representation of the various functional domains identified within the PST domain of Osf2.

5.6.2.5 The VWRPY Motif Can Act as a Repressor of Transcription

The analysis presented above suggested that the last 5 amino acids of Osf2 (VWRPY) (SEQ ID NO:69) repressed transcription. This motif is conserved in all known Runt-related proteins (Ito and Bae, 1997). To demonstrate the repression function of these 5 amino acids, six copies of the VWRPY (SEQ ID NO:69) sequence were cloned in frame between GAL4DBD and the VP16 activation domain, (FIG. 16D) and tested their functions in a DNA cotransfection assay. This multimer of VWRPY (SEQ ID NO:69) led to a 280-fold decrease in the transactivation ability of VP16 (FIG. 16E). Immunoblot analysis with an anti-GAL4DBD antibody showed that the (GAL4-6x VWRPY-VP16) fusion protein was indeed expressed in transfected cells. In a control study, an oligonucleotide encoding six copies of the 5 amino acids (GASEL; SEQ ID NO:75) located at the C-terminal end of AD3 (FIG. 16D) was also cloned at the same location. This resulted in a nearly two-fold increase in the transactivation ability of VP16 (FIG. 16E). These results demonstrate that the VWRPY (SEQ ID NO:69) motif acts as a repressor of transcription and suggest that the GASEL (SEQ ID NO:75) motif has a transactivation function.

It has been proposed that in Drosophila Runt, the VWRPY (SEQ ID NO:69) motif also acts as a repressor of transcription by interacting with Groucho, although Groucho can still prevent transactivation by Runt in the absence of this motif (Aronson et al., 1997). Thus, the inventors asked whether TLE2, a mammalian homolog of Groucho, could affect the transactivation ability of Osf2. Cotransfection of TLE2 with either Osf2 or Osf2ΔC12 (which lacks the last 12 amino acids, including VWRPY (SEQ ID NO:69)) resulted in a two-fold decrease in Osf2 transactivation ability (FIG. 16). This observation does not exclude the possibility that the VWRPY (SEQ ID NO:69) motif interacts with TLE2, but supports the hypothesis that the mechanism by which TLE2 may inhibit the transactivation function of Osf2 is not strictly dependent on the presence of the VWRPY (SEQ ID NO:69) motif.

5.6.2.6 The QA Domain Prevents Heterodimerization of Full-Length OSF2 with CBFβ

Cbfa2 and the Drosophila Runt protein can heterodimerize with the widely expressed Cbfβ protein in vertebrates (Speck and Stacy, 1995) and two homologs of Cbfβ, Brother and Big Brother, in Drosophila (Golling et al., 1996). Cbfβ does not have any intrinsic DNA-binding activity but increases the affinity of Runt and Cbfa2 for DNA (Golling et al., 1996; Bae et al., 1994). Although it has not been reported whether Cbfβ has any effect on the transactivation ability of Runt-related proteins, deletion of Cbfβ or Cbfa2 in mice results in an identical phenotype, underscoring the importance of the Cbfa2-Cbfβ interaction in vivo (Okuda et al., 1996; Wang et al., 1996a; 1996b; Sasaki et al., 1996).

Since Cbfβ is also expressed in osteoblasts, the inventors tested if Cbfβ was also a partner for Osf2 using an electrophoretic mobility shift assay (EMSA). His-Osf2 alone formed a specific complex with OSE2 and the addition of Cbf]3 resulted in intensification of the Osf2-DNA complex, but did not result in the appearance of a slower migrating protein-DNA complex (FIG. 18A, compare lanes 1 and 2). In contrast, when using His-Cbfa2 protein as a positive control, the inventors always detected heterodimerization with Cbfβ, resulting in a protein-DNA complex of slower mobility (FIG. 18A, compare lanes 3 and 4). These two results strongly suggest the absence of detectable heterodimerization of Osf2 and Cbfβ. To further establish that full-length Osf2 could not interact directly with Cbfβ, in vitro protein association assays were performed with purified recombinant glutathione-S-transferase(GST)-Cbfβ fusion protein. $^{35}$S-labeled Cbfa2 protein was bound by immobilized GST-Cbfβ, but not by GST alone (FIG. 18B, lanes 4–6). In contrast, S-labeled Osf2 protein was not bound by immobilized GST-Cbfβ protein (FIG. 18B, lanes 1–3).

The inhibition of heterodimerization may be due to one of the two major Osf2-specific domains, AD1 or AD2 (the QA domain). To test this, the amino-terminal region of Cbfa2 was swapped with the amino-terminal region of Osf2 (FIG. 18C). In EMSA, this chimeric protein (1.2.2) could not heterodimerize with Cbfβ (FIG. 18A), compare lanes 5 and 6). ΔN19.1.1, another deletion mutant of Osf2 could not heterodimerize with Cbfβ (FIG. 16A, lane 8), while a deletion mutant containing only the rant and PST domains of Osf2 (Δ.runt.PST) could heterodimerize with Cbfβ (FIG. 18A, lane 10). This indicated that it is the QA domain, present at the N-terminal end of Osf2, that probably prevents heterodimerization of the native protein with Cbfβ. Consistent with this result, cotransfection of Cbfβ with Osf2 did not increase Osf2.

5.6.3 Discussion

Osf2 is one mammalian member of the Runt-related family of transcription factors. Its critical function during skeletogenesis and the presence of stretches of amino acids in this molecule distinct from those in most other Runt-related proteins (FIG. 13) suggest that it has functional domains which could specify its unique functions in osteoblast differentiation. An extensive structure/function analysis revealed a novel functional organization for this family of proteins demonstrating that the N-terminal end and the QA domain control to a large extent its transactivation and dimerization abilities. These findings are summarized in FIG. 19.

5.6.3.1 Definition of a Short Nuclear Localization Signal in OSF2

Previous analyses of Cbfa1 had indicated that the NLS spans a broad region covering the runt and PST domains. This was based on a study of the subcellular localization of a series of deletion mutants of Cbfa1 (Lu et al., 1995). In the context of the wild-type protein, however, the NLS of Osf2 is much shorter. A 9-amino acid sequence located at the junction of the runt and PST domains is necessary and sufficient for nuclear localization of the protein. This sequence is rich in basic residues known to be important for nuclear localization of some proteins (Nigg, 1997), and is present in other Runt-related proteins as well, implying that it could perform the same function in these proteins.

5.6.3.2 Existence of an Efficient Transactivation Domain in the N-Terminal End of OSF2

N-terminal deletion mutants of Osf2 were generated, and a deletion leaving intact only the runt and PST domains was virtually inactive in the transactivation assay. This represented the first demonstration of a transactivation function in the N-terminal end of any Runt-related protein. The N-terminal end of Osf2 is substantially different from the homologous region in Cbfa2 and Runt. It contains two subdomains that are unique to Osf2. One includes the first 19 amino acid residues and the other one is the QA domain; both of these domains have a transactivation function. AD1 and AD2 sequences are unique to Osf2 and are not present in other members of this family, suggesting that the presence of transactivation domains at the N-terminal end may be specific to Osf2.

5.6.3.3 Analysis of the Transactivation Ability of the QA Domain

Runt has a stretch of 12 alanines at its N-terminal end (Kania et al., 1990), and Lozenge, a glutamine-rich region at its C-terminal end (Daga et al., 1996), but Osf2 is the only Runt-related protein to have consecutive glutamine and alanine stretches. These analyses show that, by itself, the QA domain has an important transactivation function, and that within the QA domain, the stretch of 29 glutamine residues is responsible for most, if not all, of the transactivation function. This is in agreement with studies showing that glutamine stretches have a transactivation function in several other transcription factors (Gerber et al., 1994). Expansion of this alanine stretch in humans, from 17 to 27 alanine residues, leads to a CCD phenotype, which is a loss-of-function phenotype (Mundlos et al., 1997), and alanine-rich regions have been shown to have a repressor function in several transcription factors (Han and Manley, 1993a; Han and Manley, 1993b).

There has been no other vertebrate transcription factor described with such a QA domain. In Drosophila, there are several transcription factors that have glutamine- and alanine-rich regions, and they may serve as examples to predict the function of the QA domain in Osf2. Bicoid is one of those Drosophila factors that has been intensively studied and shown to activate transcription through an interaction between its glutamine-alanine-rich region and $TAF_{110}$ and $TAF_{60}$ (Sauer et al., 1995). Thus it is possible that the QA domain of Osf2 may interact with the TAFs and/or other proteins of the general transcription machinery. Alternatively, the QA domain could also interact with cell-specific coactivators.

5.6.3.4 A Third Activation Domain is Present in the PST Domain

Deletion analysis showed that the PST domain also contains a transactivation domain the inventors term AD3. This is in agreement with what is already known for the other Runt-related proteins such as Cbfa2 (Bae et al., 1994). Although the PST domain by itself is not able to confer the transactivation function of Osf2 in a DNA cotransfection assay, genetic analysis indicates that this domain is critical for in vivo. Indeed, a nonsense mutation in the PST domain that causes CCD in humans is located in AD3 (Mundlos et al., 1997). The fact that deletion of each of the activation domains in Osf2 results in a similar decrease in the transactivation function of the protein indicates that these domains are functionally dependent on each other and that they may interact together with common coactivators. AD3 is highly homologous to the corresponding region of Cbfa2 (Bae et al., 1993), except for its C-terminal 27 amino acids. Studies conducted with human OSF2 have shown that this small region of the PST domain is also required for optimum transactivation (Geoffroyet al., 1998) and the GASEL motif at the C-terminal end of AD3 appears to have, by itself, a transactivation function.

5.6.3.5 Existence of a Large Repressor Subdomain in the PST Domain

The PST domain, as a whole, has no transactivation function in a GAL4-based cotransfection assay. This is due to the presence of a relatively large repressor domain (RD) that comprises the last 154 amino acids. This repressor domain includes the VWRPY motif, the last 5 amino acids of the molecule. Given the sequence homology between Osf2 and Cbfa2 in this repressor domain, it was interesting to determine if the corresponding region in Cbfa2 has also a repressor function.

It was shown that six copies of the VWRPY (SEQ ID NO:69) motif could inhibit the transactivation function of VP16. In Drosophila, this motif of Runt interacts with Groucho and leads to transcriptional repression. However, Groucho could still inhibit, albeit less efficiently, the transactivation function of Runt in the absence of the VWRPY (SEQ ID NO:69) motif (Aronson et al., 1997). TLE2, a mammalian homolog of Groucho, inhibits transactivation by Osf2, even in the absence of the last 5 amino acids. This is consistent with the fact that the repressor domain extends further amino terminus of the PST domain and suggests that the molecular mechanism by which TLE2 inhibits the transactivation function of Osf2 is not strictly dependent on the presence of this motif. It is possible that once recruited by Osf2, TLE2 could modify chromatin structure and thereby modulate Osf2 function (Paroush et al., 1994).

5.6.3.6 Lack of Heterodimerization of Full-Length OSF2 with CBFβ

Cbfa2 heterodimerizes with Cbfβ (Bae et al., 1994), and in Drosophila, Runt interacts with the Cbfβ homologs called Brother and Big Brother (Golling et al., 1996). Moreover, the deletion of the Cbfβ gene in mice leads to a phenotype identical to the one caused by inactivation of Cbfa2 (Okuda et al., 1996; Wang et al., 1996a; 1996b; Sasaki et al., 1996), indicating that the interaction between Cbfβ and Cbfa2 is functionally important in vivo. Therefore, it was surprising when no interaction between Osf2 and Cbfβ in DNA-binding assays could be detected. Several lines of evidence indicate that this absence of interaction is real and that the QA domain may be responsible for this absence of heterodimerization. First, in control studies, heterodimerization of Cbfa2 and Cbfβ was always observed. Second, Cbfβ colocalizes to the nucleus only with a deletion mutant of the Cbfa1 protein lacking its N-terminal end (Lu et al., 1995). This is in agreement with the absence of skeletal abnormalities in mice heterozygous for Cbfβ deletion (Sasaki et al., 1996; Wang et al., 1996b) and with the fact that Cbfβ does not increase the transactivation function of intact Osf2 in transient transfection assays. Lastly, deletion and domain-swapping studies strongly suggest the QA domain as being responsible for preventing heterodimerization with Cbfβ.

The deletion that removed AD1, left in place the amino-terminal part of Osf2 that is highly homologous to corresponding region of Cbfa2 and the QA domain. Full-length Cbfa2 heterodimerizes readily with Cbfβ, therefore it is likely that it is the QA domain that prevents heterodimerization of Osf2 with Cbfβ. This is possibly due to conformational changes imposed on the molecule by the QA domain. Alternatively, Osf2 could heterodimerize with yet unknown, and possibly cell-specific proteins.

5.7 Example 7

Transgenic Mice Overexpressing the OSF2 DNA-Binding Domain Develop an Osteopenic Phenotype Osteoblasts function is to produce bone matrix. Osf2/Cbfa1 (Osf2) is also expressed in osteoblasts postnatally. To determine whether Osf2 controls bone formation the inventors generated transgenic mice overexpressing Osf2 DNA-binding domain (ΔOsf2) in osteoblasts, only after birth. ΔOsf2 inhibits Osf2 transactivation function, and ΔOsf2-expressing mice have a normal skeleton development but an osteopenic phenotype postnatally. Histomorphometric studies showed a major decrease in the rate of bone formation in ΔOsf2-expressing mice. Remarkably, the osteoblast number was unchanged. Molecular analysis revealed that the expression of the main osteoblast-specific genes, including type I collagen, the major osteoblast biosynthetic product, was nearly abolished in transgenic mice. Osf2 also binds to, and regulates the activity of its own promoter providing a molecular mechanism to explain the severity of the phenotype. This example demonstrates that Osf2 has a dual function. Besides its developmental role, it is a positive regulator of bone formation by pre-existing osteoblasts after birth. This suggests that upregulating Osf2 expression may be a means for correcting bone loss in osteopenic conditions.

The DNA-binding domains of all runt-related proteins, including Osf2, have no detectable transactivation function. Thus, to generate an inactive form of the protein, a deletion mutant of Osf2 containing only its DNA-binding domain (called thereafter ΔOsf2) was constructed. In DNA cotransfection assays, increasing amounts of ΔOsf2 inhibited transactivation of an Osteocalcin promoter-luciferase chimeric gene by endogenous Osf2 in ROS 17/2.8 osteoblastic cells, indicating that ΔOsf2 could inhibit Osf2 transactivation function, probably by competing for binding to the same sites.

To determine if Osf2 is involved in the maintenance of osteoblast function in vivo transgenic mice overexpressing ΔOsf2 under the control of the mouse Osteocalcin gene 2 (OG2) promoter were generated. Osteocalcin is not expressed at a significant level during embryonic development and its expression is restricted to osteoblasts after birth. Thus, OG2 promoter should confer osteoblast-specific and post-natal-specific expression to ΔOsf2. For each study identical results were obtained with progenies of 2 independent transgenic lines. RT-PCR™ analysis demonstrated the bone-specific expression of the transgene. As expected ΔOsf2-expressing mice were normal at birth, in particular the skeleton was mineralized unlike what is the case for the Cbfa1-deficient mice. However, shortly after birth the ΔOsf2-expressing mice developed skeletal abnormalities. Radiological examination of 2-wk-old wild-type and mutant animals revealed that the transgenic mice had shorter long bones, a decreased cortical thickness, and a decreased bone density compared to wild-type mice. Histological analysis showed a decreased amount of trabecular and cortical bone in vertebrae and in long bones of transgenic animals compared to wild-type littermates. These findings demonstrated the existence of an osteopenia in the ΔOsf2-expressing mice.

To determine whether this decrease in bone mass was due to a block in osteoblast differentiation or to a lack of bone matrix deposition by pre-existing osteoblasts, static and dynamic histomorphometric analysis was performed after double labeling with tetracycline/calcein, a marker of the amount of de novo bone formation. At 2 wk of age there was a significant decrease in the amount of newly formed bone and a 3 to 4 fold reduction of the bone formation rate in long bones of ΔOsf2-expressing mice as compared to wild-type animals. Osteoid thickness, an indirect indicator of bone matrix deposition, was also decreased. These findings were consistent with the x-ray and the conventional histology analyses. Remarkably, this decrease in the rate of bone formation occurred while the osteoblast number, as measured by the bone surface covered with osteoblasts, was unchanged. Likewise, the number of osteoclasts, the bone resorbing cells, was identical in wild-type and transgenic mice. These results demonstrated that the osteopenic phenotype of the ΔOsf2 transgenic mice was due to a functional defect of the osteoblasts, not to a block in osteoblast differentiation. They indicate that Osf2 is required for the maintenance of the differentiated osteoblast phenotype after birth.

To decipher the molecular basis of this osteopenic phenotype in presence of a normal number of osteoblasts, the inventors studied the expression of genes encoding structural proteins of the bone matrix. The expression of Osteocalcin gene 1 (OG1), and OG2, two osteoblast-specific genes known to be regulated by Osf2, of Bone sialo protein (BSP) another osteoblast-specific gene, and of Osteopontin were all decreased. Those genes encode non-collagenous proteins that represent only a minor amount of the bone matrix proteins and their decreased expression could not alone explain the osteopenic phenotype.

Type I collagen is the major constituent of the bone matrix accounting for 90% of its protein content. The expression of α1(I) collagen and of α2(I) collagen, the 2 genes encoding Type I collagen, was markedly decreased in ΔOsf2-expressing mice compared to wild-type littermates. DNA sequence inspection and DNA binding assays identified a potential Osf2-binding site in the promoter of the mouse α1(I) collagen gene [OSE2α1(I)] and in the first exon of the α2(I) collagen gene [OSE2α2(I)]. Moreover, these sites are present at approximately the same location in the mouse, rat, and human genes. The functional relevance of OSE2α1(I) was assessed in vitro and in vivo. In DNA cotransfection assays performed in COS cells that do not express Osf2, exogenous Osf2 transactivated P40SE2α1(I) Luciferase (Luc), a construct containing 4 OSE2α1(I) sites fused to an α1(I) collagen minimal promoter. This transactivation was prevented by a mutation in the OSE2α1(I) site that abolished DNA binding. Second, in transgenic mice overexpressing multiple copies of the OSE2α1(I)element in front of the α1(I) collagen minimal promoter-luc chimeric gene luciferase activity was detected only in bone and the same 2-bp mutation as above abolished this expression. Taken together these studies strongly suggest that Osf2 contributes to the osteoblast expression of type I collagen, the major biosynthetic product of the osteoblast, in vivo, and provide a molecular basis for the osteopenic phenotype observed in the ΔOsf2-expressing mice.

To determine if the severity of the phenotype was due to a high expression of the transgene the inventors compared its expression to the expression of endogenous OSF2. Surprisingly, the level of expression of the transgene and of the endogenous gene were nearly identical. The mechanism by which ΔOsf2 should inhibit the expression of structural genes should be by competition with endogenous Osf2 for identical binding sites. Thus, this comparable level of expression of the transgene and of the endogenous gene could not explain alone the phenotype. This led the inventors to study Osf2 expression in the ΔOsf2-expressing mice in search of an additional level of regulation. Endogenous Osf2 expression was nearly abolished in every transgenic mouse analyzed indicating that Osf2 controls its own expression. Sequence inspection of the mouse 5' region of the Osf2 gene showed the presence of one consensus Osf2-binding site, 5'-ACCACA-3' (SEQ ID NO:77) upstream of the start site of transcription and of two others, side by side, in the 5' untranslated region. These exact sequences are also present, at the same location, in the human Osf2 gene. In DNA binding assay osteoblast nuclear extracts bound to oligonucleotides containing wild-type sequences for these elements, and an antibody against Osf2 caused an upward shift of the protein-DNA complex. Likewise, recombinant Osf2 bound to the wild-type elements but not to their mutated counterparts demonstrating that these sequences are bona fide OSE2 sites. Moreover, quantitative DNA binding assays using decreasing amounts of recombinant Osf2 demonstrated that the sites present in the Osf2 promoter had a 10 to 100 fold higher affinity for Osf2 than other well characterized Osf2 binding sites. In DNA cotransfection studies exogenous Osf2 transactivated an Osf2 promoter-luciferase chimeric gene containing the wild-type OSE2 elements but not a similar construct containing mutated OSE2 elements. These results, along with the down-regulation of Osf2 expression observed in the ΔOsf2-expressing mice, demonstrate that Osf2 controls positively its own expression in osteoblasts. This may be a critical means through which Osf2 controls structural gene expression in differentiated osteoblasts and thereby the rate of bone formation.

This example demonstrates that Osf2 function is not restricted to cell differentiation along the osteoblastic lineage but is also involved in cell physiology. Indeed, Osf2 is required to maintain a normal rate of bone formation by already differentiated osteoblasts. These results provide a molecular explanation for the growth retardation and other abnormal skeletal features observed in adult cleidocranial dysplasia patients. The demonstration that Osf2 is required to maintain bone formation after birth, together with the fact that haploinsufficiency for Osf2 leads to a generalized defect of bone formation suggests that an increase in Osf2 expression may be of therapeutic use in osteopenic conditions.

5.8 Example 8

Alernatively Spliced, Dominant Negative Variant of OSF2

The inventors have identified an alternatively spliced, dominant negative variant of Osf2. This variant is capable of altering the regulation of Osf2 expression and function in vivo. Because it lacks the domain responsible for the activation of transcription by Osf2 but retains the DNA-binding domain, the protein encoded by this alternatively spliced mRNA is capable of competing with the endogenous Osf2 for binding to the Osf2-binding site yet is unable to activate transcription. Therefore, the variant is capable of preventing the activation of genes by Osf2 much like the deletion mutant Δosf2.

5.8.1 Nucleic Acid Sequence of the Alternatively Spliced, Dominant Negative Variant of OSF2 (SEQ ID NO:70)

```
ATGGCGTCAAACAGCCTCTTCAGCGCAGTGACACCGTGTCAGCAAAGCTTCTTTTGGGATCCGAGCACCAGCCGGCG
CTTCAGCCCCCCCTCCAGCAGCCTGCAGCCCGGCAAGATGAGCGACGTGAGCCCGGTGGTGGCTGCGCAGCAGCAGC
AACAGCAGCAGCAGCAGCAGCAACAGCAGCAGCAACAACAGCAACAGCAACAACAGCAGCAGCAGCAGCAGCAGCAG
GAGGCGGCCGCAGCAGCAGCGGCGGCAGCGGCGGCGGCAGCAGCGGCGGCGGCCGCAGTGCCCCGATTGAGGCCGCC
GCACGACAACCGCACCATGGTGGAGATCATCGCGGACCACCCGGCCGAACTGGTCCGCACCGACAGTCCCAACTTCC
TGTGCTCCGTGCTGCCCTCGCACTGGCGGTGCAACAAGACCCTGCCCGTGGCCTTCAAGGTTGTAGCCCTCGGAGAG
GTACCAGATGGGACTGTGGTTACCGTCATGGCCGGGAATGATGAGAACTACTCCGCCGAGCTCCGAAATGCCTCCGC
TGTTATGAAAAACCAAGTAGCCAGGTTCAACGATCTGAGATTTGTGGGCCGGAGCGGACGAGGCAAGAGTTTCACCT
TGACCATAACAGTCTTCACAAATCCTCCCCAAGTGGCCACTTACCACAGAGCTATTAAAGTGACAGTGGACGGTCCC
CGGGAACCAAGAAGGCACAGACAGAAGCTTGATGACTCTAAACCTAGTTTGTTCTCTGATCGCCTCAGTGATTTAGG
GCGCATTCCTCATCCCAGTATGAGAGTAGGTGTCCCGCCTCAGAACCCACGGCCTCCCTGAACTCTGCACCAAGTC
CTTTTAATCCACAAGGACAGAGTCAGATTACAGATCCCAGGCAGGCACAGTCTTCCCCACCGTGGTCCTATGACCAG
TCTTACCCCTCCTATCTGAGCCAGATGACATCCCCATCCATCCACTCCACCACGCCGCTGTCTTCCACACGGGCAC
CGGGCTACCTGCCATCACTGACGTGCCCAGGCGTATTTCAGATTCAGAACCCAGCACCTTGGACTCACAGTCTTCCA
CCACCCTGTTCCTGTCTCCAGAGGAGCCTGGCCCCTCTACAGCAGCTCTGCCATCTCCATCCTCGTCCTGTGAGCCC
CAGCCCTTCTCTCCCAGCCCCATGTTGCCCCCTCTCCTGCAGCCTCTGTCCACTGCCTCCACAGTGCCAGCCCCTG
CGTCCGTCGGCGCACTGGGCTCTACACCATTGTGACCTCCTCCCCAGAGGCTGCACCCCACCTTGTTGACTGGATGC
CCAGCTGCCCCACTGCCACGTCCCCTGGTGTCCGAGGCAAGGATCATGAGCGGCCACAGACCATGATGGCCCCGGCC
CCAGCTCTAGCTTCAGAGAGGGGCCACAGTCAGCATGCAGGCCCTGCCAGGGATGATCATGCTGAACATCCTGGAAC
CTCCCCAAAGCCCTGTGCTCCTCCAGCCGCTGCTGCCACCTTGGAGGCCAGTGTTGGGGACATCCTGGTGGAGCTAC
GGACAATGAATGGCCATCTGGACATCATAGCAAAGGCCCTCACTAAATTGGCCTCTTCTCTGGTGCCCCAGTCTCAG
CCTGTGCCTGAAGCACCAGATGCGAATTAAAAGAGCTGGACTTCTAAACAAAGGGATGCTGAGGTACCACACATCCT
CGCTGACTCCTCTGATCCCGTCTTTGCTGGAGACAAGCAAAATCAGCAGAAGAGCCAGTTACTTAGCTTGGTTTGCT
CACACATTGGATGCCCTTGGCCTGTCACTCAAAGGATAGCAGTGTCCTGCTGGCTCCACGAGCTGACAAGCTGTAGA
CTTTCTGTGTTCCCTTTCACCTTCCAATGCCCCTCTCTCGTTCTAAATCCCCAATAGAAGAAGCACCCGAGAAGTT
CCAGGGACAAGGTGATTGGAAAGGTATCATTCCCTCCCAGTCCAGCGAACCCCCAGCCAAGCGAGCGGAGGGGAGAG
GAGGTCCTATCGTCAGAAACACTTTCTGGGCCCCTCCAGCATCCCTTTCTTGAGATGCTGATGGTGTTGCCACCTC
CAGTGGACTCCAGTGGACTTCACATATCTCTTCTTAAAGTCTCTTTAGGAAAACCAAATTGATTGTTTTTCTCATTT
ATACCTACATTTCAAAGAGTTTGGGAAATAGGCAAGGAGGGAAAAGGACAGAGCAGAAAGACGGTGGGGGCTATTTA
GGTCTTTCTTATGAATAAGAGTATCATGTGTCCTGATAAAGTGTGTGTCTATACTCTCTG
```

5.8.2 Amino Acid Sequence of the Alternatively Spliced, Dominant Negative Variant of OSF2 (SEQ ID NO:71)

```
Met Ala Ser Asn Ser Leu Phe Ser Ala Val Thr Pro Cys Gln Gln Ser

Phe Phe Trp Asp Pro Ser Thr Ser Arg Arg Phe Ser Pro Ser Ser

Ser Leu Gln Pro Gly Lys Met Ser Asp Val Ser Pro Val Val Ala Ala

Gln Gln Gln Gln Gln Gln Gln Gln Gln Gln Gln Gln Gln Gln Gln

Gln Gln Gln Gln Gln Gln Gln Gln Gln Gln Gln Gln Glu Ala Ala

Ala Ala Ala Ala Ala Ala Ala Ala Ala Ala Ala Ala Ala Ala

Val Pro Arg Leu Arg Pro Pro His Asp Asn Arg Thr Met Val Glu Ile

Ile Ala Asp His Pro Ala Glu Leu Val Arg Thr Asp Ser Pro Asn Phe

Leu Cys Ser Val Leu Pro Ser His Trp Arg Cys Asn Lys Thr Leu Pro

Val Ala Phe Lys Val Val Ala Leu Gly Glu Val Pro Asp Gly Thr Val

Val Thr Val Met Ala Gly Asn Asp Glu Asn Tyr Ser Ala Glu Leu Arg

Asn Ala Ser Ala Val Met Lys Asn Gln Val Ala Arg Phe Asn Asp Leu

Arg Phe Val Gly Arg Ser Gly Arg Gly Lys Ser Phe Thr Leu Thr Ile

Thr Val Phe Thr Asn Pro Pro Gln Val Ala Thr Tyr His Arg Ala Ile

Lys Val Thr Val Asp Gly Pro Arg Glu Pro Arg Arg His Arg Gln Lys

Leu Asp Asp Ser Lys Pro Ser Leu Phe Ser Asp Arg Leu Ser Asp Leu

Gly Arg Ile Pro His Pro Ser Met Arg Val Gly Val Pro Pro Gln Asn

Pro Arg Pro Ser Leu Asn Ser Ala Pro Ser Pro Phe Asn Pro Gln Gly

Gln Ser Gln Ile Thr Asp Pro Arg Gln Ala Gln Ser Ser Pro Pro Trp

Ser Tyr Asp Gln Ser Tyr Pro Ser Tyr Leu Ser Gln Met Thr Ser Pro

Ser Ile His Ser Thr Thr Pro Leu Ser Ser Thr Arg Gly Thr Gly Leu

Pro Ala Ile Thr Asp Val Pro Arg Arg Ile Ser Asp Ser Glu Pro Ser

Thr Leu Asp Ser Gln Ser Ser Thr Thr Leu Phe Leu Ser Pro Glu Glu

Pro Gly Pro Ser Thr Ala Ala Leu Pro Ser Pro Ser Ser Cys Glu

Pro Gln Pro Phe Ser Pro Ser Pro Met Leu Pro Pro Leu Leu Gln Pro

Leu Ser Thr Ala Ser Thr Val Pro Ala Pro Cys Val Arg Arg Arg Thr

Gly Leu Tyr Thr Ile Val Thr Ser Ser Pro Glu Ala Ala Pro His Leu

Val Asp Trp Met Pro Ser Cys Pro Thr Ala Thr Ser Pro Gly Val Arg

Gly Lys Asp His Glu Arg Pro Gln Thr Met Met Ala Pro Ala Pro Ala

Leu Ala Ser Glu Arg Gly His Ser Gln His Ala Gly Pro Ala Arg Asp

Asp His Ala Glu His Pro Gly Thr Ser Pro Lys Pro Cys Ala Pro Pro

Ala Ala Ala Ala Thr Leu Glu Ala Ser Val Gly Asp Ile Leu Val Glu

Leu Arg Thr Met Asn Gly His Leu Asp Ile Ile Ala Lys Ala Leu Thr

Lys Leu Ala Ser Ser Leu Val Pro Gln Ser Gln Pro Val Pro Glu Ala

Pro Asp Ala Asn
```

5.9 Example 9

Nucleic Acid Sequence of the OSF2 Promoter and
5' Untranslated Region (SEQ ID NO:72)

```
GGAATTAATTCGGATCCGTATTCCACTGCTTCATTTTCAATATTCTTTCTGTATTGTTAATTATGCCTGAACTCA

CCATAAATTATACATAAAGCTTAATAGAGACCTCAATCCACAATAGCCTTTTCTGAACCCAATGAGAAATCTATA

CACGGCAATGAAACTGGCATGCAAATAAAAGAACTGTCAAGACATGTACTCCTGAAATAACCCTACAATAACTAT

TCTAAAGGCTGTGTGTGGTCTCACCCATAGATTTTGGCAAGATGCACTTTCTCCGACCACAGTCAGATTCATCCA

AAAGCAGTGGCACTGGAGAGCCTCTGTCTCACCTGTCAAACTTGAGAAACATTCTTGCAAAGACCACCATGAGTC

GGTGGAGAAAGCCACGCTGCGACAGCTGTTCTTGATAAGCATCTTCTAAAGTGGGGAACTCCAACAATTAAGCAA

ATCATCCTTAAAGGAGATATAGACAGCAACACCCAAACCTAAATGCTGAGATGTTCCAAAATCAAACATGGGTAA

TCCAGACATCCTGCAATATGCAGAGGGGCCATTCATAAGTGATACTGACAGTCTTTCCTTATCATCTAATACAAT

CTCTTAACATTATTTGCCAACTTAAAAACTATGTATCCTTTTTTAATATTTGGCCAACCTCCTTTGTAAAACCTT

AAAATACATATAAATTTTCAAGTATTAAATTCATCAAAATTGCTGAAGTTTGACAACTAAAAGCTCAATAGCTGA

AGACTTATAAATGGGAACATTAAATATATTAAAATCTGATCTTTTTATGATACATTGATACATTTTTAGCCACAT

CAAATAAAAGTTCACTTTTGCTTTGCCTTGACTTCATCAAGTTTATGGACAGAAGGGGAACGTATGGATACAATG

GTGAGAGAGACAATTACTCAGAAAAGAAGGATGCCTCACTGGGCTTGACTCAAGTTGGGGCCACTACCCAACAAC

AAATGATAAGTCAGACTTTTAAAAACTGCACCTGGCTCTCTACAAAGCTTACATAAGACCAACAGTATCTAAAAT

TGTAACTTTGTTGCCTTTTGGGTGACAGGCTCCTCTAACTCTGTTCAATACAAGAACAATTCAAGTGAACAAGAG

AGTGGTGGCCTATAGGGCCTTTTCCAAGACAAGGGACACCAATTAAGTTCTCACTTCAGAATAATGTCATCTGCA

GTAAAGTCCTAAATCACAAAGACAAAGTGACAATCAAGGTTCCCATGTATTAGGCTGCCCCACACTTACCCCTTA

CTATGCAAGCACAAAAGTTAGTTTCACTTTTCCCTAGATACACTAACTTGCATAACTAGGATATTATTTTTCTTT

GGTTTGGTCAGAAGCATGTTTGATATAAATTTTATTAAGTGGTAGTGTATGTAACATTGCATTGTGGGTAGTCGT

TTCCTGCTTTAGTCTGGCCACATCCTCAGCTGTCATACAAGCATGTTGCCCACATTTTGTGCAAGTTGTCACCTT

TTTTAAAAAAAAAATCTTACAAAAATGACACGAAGATGAATTGCTTTAATAATTATAAGAAACATAAAATATTTT

ATACAGATACATTACAGAAGTATAGACCACCACTCTTCAGAGAGCAATGCCTCACAATCAGAGTGCTAATGTCAT

ACATAACAATATGCCTAAGTAAAAGAGCATAAAGGAAAGGGTCAAGGGACAGACTGGCAGAAATAAAACATTCCT

GGACAGAGCTGTCAATGATCTCTAAGACCTGAGGTACAGTACACCGCAGTGTGCACAAAGGGCTGCACTTCAGAC

CTGTGAGGTGCTCATTAGTGAGTGCTACAATGTCGATATTCCTCAATAGAATTTTAAGAAAGTTCTGAATATATA

GAAACGTGAAAGCATGGAAAAAGAAAAGTAAAAAGCCTGGAGCTGGAGTAGAAAGGAAAAAGAGAGGAACAGAAA

TGAAGGAGGAGGGACCATAGGAGGGGGGTGTGGAGGGGGAAGGAGGGGAAGGAGGAGGGAGGAGGTAAGATGT

GGACACTAACTTAGGATGTTCTCTCTGGGCATCCAATCTGCATATTACATCACACTTAGAAAGACCACTGCCAGG

AGTACACACGCATGAAATCAGTAAACAAGAAAACTGTGGTACTTTTTAAAATATTATCTAATTTAAAACCTCATA

GCCAAGTTCAAAATACTCTGTACTCACAACCAGATATGCTTTCTTATATTTGTAATATAAAGCATGAGAGTTAAT

ATCTCATAATCATAATTCAGAATATAAAACTATAATGTTTTGCTAACACAGAACAATTTCACGTCTTTAATAAAA

GTTTGATAAATGCTAGGTGAACTTAAACAGCTATGCATTAAACCTGAAAAAGAAAAAATTACCCACCAATGGAAA

ACACAAATTACTAAATATTAAGTTAAAATGAATTAAGAAAGTCCCTAGCCCAAGTCTCATAAGCAGACTATTTTA

AGCCAGAGTGGGCACCTAGAGTTTGTTAGTCATTTTCTTACTGTTTCGATTAAAAGAATAGAAAAGCAACAACTA

TACATCCAAAGGAATCCTTCTTTAGAGCACAGATATTGGCACAGTATTGGTAAAGTAAGGCTACTGTGTTCAAGT

GCAAGCAGGAACCGATCAAATAAAAATCAATTCAAATGGTAACATTGAAGAAATGTATAGTATTTAAGATATTAC

TATACTGTTATATTCACATGTCTTGATATTTTAAGAACTTTGACAAATCTGAAAAAATTATTAAATTGTAAAAAA
```

-continued

```
ACAAGAAAGCAAGACAATAATTTCATGATTTAAGACTGATTTCAAATTTAAAGCTGTATTTCATTGTTATTGCAT
GAAAACACAGAATTTATAGGGCACAACTAAACTTGTTACTTACTTCACAGCAATTGCTAGCATATCCTCCAAAAG
GATTACATTTAAAAGATCTTTAAAGAGAGTCTGTGGTTTCCATTTCTGAATATAAGCATGGTAAAAGTCTCTAAA
CAAGCGCTTTCTGCCATGGCTTTTCAAAGCTGGCTCCCTCTCTCCATCTCTAGCAGCCATTTCTAAGGAAATGCA
GTCAGTATCAAAGATGTTACCACTCACCAGTGTTGTCTTTAAATTTCCACCACAGTGTACAGGTTGCTCCTGAGT
CTAGTTTGAATTGGGAGGGGTACGTGGACAATGAATGCATAAATTTAACCACAAATGTAACATTCCTGTTTTTAT
CCTGCCAGAATGTGATGGACTATACACAATACATAAAGGCCACGTTCAGCAACCTCTACTAAACTCTTGTATCAT
GAGATACAGACCATAACTCACAGACACAGGAAATAGGGTTAGGTTACCTGCAAAACAGACCATGTGACTACTCAT
CTGATAAATGAGATGGTGGTAAAATTTATTCAAATTCATTTTAGATCAATTTGAATACCAAAATGTATATACCTT
TTTTTAAAAAATGTAAGGGAAAAATTATTGCATGAAAAATTAGGACATAAAAGACCTGGGCACTCTAAAAGAAAA
GCATTTGCTTACTATCCTATAGCAACTACGCAAACATCTTCAACTGCCAAGTGCTGTGATTCCTTGTACATATGG
AACTAAGTTCAGAAACTCCACAAATTATATAGACAAAACCCTTTTTTATTTACTTTGAATAATAGAGATAAAGA
TCACACTGGCACACTTTATTTATGAAAGAGGATAATAGAGTAACTTTTTTCTCCTCTGCATGAATAATGACCCTA
AATGAAAACTTCAGTATAAATATCTGTTTTACAGTAAAACATGAGTCTAGCCTCAAAAATCAAACAAAGAATGT
ATTTCTGTGGTTTTGTCATTAAAACTTTATTCTGAAAAATTAAATAAATAAACCTAGATTCTTGAAAAATAAGGG
GTTAAAAGCATTACCATGTCTTTCCAGTATATAGAGAATAAATGTTTAAAGAATCTTATGAACATGATTTCATAG
ATAACTTTAACTAAGAGGAAACAAAAACAGACAATGAGTTATTTTGGGGTGTACAGACACAAGAATATTTTACTT
CTGTCACCCTCTAAGTCACTCCCTCTTACCTCCACTGTGCACCCCAAATAATTTCTTGTACTTCTGTGCCCCCAC
CCACCATCACAGTCATCCGTTCCATGCCACTCCTGGTTACCATCACACTAGGAAGAAATCTAACATGCAAATTCA
GAGTGGCGTGGATAAATGGCAAAAAATGCCTAGGAAATTGGTCTGCTCGCCTTTATAATGTTTGTTGAAAAATCC
TCCATCGCTCCCAACTAATGAAAACAGGAAGCTCTATTCATAAATGTGAAATTCACTGCCTATGATATATAATCA
TCCTAATAAGAAAATGAGCTCTAGACATACATGTCCAAGAGGGCAAAAGAAGAGATAGTTTCCCAAAGATGGTTT
CAATTTTCTTCTGAATCAGAATTAGCAAATCAAGACGACTAACATACTCTGTCTGTGTGCATTATTCCTTACTAC
ACACAGCATTTTGTAATTTATTTCAAAGCTTCCATTATAAACAACAAAAACTTACAGTTTCTGTTAACCCCCTCT
ATTCTGAGCTATGGAAATTACTGCATATTTCATTATATATGCAGAACTGCACCCAAAGTCCTGTTACAGTCACTG
TCCACGCTGATGAAAGAATTATACAAAACATTTCTTTGAAAGATAAAATCCAATCATACAGAAAACTAACATTAG
TCCAACAAAATGTCCACCACAATTCCTGACATTTGTTTTTTAAGATCTTCAAAGTAACCATGGGATGATGGCAAA
AATAATGTAAACGATACTAATTACATTTAATCTTTATTGTAAGAGCCGCCACGTAATAAAAAAAAAAAAAAAATCA
ACTACACAGCCATGATTTAATATTTGTAAAGGAATCCCCAGGCTAACACTTTTGTGACAGCCAATTACAGTCGAT
CCCGATCCCGGCAAGGAGTTTGCAAGCAGAGCTCTGGAAAGGTAAACTCCTTTTTACAATGAGTTACAGATCCCC
AAGCTTAGGAAGACAAGCAAAAGGCAAACAGAAGGAAGCAGCCACCCTGGGAAATCCGAAGCAGCCTTGCAAGTG
ATACAATCCCAAGATGCGAATTACTGCAAAGCAGCACTGTTGCTCAGAACGCCACACACTCAGTTGAGACAATTT
TGCTCACTTTTCCATAGACATAATAATGAAGGAAAGGGAGGAGGGGTAGAGAAGAGAGATGAAAAAGCAGAGGAG
GGAAGGGGAGTAGGGAGGTGGCAGAAAGGAAAAGCCTTAGCTACAGAGTTCTGCTCTCCAGAGGCTTAACCTTA
CAGGAGTGTGGGCTCCTTCAGCATTTGTGTTCTAGCCAAATCCTCATGAGTCACAAAAATTAAAAAGCTATAACC
TTCTGAATGCCAGGAAGGCCTTACCACAAGCCTTTTGTCAGAGGGAGAAAGGGAGAGAGAGGGAGAGAGAG
GGAGAGAGGGAGGGAGAGAGGAAGGGAAGGAGAGACAGAGGAACACCCATAAGTAAAGAGACAGAAGGAAGGAAA
GGGAGAGGACAAGAGAAGAGAAAGGAGGGAGGGGAGGGAGAAGGAAAAAGATTGAGAAAGAGGGAGGGAAGAGA
GCAAGGGGAAGCCACAGTGGTAGGCAGTCCCACTTTACTTTGAGTACTGTGAGGTCACAAACCACATGATTCTGT
CTCTCCAGTAATAGTGCTTGCAAAAAATAGGAGTTTTAAAGCTTTTGCTTTTTTGGATTGTGTGAATGCTTCATT
```

```
-continued
CGCCTCACAAACAACCACAGAACCACAAGTGCGGTGCAAACTTTCTCCAGGAAGACTGCAAGAAGGCTCTGGCGT

TTAAATGGTTAATCTCTGCAGGTCACTACCAGCCACCGAGACCAACCGAGTCAGTGAGTGCTCTAACCACAGTCC

ATGCAGGAATAGTAGGTCCTTCAAATATTTGCTCACTCCGTTTTGTTTTGTTTCCTTGCTTTTCACATGTTACCA

GCTACATAATTTCTTGACAGAAAAAAATAAATATAAAGTCTATGTACTCCAGGCATACTGTACAACTAAAACAGG

GACTGGGTATGGTTTGTATTTTCAGTTTAAGGCTGCAAGCAGTATTTACAACAGAGGGCACAAGTTCTATCTGGA

AAAAAAAGGAGGGACTATGGCGTCAAAC
```

6.0 REFERENCES

The following references, to the extent that they provide exemplary procedural or other details supplementary to those set forth herein, are specifically incorporated herein by reference: U.S. Pat. No. 3,791,932, issued Feb. 12, 1974.

U.S. Pat. No. 3,949,064, issued Apr. 6, 1976.
U.S. Pat. No. 4,174,384, issued Nov. 13, 1979.
U.S. Pat. No. 4,196,265, issued Apr. 1, 1980.
U.S. Pat. No. 4,237,224, issued Dec. 2, 1980.
U.S. Pat. No. 4,271,147, issued Jun. 2, 1981.
U.S. Pat. No. 4,358,535, issued Nov. 9, 1982.
U.S. Pat. No. 4,883,750, issued Nov. 28, 1989.
U.S. Pat. No. 4,514,498, issued Apr. 30, 1985.
U.S. Pat. No. 4,554,101, issued Nov. 19, 1985.
U.S. Pat. No. 4,578,770, issued Mar. 25, 1986.
U.S. Pat. No. 4,596,792, issued Jun. 24, 1986.
U.S. Pat. No. 4,599,230, issued Jul. 8, 1986.
U.S. Pat. No. 4,599,231, issued Jul. 8, 1986.
U.S. Pat. No. 4,601,903, issued Jul. 22, 1986.
U.S. Pat. No. 4,608,251, issued Aug. 26, 1986.
U.S. Pat. No. 4,683,195, issued Jul. 28, 1987.
U.S. Pat. No. 4,683,202, issued Jul. 28, 1987.
U.S. Pat. No. 4,740,467, issued Apr. 26, 1988.
U.S. Pat. No. 4,795,804, issued Jan. 3, 1989.
U.S. Pat. No. 4,800,159, issued Jan. 24, 1989.
U.S. Pat. No. 4,883,750, issued Nov. 28, 1989.
U.S. Pat. No. 4,877,864, issued Oct. 31, 1989.
U.S. Pat. No. 4,965,188, issued Oct. 23, 1990.
U.S. Pat. No. 4,968,590, issued Nov. 6, 1990.
U.S. Pat. No. 4,987,071, issued Jan. 22, 1991.
U.S. Pat. No. 5,011,691, issued Apr. 30, 1991.
U.S. Pat. No. 5,013,649, issued May 7, 1991.
U.S. Pat. No. 5,106,748, issued Apr. 21, 1992.
U.S. Pat. No. 5,108,753, issued Apr. 28, 1992.
U.S. Pat. No. 5,108,922, issued Apr. 28, 1992.
U.S. Pat. No. 5,116,738, issued May 26, 1992.
U.S. Pat. No. 5,141,905, issued Aug. 25, 1992.
U.S. Pat. No. 5,166,058, issued Nov. 24, 1992.
U.S. Pat. No. 5,176,995, issued Jan. 5, 1993.
U.S. Pat. No. 5,187,076, issued Feb. 16, 1993.
U.S. Pat. No. 5,334,711, issued Aug. 2, 1994.
U.S. Pat. No. 5,354,855, issued Oct. 11, 1994.
U.S. Pat. No. 5,399,346, issued Mar. 21, 1995.
U.S. Pat. No. 5,518,913, issued May 21, 1996.
U.S. Pat. No. 5,585,362, issued Dec. 17, 1996.
U.S. Pat. No. 5,616,326, issued Apr. 1, 1997.
U.S. Pat. No. 5,631,359, issued May 20, 1997.
U.S. Pat. No. 5,698,202, issued Dec. 16, 1997.
U.S. Pat. No. 5,700,922, issued Dec. 23, 1997.
Eur. Pat. Appl. Publ. No. EP 0273085.
Eur. Pat. Appl. Publ. No. EP 320308.
Eur. Pat. Appl. Publ. No. EP 0360257.
Eur. Pat. Appl. Publ. No. EP 92110298.4.
Great Britain Pat. Appl. Publ. No. GB 2,202,328.
Intl. Pat. Appl. Publ. No. PCT/US87/00880.
Intl. Pat. Appl. Publ. No. WO 88/10315.
Intl. Pat. Appl. Publ. No. WO 89/06700.
Intl. Pat. Appl. Publ. No. WO 91/03162.
Intl. Pat. Appl. Publ. No. WO 92/07065.
Intl. Pat. Appl. Publ. No. WO 93/15187.
Intl. Pat. Appl. Publ. No. WO 93/23569.
Intl. Pat. Appl. Publ. No. WO 94/02595.
Intl. Pat. Appl. Publ. No. WO 94/13688.
Intl. Pat. Appl. Publ. No. PCT/US89/01025.

Adelman, Hayflick, Vasser, Seeburg, "In vitro deletional mutagenesis for bacterial production of the 20,000-dalton form of human pituitary growth hormone," *DNA*, 2(3): 183–193, 1983.

Ahn, Bae, Maruyama, Ito, "Comparison of the human genomic structure of the Runt domain-encoding PEBP2/CBF(alpha) gene family," *Gene*, 168:279–280, 1996.

Allen and Choun, "Large unilamellar liposomes with low uptake into the reticuloendothelial system," *FEBS Lett.*, 223:42–46, 1987.

Alper, "Boning up: newly isolated proteins heal bad breaks," *Science*, 263:324–325,1994.

Altschul et al., "Basic local alignment search tool," *J. Mol. Biol.*, 215:403–410, 1990.

Andersson and Marks, "Tartrate-resistant acid ATPase as a cytochemical marker for osteoclasts," *J. Histochem. Cytochem.*, 37(1):115–117, 1989.

Ansari-Lari, Jones, Timms, Gibbs, "Improved ligation-anchored PCR™ strategy for identification of 5' ends of transcripts," *Biotechniques*, 21:34–38, 1996.

Armitage et al., *Proc. Natl. Acad, Sci. USA*, 94(23): 12320–12325, 1997.

Aronson, Fisher, Blechman, Caudy, Gergen, "Groucho-dependent and -independent repression activities of runt domain proteins," *Mol. Cell. Biol.*, 17:5581–5587, 1997.

Asahina, Sampath, Nishimura, Hauschka, "Human osteogenic protein-1 induces both chondroblastic and osteoblastic differentiation of osteoprogenitor cells derived from newborn rat calvaria," *J. Cell Biol.*, 123:921–933, 1993.

Aubin and Liu. "The osteoblast lineage," In: *Principles of Bone Biology*, Bilezikian et al. eds. San Diego, Calif., Academic Press, pp. 51–67, 1996.

Ausubel, Brent, Kingston, Moore, Seidman, Smith, Strul (ed.), In: *Current protocols in Molecular Biology*. John Wiley & Sons, Inc., New York, 1994.

Bae, Ogawa, Maruyama, Oka, Satake, Shigesada, Jenkins, Gilbert, Copeland, Ito, PEBP2αB/Mouse AML1 consists of multiple isoforms that possess differential transactivation potentials," *Mol. Cell. Biol.*, 14:3242–3252, 1994.

Bae, Takahashi, Zhang, Ogawa, Shigesada, Namba, Satake, Ito, "Cloning, mapping and expression of PEBP2αC, a third gene encoding the mammalian runt domain," *Gene*, 159:245–248, 1995.

Bae, Yamaguchi-Iwai, Ogawa, Maruyama, Inuzuka, Kagoshima, Shigesada, Satake, Ito, "Isolation of PEBP2αB cDNA representing the mouse homolog of human acute myeloid leukemia gene," *Oncogene*, 8:809–814, 1992.

Bae, Yamaguchi-Iwai, Ogawa, Maruyama, Inuzuka, Kagoshima, Shigesada, Satake, Ito, "Isolation of PEBP2αB cDNA representing the mouse homolog of human acute myeloid leukemia gene, AML1," *Oncogene*, 8:809–814, 1993.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Bayer and Wilchek, "The use of the avidin-biotin complex as a tool for molecular biology," In: *Methods of Biochemical Analysis*, Glick, D., John Wiley and Sons, New York, 1980.

Benvenisty and Reshef, "Direct introduction of genes into rats and expression of the genes," *Proc. Natl. Acad. Sci. USA*; 83(24): 9551–9555, 1986.

Bodem et al., "Regulation of gene expression by human foamy virus and potentials of foamy viral vectors," *Stem Cells*, 15 (Suppl. 1):1:141–147, 1997.

Boden et al., "Estrogen receptor mRNA expression in callus during fracture healing in the rat," *Calcif. Tissue Int.*, 45:34–325, 1989.

Boffa, Carpaneto, Allfrey, *Proc. Natl. Acad. Sci. USA*, 92:1901–1905, 1995.

Boffa, Morris, Carpaneto, Louissaint, Allfrey, *J. Biol. Chem.*, 271:13228–13233, 1996.

Bogdanovic, Bedalov, Krebsbach, Pavlin, Woody, Clark, Thomas, Rowe, Kream, Lichtler, "Regulation of COL1A1 expression in type I collagen producing tissues: identification of a 49 base pair region which is required for transgene expression in bone of transgenic mice," *J. Bone Min. Res.*, 9:285–291, 1994.

Bolivar, Rodriguez, Betlach, Boyer, "Construction and characterization of new cloning vehicles. I. Ampicillin-resistant derivatives of the plasmid pMB9," *Gene*, 2(2): 75–93, 1977.

Bonadio, Saunders, Tsai, Goldstein, Morris-Winam, Brinkley, Dolan, Altschuler, Hawkins, Bateman, Mascara, Jaenisch, *Proc. Natl. Acad. Sci. USA*, 87:7145–7149, 1990.

Bradley, In: *Teratocarcinomas and Embryonic Stem Cells: A Practical Approach*, (ed. Robinson, E. J.) 113–151, IRL, Oxford, 1987.

Brown, "Southern blotting onto a nylon membrane with an alkaline buffer," In: *Current Protocols in Molecular Biology*, Boston, John Wiley and Sons, Ausubel et al. Eds., Vol. 1, p. 297, 1993.

Byers and Steiner, "Osteogenesis imperfecta," *Annu. Rev. Med.*, 43:269–282, 1992.

Campbell, In: *Monoclonal Antibody Technology, Laboratory Techniques in Biochemistry and Molecular Biology*, Burden and Von Knippenberg, Eds., Vol. 13, pp. 75–83, Elsevier, Amsterdam, 1984.

Capecchi, "High efficiency transformation by direct microinjection of DNA into cultured mammalian cells," *Cell*, 22(2):479–488, 1980.

Carlsson et al., *Nature*, 380:207, 1996.

Carroll and Moss, *Curr. Opin. Biotechnol.*, 8(5):573–577, 1997.

Cech et al., "In vitro splicing of the ribosomal RNA precursor of Tetrahymena: involvement of a guanosine nucleotide in the excision of the intervening sequence," *Cell*, 27(3 Pt 2):487–496, 1981.

Celeste, Rosen, Buecker, Kriz, Wang, Wozney, "Isolation of the human gene for bone gla protein utilizing the mouse and rat cDNA clones," *EMBO J.*, 5:1885–1890, 1986.

Chang et al., "Foreign gene delivery and expression in hepatocytes using a hepatitis B virus vector," *Hepatology*, 14:134A, 1991.

Chang, Nunberg, Kaufinan, Erlich, Schimke, Cohen, "Phenotypic expression in *E. coli* of a DNA sequence coding for mouse dihydrofolate reductase", *Nature*, 275(5681): 617–624, 1978.

Chen and Okayama, "High-efficiency transformation of mammalian cells by plasmid DNA," *Mol. Cell. Biol.*, 7:2745–2752, 1987.

Chen et al., *Nucl. Acids Res.*, 20:4581–4589, 1992.

Chen, Harless, Wright, Kellems, "Identification and characterization of transcriptional arrest sites in exon 1 of the human adenosine deaminase gene," *Mol. Cell. Biol.*, 10:4555–4564, 1990.

Chou and Fasman, "Conformational Parameters for Amino Acides in Helical, β-Sheet, and Random Coil Regions Calculated from Proteins," *Biochemistry*, 13(2):211–222, 1974b.

Chou and Fasman, "Empirical Predictions of Protein Conformation," *Ann. Rev. Biochem.*, 47:251–276, 1978b.

Chou and Fasman, "Prediction of β-Turns," *Biophys. J.*, 26:367–384, 1979.

Chou and Fasman, "Prediction of Protein Conformation," *Biochemistry*, 13(2):222–245, 1974a.

Chou and Fasman, "Prediction of the Secondary Structure of Proteins from Their Amino Acid Sequence," *Adv. Enzymol. Relat. Areas Mol. Biol.*, 47:45–148, 1978a.

Chowrira and Burke, *Nucl. Acids Res.*, 20:2835–2840, 1992.

Christensen et al., *J. Pept. Sci.*, 1(3):175–183, 1995.

Clapp, "Somatic gene therapy into hematopoietic cells. Current status and future implications," *Clin. Perinatol.*, 20(1):155–168, 1993.

Coffin, "Retroviridae and their replication," In: *Virology*, Fields et al. (eds.), New York: Raven Press, pp. 1437–1500, 1990.

Coffman, Kirchhamer, Harrington, Davidson, "SpRunt-1, a new member of the runt domain family of transcription factors, is a positive regulator of the aboral ectoderm-specific CyIIIM gene in sea urchin embryos," *Dev. Biol.*, 174:43–54, 1996.

Cohn and Tickle, "Limbs: a model for pattern formation within the vertebrate body plan," *Trends Gent.*, 12:253–258, 1996.

Collins and Olive, *Biochem.*, 32:2795–2799, 1993.

Comstock et al., *Methods Mol. Biol.*, 62:207–222, 1997.

Corey, *Trends Biotechnol.*, 15(6):224–229, 1997.

Couch et al., "Immunization with types 4 and 7 adenovirus by selective infection of the intestinal tract," *Am. Rev. Resp. Dis.*, 88:394–403, 1963.

Coune, "Liposomes as drug delivery system in the treatment of infectious diseases: potential applications and clinical experience," *Infection*, 16(3):141–147, 1988.

Coupar et al., "A general method for the construction of recombinant vaccinia virus expressing multiple foreign genes," *Gene*, 68:1–10, 1988.

Couvreur et al., "Nanocapsules, a new lysosomotropic carrier," *FEBS Lett.*, 84:323–326, 1977.

Couvreur, "Polyalkyleyanoacrylates as colloidal drug carriers," *Crit. Rev. Ther. Drug Carrier Syst.*, 5:1–20, 1988.

Curiel, Agarwal, Wagner, Cotten, "Adenovirus enhancement of transferrin-polylysine-mediated gene delivery," *Proc. Natl. Acad. Sci. USA*, 88(19):8850–8854, 1991.

Curiel, Wagner, Cotten, Birnstiel, Agarwal, Li, Loechel, Hu, "High-efficiency gene transfer mediated by adenovirus coupled to DNA-polylysine complexes," *Hum. Gen. Ther.*, 3(2):147–154, 1992.

Daga, Karlovich, Dumstrei, Banerjee, "Patterning of cells in the Drosophila eye by Lozenge, which shares homologous domains with AML1," *Genes Dev.*, 10:1194–1205, 1996.

Desbois, Hogue, Karsenty, "The mouse osteocalcin gene cluster contains three genes with two separate spatial and temporal patterns of expression," *J. Biol. Chem.*, 269(2):1183–1190, 1994.

Desiderio and Campbell, "Liposome-encapsulated cephalotin in the treatment of experimental murine-salmonellosis," *J. Reticuloendothel. Soc.*, 34:279–287, 1983.

Dingwall and Laskey, "Nuclear targeting sequences—a consensus," *Trends Biochem. Sci.*, 16:478–481, 1991.

Dropulic et al., *J. Virol.*, 66:1432–41, 1992.

Dubensky et al., "Direct transfection of viral and plasmid DNA into the liver or spleen of mice," *Proc. Nat. Acad. Sci. USA*, 81:7529–7533, 1984.

Ducy and Karsenty, "Two distinct osteoblast-specific cis-acting elements control expression of a mouse osteocalcin gene," *Mol. Cell. Biol.*, 15:1858–1869, 1995.

Ducy, Zhang, Geoffroy, Ridall, Karsenty, "Osf2/Cbfa1: a transcriptional activator of osteoblast differentiation," *Cell*, 89:747–754, 1997.

Duehohn et al., *J. Org. Chem.*, 59:5767–5773, 1994.

Edmonson and Olson, "Helix-loop-helix proteins as regulators of muscle-specific transcription," *J. Biol. Chem.*, 268:755–758, 1993.

Egholm et al., *Nature*, 365:566–568, 1993.

Eglitis and Anderson, "Retroviral vectors for introduction of genes into mammalian cells," *Biotechniques*, 6(7):608–614, 1988.

Eglitis, Kantoff, Kohn, Karson, Moen, Lothrop, Blaese, Anderson, "Retroviral-mediated gene transfer into hemopoietic cells," *Avd. Exp. Med. Biol.*, 241:19–27, 1988.

Eichenlaub, *J. Bacteriol.*, 138(2):559–566, 1979.

Elroy-Stein and Moss, *Proc. Natl. Acad. Sci. USA*, 87:6743–7, 1990.

Erlebacher et al. "Toward a molecular understanding of skeletal development," *Cell*, 80:371–378, 1995.

Faller and Baltimore, "Liposome encapsulation of retrovirus allows efficient super infection of resistant cell lines," *J. Virol.*, 49(1):269–272, 1984.

Fechheimer et al., "Transfection of mammalian cells with plasmid DNA by scrape loading and sonication loading," *Proc. Natl. Acad. Sci. USA*, 84:8463–8467, 1987.

Ferkol, Lindberg, Chen, Perales, Crawford, Ratnoff, Hanson, "Regulation of the phosphoenolpyruvate carboxykinase/human factor IX gene introduced into the livers of adult rats by receptor-mediated gene transfer," *FASEB J.*, 7(11):1081–1091, 1993.

Fiers, Contreras, Haegemann, Rogiers, Van de Voorde, Van Heuverswyn, Van Herreweghe, Volckaert, Ysebaert, "Complete nucleotide sequence of SV40 DNA," *Nature*, 273(5658):113–120, 1978.

Footer, Engholm, Kron, Coull, Matsudaira, *Biochemistry*, 35:10673–10679, 1996.

Forster and Symons, "Self-cleavage of plus and minus RNAs of a virusoid and a structural model for the active sites," *Cell*, 49:211–220, 1987.

Fraley et al., "Entrapment of a bacterial plasmid in phospholipid vesicles: Potential for gene transfer," *Proc. Natl. Acad. Sci. USA*, 76:3348–3352, 1979.

Friedmann, "Progress toward human gene therapy," *Science*, 244:1275–1281, 1989.

Frohman, M. A., In: "PCR Protocols: A Guide to Methods and Applications," Academic Press, New York, 1990.

Fromm, Taylor, Walbot, "Expression of genes transferred into monocot and dicot plant cells by electroporation," *Proc. Natl. Acad. Sci. USA*, 82(17):5824–5828, 1985.

Furukawa, Yamaguchi, Ogawa, Shigesada, Satake, Ito, "A ubiquitous repressor interacting with an F9 cell-specific silencer and its functional suppression by differentiated cell-specific positive factors," *Cell Growth Diff.*, 1:135–147, 1990.

Fynan, Webster, Fuller, Haynes, Santoro, Robinson, "DNA vaccines: protective immunizations by parenteral, mucosal, and gene gun inoculations," *Proc. Natl. Acad. Sci. USA*, 90(24):11478–11482, 1993.

Gabizon and Papahadjopoulos, "Liposomes formulations with prolonged circulation time in blood and enhanced uptake by tumors," *Proc. Natl. Acad. Sci. USA*, 85:6949–6953, 1988.

Gambacorti-Passerini et al., *Blood*, 88:1411–1417, 1996.

Gao and Huang, *Nucl. Acids Res.*, 21:2867–2872, 1993.

Gefter, Margulies, Scharff, "A simple method for polyethylene glycol-promoted hybridization of mouse myeloma cells," *Somat. Cell Genet.*, 3(2):231–236, 1977.

Geoffroy, Ducy, Karsenty, "A PEBP2/AML-I-related factor increases osteocalcin promotor activity through its binding to an osteoblast-specific cis-acting element," *J. Biol. Chem.*, 270:30973–30979, 1995.

Gerber, Seipel, Georgiev, Hofferer, Hug, Rusconi, Schaffner, "Transcriptional activation modulated by homopolymeric glutamine and proline stretches," *Science*, 263:808–811, 1994.

Gergen and Wieschaus, "The localized requirements for a gene affecting segmentation in Drosophila: analysis of larvae mosaic for runt," *Dev. Biol.*, 109:321–335, 1985.

Gerlach et al., "Construction of a plant disease resistance gene from the satellite RNA of tobacco rinspot virus," *Nature* (London), 328:802–805, 1987.

Ghosh-Choudhury et al., "Protein IX, a minor component of the human adenovirus capsid, is essential for the packaging of full-length genomes," *EMBO J.*, 6:1733–1739, 1987.

Ghosh and Bachhawat, "Targeting of liposomes to hepatocytes," In: *Liver diseases, targeted diagnosis and therapy using specific receptors and ligands*, Wu G. and C. Wu ed., New York: Marcel Dekker, pp. 87–104, 1991.

Ghozi, Bernstein, Negreanu, Levanon, Groner, "Expression of the acute myeloid leukemia gene AML1 is regulated by two promoter regions," *Proc. Natl. Acad. Sci. USA*, 93:1935–1940, 1996.

Giese, Kingsley, Kirshner, Grosschedl, "Assembly and function of a TCRα enhancer complex is dependent on LEF-1-induced DNA binding and multiple protein-protein interactions," *Genes and Dev.*, 9:995–1008, 1995.

Goding, "Monoclonal Antibodies: Principles and Practice," pp. 60–74. 2nd Edition, Academic Press, Orlando, Fla., 1986.

Goeddel, Heyneker, Hozumi, Arentzen, Itakura, Yansura, Ross, Miozzari, Crea, Seeburg, "Direct expression in *Escherichia coli* of a DNA sequence for human growth hormone," *Nature*, 281(5732):544–548, 1979.

Goeddel, Shepard, Yelverton, Leung, Crea, Sloma, Pestka, "Synthesis of human fibroblast interferon by *E. coli*," *Nucl. Acids Res.*, 8(18):4057–4074, 1980.

Golling, Li, Pepling, Stebbins, Gergen, "Drosophila homologs of the proto-oncogene product PEBP2/CBFβ regulate the DNA-binding properties of Runt. *Mol. Cell. Biol.*, 16:932–942, 1996.

Gomez-Foix, Coats, Baque, Alam, Gerard, Newgard, "Adenovirus-mediated transfer of the muscle glycogen phosphorylase gene into hepatocytes confers altered regulation of glycogen metabolism," *J. Biol. Chem.*, 267(35): 25129–25134, 1992.

Good and Nielsen, *Antisense Nucleic Acid Drug Dev.*, 7(4):431–437, 1997.

Goodman et al. "Development of a dynamic bone in patients with secondary hyperparathyroidism after intermittent calcitrol therapy," *Kidney Int.*, 46:1160–1166, 1994.

Gopal, "Gene transfer method for transient gene expression, stable transfection, and cotransfection of suspension cell cultures," *Mol. Cell Biol.*, 5:1188–1190, 1985.

Graham and Prevec, "Adenovirus-based expression vectors and recombinant vaccines," *Biotechnology*, 20:363–390, 1992.

Graham and Prevec, "Manipulation of adenovirus vector," In: *Methods in Molecular Biology: Gene Transfer and Expression Protocol*, E. J. Murray (ed.), Clifton, N.J.: Humana Press, 7:109–128, 1991.

Graham and van der Eb, "Transformation of rat cells by DNA of human adenovirus 5," *Virology*, 54(2):536–539, 1973.

Graham et al., "Characteristics of a human cell line transformed by DNA from human adenovirus type 5", *J. Gen. Virol.*, 36:59–72, 1977.

Green, Issemann, Sheer, "A versatile in vivo and in vitro eukaryotic expression vector for protein engineering,", *Nucl. Acids Res.*, 16(1):369, 1988.

Griffith et al., *J. Am. Chem. Soc.*, 117:831–832, 1995.

Grunhaus and Horwitz, "Adenovirus as cloning vector," *Seminar in Virology*, 3:237–252, 1992.

Guerrier-Takada et al., *Cell*, 35:849, 1983.

Gundberg, Hauschka, Lian, Gallop, "Osteocalcin: isolation, characterization, and detection," *Methods Enzymol.*, 107:516–544, 1984.

Haaima, Lohse, Buchardt, Nielsen, *Angew. Chem., Int. Ed. Engl.*, 35:1939–1942, 1996.

Hahn, Vogel, Delling, *Virchows Arch. A. Pathol. Anat. Histopathol.*, 418:1–7, 1991.

Hampel and Tritz, *Biochem.*, 28:4929, 1989.

Hampel et al., *Nucl. Acids Res.*, 18:299, 1990.

Han and Manley, "Functional domains of the Drosophila Engrailed protein," *EMBO J.*, 12:2723–2733, 1993b.

Han and Manley, "Transcriptional repression by the Drosophila even-skipped protein: definition of a minimal repression domain," *Genes Dev.*, 7:491–503, 1993a.

Hanvey et al., *Science*, 258:1481–1485, 1992.

Harland and Weintraub, "Translation of mammalian mRNA injected into Xenopus oocytes is specifically inhibited by antisense RNA," *J. Cell Biol.*, 101:1094–1099, 1985.

Harlow and Lane, In: *Antibodies: A Laboratory Manual*, Cold Spring Harbor Laboratory, Cold Spring Harbor, N.Y., 1988.

Hauschka, Lian, Cole, Gundberg, "Osteocalcin and matrix Gla protein: vitamin K-dependent proteins in bone," *Physiol. Rev.*, 69:990–1047, 1989.

Heath and Martin, "The development and application of protein-liposome conjugation techniques," *Chem. Phys. Lipids*, 40:347–358, 1986.

Heath et al., "Liposome-mediated delivery of pteridine antifolates to cells: in vitro potency of methotrexate and its alpha and gamma substituents," *Biochim. Biophys. Acta*, 862:72–80, 1986.

Henry-Michelland et al., "Attachment of antibiotics to nanoparticles; Preparation, drug-release and antimicrobial activity in vitro," *Int. J. Pharm.*, 35:121–127, 1987.

Hermonat and Muzycska, "Use of adenoassociated virus as a mammalian DNA cloning vector: Transduction of neomycin resistance into mammalian tissue culture cells," *Proc. Natl. Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Natl. Acad. Sci. USA*, 90:2812–2816, 1993.

Hess et al., *J. Adv. Enzyme Reg.*, 7:149, 1968.

Hitzeman, Clarke, Carbon, "Isolation and characterization of the yeast 3-phosphoglycerokinase gene (PGK) by an immunological screening technique," *J. Biol. Chem.*, 255(24):12073–12080, 1980.

Hogan, "Bone morphogenetic proteins: multifunctional regulators of vertebrate development," *Genes Dev.*, 10:1580–1594, 1996.

Holland and Holland, "Isolation and identification of yeast messenger ribonucleic acids coding for enolase, glyceraldehyde-3-phosphate dehydrogenase, and phosphoglycerate kinase," *Biochemistry*, 17(23):4900–4907, 1978.

Hoover et al., (Eds.), "*Remington's Pharmaceutical Sciences*," 15th Edition, pp. 1035–1038 and 1570–1580, Mack Publishing Co., Easton, Pa., 1975.

Horowitz et al., "Functional and molecular changes in colony stimulating factor secretion by osteoblasts," *Connective Tissue Res.*, 20:159–168, 1989.

Horton, "Connective tissue and its heritable disorders," In: *Morphology of connective tissue: cartilage*. Chichester, UK. Wiley-Liss, Inc. pp. 73–84, 1993.

Horwich et al. "Synthesis of hepadenovirus particles that contain replication-defective duck hepatitis B virus genomes in cultured HuH7 cells," *J. Virol.*, 64:642–650, 1990.

Huang, *Curr. Opin. Biotechnol.*, 7(5):531–535, 1996.

Hyrup and Nielsen, *Bioorg. Med. Chem.*, 1996.

Ilan et al., *J. Clin. Invest.*, 99(5):1098–1106, 1997.

Imaizumi et al., "Liposome-entrapped superoxide dismutase ameliorates infarct volume in focal cerebral ischemia," *Acta. Neurochirurgica Suppl.*, 51:236–238, 1990b.

Imaizumi et al., "Liposome-entrapped superoxide dismutase reduces cerebral infarction in cerebral ischemia in rats," *Stroke*, 21(9):1312–1317, 1990a.

Itakura, Hirose, Crea, Riggs, Heyneker, Bolivar, Boyer, "Expression in *Escherichia coli* of a chemically synthesized gene for the hormone somatostatin," *Science*, 198(4321):1056–1063, 1977.

Ito and Bae, "The runt domain transcription factor, PEBP2/CBF, and its involvement in human leukemia," In: *Cell cycle regulators and chromosomal translocation*, Yaniv M., and Ghysdael K., (ed.), Birkhauser Verlag, Basel, Switzerland, 1997.

Ito, "Structural alterations in the transcription factor PEBP2/CBF linked to four different types of leukemia," *J. Cancer Res. Clin. Oncol.*, 122:266–274, 1996.

Jaeger et al., *Proc. Natl. Acad. Sci. USA*, 86:7706–7710, 1989.

Jameson and Wolf, "The Antigenic Index: A Novel Algorithm for Predicting Antigenic Determinants," *Compu. Appl. Biosci.*, 4(1):181–6, 1988.

Jensen et al., *Biochemistry*, 36(16):5072–5077, 1997.

Jingushi et al., "Acidic fibroblast growth factor injection stimulates cartilage enlargement and inhibits cartilage gene expression in rat fracture healing," *J. Orthop. Res.*, 8:364–371, 1990.

Johnson et al. "Pleitropic effects of a null mutation in the c-fos proto-oncogene," *Cell*, 71(4):577–586, 1992.

Johnson et al., "Peptide Turn Mimetics" In: *Biotechnology and Pharmacy*, Pezzuto et al., eds., Chapman and Hall, New York, 1993.

Jones and Morikawa, *Curr. Opin. Biotechnol.*, 7(5): 512–516, 1996.

Jones and Shenk, "Isolation of deletion and substitution mutants of adenovirus type 5," *Cell*, 13:181–188, 1978.

Jones, "Proteinase mutants of *Saccharomyces cerevisiae*," *Genetics*, 85(1):23–33, 1977.

Jones, In: *Smith's recognizable patterns of human malformation*, W.B. Saunders Company, Philadelphia, 1997.

Joyce, "RNA evolution and the origins of life," *Nature*, 338:217–244, 1989.

Kafri et al., "Sustained expression of genes delivered directly into liver and muscle by lentiviral vectors," *Nat. Genet.*, 17(3):314–317, 1997.

Kagoshima, Akamatsu, Ito, Shigesada, "Functional dissection of the α and β subunits of transcription factor PEBP2α and the redox susceptibility of its DNA-binding activity," *J. Biol. Chem.*, 271(51):33074–33082, 1996.

Kagoshima, Shigesada, Satake, Ito, Miyoshi, Ohki, Pepling, Gergen, "The Runt domain identifies a new family of heteromeric transcriptional regulators," *Trends in Genet.*, 9:338–341, 1993.

Kaneda, Iwai, Uchida, "Introduction and expression of the human insulin gene in adult rat liver," *J. Biol. Chem.*, 264(21):12126–12129, 1989.

Kania, Bonner, Duffy, Gergen, "The Drosophila segmentation gene runt encodes a novel nuclear regulatory protein that is also expressed in the developing nervous system," *Genes Dev.*, 4:1701–1713, 1990.

Karaplis et al. "Lethal skeletal dysplasia from targeted disruption of the parathyroid hormone-related peptide gene," *Genes Dev.*, 8(3):277–289, 1994.

Karlsson, Van Doren, Schweiger, Nienhuis, Gluzrnan, "Stable gene transfer and tissue-specific expression of a human globin gene using adenoviral vectors," *EMBO J.*, 5(9):2377–2385, 1986.

Kashani-Saber et al., *Antisense Res. Dev.*, 2:3–15, 1992.

Katagii, Yamaguchi, Ikeda, Yoshiki, Wozney, Rosen, Wang, Tanaka, Omura, Suda, "The non-osteogenic mouse pluripotent cell line, C3H10T1/s, is induced to differentiate into osteoblastic cells by recombinant human bone morphogenetic protein-2," *Biochem. Biophys. Res. Commun.*, 172:295–299, 1990.

Kato et al., "Expression of hepatitis β virus surface antigen in adult rat liver," *J. Biol. Chem.*, 266:3361–3364, 1991.

Kaufman, "*The Atlas of Mouse Development*," M. H. Kaufinan, ed., San Diego, Calif.: Academic Press, pp. 389–407, 1992.

Kesterson, Stanley, DeMayo, Finegold, Pike, "The human osteocalcin promoter directs bone-specific vitamin D-regulatable gene expression in transgenic mice," *Mol. Endocrinol.*, 7:462–467, 1993.

Khatri et al., *Virology*, 239(1):226–237, 1997.

Kim and Cech, "Three-dimensional model of the active site of the self-splicing rRNA precursor of Tetrahymena," *Proc. Natl. Acad. Sci. USA*, 84(24):8788–8792, 1987.

Kim and Spiegelman, "ADD1/SREBP1 promotes adipocyte differentiation and gene expression linked to fatty acid metabolism," *Genes Dev.*, 10:1096–1107, 1996.

Kim et al., *J. Virol.*, 72(2):994–1004, 1998.

Kingsley, "The TGF-β superfamily: new members, new receptors and new genetic tests of function in different organisms," *Genes Dev.*, 8:133–146, 1994.

Kingsman, Clarke, Mortimer, Carbon, "Replication in Saccharomyces cerevisiae of plasmid pBR313 carrying DNA from the yeast trpl region," *Gene*, 7(2):141–152, 1979.

Klein, Komstein, Sanford, Fromm, *Nature*, 327:70–73, 1987.

Koch et al., *Tetrahedron Lett.*, 36:6933–6936, 1995.

Koh et al., *Biotechniques*, 23(4):622–624, 1997.

Kohler and Milstein, "Continuous cultures of fused cells secreting antibody of predefined specificity," *Nature*, 256 (5517):495–497, 1975.

Kohler and Milstein, "Derivation of specific antibody-producing tissue culture and tumor lines by cell fusion," *Eur. J. Immunol.*, 6(7):511–519, 1976.

Komori, Yagi, Nomura, Yamaguchi, Sasaki, Deguchi, Shimizu, Bronson, Gao, Inada, Sato, Okamoto, Kitamura, Yoshiki, Kishimoto, "Targeted disruption of Cbfa1 results in a complete lack of bone formation owing to maturational arrest of osteoblasts," *Cell*, 89:755–764, 1997.

Koppelhus, *Nucleic Acids Res.*, 25(11):2167–2173, 1997.

Kozak, "An analysis of 5'-noncoding sequences of 699 vertebrate messenger RNAs," *Nucleic Acids Res.*, 15:8125–8148, 1987.

Kozak, "The scanning model for translation: an update," *J. Cell Biol.*, 108:229–241, 1989.

Kremsky et al., *Tetrahedron Lett.*, 37:4313–4316, 1996.

Kuby, In: *Immunology*, 2nd Edition. W.H. Freeman & Company, New York, 1994.

Kuo, Conley, Chen, Sladek, Darnell Jr., Crabtree, "A transcriptional hierarchy involved in mammalian cell-type specification," *Nature*, 355:457–461, 1992.

Kurokawa, Tanaka, Tanaka, Hirano, Ogawa, Mitani, Yazaki, Hirai, "A conserved cysteine residue in the runt homology domain of AML1 is required for the DNA-binding ability and the transforming activity on fibroblasts," *J. Biol. Chem.*, 271:16870–16876, 1996a.

Kurokawa, Tanaka, Tanaka, Ogawa, Mitani, Yazaki, Hirai, "Overexpression of the AML1 proto-oncoprotein in NIH3T3 cells leads to neoplastic transformation depending on the DNA-binding and transcriptional potencies," *Oncogene*, 12:883–892, 1996b.

Kwoh et al., *Proc. Natl. Acad. Sci. USA*, 86(4):1173–1177, 1989.

Kyte and Doolittle, "A simple method for displaying the hydropathic character of a protein," *J. Mol. Biol.*, 157(1): 105–132, 1982.

L'Huillier et al., *EMBO J.*, 11:4411–4418, 1992.

Landsdorp et al., *Hum. Mol. Genet.*, 5:685–691, 1996.

Le Gal La Salle et al., "An adenovirus vector for gene transfer into neurons and glia in the brain," *Science*, 259:988–990, 1993.

Lee, Thirunavukkarasu, Zhou, Pastore, Baldini, Hecht, Geoffroy, Ducy, Karsenty, "Missense mutations abolishing DNA-binding of the osteoblast-specific transcription factor OSF2/CBFA1 in cleidocranial dysplasia," *Nature Genet.*, 16:307–310, 1997.

Lenny, Meyers, Hiebert, "Functional domains of the t(8;21) fusion protein, AML-1/ETO, *Oncogene*, 11:1761–1769, 1995.

Levanon, Negreanu, Bernstein, Bar-Am, Avivi, Groner, "AML1, AML2, and AML3, the human members of the runt domain gene-family: cDNA structure, expression, and chromosomal localization," *Genomics*, 23:425–432, 1994.

Levrero et al., "Defective and nondefective adenovirus vectors for expressing foreign genes in vitro and in vivo," *Gene*, 101:195–202, 1991.

Li and Garoff, *Proc. Natl. Acad. Sci. USA*, 93(21): 11658–11663, 1996.

Lian, Stewart, Puchacz, Mackowiak, Shalhoub, Collart, Zambetti, Stein, "Structure of the rat osteocalcin gene and regulation of vitamin D-dependent expression," *Proc. Natl. Acad. Sci. USA*, 86(4):1143–1147, 1989.

Liddell and Cryer, "A Practical Guide to: Monoclonal Antibodies," John Wiley & Sons, New York, 1991.

Lieber et al., *Methods Enzymol.*, 217:47–66, 1993.

Lisziewicz et al., *Proc. Natl. Acad. Sci. USA*, 90:8000–8004, 1993.

Lopez-Berestein et al., "Liposomal amphotericin B for the treatment of systemic fingal infections in patients with cancer: a preliminary study" *J. Infect. Dis.*, 2151:704, 1985a.

Lopez-Berestein et al., "Protective effect of liposomal-amphotericin B against *C. albicans* infection in mice," *Cancer Drug Delivery*, 2:183, 1985b.

Lu, Maruyama, Satake, Bae, Ogawa, Kagoshima, Shigesada, Ito, "Subcellular localization of the α and β subunits of the acute myeloid leukemia-linked transcription factor PEBP2/CBF," *Mol. Cell. Biol.*, 15:1651–1661, 1995.

Lu, Xiao, Clapp, Li, Broxmeyer, "High efficiency retroviral mediated gene transducion into single isolated immature and replatable CD34(3+) hematopoietic stem/progenitor cells from human umbilical cord blood," *J. Exp. Med.*, 178(6):2089–2096, 1993.

Lundstrom, *Curr. Opin. Biotechnol.*, 8(5):578–582, 1997.

Luo et al. "Recombinant NFAT1 ($NFAT_p$) is regulated by calcineurin in T cells and mediates transcription of several cytokine genes," *Mol. Cell. Biol.*, 16(7):3955–3966, 1996a.

Luo, D'Souza, Hogue, Karsenty, "The matrix gla protein gene is a marker of the chondrogenesis cell lineage during mouse development," *J. Bone Miner. Res.*, 10:325–334, 1995.

Luo, Ducy, McKee, Pinero, Loyer, Behringer, Karsenty, "Spontaneous calcification of arteries and cartilage in mice lacking matrix GLA protein," *Nature*, 386(6620): 7881, 1997.

Luyten et al., "Purification and partial amino acid sequence of osteogenic, a protein initiating bone differentiation," *J. Biol. Chem.*, 264:13377–13380, 1989.

Macejak and Sarnow, "Internal initiation of translation mediated by the 5' leader of a cellular mRNA," *Nature*, 353:90–94, 1991.

Maloy et al., "Microbial Genetics," 2nd Edition. Jones and Barlett Publishers, Boston, Mass., 1994.

Maloy, "Experimental Techniques in Bacterial Genetics" Jones and Bartlett Publishers, Boston, Mass., 1990.

Maniatis et al., "Molecular Cloning: a Laboratory Manual," Cold Spring Harbor Laboratory, Cold Spring Harbor, N.Y., 1982.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

McMahon and Bradley, "The Wnt-1 (int-1) proto-oncogene is required for development of a large region of the mouse brain," *Cell*, 62(6):1073–1085, 1990.

Merriman, van Wijnen, Hiebert, Bidwell, Fey, Lian, Stein, Stein, "The tissue-specific nuclear matrix protein, NMP-2, is a member of the AML/CBF/PEBP2/Runt domain transcription factor family: interactions with the osteocalcin gene promoter," *Biochemistry*, 34:13125–13132, 1995.

Meyers, Downing, Hiebert, "Identification of AML-1 and the (8;21) translocation protein (AML-1ETO) as sequence-specific DNA-binding proteins: the runt homology domain is required for DNA binding and protein-protein interactions," *Mol. Cell. Biol.*, 13:6336–6345, 1993.

Meyers, Lenny, Hiebert, "The (8;21) fusion protein interferes with AML-1B-dependent transcriptional activation," *Mol. Cell. Biol.*, 15:1974–1982, 1995.

Michael, *Biotechniques*, 16:410–412, 1994.

Michel and Westhof, "Modeling of the three-dimensional architecture of group I catalytic introns based on comparative sequence analysis," *J. Mol. Biol.*, 216:585–610, 1990.

Molkentin and Olson. "Combinatorial control of muscle development by basic helix-loop-helix and MADS-box transcription factors," *Proc. Natl. Acad. Sci. USA*, 93:9366–9373, 1996.

Mollegaard, Buchardt, Egholm, Nielsen, *Proc. Natl. Acad. Sci. USA*, 91:3892–3895, 1994.

Mori and Fukatsu, "Anticonvulsant effect of DN-1417 a derivative of thyrotropin-releasing hormone and liposome-entrapped DN-1417 on amygdaloid-kindled rats," *Epilepsia*, 33(6):994–1000, 1992.

Muller et al., "Efficient transfection and expression of heterologous genes in PC12 cells," *Cell. Biol.*, 9(3):221–229, 1990.

Mulligan, "The basic science of gene therapy," *Science*, 260:926–932, 1993.

Mundlos, Mulliken, Abramsonm, Warman, Knoll, Olsen, "Genetic mapping of cleidocranial dysplasia and evidence of a microdeletion in one family," *Hum. Molec. Genet.*, 4:71–75, 1995.

Mundlos, Otto, Mundlos, Mulliken, Aylsworth, Albright, Lindhout, Cole, Henn, Knoll, Owen, Mertelsmann, Zabel, Olsen, "Mutations involving the transcription factor CBFA1 cause cleidocranial dysplasia," *Cell*, 89:773–779, 1997.

Muragaki, Mundlos, Upton, Olsen, "Altered growth and branching patterns in synpolydactyly caused by mutations in HOXD13," *Science*, 272:548–551, 1996.

Murakami, Watanabe, Nikura, Kameda, Saitoh, Yamamoto, Yokouchi, Kuroiwa, Mizumoto, "High-level expression of exogenous genes by replication-competent retrovirus vectors with an internal ribosomal entry site," *Gene*, 202(1–2):23–29, 1997.

Nakamura et al., "Enzyme Immunoassays: Heterogenous and Homogenous Systems," Chapter 27, 1987.

Neilsen, In: *Perspectives in Drug Discovery and Design* 4, Escom Science Publishers, pp. 76–84, 1996.

Nicolas and Rubinstein, "Retroviral vectors," In: *Vectors: A survey of molecular cloning vectors and their uses*, Rodriguez and Denhardt (eds.), Stoneham: Butterworth, pp. 494–513, 1988.

Nicolau and Gersonde, "Incorporation of inositol hexaphosphate into intact red blood cells, I, fusion of effector-containing lipid vesicles with erythrocytes," *Naturwissenschaften (Germany)*, 66(11):563–566, 1979.

Nicolau and Sene, "Liposome-mediated DNA transfer in eukaryotic cells," *Biochem. Biophys. Acta*, 721:185–190, 1982.

Nicolau et al., "Liposomes as carriers for in vivo gene transfer and expression," *Methods Enzymol.*, 149:157–176, 1987.

Nielsen et al., *Anticancer Drug Des.*, 8(1):53–63, 1993b.

Nielsen, Egholm, Berg, Buchardt, *Science*, 254:1497–1500, 1991.

Nigg, "Nucleocytoplasmic transport: signals, mechanisms and regulation," *Nature*, 386:779–787, 1997.

Norton, Piatyszek, Wright, Shay, Corey, *Nat. Biotechnol.*, 14:615–620, 1996.

Norton, Waggenspack, Varnum, Corey, *Bioorg Med Chem.*, 3:437–445, 1995.

Nucifora and Rowley, "AML1 and the 8;21 and 3;21 translocations in acute and chronic myeloid leukemia," *Blood*, 86(1):1–14, 1995.

O'Reilly, *Methods Mol. Biol.*, 62:235–246, 1997.

Oertli et al., *Langenbecks Arch Chir Suppl Kongressbd*, 114:79–84, 1997.

Ogawa, Inuzuka, Maruyama, Satake, Naito-Fujimoto, Ito, Shigesada, "Molecular cloning and characterization of PEBP2β, the heterodimeric partner of a novel Drosophila runt-related DNA binding protein PEBP2a," *Virology*, 194:314–331, 1993a.

Ogawa, Maruyama, Kagoshima, Inuzuka, Lu, Satake, Shigesada, Ito, "PEBP2/PEA2 represents a family of transcription factors homologous to the products of the Drosophila runt gene and the human AML1 gene," *Proc. Natl. Acad. Sci. USA*, 90:6859–6863, 1993b.

Ohara et al., *Proc. Natl. Acad. Sci. USA*, 86(15):5673–5677, 1989.

Ohkawa et al., *Nucl. Acids Symp. Ser.*, 27:15–6, 1992.

Ojwang et al., *Proc. Natl. Acad. Sci. USA*, 89:10802–10806, 1992.

Okuda, Deursen, Hiebert, Grosveld, Downing, "AML1, the target of multiple chromosomal translocations in human leukemia, is essential for normal fetal liver hematopoiesis," *Cell*, 84:321–330, 1996.

Oldberg, Franzen, Heinegrad, "Cloning and sequence analysis of rat bone sialoprotein (osteopontin) cDNA reveals an Arg-Gly-Asp cell-binding sequence," *Proc. Natl. Acad. Sci. USA*, 83(23):8819–8823, 1986.

Olson, Perry, Schulz, "Regulation of muscle differentiation by the MEF2 family of MADS box transcription factors," *Dev. Biol.*, 172:2–14, 1995.

Orkins, "Transcription factors and hematopoietic development," *J. Biol. Chem.*, 270:4955–4958, 1995.

Orum, Nielsen, Egholm, Berg, Buchardt, Stanley, *Nucl. Acids Res.*, 21:5332–5336, 1993.

Orum, Nielsen, Jorgensen, Larsson, Stanley, Koch, *BioTechniques*, 19:472–480, 1995.

Otto, Thornell, Crompton, Denzel, Gilmour, Rosewell, Stamp, Beddington, Mundlos, Olsen, Selby, Owen, "Cbfa1, a candidate gene for the cleidocranial dysplasia syndrome, is essential for osteoblast differentiation and bone development," *Cell*, 89(5):765–771, 1997.

Ozkaynak et al., "OP-1 cDNA encodes an osteogenic protein in the TGF-b famil." *EMBO J.*, 9:2085–2093, 1990.

Palaparti, Baratz, Stifani, "The Groucho/transducin-like enhancer of split transcriptional repressors interact with the genetically defmd amino-terminal silencing domain of Histone H3," *J. Biol. Chem.*, 272:26604–26610, 1997.

Pardridge, Boado, Kang, *Proc. Natl. Acad. Sci. USA*, 92:5592–5596, 1995.

Parfitt, Drezner, Glorieux, Kanis, Malluche, Meunier, Ott, Recker, *J. Bone Mineral Res.*, 2:595–610, 1987.

Parfitt, Mathews, Villanueva, Kleerekoper, Frame, Rao, *J. Clin. Invest.*, 72:1396–1409, 1983.

Parfitt, Riggs, Melton, *Osteoporosis: Etiology, Diagnosis and Management*, (eds.), p. 501, Raven Press, N.Y., 1988.

Paroush, Finley Jr., Kidd, Wainwright, Ingham, Brent, Ish-Horowicz, "Groucho is required for Drosophila neurogenesis, segmentation, and sex determination and interacts directly with Hairy-related bHLH proteins," *Cell*, 79:805–815, 1994.

Paskind et al., "Dependence of moloney murine leukemia virus production on cell growth," *Virology*, 67:242–248, 1975.

Pelletier and Sonenberg, "Internal initiation of translation of eukaryotic mRNA directed by a sequence derived from poliovirus RNA," *Nature*, 334:320–325, 1988.

Perales et al., *Proc. Natl. Acad. Sci. USA*, 91:4086–4090, 1994.

Perrault et al., *Nature*, 344:565, 1990.

Perrotta and Been, *Biochem.*, 31:16, 1992.

Perry-O'Keefe, Yao, Coull, Fuchs, Egholm, *Proc. Natl. Acad. Sci. USA*, 93:14670–14675, 1996.

Petersen, Jensen, Egholm, Nielsen, Buchardt, *Bioorg. Med. Chem. Lett.*, 5:1119–1124, 1995.

Piccolo, Sasai, Lu, De Robertis, "Dorsoventral patterning in xenopus: inhibition of ventral signals by direct binding of chordin to BMP-4," *Cell*, 86:589–598, 1996.

Pieken et al., *Science*, 253:314, 1991.

Pikul et al., "In vitro killing of melanoma by liposome-delivered intracellular irradiation, *Arch. Surg.*, 122(12):1417–1420, 1987.

Poli, Balena, Fattori, Markators, Yamamoto, Tanaka, Ciliberto, Rodan, Costantini, "Interleukin-6 deficient mice are protected from bone loss caused by estrogen depletion," *EMBO J.*, 13(5):1189–1196, 1994.

Possee, *Curr. Opin. Biotechnol.*, 8(5):569–572, 1997.

Potter et al., "Enhancer-dependent expression of human k immunoglobulin genes introduced into mouse pre-B lymphocytes by electroporation," *Proc. Natl. Acad. Sci. USA*, 81:7161–7165, 1984.

Prockop, "Mutations that alter the primary structure of type I collagen. The perils of a system for generating large structures by the principle of nucleated growth," *J. Biol. Chem.*, 265:15349–15352, 1990.

Prokop and Bajpai, "Recombinant DNA Technology I," Conference on Progress in Recombinant DNA Technology Applications, Potosi, Mich., Jun. 3–8, 1990, *Ann. N.Y. Acad. Sci.*, 646:1–383, 1991.

Racher et al., *Biotechnology Techniques*, 9:169–174, 1995.

Ragot et al., "Efficient adenovirus-mediated transfer of a human minidystrophin gene to skeletal muscle of mdx mice," *Nature*, 361:647–650, 1993.

Raisz and Kream, "Regulation of bone formation," *N. Engl. J. Med.*, 309:29–35, 1983.

Ramirez-Solis, Davis, Bradley, *Methods Enzymol.*, 225:855–878, 1993.

Rawn, "Biochemistry" Harper & Row Publishers, New York, 1983.

Reddi, "Bone and cartilage differentiation," *Curr. Opin. Genet. Dev.*, 4:737–744, 1994.

Reinhold-Hurek and Shub, "Self-splicing introns in tRNA genes of widely divergent bacteria," *Nature*, 357:173–176, 1992.

Renan, "Cancer genes: current status, future prospects, and applicants in radiotherapy/oncology," *Radiother. Oncol.*, 19:197–218, 1990.

Renneisen et al., "Inhibition of expression of human immunodeficiency virus-1 in vitro by antibody-targeted liposomes containing antisense RNA to the env region," *J. Biol. Chem.*, 265(27):16337–16342, 1990.

Reynolds, "The effect of ascorbic acid on the growth of chick bone rudiments in vitro," *Exp. Cell. Res.*, 47:42–48, 1967.

Rhodes, DiMattia, Rosenfeld, "Transcriptional mechanisms in anterior pituitary cell differentiation," *Curr. Opin. Genet. Dev.*, 4:709–717, 1994.

Rich et al., "Development and analysis of recombinant adenoviruses for gene therapy of cystic fibrosis," *Hum. Gene Ther.*, 4:461–476, 1993.

Ridgeway, "Mammalian expression vectors," In: *Vectors: A survey of molecular cloning vectors and their uses*, Rodriguez R L, Denhardt D T, ed., Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rodan and Martin, "Role of the osteoblasts in hormonal control of bone resorption. A hypothesis," *Calcif. Tissue Int.*, 33:349–352, 1981.

Rodan et al. "Pathophysiology of osteoporosis," *Principles of Bone Biology*. Bilezikian et al. eds. San Diego, Calif. Academic Press. pp. 979–990. 1996.

Rose, *Anal. Chem.*, 65(24):3545–3549, 1993.

Rosenfeld et al., "Adenovirus-mediated transfer of a recombinant α1-antitrypsin gene to the lung epithelium in vivo," *Science*, 252:431434, 1991.

Rosenfeld et al., "In vivo transfer of the human cystic fibrosis transmembrane conductance regulator gene to the airway epithelium," *Cell*, 68:143–155, 1992.

Rossert, Chen, Eberspaecher, Smith, de Chrombrugghe, "Identification of a minimal sequence of the mouse pro-α1 (I) collagen promoter that confers high-level osteoblast expression in transgenic mice and that binds a protein selectively present in osteoblasts," *Proc. Natl. Acad. Sci. USA*, 93:1027–1031, 1996.

Rossi et al., *Aids Res. Hum. Retrovir.*, 8:183, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Ruskowski et al., *Cancer*, 80(12 Suppl):2699–2705, 1997.

Sadowski and Ptashne, "A vector for expressing GAL4 (1–147) fusion in mammalian cells," *Nucl. Acids Res.*, 17:7539, 1989.

Sambrook, Fristch, Maniatis, *"Molecular Cloning: A Laboratory Manual,"* C. Nolan, ed., Cold Spring Harbor Laboratory Press, Cold Spring Harbor, N.Y., 1989.

Sampath, Maliakal, Hauschka, Jones, Sasak, Tucker, White, Coughlin, Tucker, Pang, Corbett, Ozkaynak, Oppermann, Rueger, "Recombinant human osteogenic protein-1 (hOP-1) induces new bone formation in vivo with a specific activity comparable with natural bovine osteogenic protein and stimulates osteoblast proliferation and differentiation in vitro," *J. Biol. Chem.*, 267:20352–20362, 1992.

Sarver et al., *Science*, 247:1222–1225, 1990.

Sasaki, Yagi, Bronson, Tominaga, Matsunashi, Deguchi, Tani, Kishimoto, Komori, "Absence of fetal liver hematopoiesis in mice deficient in transcriptional coactivator core binding factor β," *Proc. Natl. Acad. Sci. USA*, 93:12359–12363, 1996.

Satake, Nomura, Yamagushi-Iwai, Takahama, Hashimoto, Niki, Kitamura, Ito, "Expression of the runt domain-encoding PEBP2α genes in T cells during thymic development," *Mol. Cell. Biol.*, 15:1662–1670, 1995.

Sauer, Hansen, Tjian, "Multiple $TAF_{IIS}$ directing synergistic activation of transcription," *Science*, 270:1783–1788, 1995.

Saville and Collins, *Cell*, 61:685–696, 1990.

Saville and Collins, *Proc. Natl. Acad. Sci. USA*, 88:8826–8830, 1991.

Scanlon et al., *Proc. Natl. Acad. Sci. USA*, 88:10591–10595, 1991.

Scaringe et al., *Nuc. Acids Res.*, 18:5433–5441, 1990.

Sculier et al., "Pilot study of amphotericin B entrapped in sonicated liposomes in cancer patients with fuingal infections," *J. Cancer Clin. Oncol.*, 24(3):527–538, 1988.

Seeger et al., *Biotechniques*, 23(3):512–517, 1997.

Segal, "Biochemical Calculations" 2nd Edition. John Wiley & Sons, New York, 1976.

Seitz et al., "Effect of transforming growth factor β on parathyroid hormone receptor binding and cAMP formation in rat osteosarcoma cells," *J. Bone Min. Res.*, 7:541–546, 1992.

Selby and Selby, "Gamma-ray-induced dominant mutations that cause skeletal abnormalities in mice. II. Description of proved mutations," *Mut. Res.*, 51:199–236, 1978.

Selvamurugan, Pearmen, Chou, Pulumati, Brown, Baumann, Angel, Partridge, "Parathyroid hormone regulates the rodent collagenase gene through the AP-1 site together with an upstream regulatory element," Abstr. T460, Abstr. 18th *Annu. Meet. Am. Soc. Bone Min. Res.*, p. S414, 1996.

Shimell et al., "The Drosophila dorsal-ventral patterning gene tolloid is related to human bone morphogenetic protein 1," *Cell*, 67:469–481, 1991.

Sillence et al., "Animal model: skeletal abnormalities in mice with cleidocranial dysplasia," *Am. J. Med. Genet.*, 27:75–85, 1987.

Simeone, Daga, Calabi, "Expression of runt in the mouse embryo," *Dev. Dyn.*, 203(1):61–70, 1995.

Soriano, Montgomery, Geske, Bradley, "Targeted disruption of the c-src proto-oncogene leads to osteopetrosis in mice," *Cell*, 64(4):693–702, 1991.

Speck and Stacy, "A new transcription factor family associated with human leukemias," *Crit. Rev. Euk. Gene Exp.*, 5:337–364, 1995.

Spiegelman and Flier, "Adipogenesis and obesity: rounding out the big picture," *Cell*, 87:377–389, 1996.

Spoerel and Kafatos, "Identification of genomic sequences corresponding to cDNA clones," *Methods Enzymol.*, 152:588–597, 1987.

Stetsenko, Lubyako, Potapov, Azhikina, Sverdlov, *Tetrahedron Lett.*, 37:3571–3574, 1996.

Stinchcomb, Struhl, Davis, "Isolation and characterization of a yeast chromosomal replicator," *Nature*, 282(5734):39, 1979.

Stratford-Perricaudet and Perricaudet, "Gene transfer into animals: the promise of adenovirus," p. 51–61, In: *Human Gene Transfer*, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Strauss, "Preparation of genomic DNA from mammalian tissue," In: *Current Protocols in Molecular Biology*, Boston, John Wiley and Sons, Ausubel et al. Eds., Vol. 1, pp. 221–223, 1994.

Suda, Takahashi, Martin, "Modulation of osteoclast differentiation," *Endocrine Rev.*, 13:66–80, 1992.

Sudo, Kodama, Amagai, Yamamoto, Kasai, "In vitro differentiation and calcification of a new clonal osteogenic cell line derived from newborn mouse calvaria," *J. Cell Biol.*, 96:191–198, 1983.

Sundin, Busse, Rogers, Gudas, Eichele, "Region-specific expression in early chick and mouse embryo of Ghox-lab and Hox 1.6, vertebrate homeobox-containing genes related to Drosophila labial," *Development*, 108:47–58, 1990.

Tabin, "Retinoids, homeoboxes, and growth factors: toward molecular models for limb development," *Cell*, 66:199–217, 1991.

Tairaet al., *Nucl. Acids Res.*, 19:5125–5130, 1991.

Taylor and Jones. "Multiple new phenotypes induced in 10T1/2 and 3T3 cells treated by 5-azacytidine," *Cell*, 17:771–779, 1979.

Temin, "Retrovirus vectors for gene transfer: Efficient integration into and expression of exogenous DNA in vertebrate cell genome," In: *Gene Transfer*, Kucherlapati (ed.), New York: Plenum Press, pp. 149–188, 1986.

Thiede, Bayerdorffer, Blasczyk, Wittig, Neubauer, *Nucleic Acids Res.*, 24:983–984, 1996.

Thisted, Just, Petersen, Hyldig-Nielsen, Godtfredsen, *Cell Vision*, 3:358–363, 1996.

Thomson et al., *Tetrahedron*, 51:6179–6194, 1995.

Tomanin et al., *Gene*, 193(2):129–140, 1997.

Tomic et al., *Nucl. Acids Res.*, 12:1656, 1990.

Tontonoz et al., "Stimulation of adipogenesis in fibroblasts by PPAR 2, a lipid-activated transcription factor," *Cell*, 79:1147–1156, 1994.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Towler, Bennett, Rodan, "Activity of the rat osteocalcin basal promoter in osteoblastic cells is dependent upon homeodomain and CP1 binding motifs," *Mol. Endocrinol.*, 8:614–624, 1994.

Tsai and Gergen, "Gap gene properties of the pair-rule gene runt during Drosophila segmentation," *Development*, 120:1671–1683, 1994.

Tschumper and Carbon, "Sequence of a yeast DNA fragment containing a chromosomal replicator and the TRP1 gene," *Gene*, 10(2):157–166, 1980.

Tubulekas et al., *Gene*, 190(1):191–195, 1997.

Tur-Kaspa et al., "Use of electroporation to introduce biologically active foreign genes into primary rat hepatocytes," *Mol. Cell Biol.*, 6:716–718, 1986.

Ulmann, Will, Breipohl, Langner, Ryte, *Angew. Chem., Int. Ed. Engl.*, 35:2632–2635, 1996.

Upender et al., *Biotechniques*, 18:29–31, 1995.

Usman and Cedergren, *TIBS*, 17:34, 1992.

Usman et al., *J. Am. Chem. Soc.*, 109:7845–7854, 1987.

Van Dyke, Sirito, Sawadogo, "Single-step purification of bacterially expressed polypeptides containing an oligo-histidine domain," *Gene*, 111:99–104, 1992.

Varmus et al., "Retroviruses as mutagens: Insertion and excision of a nontransforming provirus alter the expression of a resident transforming provirus," *Cell*, 25:23–36, 1981.

Ventura et al., *Nucl. Acids Res.*, 21:3249–3255, 1993.

Veselkov, Demidov, Nielsen, Frank-Kamenetskii, *Nucl. Acids Res.*, 24:2483–2487, 1996.

Vickers, Griffith, Ramasamy, Risen, Freier, *Nucl. Acids Res.*, 23:3003–3008, 1995.

Vignery and Baron, "Dynamic histomorphometry of alveolar bone remodeling in the adult rat," *Anat. Rec.*, 196(2):191–200, 1980.

Voss and Rosenfeld, "Anterior pituitary development: short tales from dwarf mice," *Cell.* 70:527–530, 1992.

Wagner, Matteucci, Lewis, Gutierrez, Moulds, Froehler, "Antisense gene inhibition by oligonucleotides containing C-5 propyne pyrimidines," *Science*, 260(5113):1510–1513, 1993.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.

Walker et al., *Proc. Natl. Acad. Sci. USA*, 89(1):392–396, 1992.

Wang et al., "Bone and haematopoietic defects in mice lacking c-fos," *Nature*, 360(6406):741–745, 1992.

Wang et al., *Methods enzymol.*, 288:38–55, 1997.

Wang, *J. Am. Chem. Soc.*, 118:7667–7670, 1996.

Wang, Stacy, Binder, Marin-Padilla, Sharpe, Speck, "Disruption of the Cbfa2 gene causes necrosis and hemorrhaging in the central nervous system and blocks definitive hematopoiesis," *Proc. Natl. Acad. Sci. USA*, 93:3444–3449, 1996a.

Wang, Stacy, Miller, Lewis, Gu, Huang, Bushweller, Bories, Alt, Ryan, Liu, Wynshaw-Boris, Binder, Marin-Padilla, Sharpe, Speck, "The Cbfβ subunit is essential for CBFα2 (AML1) function in vivo," *Cell*, 87:697–708, 1996b.

Wang, Wang, Crute, Melnikova, Keller, Speck, "Cloning and characterization of subunits of the T-cell receptor and murine leukemia virus enhancer core-binding factor," *Mol. Cell. Biol.*, 13:3324–3339, 1993.

Watson, J. D. et al., *Molecular Biology of the Gene*, 4th Ed., W. A. Benjamin, Inc., Menlo Park, Calif., 1987.

Webb and Hurskainen, *J. Biomol. Screen.*, 1:1 19–121, 1996.

Weerasinghe et al., *J. Virol.*, 65:5531–5534, 1991.

Weinreb, Shinar, Rodan, "Different pattern of alkaline phosphatase, osteopontin, and osteocalcin expression in developing rat bone visualized by in situ hybridization," *J. Bone. Miner. Res.*, 5:831–842, 1990.

Wijmenga, Speck, Dracopoli, Hofker, Liu, Collins, "Identification of a new murine runt domain-containing gene, Cbfa3, and localization of the human homolog, CBFA3, to chromosome 1p35-pter," *Genomics*, 26:611–614, 1995.

Wilkinson, "In situ hybridization," In: *In situ hybridization: A practical approach*, New York, N.Y.: IRL Press at Oxford University, 11:257–263, 1992.

Wolf et al., "An Integrated Family of Amino Acid Sequence Analysis Programs," *Compu. Appl. Biosci.*, 4(1):187–91, 1988.

Wong and Neumann, "Electric field mediated gene transfer," *Biochim. Biophys. Res. Commun.*, 107(2):584–587, 1982.

Wong et al., "Appearance of β-lactamase activity in animal cells upon liposome mediated gene transfer," *Gene*, 10:87–94, 1980.

Woolf et al., *Proc. Natl. Acad. Sci. USA*, 89:7305–7309, 1992.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Wu et al., *Gene*, 190(1):157–162, 1997.

Wu, S. J. and Dean, D. H., "Functional significance of loops in the receptor binding domain of *Bacillus thuringiensis* CryIIIA δ-endotoxin," *J. Mol. Biol.* 255(4):628–640, 1996.

Yang et al., "In vivo and in vitro gene transfer to mammalian somatic cells by particle bombardment," *Proc. Natl. Acad. Sci. USA*, 87:9568–9572, 1990.

Yang, Zhang, Davey, Mulligan, Cocking, *Plant Cell Rep*, 7:421–425, 1988.

Young and Davis, "Efficient isolation of genes by using antibody probes," *Proc. Natl. Acad. Sci. USA*, 80:1194–1198, 1983.

Yu et al., *Proc. Natl. Acad. Sci. USA*, 90:6340–6344, 1993.

Zatloukal, Wagner, Cotten, Phillips, Plank, Steinlein, Curiel, Birnstiel, "Transferrinfection: a highly efficient way to express gene constructs in eukaryotic cells," *Ann. N.Y. Acad. Sci*, 60:136–153, 1992.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

Zhang et al. "1,25(OH)2 vitamin $D_3$ inhibits Osteocalcin expression in mouse through an indirect mechanism," *J. Biol. Chem.*, 272:110–116, 1997.

Zhou et al., *Mol. Cell Biol.*, 10:4529–4537, 1990.

---

What is claimed is:

1. A polynucleotide that encodes an Osf2/Cbfa1 polypeptide comprising the contiguous amino acid sequence of SEQ ID NO:2 or SEQ ID NO:71.

2. The polynucleotide of claim 1, further defined as DNA.

3. The polynucleotide of claim 1, comprising a human Osf2/Cbfa1 gene.

4. The polynucleotide of claim 1, operably linked to a promoter.

5. The polynucleotide of claim 4, wherein said promoter is selected from the group consisting of a polyoma, Adenovirus 2, Simian Virus 40, β-lactamase, an Osf2/Cbfa1, lac, tac, trp, Osf, Runt, 3-phosphoglycerate kinase, enolase, alcohol dehydrogenase 2, isocytochrome C, acid phosphatase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and a glucokinase promoter.

6. The polynucleotide of claim 1, further comprising a vector.

7. The polynucleotide of claim 6, wherein said vector is a plasmid or viral vector.

8. The polynucleotide of claim 1, comprising the contiguous nucleic acid sequence of SEQ ID NO:1 or SEQ ID NO:70.

9. An isolated host cell comprising the vector of claim 6.

10. The host cell of claim 9, wherein said host cell is bacterial cell or a mammalian cell.

11. A polynucleotide comprising the contiguous nucleotide sequence of SEQ ID NO:72.

12. An isolated host cell comprising a nucleic acid segment that encodes an Osf2/Cbfa1 polypeptide comprising the contiguous amino acid sequence of SEQ ID NO:2 or SEQ ID NO:71.

13. The host cell of claim 12, further defined as a bacterial or animal host cell.

14. The host cell of claim 12, comprised within a non-human transgenic animal.

15. The host cell of claim 12, wherein said host cell expresses said Osf2/Cbfa1 polypeptide.

16. A composition comprising a polypeptide having an amino acid sequence that comprises at least 12 contiguous amino acid residues from SEQ ID NO:2 or SEQ ID NO:71, said polypeptide having osteoblast-specific transcription factor activity.

17. The composition of claim 16, wherein said polypeptide comprises the amino acid sequence of SEQ ID NO:2 or SEQ ID NO:71.

18. A purified antibody that specifically binds to a polypeptide having an amino acid sequence that comprises at least 12 contiguous amino acid residues from SEQ ID NO:2 or SEQ ID NO:71.

19. The antibody of claim 18, wherein said antibody specifically binds to a polypeptide comprising the amino acid sequence of SEQ ID NO:2 or SEQ ID NO:71.

20. The antibody of claim 18, wherein said antibody is linked to a detectable label.

21. The antibody of claim 20, wherein said antibody is linked to a radioactive label, a fluorogenic label, a nuclear magnetic spin resonance label, biotin or an enzyme that generates a colored product upon contact with a chromogenic substrate.

22. The antibody of claim 21, wherein said antibody is linked to an alkaline phosphatase, hydrogen peroxidase or glucose oxidase enzyme.

23. A method for detecting an Osf2/Cbfa1 polypeptide in a sample, comprising the steps of:
 (a) obtaining a sample suspected of containing an Osf2/Cbfa1 polypeptide;
 (b) contacting said sample with a first antibody that binds to an Osf2/Cbfa1 polypeptide, under conditions effective to allow the formation of immune complexes; and
 (c) detecting the immune complexes so formed.

24. The method of claim 23, wherein said antibody is linked to a radioactive label, a fluorogenic label, a nuclear magnetic spin resonance label, biotin or an enzyme that generates a colored product upon contact with a chromogenic substrate.

25. An immunodetection kit comprising, in suitable container means, a polypeptide comprising the amino acid sequence of SEQ ID NO:2 or SEQ ID NO:71, or a first antibody that binds to a polypeptide comprising the amino acid sequence of SEQ ID NO:2 or SEQ ID NO:71, and at least one immunodetection reagent.

26. The immunodetection kit of claim 25, wherein the immunodetection reagent is a detectable label that is linked to said polypeptide or said first antibody.

27. The immunodetection kit of claim 25, wherein said immunodetection reagent is a detectable label that is linked to a second antibody that has binding affinity for said polypeptide or said first antibody.

28. The immunodetection kit of claim 25, wherein the immunodetection reagent is a detectable label that is linked to a second antibody that has binding affinity for a human antibody.

29. A method of generating an immune response, comprising administering to an animal a pharmaceutical composition comprising an immunologically effective amount of an Osf2/Cbfa1 composition.

30. A method of detecting a polypeptide that interacts with an Osf2 binding site, said method comprising the steps of:
 (a) obtaining a labeled Osf2 binding site;
 (b) screening an expression library with said labeled Osf2 binding site;
 (c) identifying in said library one or more polypeptides that interacts with said Osf2 binding site; and
 (d) obtaining said interacting polypeptide from said expression library.

* * * * *